(12) United States Patent
Otto et al.

(10) Patent No.: US 6,949,522 B2
(45) Date of Patent: Sep. 27, 2005

(54) β-2'- OR 3'-HALONUCLEOSIDES

(75) Inventors: Michael J. Otto, Lilburn, GA (US); Junxing Shi, Duluth, GA (US); Chung K. Chu, Athens, GA (US); Raymond F. Schinazi, Decatur, GA (US); Giuseppe Gumina, Athens, GA (US); Youhoon Chong, Athens, GA (US); Yongseok Choi, Frederick, MD (US)

(73) Assignees: Pharmasset, Inc., Tucker, GA (US); The University of Georgia Research Foundation, Inc., Athens, GA (US); Emory University, Atlanta, GA (US)

(*) Notice: Subject to any disclaimer, the term of this patent is extended or adjusted under 35 U.S.C. 154(b) by 0 days.

(21) Appl. No.: 10/179,612

(22) Filed: Jun. 24, 2002

(65) Prior Publication Data

US 2005/0119286 A1 Jun. 2, 2005

Related U.S. Application Data

(60) Provisional application No. 60/305,386, filed on Jul. 13, 2001, and provisional application No. 60/300,356, filed on Jun. 22, 2001.

(51) Int. Cl.$^7$ ............................ A01N 43/04; A61K 31/70
(52) U.S. Cl. ............................ 514/45; 514/42; 514/43; 514/46; 514/47; 514/48
(58) Field of Search ............................ 514/42, 43, 45, 514/46, 47, 48

(56) References Cited

U.S. PATENT DOCUMENTS

| | | | |
|---|---|---|---|
| 4,211,773 A | 7/1980 | Lopez et al. | |
| 4,625,020 A | 11/1986 | Brundidge et al. | |
| 4,666,892 A | 5/1987 | Fox et al. | |
| 4,681,933 A | 7/1987 | Chu et al. | |
| 4,963,662 A | 10/1990 | Matthes et al. | |
| 5,034,518 A | 7/1991 | Montgomery et al. | |
| 5,128,458 A | 7/1992 | Montgomery et al. | |
| 5,215,970 A | 6/1993 | Datema et al. | |
| 5,246,924 A | 9/1993 | Fox et al. | |
| 5,336,764 A | 8/1994 | Marquez et al. | |
| 5,424,416 A | 6/1995 | Jones et al. | |
| 5,426,183 A | 6/1995 | Kjell | |
| 5,446,029 A | 8/1995 | Eriksson et al. | |
| 5,565,438 A | 10/1996 | Chu et al. | |
| 5,567,688 A | 10/1996 | Chu et al. | |
| 5,574,149 A | 11/1996 | Van Tuttle et al. | |
| 5,587,362 A | 12/1996 | Chu et al. | |
| 5,637,574 A | 6/1997 | Burns et al. | |
| 5,663,154 A | 9/1997 | Burns et al. | |
| 5,703,058 A | 12/1997 | Schinazi et al. | |
| 5,817,799 A | 10/1998 | Marquez et al. | |
| 6,348,587 B1 | 2/2002 | Schinazi et al. | |
| 6,355,790 B1 * | 3/2002 | Rosenblatt et al. | 536/24.5 |

FOREIGN PATENT DOCUMENTS

| | | |
|---|---|---|
| EP | 0 292 023 | 11/1988 |
| EP | 0 316 017 | 5/1989 |
| EP | 0 352 248 | 1/1990 |
| EP | 0 357 571 | 3/1990 |
| EP | 0 409 227 A2 | 1/1991 |
| EP | 0 463 470 | 1/1992 |
| WO | WO 88/09001 | 10/1988 |
| WO | WO 92/08727 | 5/1992 |
| WO | WO 94/14831 | 7/1994 |
| WO | WO 99/43691 | 9/1999 |
| WO | WO 01/90121 | 11/2001 |
| WO | WO 01/92282 | 12/2001 |

OTHER PUBLICATIONS

Koshida et al. Antimicrobial Agents and Chemotherapy, 1989, pp. 2083–2088.*

Pai Balakrishna, et al., Inhibition of Hepatitis B Virus by a Novel L–Nucleoside, 2'–Fluoro–5–Methyl–β–L–arabinofuranosyl Uracil, *Antimicrobial Agents and Chemotherapy*, Feb. 1996, 380–356.

Belen'kii, S. M.; Schinazi, R. S. Multiple drug effect analysis with confidence interval. *Antiviral. Res.* 1994, 25, 1–11.

Bobek, M.; Bloch, A.; Parthasarathy, R.; Whistler, R. L. Synthesis and biological activity of 5–fluoro–4'–thiouridine and some related nucleosides. *J. Med. Chem.* 1975, 18, 784–787), including 9–(4–thio–D–xylofuranosyl)adenine.

Choi, Y.; Choo, H.; Chong, Y.; Lee, S.; Olgen, S.; Schinazi, R. F.; Chu, C. K. Synthesis and potent anti–HIV activity of L–2',3'–didehydro–2',3'–dideoxy–2'–fluoro–4'–thiocytidine. *Org. Lett.* 2002, 4, 305–307.

Chong, Y.; Gumina, G.; Chu, C. K. *Tetrahedron Asymmetry.* 2000, 11, 4853–4875.

Chu, et al., Use of 2'–Fluoro–5–methyl–β–L–arabinofuranosyluracil as a Novel Antiviral Agent for Hepatitis B Virus and Epstein–Barr Virus; *Antimicrobial Agents and Chemotherapy*, Apr. 1995, 979–981.

Cooperwood et al. *Nucleosides Nucleotides* 2000, 19 (1&2), 219.

Desgranges, C.; Razaka, G.; Rabaud, M.; Bricaud, H.; Balzarini, J.; De Clercq, E. Phosphorolysis of (E)–5–(2–bromovinyl)–2'–deoxyuridine (BVDU) and other 5–substituted–2'–deoxyuridines by purified human thymidine phosphorylase and intact blood–platelets. *Biochem. Pharmacol.* 1983, 32, 3583–3590.

Dyson, M. R.; Coe, P. L.; Walker, R. T. The synthesis and antiviral properties of E–5–(2–bromovinyl)–4'–thio–2'–deoxyuridine. *J. Chem. Soc., Chem. Commun.* 1991, 741–742.

Dyson, M. R.; Coe, P. L.; Walker, R. T. The synthesis and antiviral activity of some 4'–thio–2'–deoxy nucleoside analogs. *J. Med. Chem.* 1991, 34, 2782–2786.

(Continued)

*Primary Examiner*—James O. Wilson
*Assistant Examiner*—Patrick T. Lewis

(57) ABSTRACT

The present invention includes compounds and compositions of β-halonucleosides, as well as methods to treat HIV, HBV or abnormal cellular proliferation comprising administering said compounds or compositions.

44 Claims, 18 Drawing Sheets

OTHER PUBLICATIONS

Ford, H. Jr.; Dai, F.; Mu, L.; Siddiqui, M. A.; Nicklaus, M. C.; Anderson, L.; Marquez, V. E.; Barchi, J. J. Jr. Adenosine deaminase prefers a distinct sugar ring conformation for binding and catalysis: Kinetic and structural studies. *Biochemistry,* 2000, 39, 2581–2592.

Fu, Y.–L.; Bobek, M. In *Nucleic Acid Chemistry;* Townsend, L.; Tipson, R. S., Eds.; John Wiley & Sons: New York, 1978; pp 317–323.

Hanessian, S.; Murray, P. J. Stereochemical control of nature's biosynthetic pathways: A general strategy for the synthesis of polypropionate–derived structural units from a single chiral progenitor. *Tetrahedron* 1987, 43, 5055–5072.

Herdewijn, P. Structural requirements for activiral activity in nucleosides. *Drug Discov. Today,* 1997, 2, 235–242.

Borthwick, et al., Synthesis and Enzymatic Resolution of Carbocyclic 2'-Ara–fluoro–Guanosine: A Potent New Anti–Herpetic Agent, *J. Chem. Soc., Chem. Commun,* 1988.

Bouffard, Kinetic Studies of 2',2'-difluorodeoxycytidine (Gemcitabine) with Purified Human Deoxycytidine Kinase and Cytidine Deaminase, *BioChemical Pharmacology,* vol. 45 (No. 9) pp. 4857–1861, 1993.

Lee et al. *J. Med. Chem.* 2002, 45, 1313–1320.

Lee, K.; Choi, Y.; Gullen, E.; Schlueter–Wirtz, S.; Schinazi, R. F.; Cheng, Y.–C.; Chu, C. K. Synthesis and anti–HIV and anti–HBV activities of 2'-fluoro-2',3'-unsaturated L–nucleosides. *J. Med. Chem.* 1999, 42, 1320–1328.

Lee, K.; Chu, C. K. Molecular modeling approach to understanding the mode of action of L–nucleosides as antiviral agents. *Antimicrob. Agents Chemother.* 2001, 45, 138–144.

Ma et al., *J. Med. Chem.* 1996, 39 (14), 2835.

Marquez, V. E.; Tseng, C. K.–H.; Mitsuya, H.; Aoki, S.; Kelley, J. A.; Ford, H. Jr.; Roth, J. S.; Broder, S.; Johns, D. G.; Driscoll, J. S. Acid–stable 2'-fluoro purine dideoxynucleosides as active agents against HIV. *J. Med. Chem.* 1990, 33, 978–985.

Martin, et.al., Synthesis and Antiviral Activity of Monofluoro and Difluoro Analogues of Pyrimidine Deoxyribonucleosides against Human Immunodeficiency Virus (HIV–1), *J. Med. Chem.* 1990, 33, 2137–2145.

Ototani, N.; Whistler, R. L. Preparation and antitumor activity of 4'-thio analogs of 2,2'-anhydro–1–β–D–arabinofuranosylcytosine. *J. Med. Chem.* 1974, 17, 535–537.

Parks, R. E., Jr.; Stoeckler, J. D.; Cambor, C.; Savarese, T. M.; Crabtree, G. W.; Chu, S.–H. In Molecular Actions and Targets for Cancer Chemotherapeutic Agents; Sartorelli, A. C. Lazo, J. S., Bertino, J. R., Eds.; Academic Press: New York, 1981; pp 229–252.

Philpott, M.S., Ebner, J.P., Hoover, E.A., "Evaluation of 9–(2-phosphonylmethoxyethyl) adenine therapy for feline immunodeficiency virus using a quantitative polymerase chain reaction," *Vet. Immunol. Immunopathol.* 35:155166, 1992.

Reist, E. J.; Gueffroy, D. E.; Goodman, L. Synthesis of 4–thio–D–& L–ribofuranose and corresponding adenine nucleosides. *J. Am. Chem. Soc.* 1964, 86, 5658–5663.

Reist, E. J.; Fisher, L. V.; Gueffroy, E.; Goodman, L. Neighboring–group participation. Preparation of dithiopentose sugars via a thioacylonium ion intermediate. *J. Org. Chem.* 1968, 33, 189–192.

Secrist III, J. A.; Riggs, R. H.; Tiwari, K. N.; Montgomery, J. A. Synthesis and anti–HIV activity of 4'-thio–2', 3'-dideoxynucleosides. *J. Med. Chem.* 1992, 35, 533–538.

Secrist III, J. A.; Tiwari, K. N.; Riordan, J. M.; Montgomery, J. A. Synthesis and biological activity of 2'-deoxy–4–'thio pyrimidine nucleosides, *J. Med. Chem.* 1991, 34, 2361–2366.

Secrist, J. A.; Tiwari, K. N.; Shortnacy–Fowler, A. T.; Messini, L.; Riordan, J. M.; Montgomery, J. A. Synthesis and biological activity of certain 4'-thio–D–arabinofuranosylpurine nucleosides. *J. Med. Chem.* 1998, 41, 3865–3871.

Sellon D.C., "Equine Infectious Anemia," *Vet. Clin. North Am. Equine Pract. United States,* 9: 321–336, 1993.

Sterzycki, et al., Synthesis and Anti–HIV Activity of Several 2'-Fluoro–Containing Pyrimidine Nucleosides, *J. Med. Chem.* 1990.

Takagi, R.; Nakamura, M.; Hashizume, M.; Kojima, S.; Ohkata, K. Stereoselective cyclopropanation of 3–aryl–2–phosphonoacrylates induced by the (–)–8–phenylmenthyl group as a chiral auxiliary. *Tetrahedron lett.* 2001, 42, 5891–5895.

Uenishi, J.; Motoyama, M.; Nishiyama, Y.; Wakabayashi, S. Stereocontrolled preparation of cyclic xanthate—A novel synthetic route to 4–thiofuranose and 4'-thionucleoside. *J. Chem. Soc., Chem. Commun.* 1991, 1421–1422.

Wang, P.; Hong, J. H.; Cooperwood, J. S.; Chu, C. K. Recent advances in L–nucleosides: chemistry and biology. *Antiviral Res.* 1998, 40, 19–44.

Wantanabe, et al., Synthesis and Anti–HIV Activity of 2'–"Up"–Fluoro Analogues of Active Anti–Aids Nucleosides 3'-Azido–3'-deoxythymidine (AZT) and 2',3'-deoxythymidine (AZT) and 2',3'-dideoxycytidine (DDC), *J. Med. Chem.* 1990, 33, 2145–2150.

Whistler, R. L.; Doner, L. W.; Nayak, U. G. 4–Thio–D–arabinofuranosylpyrimidine nucleosides. *J. Org. Chem.* 1971, 36, 108–110.

Yoshimura, Y.; Kitano, K.; Yamada, K.; Satoh, H.; Watanabe, M.; Miura, S.; Sakata, S.; Sasaki, T.; Matsuda, A. A novel synthesis of 2'-modified 2'-deoxy–4'-thiocytidines from D–glucose. *J. Org. Chem.* 1997, 62, 3140–3152.

Yoshimura, Y.; Watanabe, M.; Satoh, H.; Ashida, N.; Ijichi, K.; Sakata, S.; Machida, H.; Matsuda, A. A facile, alternative synthesis of 4'-thioarabinonucleosides and their biological activities. *J. Med. Chem.* 1997, 40, 2177–2183.

Young, R. J.; Shaw–Ponter, S.; Thomson, J. B.; Miller, J. A.; Cumming, J. G.; Pugh, A. W.; Rider, P. Synthesis and antiviral evaluation of enantiomeric 2',3'-dideoxy– and 2',3'-didehydro–2',3'-dideoxy–4'-thionucleosides. *Bioorg. Med. Chem. Lett.* 1995, 5, 2599–2604.

* cited by examiner

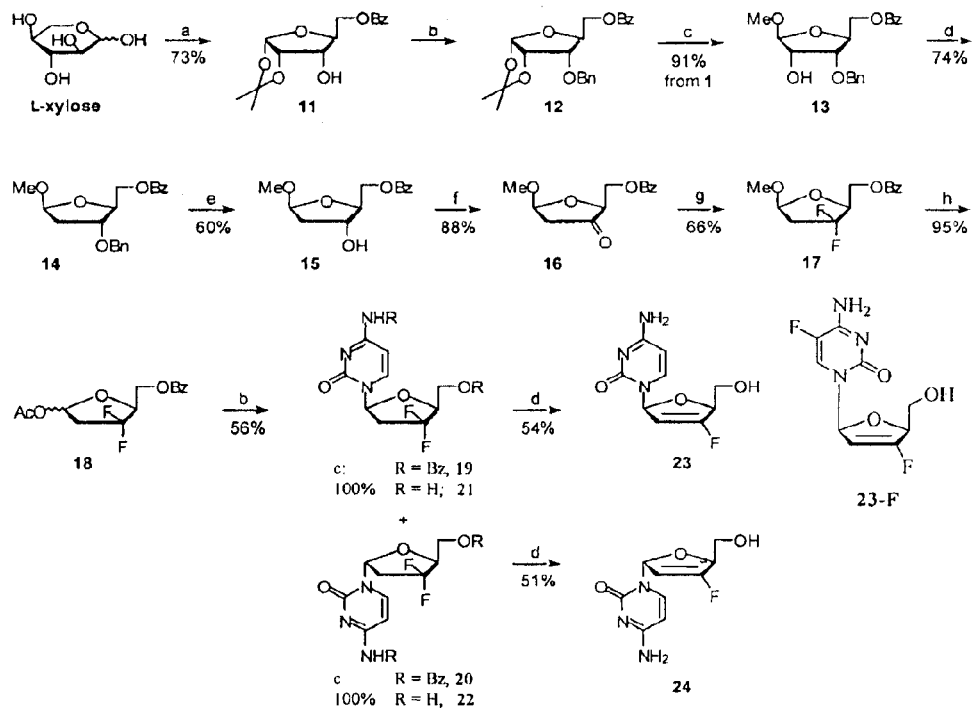
FIGURE 2A
FIGURE 2B
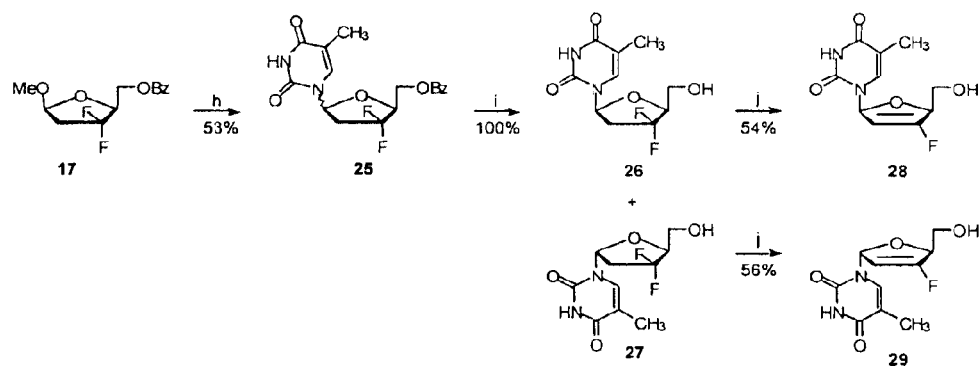

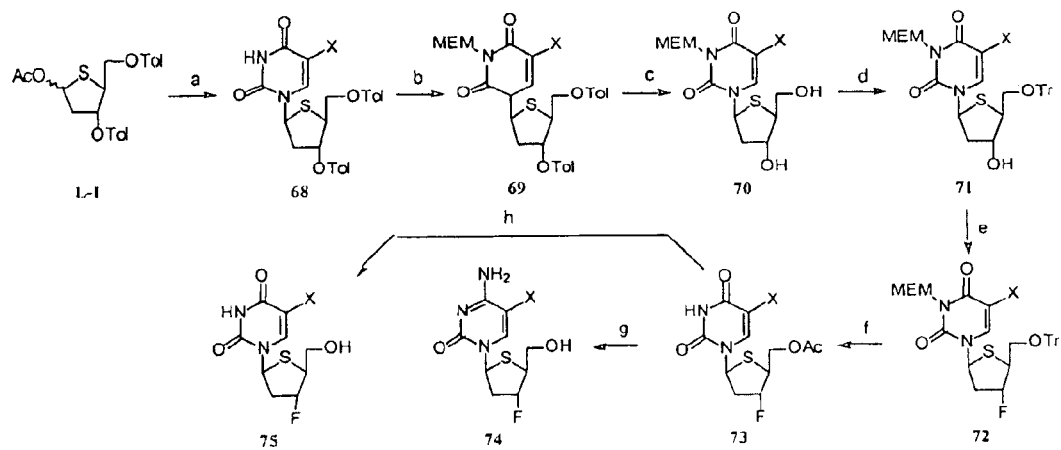
FIGURE 9
FIGURE 10
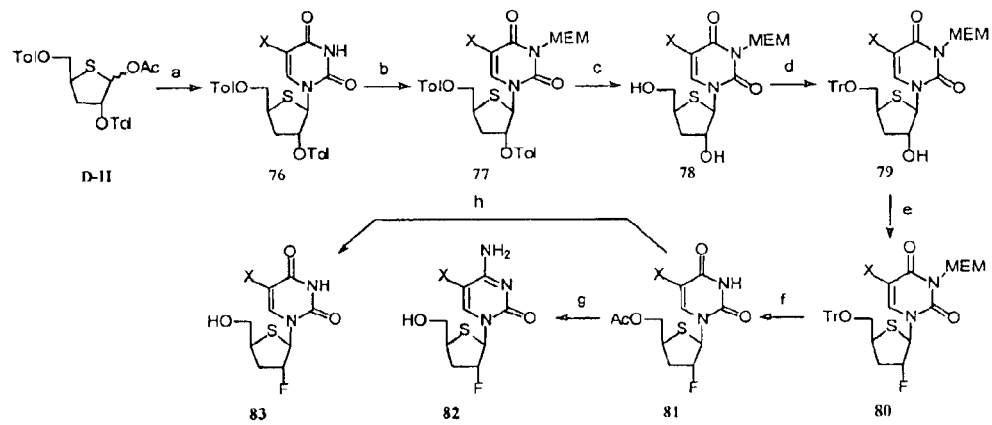

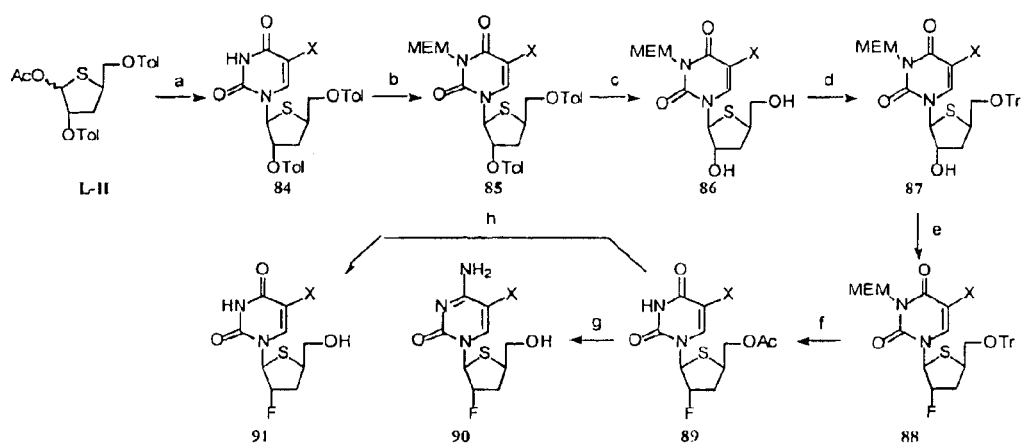
FIGURE 11
FIGURE 12
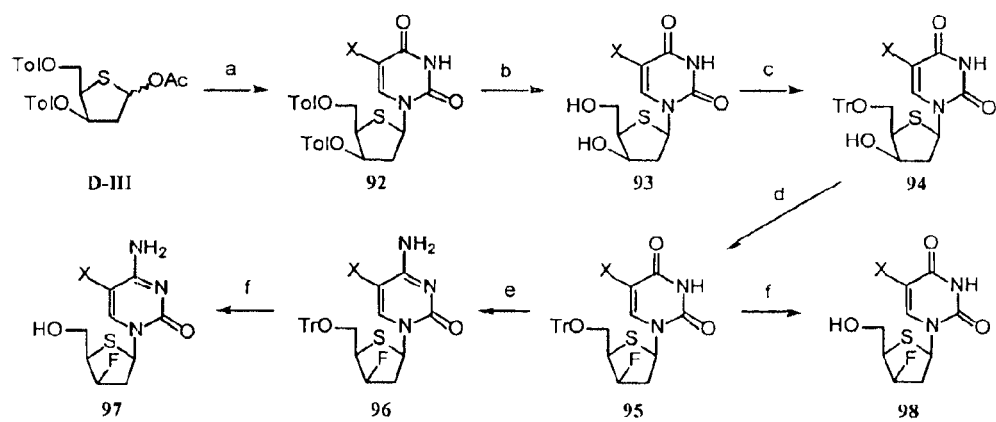

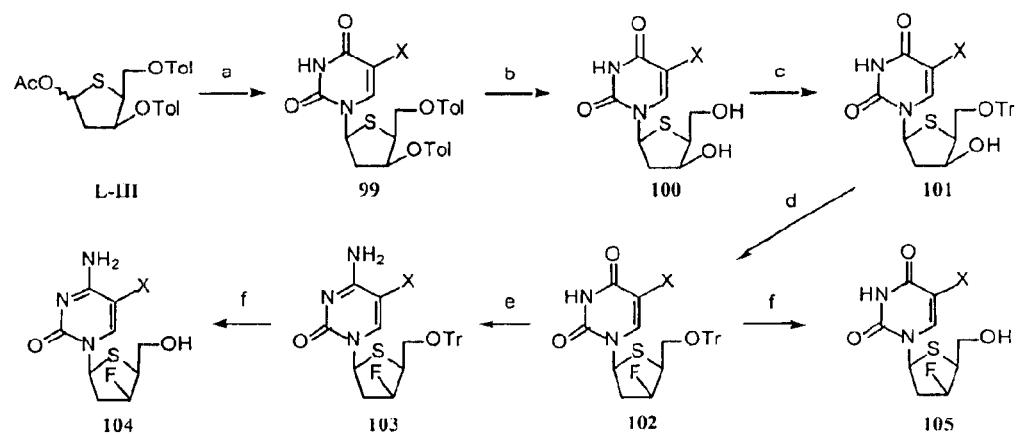
FIGURE 13
FIGURE 14
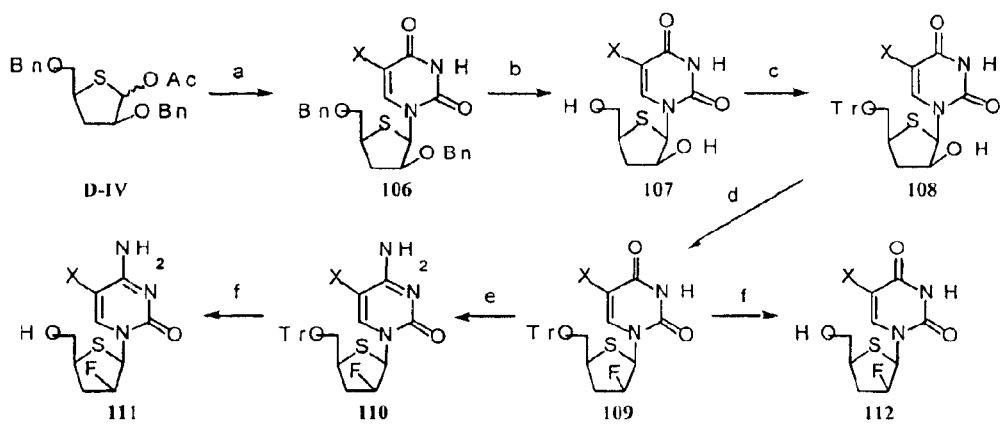

β-2'- OR 3'-HALONUCLEOSIDES

This application claims priority to U.S. Provisional Application No. 60/300,356, filed on Jun. 22, 2001, and U.S. Provisional Application No. 60/305,386, filed on Jul. 13, 2001.

The invention described herein was made with Government support under grant number AI32351 and AI25899 awarded by the National Institutes of Health, as well as grant numbers 1R37AI-41890 and 1RO1AI-32351. The United States Government has certain rights to this invention.

FIELD OF THE INVENTION

This invention is in the area of pharmaceutical chemistry, and in particular, describes β-2'- or 3'-halonucleosides and methods for their preparation and use.

BACKGROUND OF THE INVENTION

Synthetic nucleosides such as 5-iodouracil and 5-fluorouracil have been used for the treatment of cancer for many years. Since the 1980's, synthetic nucleosides have also been a focus of interest for the treatment of HIV and hepatitis.

In 1981, acquired immune deficiency syndrome (AIDS) was identified as a disease that severely compromises the human immune system, and that almost without exception leads to death. In 1983, the etiological cause of AIDS was determined to be the human immunodeficiency virus (HIV). In 1985, it was reported that the synthetic nucleoside 3'-azido-3'-deoxythymidine (AZT) inhibits the replication of human immunodeficiency virus. Since then, a number of other synthetic nucleosides, including 2',3'-dideoxyinosine (DDI), 2',3'-dideoxycytidine (DDC), and 2',3'-dideoxy-2',3'-didehydrothymidine (D4T), have been proven to be effective against HIV. After cellular phosphorylation to the 5'-triphosphate by cellular kinases, these synthetic nucleosides are incorporated into a growing strand of viral DNA, causing chain termination due to the absence of the 3'-hydroxyl group. They can also inhibit the viral enzyme reverse transcriptase.

The success of various synthetic nucleosides in inhibiting the replication of HIV in vivo or in vitro has led a number of researchers to design and test nucleosides that substitute a heteroatom for the carbon atom at the 3'-position of the nucleoside. European Patent Publication No. 0 337 713 and U.S. Pat. No. 5,041,449, assigned to BioChem Pharma, Inc., disclose 2-substituted-4-substituted-1,3-dioxolanes that exhibit antiviral activity. U.S. Pat. No. 5,047,407 and European Patent Publication No. 0 382 526, also assigned to BioChem Pharma, Inc., disclose that a number of 2-substituted-5-substituted-1,3-oxathiolane nucleosides have antiviral activity, and specifically report that 2-hydroxymethyl-5-(cytosin-1-yl)-1,3-oxathiolane (referred to below as BCH-189) has approximately the same activity against HIV as AZT, with little toxicity.

It has also been disclosed that cis-2-hydroxymethyl-5-(5-fluorocytosin-1-yl)-1,3-oxathiolane ("FTC") has potent HIV activity. Schinazi, et al., "Selective Inhibition of Human Immunodeficiency viruses by Racemates and Enantiomers of cis-5-Fluoro-1-[2-(Hydroxymethyl)-1,3-Oxathiolane-5-yl]-Cytosine" Antimicrobial Agents and Chemotherapy, November 1992, 2423–2431. See also U.S. Pat. Nos. 5,210, 085; 5,814,639; and 5,914,331.

Another virus that causes a serious human health problem is the hepatitis B virus (referred to below as "HBV"). HBV is second only to tobacco as a cause of human cancer. The mechanism by which HBV induces cancer is unknown. It is postulated that it may directly trigger tumor development, or indirectly trigger tumor development through chronic inflammation, cirrhosis, and cell regeneration associated with the infection.

After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed.

Patients typically recover from acute hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is very similar to that of acquired immune deficiency syndrome, which accounts for why HBV infection is common among patients with AIDS or AIDS related complex. However, HBV is more contagious than HIV.

Both FTC and 3TC exhibit activity against HBV. Furman, et al., "The Anti-Hepatitis B Virus Activities, Cytotoxicities, and Anabolic Profiles of the (−) and (+) Enantiomers of cis-5-Fluoro-1-[2-(Hydroxymethyl)-1,3-oxathiolane-5-yl]-Cytosine" Antimicrobial Agents and Chemotherapy, December 1992, pp. 2686–2692; and Cheng, et al., Journal of Biological Chemistry, Volume 267(20), pp. 13938–13942 (1992). Other compounds that exhibit activity against HBV in humans include L-FMAU (Triangle Pharmaceuticals, Inc. under license from The University of Georgia Research Foundation and Yale University), and L-dT and L-dC (Idenix Pharmaceuticals, Inc.).

HCV is the major causative agent for post-transfusion and for sporadic non A, non B hepatitis (Alter, H. J. (1990) J. Gastro. Hepatol. 1:78–94; Dienstag, J. L. (1983) Gastro 85:439–462). Despite improved screening, HCV still accounts for at least 25% of the acute viral hepatitis in many countries (Alter, H. J. (1990) supra; Dienstag, J. L. (1983) supra; Alter M. J. et al. (1990a) J.A.M.A. 264:2231–2235; Alter M. J. et al (1992) N. Engl. J. Med. 327:1899–1905; Alter, M. J. et al. (1990b) N. Engl. J. Med. 321:1494–1500). Infection by HCV is insidious in a high proportion of chronically infected (and infectious) carriers who may not experience clinical symptoms for many years. The high rate of progression of acute infection to chronic infection (70–100%) and liver disease (>50%), its world-wide distribution and lack of a vaccine make HCV a significant cause of morbidity and mortality. Currently, there are three types of interferon and a combination of interferon and ribavirin used to treat hepatitis C. Selection of patients for treatment may be determined by biochemical, virologic, and when necessary, liver biopsy findings, rather than presence or absence of symptoms.

Interferon is given by injection, and may have a number of side effects including flu-like symptoms including headaches, fever, fatigue, loss of appetite, nausea, vomiting, depression and thinning of hair. It may also interfere with the production of white blood cells and platelets by depressing the bone marrow. Periodic blood tests are required to monitor blood cells and platelets. Ribavirin can cause sudden, severe anemia, and birth defects so women should avoid pregnancy while taking it and for 6 months following treatment. The severity and type of side effects differ for each individual. Treatment of children with HCV is not currently approved but is under investigation. While 50–60% of patients respond to treatment initially, lasting clearance of the virus occurs in only about 10–40% of patients. Treatment may be prolonged and given a second time to those who relapse after initial treatment. Re-treatment with bioengineered consensus interferon alone results in elimination of the virus in 58% of patients treated for one year. Side effects occur but the medication is usually well tolerated. Combined therapy (interferon and ribavirin) shows elimination of the virus in 47% after 6 months of therapy. Side effects from both drugs may be prominent.

A tumor is an unregulated, disorganized proliferation of cell growth. A tumor is malignant, or cancerous, if it has the properties of invasiveness and metastasis. Invasiveness refers to the tendency of a tumor to enter surrounding tissue, breaking through the basal laminas that define the boundaries of the tissues, thereby often entering the body's circulatory system. Metastasis refers to the tendency of a tumor to migrate to other areas of the body and establish areas of proliferation away from the site of initial appearance.

Cancer is now the second leading cause of death in the United States. Over 8,000,000 persons in the United States have been diagnosed with cancer, with 1,208,000 new diagnoses expected in 1994. Over 500,000 people die annually from the disease in this country.

Cancer is not fully understood on the molecular level. It is known that exposure of a cell to a carcinogen such as certain viruses, certain chemicals, or radiation, leads to DNA alteration that inactivates a "suppressive" gene or activates an "oncogene." Suppressive genes are growth regulatory genes, which upon mutation, can no longer control cell growth. Oncogenes are initially normal genes (called prooncongenes) that by mutation or altered context of expression become transforming genes. The products of transforming genes cause inappropriate cell growth. More than twenty different normal cellular genes can become oncongenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

All of the various cell types of the body can be transformed into benign or malignant tumor cells. The most frequent tumor site is lung, followed by colorectal, breast, prostate, bladder, pancreas and then ovary. Other prevalent types of cancer include leukemia, central nervous system cancers, including brain cancer, melanoma, lymphoma, erythroleukemia, uterine cancer, and head and neck cancer.

Cancer is now primarily treated with one or a combination of three years of therapies: surgery, radiation and chemotherapy. Surgery involves the bulk removal of diseased tissue. While surgery is sometimes effective in removing tumors located at certain sites, for example, in the breast, colon and skin, it cannot be used in the treatment of tumors located in other areas, such as the backbone, or in the treatment of disseminated neoplastic conditions such as leukemia.

Chemotherapy involves the disruption of cell replication or cell metabolism. It is used most often in the treatment of leukemia, as well as breast, lung, and testicular cancer.

There are five major classes of chemotherapeutic agents currently in use for the treatment of cancer: natural products and their derivatives; anthacyclines; alkylating agents; antiproliferatives (also called antimetabolites); and hormonal agents. Chemotherapeutic agents are often referred to as antineoplastic agents.

The alkylating agents are believed to act by alkylating and cross-linking guanine and possibly other bases in DNA, arresting cell division. Typical alkylating agents include nitrogen mustards, ethyleneimine compounds, alkyl sulfates, cisplatin and various nitrosoureas. A disadvantage with these compounds is that they not only attach malignant cells, but also other cells which are naturally dividing, such as those of bone marrow, skin, gastrointestinal mucosa, and fetal tissue.

Antimetabolites are typically reversible or irreversible enzyme inhibitors, or compounds that otherwise interfere with the replication, translation or transcription of nucleic acids.

Several synthetic nucleosides have been identified that exhibit anticancer activity. A well known nucleoside derivative with strong anticancer activity is 5-fluorouracil. 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation and edema. Derivatives of 5-fluorouracil with anticancer activity have been described in U.S. Pat. No 4,336,381, and in Japanese patent publication Nos. 50-50383, 50-50384, 50-64281, 51-146482, and 53-84981.

U.S. Pat. No. 4,000,137 discloses that the peroxidate oxidation product of inosine, adenosine or cytidine with methanol or ethanol has activity against lymphocytic leukemia.

Cytosine arabinoside (also referred to as Cytarabin, araC, and Cytosar) is a nucleoside analog of deoxycytidine that was first synthesized in 1950 and introduced into clinical medicine in 1963. It is currently an important drug in the treatment of acute myeloid leukemia. It is also active against acute lymphocytic leukemia, and to a lesser extent, is useful in chronic myelocytic leukemia and non-Hodgkin's lymphoma. The primary action of araC is inhibition of nuclear DNA synthesis. Handschumacher, R. and Cheng, Y., "Purine and Pyrimidine Antimetabolites" Cancer Medicine, Chapter XV-1, 3rd Edition, Edited by J. Holland, et al., Lea and Febigol, publishers.

5-Azacytidine is a cytidine analog that is primarily used in the treatment of acute myclocytic leukemia and myelodysplastic syndrome.

2-Fluoroadenosine-5'-phosphate (Fludara, also referred to as FaraA)) is one of the most active agents in the treatment of chronic lymphocytic leukemia. The compound acts by inhibiting DNA synthesis. Treatment of cells with F-araA is associated with the accumulation of cells at the G1/S phase boundary and in S phase; thus, it is a cell cycle S phase-specific drug. Incorporation of the active metabolite, F-araATP, retards DNA chain elongation. F-araA is also a potent inhibitor of ribonucleotide reductase, the key enzyme responsible for the formation of dATP.

2-Chlorodeoxyadenosine is useful in the treatment of low grade B-cell neoplasms such as chronic lymphocytic leukemia, non-Hodgkins' lymphoma, and hairy-cell leukemia.

In designing new nucleosides, there have been a number of attempts to incorporate a fluoro substituent into the carbohydrate ring of the nucleoside. Fluorine has been suggested as a substituent because it might serve as an isopolar and isosteric mimic of a hydroxyl group as the C—F bond length (1.35 Å) is so similar to the C—O bond length (1.43 Å) and because fluorine is a hydrogen bond acceptor. Fluorine is capable of producing significant electronic changes in a molecule with minimal steric perturbation. The substitution of fluorine for another group in a molecule can cause changes in substrate metabolism because of the high strength of the C—F bond (116 kcal/mol vs. C—H=100 kcal/mol).

A number of references have reported the synthesis and use of 2'-arabinofluoro-nucleosides (i.e., nucleosides in which a 2'-fluoro group is in the "up"-configuration). There have been several reports of 2-fluoro-β-D-arabinofuranosyl nucleosides that exhibit activity against hepatitis B and herpes. See, for example, U.S. Pat. No. 4,666,892 to Fox, et al.; U.S. Pat. No. 4,211,773 to Lopez, et al; Su, et al., Nucleosides. 136. Synthesis and Antiviral Effects of Several 1-(2-Deoxy-2-fluoro-β-D-arabinofuranosyl)-5-alkyluracils. Some Structure-Activity Relationships, J. Med. Chem., 1986, 29, 151–154; Borthwick, et al., Synthesis and Enzymatic Resolution of Carbocyclic 2'-Ara-fluoro-Guanosine: A Potent New Anti-Herpetic Agent, J. Chem. Soc., Chem. Commun, 1988; Wantanabe, et al., Synthesis and Anti-HIV Activity of 2'-"Up"-Fluoro Analogues of Active Anti-Aids Nucleosides 3'-Azido-3'-deoxythymidine (AZT) and 2',3'-deoxythymidine (AZT) and 2',3'-dideoxycytidine (DDC), J. Med. Chem. 1990, 33, 2145–2150; Martin, et.al., Synthesis and Antiviral Activity of Monofluoro and Difluoro Analogues of Pyrimidine Deoxyribonucleosides against Human Immunodeficiency Virus (HIV-1), J. Med. Chem. 1990, 33, 2137–2145; Sterzycki, et al., Synthesis and Anti-HIV Activity of Several 2'-Fluoro-Containing Pyrimidine Nucleosides, J. Med. Chem. 1990, as well as EPA 0 316 017 also filed by Sterzycki, et al.; and Montgomery, et al., 9-(2-Deoxy-2-fluoro-β-D-arabinofuranosyl)-guanine: A Metabolically Stable Cytotoxic Analogue of 2'-Deoxyguanosine. U.S. Pat. No. 5,246,924 discloses a method for treating a hepatitis infection that includes the administration of 1-(2'-deoxy-2'-fluoro-β-D-arabinofuranosyl)-3-ethyluracil), also referred to as "FEAU." U.S. Pat. No. 5,034,518 discloses 2-fluoro-9-(2-deoxy-2-fluoro-β-D-arabino-furanosyl)adenine nucleosides which exhibit anticancer activity by altering the metabolism of adenine nucleosides by reducing the ability of the compound to serve as a substrate for adenosine. EPA 0 292 023 discloses that certain β-D-2'-fluoroarabinonucleosides are active against viral infections.

U.S. Pat. No. 5,128,458 discloses β-D-2',3'-dideoxy-4'-thioribonucleosides as antiviral agents. U.S. Pat. No. 5,446,029 discloses that 2',3'-didcoxy-3'-fluoro-nucleosides have anti-hepatitis activity.

European Patent Publication No. 0 409 227 A2 discloses certain 3'-substituted β-D-pyrimidine and purine nucleosides for the treatment of hepatitis B.

It has also been disclosed that L-FMAU (2'-fluoro-5-methyl-β-L-arabinofuranosyl-uracil) is a potent anti-HBV and anti-EBV agent. See Chu, et al., Use of 2'-Fluoro-5-methyl-β-L-arabinofuranosyluracil as a Novel Antiviral Agent for Hepatitis B Virus and Epstein-Barr Virus; Antimicrobial Agents and Chemotherapy, April 1995, 979–981; Balakrishna, et al., Inhibition of Hepatitis B Virus by a Novel L-Nucleoside, 2'-Fluoro-5-Methyl-β-L-arabinofuranosyl Uracil, Antimicrobial Agents and Chemotherapy, February 1996, 380–356; U.S. Pat. Nos. 5,587,362; 5,567,688; and 5,565,438.

U.S. Pat. Nos. 5,426,183 and 5,424,416 disclose processes for preparing 2'-deoxy-2',2'-difluoronucleosides and 2'-deoxy-2'-fluoro nucleosides. See also Kinetic Studies of 2',2'-difluorodeoxycytidine (Gemcitabine) with Purified Human Deoxycytidine Kinase and Cytidine Deaminase, BioChemical Pharmacology, Vol. 45 (No. 9) pages 4857–1861, 1993.

U.S. Pat. No. 5,446,029 to Eriksson, et al., discloses that certain 2',3'-dideoxy-3'-fluoronucleosides have hepatitis B activity. U.S. Pat. No. 5,128,458 discloses certain 2',3'-dideoxy-4'-thioribonucleosides wherein the 3'-substituent is H, azide or fluoro. WO 94/14831 discloses certain 3'-fluoro-dihydropyrimidine nucleosides. WO 92/08727 discloses β-L-2'-deoxy-3'-fluoro-5-substituted uridine nucleosides for the treatment of herpes simplex 1 and 2.

European Patent Publication No. 0 352 248 discloses a broad genus of L-ribofuranosyl purine nucleosides for the treatment of HIV, herpes, and hepatitis. While certain 2'-fluorinated purine nucleosides fall within the broad genus, there is no information given in the specification on how to make these compounds in the specification, and they are not among specifically disclosed or the preferred list of nucleosides in the specification. The specification does disclose how to make 3'-ribofuranosyl fluorinated nucleosides. A similar specification is found in WO 88/09001, filed by Aktiebolaget Astra.

European Patent Publication No. 0 357 571 discloses a broad group of β-D and α-D pyrimidine nucleosides for the treatment of AIDS which among the broad class generically includes nucleosides that can be substituted in the 2' or 3'-position with a fluorine group. Among this broad class, however, there is no specific disclosure of 2'-fluorinated nucleosides or a method for their production.

European Patent Publication No. 0 463 470 discloses a process for the preparation of (5S)-3-fluoro-tetrahydro-5-[(hydroxy)methyl]-2-(3H)-furanone, a known intermediate in the manufacture of 2'-fluoro-2',3'-dideoxynucleosides such as 2'-fluoro-2',3'-dideoxycytidine.

U.S. Pat. Nos. 5,817,799 and 5,336,764 disclose β-D-2'-fluoroarabino-furanosyl nucleosides, and a method for their production, which are intermediates in the synthesis of 2',3'-dideoxy-2'-fluoroarabinosyl nucleosides.

U.S. Pat. No. 4,625,020 discloses a method of producing 1-halo-2-deoxy-2-fluoroarabinofuranosyl derivatives bearing protective ester groups from 1,3,5-tri-O-acyl-ribofuranose.

U.S. Pat. No. 6,348,587 and International Publication No. WO 99/43691 disclose certain 2'-fluoronucleosides, including certain 2'-fluoro-2',3'-dideoxy-2',3'-didehydro-4'-((S, $CH_2$ or CHF))-nucleosides, and their uses for the treatment of HIV, hepatitis (B or C), or proliferative conditions.

International Publication Nos. WO 01/90121 and WO 01/92282 disclose a wide variety of nucleosides for the treatment of HCV and flaviviruses and pestiviruses, respectively, including certain 2'-halo-2',3'-dideoxy-2',3'-didehydro-4'-(O, S, $SO_2$ or $CH_2$)-nucleosides.

The first example of 4'-thionucleosides was reported in 1964 by Reist et al., who synthesized the 4'-thio counterpart of naturally occurring adenosine (Reist, E. J.; Gueffroy, D. E.; Goodman, L. Synthesis of 4-thio-D-& L-ribofuranose and corresponding adenine nucleosides. J. Am. Chem. Soc. 1964, 86, 5658–5663).

A report by Young et al., emphasized the importance of this class of nucleosides, in which L-4'-thio-d4C analogues showed marked anti-HBV as well and anti-HIV activity (Young, R. J.; Shaw-Ponter, S.; Thomson, J. B.; Miller, J. A.; Cumming, J. G.; Pugh, A. W.; Rider, P. Synthesis and antiviral evaluation of enantiomeric 2',3'-dideoxy- and 2',3'-didehydro-2',3'-dideoxy-4'-thionucleosides. *Bioorg. Med. Chem. Lett.* 1995, 5, 2599–2604).

Since then, several classes of 4'-thionucleosides have been reported, (Whistler, R. L.; Doner, L. W.; Nayak, U. G. 4-Thio-D-arabinofuranosylpyrimidine nucleosides. *J. Org. Chem.* 1971, 36, 108–110; Bobek, M.; Bloch, A.; Parthasarathy, R.; Whistler, R. L. Synthesis and biological activity of 5-fluoro-4'-thiouridine and some related nucleosides. *J. Med. Chem.* 1975, 18, 784–787), including 9-(4-thio-D-xylofuranosyl)adenine (Reist, E. J.; Fisher, L. V.; Gueffroy, E.; Goodman, L. Neighboring-group participation. Preparation of dithiopentose sugars via a thioacylonium ion intermediate. *J. Org. Chem.* 1968, 33, 189–192), 9-(4-thio-D-arabinofuranosyl)adenine (Reist, E. J.; Fisher, L. V.; Gueffroy, E.; Goodman, L. Neighboring-group participation. Preparation of dithiopentose sugars via a thioacylonium ion intermediate. *J. Org. Chem.* 1968, 33, 189–192), and 4'-thio-araC (Ototani, N.; Whistler, R. L. Preparation and antitumor activity of 4'-thio analogs of 2,2'-anhydro-1-β-D-arabinofuranosylcytosine. *J. Med. Chem.* 1974, 17, 535–537).

However, the difficulty of synthesizing optically pure 4'-thionucleosides has impaired additional syntheses of these analogues, and only a few examples have been known until recently (Fu, Y. -L.; Bobek, M. In *Nucleic Aicd Chemistry*; Townsend, L.; Tipson, R. S., Eds.; John Wiley & Sons: New York, 1978; pp 317–323). Moreover, biologically interesting 2'-deoxy-4'-thionucleosides had not been synthesized until Walker and Secrist independently reported the syntheses of pyrimidine 2'-deoxy-4'-thionucleosides in 1991 (Dyson, M. R.; Coe, P. L.; Walker, R. T. The synthesis and antiviral properties of E-5-(2-bromovinyl)-4'-thio-2'-deoxyuridine. *J. Chem. Soc., Chem. Commun.* 1991, 741–742; Dyson, M. R.; Coe, P. L.; Walker, R. T. The synthesis and antiviral activity of some 4'-thio-2'-deoxy nucleoside analogs. *J. Med. Chem.* 1991, 34, 2782–2786; Secrist, J. A.; Tiwari, K. N.; Riordan, J. M.; Montgomery, J. A. Synthesis and biological activity of 2'-deoxy-4'-thiopyrimidine nucleosides. *J. Med. Chem.* 1991, 34, 2361–2366), which were followed by an alternative synthesis of 2'-deoxy-4'-thionucleosides using the Sharpless asymmetric epoxidation (Uenishi, J.; Motoyama, M.; Nishiyama, Y.; Wakabayashi, S. Stereocontrolled preparation of cyclic xanthate—A novel synthetic route to 4-thiofuranose and 4'-thionucleoside. *J. Chem. Soc., Chem. Commun.* 1991, 1421–1422; Uenishi, J.; Takahashi, K.; Motoyama, M.; Akashi, H.; Sasaki, T. Syntheses and antitumor activities of D-2'-deoxy-4'-thio and L-2'-deoxy-4'-thio pyrimidine nucleosides. *Nucleosides Nucleotides* 1994, 13, 1347–1361), synthesis of 4'-thio-2',3'-dideoxynucleosides (Secrist, J. A.; Riggs, R. M.; Tiwari, K. N.; Montgomery, J. A. Synthesis and anti-HIV activity of 4'-thio-2',3'-dideoxynucleosides. *J. Med. Chem.* 1992, 35, 533–538), and the syntheses of 4'-thioarabinonucleosides (Secrist, J. A.; Tiwari, K. N.; Shortnacy-Fowler, A. T.; Messini, L.; Riordan, J. M.; Montgomery, J. A. Synthesis and biological activity of certain 4'-thio-D-arabinofuranosylpurine nucleosides. *J. Med. Chem.* 1998, 41, 3865–3871; Yoshimura, Y.; Watanabe, M.; Satoh, H.; Ashida, N.; Ijichi, K.; Sakata, S.; Machida, H.; Matsuda, A. A facile, alternative synthesis of 4'-thioarabinonucleosides and their biological activities. *J. Med. Chem.* 1997, 40, 2177–2183) as well as 2'-modified 2'-deoxy-4'-thiocytidines (Yoshimura, Y.; Kitano, K.; Yamada, K.; Satoh, H.; Watanabe, M.; Miura, S.; Sakata, S.; Sasaki, T.; Matsuda, A. A novel synthesis of 2'-modified 2'-deoxy4'-thiocytidines from D-glucose. *J. Org. Chem.* 1997, 62, 3140–3152). The synthesized 4'-thio-2'-deoxy, 4'-thio-2',3'-dideoxy and 4'-thioarabino nucleosides have shown to have potent anti-herpes, anti-HIV and anti-cytomegalovirus activities, respectively, and some analogues, especially 4'-thiothymidine and 2'-deoxy-4'-thiocytidine, have exhibited potent cytotoxicity. The 4'-thionucleosides are usually resistant to hydrolytic cleavage of glycosyl linkage catalyzed by nucleoside phosphorylase, which is one of the advantages of 4'-thionucleosides compared with several metabolically unstable "4'-oxy" antiviral agents which are substrates for nucleoside phosphorylase (Parks, R. E., Jr.; Stoeckler, J. D.; Cambor, C.; Savarese, T. M.; Crabtree, G. W.; Chu, S. -H. In Molecular Actions and Targets for Cancer Chemotherapeutic Agents; Sartorelli, A. C., Lazo, J. S., Bertino, J. R., Eds.; Academic Press: New York, 1981; pp 229–252; Desgranges, C.; Razaka, G.; Rabaud, M.; Bricaud, H.; Balzarini, J.; De Clercq, E. Phosphorolysis of (E)-5-(2-bromovinyl)-2'-deoxyuridine (BVDU) and other 5-substituted-2'-deoxyuridines by purified human thymidine phosphorylase and intact blood-platelets. *Biochem. Pharmacol.* 1983, 32, 3583–3590; Samuel,. J.; Gill, M. J.; Iwashina, T.; Tovell, D. R.; Tyrrell, D. L.; Knaus, E. E.; Wiebe, L. I. Pharmacokinetics and metabolism of E-5-(2-[I-131]iodovinyl)-2'-deoxyuridine in dogs. *Antimicrob. Agents Chemother.* 1986, 29, 320–324).

Even though 4'-thionucleosides have recently received considerable attention as potential antiviral agents, their 2',3'-unsaturated analogues have not been well investigated probably because of the synthetic difficulties. The known synthetic methods employ either nucleophilic attack of dimesylate by disulfide anion (Yoshimura, Y.; Watanabe, M.; Satoh, H.; Ashida, N.; Ijichi, K.; Sakata, S.; Machida, H.; Matsuda, A. A facile, alternative synthesis of 4'-thioarabinonucleosides and their biological activities. *J. Med. Chem.* 1997, 40, 2177–2183; Yoshimura, Y.; Kitano, K.; Yamada, K.; Satoh, H.; Watanabe, M.; Miura, S.; Sakata, S.; Sasaki, T.; Matsuda, A. A novel synthesis of 2'-modified 2'-deoxy-4'-thiocytidines from D-glucose. *J. Org. Chem.* 1997, 62, 3140–3152), ring closure of dithioacetal (Secrist, J. A.; Tiwari, K. N.; Shortnacy-Fowler, A. T.; Messini, L.; Riordan, J. M.; Montgomery, J. A. Synthesis and biological activity of certain 4'-thio-D-arabinofuranosylpurine nucleosides. *J. Med. Chem.* 1998, 41, 3865–3871) or reductive cyclization of thioacetic acid ester (Secrist, J. A.; Riggs, R. M.; Tiwari, K. N.; Montgomery, J. A. Synthesis and anti-HIV activity of 4'-thio-2',3'-dideoxynucleosides. *J. Med. Chem.* 1992, 35, 533–538).

The stereoselective synthesis of the β-L-2'-F4'-Sd4C, which showed potent anti-HIV activity ($EC_{50}$ 0.12 $\mu$M) in human peripheral blood monomuclear (PBM) cells, was reported (Choi, Y.; Choo, H.; Chong, Y.; Lee, S.; Olgen, S.; Schinazi, R. F.; Chu, C. K. Synthesis and potent anti-HIV activity of L-2',3'-didehydro-2',3'-dideoxy-2'-fluoro4'-thiocytidine. *Org. Lett.* 2002, 4, 305–307).

In light of the fact that acquired immune deficiency syndrome, AIDS-related complex, hepatitis B virus and hepatitis C virus have reached epidemic levels worldwide, and have tragic effects on the infected patient, there remains a strong need to provide new effective pharmaceutical agents to treat these diseases that have low toxicity to the host. Further, there is a need to provide new antiproliferative agents, Therefore, it is an object of the present invention to provide a method and composition for the treatment of human patients or other host animals infected with HIV.

It is another object of the present invention to provide a method and composition for the treatment of human patients infected with hepatitis B or C.

It is a further object of the present invention to provide new antiproliferative agents.

It is still another object of the present invention to provide a new process for the preparation of β-halonucleosides of the present invention.

SUMMARY OF THE INVENTION

The present invention includes β-D and β-L-3'-halonucleosides, pharmaceutical compositions comprising such compounds, as well as methods to treat or prevent an HIV infection, HBV infection or abnormal cellular proliferation comprising administering said compounds or compositions. In addition, the present invention includes the process for the preparation of such compounds, and the related β-D and β-L-2'-halo-4'-thionucleosides.

In one embodiment of the invention, the β-D and β-L-3'-halonucleoside is of the formula (I):

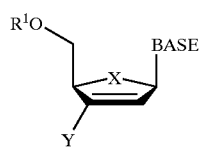

(I)

or its enantiomer, or its pharmaceutically acceptable salt or prodrug, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

X is O, S, $SO_2$ or $CH_2$;

Y is fluoro, chloro, bromo or iodo; and

BASE is a purine or pyrimidine base that may optionally be substituted, or provided in prodrug form, such as an alkylated or acylated form.

In a particular sub-embodiment of the invention, the β-D and β-L-3'-halonucleoside is of the formula (II):

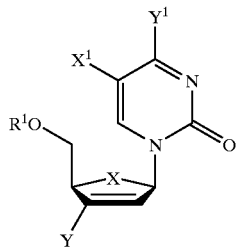

(II)

or its enantiomer, or its pharmaceutically acceptable salt or prodrug, wherein $R^1$, X and Y are as defined above;

$Y^1$ is OH, $OR^2$, $NH_2$, $NHR^2$, $NR^2R^3$, SH, $SR^2$ or halogen (F, Cl, Br or I);

$X^1$ and $X^2$ are independently selected from the group consisting of H, straight chained, branched or cyclic alkyl, CO-alkyl, CO-aryl, CO-alkoxyalkyl, halogen (F, Cl, Br or I), OH, $OR^4$, $NH_2$, $NHR^2$, $NR^4R^5$, SH or $SR^4$; and $R^2$, $R^3$, $R^4$ and $R^5$ are independently H, straight chained, branched or cyclic alkyl (especially cyclopropyl), dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In another sub-embodiment of the invention, the β-D and β-L-3'-halonucleoside is of the formula (III):

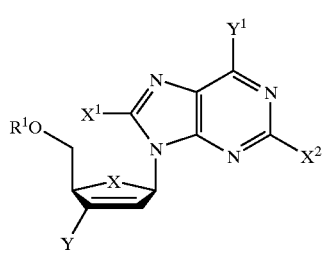

(III)

or its enantiomer, or its pharmaceutically acceptable salt or prodrug, wherein $R^1$, X, Y, $X^1$ and $Y^1$ are as defined above.

In a particular sub-embodiment, the β-D and β-L-3'-halonucleoside is a β-D and β-L-3'-halocytidine of the formula (IV):

(IV)

or its enantiomer, or its pharmaceutically acceptable salt or prodrug, wherein $R^1$, X, Y, $X^1$ $R^2$ and $R^3$ are as defined above.

In a preferred embodiment, X is O for the compounds of the formula (I)–(IV).

In an alternatively preferred embodiment, X is S for the compounds of the formula (I)–(IV).

In a preferred embodiment, Y is F for the compounds of the formula (I)–(IV).

In one embodiment of the present invention, the compounds of the formula (I)–(IV) are in the β-D configuration. In an alternate embodiment of the present invention, the compounds of formula (I)–(IV) are in the β-L configuration.

In a second embodiment of the invention, the β-D and β-L-3'-halonucleoside is of the formula (V):

(V)

or its enantiomer, or its pharmaceutically acceptable salt or prodrug, wherein $R^1$, Y and BASE are as defined above.

In a particular sub-embodiment of the invention, the β-D and β-L-3'-halonucleoside is of the formula (VI):

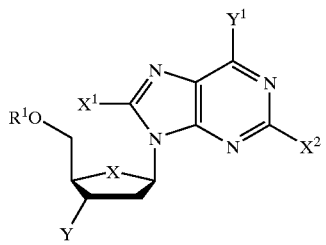

(VI)

or its enantiomer, or its pharmaceutically acceptable salt or prodrug, wherein
$R^1$, Y, $X^1$, $X^2$ and $Y^1$ are as defined above.

In another sub-embodiment of the invention, the β-D and β-L-3'-halonucleoside is of the formula (VII):

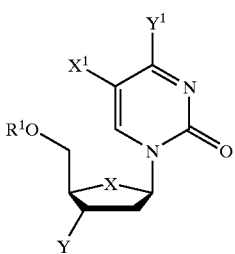

(VII)

or its enantiomer, or its pharmaceutically acceptable salt or prodrug, wherein
$R^1$, X, Y, $X^1$ and $Y^1$ are as defined above.

In a particular sub-embodiment, the β-D and β-L-3'-halonucleoside is of the formula (VIII):

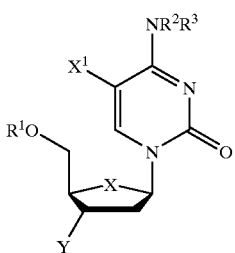

(VIII)

or its enantiomer, or its pharmaceutically acceptable salt or prodrug, wherein
$R^1$, X, Y, $X^1$ $R^2$ and $R^3$ are as defined above.

In a preferred embodiment, X is O for the compounds of the formula (V)–(VIII).

In an alternatively preferred embodiment, X is S for the compounds of the formula (V)–(VIII).

In a preferred embodiment, Y is F for the compounds of the formula (V)–(VIII).

In one embodiment of the present invention, the compounds of the formula (V)–(VIII) are in the β-D configuration. In an alternate embodiment of the present invention, the compounds of formula (V)–(VIII) are in the β-L configuration.

The β-halonucleosides depicted above are in the β-D configuration, however, it should be understood that the β-halonucleosides can be either in the β-L or β-D configuration.

The β-halonucleosides of the present invention are biologically active molecules that are useful in the treatment or prophylaxis of viral infections, and in particular an human immunodeficiency virus (HIV) and/or hepatitis B virus (HBV) infection. The compounds are also useful for the treatment of abnormal cellular proliferation, including tumors and cancer. In another embodiment of the present invention, any of the active compounds are useful in the treatment of HCV. One can easily determine the spectrum of activity by evaluating the compound in the assays described herein or with another confirmatory assay.

For instance, in one embodiment the efficacy of the antiviral compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 15 or preferably, less than 10 micromolar in vitro.

In another embodiment, for the treatment or prophylaxis of a viral infection, and in particular an HIV or HBV infection, in a host, the active compound or its derivative or salt can be administered in combination or alternation with another antiviral agent, such as an anti-HIV agent or anti-hepatitis agent, including those of the formula above. Alternatively, for the treatment of abnormal cellular proliferation, such as tumors and cancer, in a host, the active compound or its derivative or salt can be administered in combination or alternation with another antiproliferative agent, such as an anti-neoplastic agent, including those of the formula above. In general, in combination therapy, effective dosages of two or more agents are administered together, whereas during alternation therapy, an effective dosage of each agent is administered serially. The dosages will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include 2-hydroxymethyl-5-(5-fluorocytosin-1-yl)-1,3-oxathiolane (FTC); the (−)-enantiomer of 2-hydroxymethyl-5(cytosin-1-yl)-1,3-oxathiolane (3TC); carbovir, acyclovir, interferon, famciclovir, penciclovir, AZT, DDI, DDC, D4T, abacavir, L-(−)-FMAU, L-DDA phosphate prodrugs, and β-D-dioxolane nucleosides such as β-D-dioxolanyl-guanine (DG), β-D-dioxolanyl-2,6-diaminopurine (DAPD), and β-D-dioxolanyl-6-chloropurine (ACP), non-nucleoside room temperature inhibitors such as nevirapine, MKC-442, DMP-266 (sustiva) and also protease inhibitors such as indinavir, saquinavir, AZT, DMP-450 and others.

The compounds can also be used to treat equine infectious anemia virus (EIAV), feline immunodeficiency virus, and simian immunodeficiency virus. (Wang, S., Montelaro, R., Schinazi, R. F., Jagerski, B., and Mellors, J. W.: "Activity of nucleoside and non-nucleoside reverse transcriptase inhibitors (NNRTI) against equine infectious anemia virus (EIAV)." *First National Conference on Human Retro viruses and Related Infections*, Washington, D.C., Dec. 12–16, 1993; Sellon D. C., "Equine Infectious Anemia," *Vel. Clin. North Am. Equine Pract. United States*, 9: 321–336, 1993; Philpott, M. S., Ebner, J. P., Hoover, E. A., "Evaluation of 9-(2-phosphonylmcthoxyethyl) adenine therapy for feline immunodeficiency virus using a quantitative polymerase chain reaction," *Vet. Immunol. Immunopathol.* 35:155166, 1992.)

The present invention also provides a pharmaceutical composition for the treatment and/or prophylaxis of a. viral infection, and in particular a HBV or HIV infection, in a host, preferably a human, comprising an effective amount of an active compound of the present invention, optionally in a pharmaceutically acceptable carrier.

The present invention also provides a pharmaceutical composition for the treatment and/or prophylaxis of an abnormal cellular proliferation, such as tumors and cancer, in a host, preferably a human, comprising an effective amount of an active compound of the present invention, optionally in a pharmaceutically acceptable carrier.

The present invention also provides a pharnaceutical composition for the treatment and/or prophylaxis of a viral infection, and in particular a HBV or HIV infection, in a host, preferably a human, comprising an effective amount of an active compound of the present invention, in combination with one or more other effective antiviral agent, and in particular an anti-HBV or anti-HIV agent, optionally in a pharmaceutically acceptable carrier.

The present invention also provides a pharmaceutical composition for the treatment and/or prophylaxis of an abnormal cellular proliferation, such as tumors and cancer, in a host, preferably a human, comprising an effective amount of an active compound of the present invention, in combination with one or more other effective antiproliferative agent, such as an antineoplastic agent, optionally in a pharmaceutically acceptable carrier.

The present invention also provides a method for the treatment and/or prophylaxis of a viral infection, and in particular a HBV or HIV infection, in a host, preferably a human, comprising administering to the host an effective amount of an active compound of the present invention, optionally in a pharmaceutically acceptable carrier.

The present invention also provides a method for the treatment and/or prophylaxis of an abnormal cellular proliferation, such as tumors and cancer, in a host, preferably a human, comprising administering to the host an effective amount of an active compound of the present invention, optionally in a pharmaceutically acceptable carrier.

The present invention also provides a method for the treatment and/or prophylaxis of a viral infection, and in particular a HBV or HIV infection, in a host, preferably a human, comprising administering to the host an effective amount of an active compound of the present invention, in combination and/or alternation with one or more other effective antiviral agent, and in particular an anti-HBV or anti-HIV agent, optionally in a pharmaceutically acceptable carrier.

The present invention also provides a method for the treatment and/or prophylaxis of an abnormal cellular proliferation, such as tumors and cancer, in a host, preferably a human, comprising administering to the host an effective amount of an active compound of the present invention, in combination and/or alternation with one or more other effective antiproliferative agent, such as an antineoplastic agent, optionally in a pharmaceutically acceptable carrier.

The present invention also provides a use of an active compound of the present invention, optionally in a pharmaceutically acceptable carrier, for the treatment and/or prophylaxis of a viral infection, and in particular a HBV or HIV infection, in a host, preferably a human.

The present invention also provides a use of an active compound of the present invention, optionally in a pharmaceutically acceptable carrier, for the treatment and/or prophylaxis of an abnormal cellular proliferation, such as tumors and cancer, in a host, preferably a human.

The present invention also provides a use of an active compound of the present invention, in combination and/or alternation with one or more other effective antiviral agent, and in particular an anti-HBV or anti-HIV agent, optionally in a pharmaceutically acceptable carrier, for the treatment and/or prophylaxis of a viral infection, and in particular a HBV or HIV infection, in a host, preferably a human.

The present invention also provides a use of an active compound of the present invention, in combination and/or alternation with one or more other effective antiproliferative agent, such as an antineoplastic agent, optionally in a pharmaceutically acceptable carrier, for the treatment and/or prophylaxis of an abnormal cellular proliferation, such as tumors and cancer, in a host, preferably a human.

The present invention also provides a use of an active compound of the present invention, optionally in a pharmaceutically acceptable carrier, in the manufacture of a medicament for the treatment and/or prophylaxis of a viral infection, and in particular a HBV or HIV infection, in a host, preferably a human.

The present invention also provides a use of an active compound of the present invention, optionally in a pharmaceutically acceptable carrier, in the manufacture of a medicament for the treatment and/or prophylaxis of an abnormal cellular proliferation, such as tumors and cancer, in a host, preferably a human.

The present invention also provides a use of an active compound of the present invention, in combination and/or alternation with one or more other effective antiviral agent, and in particular an anti-HBV or anti-HIV agent, optionally in a pharmaceutically acceptable carrier, in the manufacture of a medicament for the treatment and/or prophylaxis of a viral infection, and in particular a HBV or HIV infection, in a host, preferably a human.

The present invention also provides a use of an active compound of the present invention, in combination and/or alternation with one or more other effective antiviral agent, and in particular an anti-HCV agent, optionally in a pharmaceutically acceptable carrier, in the manufacture of a medicament for the treatment and/or prophylaxis of a viral infection, and in particular a HCV infection, in a host, preferably a human.

The present invention also provides a use of an active compound of the present invention, in combination and/or alternation with one or more other effective antiproliferative agent, such as an antineoplastic agent, optionally in a pharmaceutically acceptable carrier, in the manufacture of a medicament for the treatment and/or prophylaxis of an abnormal cellular proliferation, such as tumors and cancer, in a host, preferably a human.

The invention also provides synthetic methods useful for preparing the compounds of the invention, as well as intermediates disclosed herein that are useful in the preparation of the compounds of the present invention.

In particular, in one embodiment of the present invention, a process for the preparation of the β-D or β-L-3'-halonucleoside of the formula (I):

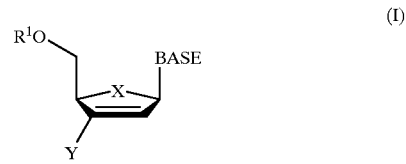

wherein Y, $R^1$ and BASE are as defined above; and

X is O, S or SO$_2$; is provided, comprising
(a) obtaining an optionally protected compound of the formula (A):

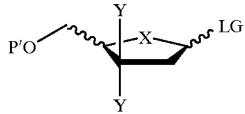
(A)

wherein P" is independently hydrogen or a suitable oxygen protecting group such as alkyl, acyl or silyl; and LG is a suitable leaving group, such as OAcyl, and in particular OAc;
(b) coupling the compound of formula (A) with a purine or pyrimidine base to obtain the compound of formula (B):

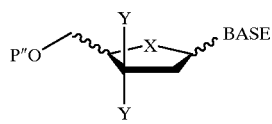
(B)

(c) eliminating and deprotecting, if necessary, the compound of formula (B) to obtain the compound of formula (I).

In a particular embodiment of the present invention, a process for the preparation of the compound of formula (A) is provided, comprising
(a) obtaining an optionally protected of the formula (C):

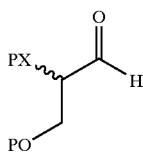
(C)

wherein each P is independently H or a suitable protecting group such as alkyl, acyl or silyl;
(b) coupling the compound of formula (C) with an optionally protected acetaldehyde to obtain a compound of formula (D):

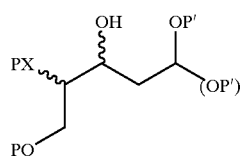
(D)

wherein each P' is independently a suitable oxygen protecting group such as alkyl, acyl or silyl;
(c) oxidizing the compound of formula (D) to obtain a compound of formula (E):

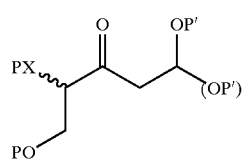
(E)

(d) halogenating the compound of formula (E) to obtain a compound of formula (F):

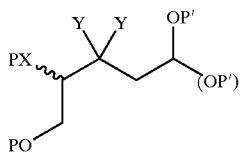
(F)

wherein each Y is independently fluoro, chloro, bromo or iodo;
(e) selectively deprotecting, if necessary; cyclizing; and activating, if necessary, the compound of formula (F) to obtain a compound of formula (A).

Alternately, in another particular embodiment of the present invention, a process for the preparation of the compound of formula (A) is provided, comprising
(a) obtaining an optionally protected of the formula (G):

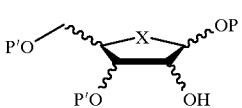
(G)

wherein each P and P" is independently a suitable oxygen protecting group such as alkyl, acyl or silyl;
(b) activating the compound of formula (G) to obtain a compound of formula (H):

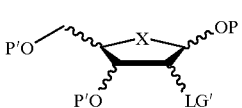
(H)

wherein LG' is a suitable leaving group, such as phenyl thionoformate;
(c) reducing the compound of formula (H) to obtain a compound of formula (J):

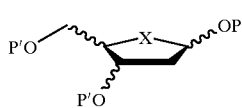
(J)

(d) selectively deprotecting, if necessary, and oxidizing the compound of formula (J) to obtain a compound of formula (K):

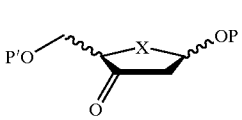
(K)

(f) halogenating the compound of formula (K) to obtain a compound of formula (L):

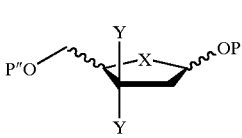
(L)

(g) selectively deprotecting, if necessary, and activating the compound of formula (L) to obtain a compound of formula (A).

In one embodiment of the present invention, the compound of formula (I) can be reduced to obtain a compound of formula (V).

In particular, in a second embodiment of the present invention, a process for the preparation of a β-D or β-L 3'-halonucleoside of the formula (V):

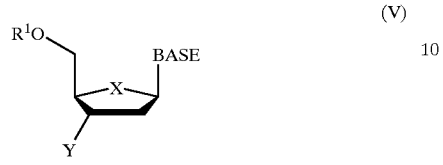

(V)

wherein Y, $R^1$ and BASE are as defined above; is provided, comprising (a) obtaining an optionally protected of the formula (M):

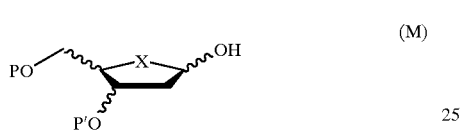

(M)

wherein each P and P' is independently a suitable oxygen protecting group such as alkyl, acyl or silyl;

(b) activating the compound of formula (M) to obtain a compound of formula (N):

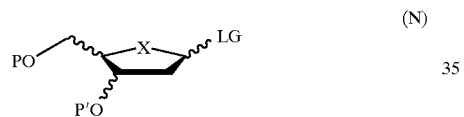

(N)

wherein LG is a suitable leaving group, such as OAcyl, and in particular OAc;

(c) coupling the compound of formula (N) with a purine or pyrimidine base to obtain the compound of formula (O):

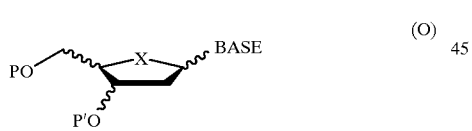

(O)

(d) selectively deprotecting, if necessary, and substituting with a halogen group to obtain the compound of formula (V).

In particular, in a third embodiment of the present invention, a process for the preparation of a β-D or β-L-2'-halo-4'-thionucleoside of the formula (IX):

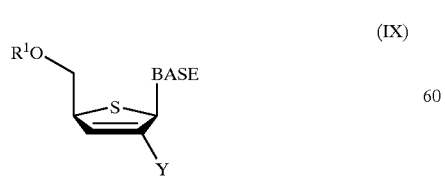

(IX)

wherein $R^1$, Y and BASE are as defined above; is provided, comprising (a) obtaining an optionally protected compound of the formula (P):

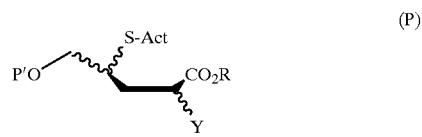

(P)

wherein P' is a suitable oxygen protecting group such as alkyl, acyl or silyl; S-Act is an activated sulfur moiety, such as S-Acyl, and in particular S-Ac, and OR is a suitable oxygen leaving group, such as O-Alkyl and in particular OMe or OEt;

(b) cyclizing the compound of formula (P) to obtain a compound of formula (Q):

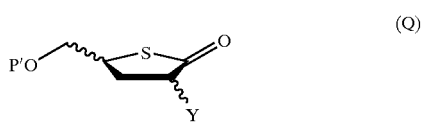

(Q)

(c) reacting the compound of formula (Q) with an electrophile to obtain a compound of formula (R):

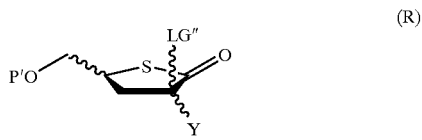

(R)

wherein LG" is a suitable leaving group, such as phenyl selenium or phenylsulfide;

(d) activating the compound of formula (R) to obtain a compound of formula (S):

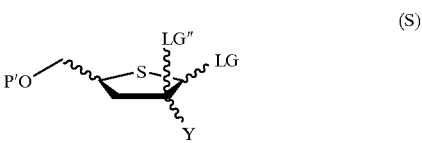

(S)

wherein LG is a suitable leaving group, such as OAcyl, and in particular OAc;

(e) coupling the compound of formula (S) with a purine or pyrimidine base to obtain a compound of formula (T):

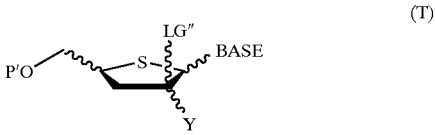

(T)

(f) eliminating and optionally deprotecting, if necessary the compound of formula (T) to obtain the compound of formula (IX).

In a particular embodiment of the present invention, a process for the preparation of the compound of formula (P) is provided, comprising (a) obtaining an optionally protected of the formula (U):

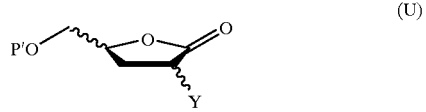

wherein each P' is independently H or a suitable protecting group such as alkyl, acyl or silyl;
(b) reacting the compound of formula (U) with an activated sulfur to obtain the compound of formula (P).

In one embodiment, the compound of formula (U) is first reacted with a nucleophilic halogen, such as iodine (optionally in the presence of triphenylphosphine), prior to reaction with the activated sulfur.

Alternately, in another particular embodiment of the present invention, the compound of formula (P) is obtained from an appropriately protected D- or L-Glutamic Acid. The D- or L-Glutamic acid can be purchased, which can then be converted to the thio derivative by means well known in the art. Examples of such protocol are Cervinka, O.; Hub, L. Asymmetric reactions. XXVII. Absolute configurations of γ-butyrolactone-γ-carboxylic acid and γ-valerolactone-γ-carboxylic acid. *Collect. Czech. Chem. Commun.* 1968, 33, 2927–2932; Hanessian, S.; Murray, P. J. Stereochemical control of nature's biosynthetic pathways: A general strategy for the synthesis of polypropionate-derived structural units from a single chiral progenitor. *Tetrahedron* 1987, 43, 5055–5072; Secrist III, J. A.; Riggs, R. H.; Tiwari, K. N.; Montgomery, J. A. Synthesis and anti-HIV activity of 4'-thio-2',3'-dideoxynucleosides. *J. Med. Chem.* 1992, 35, 533–538.

BRIEF DESCRIPTION OF THE FIGURES

FIG. 2 are two a nonlimiting illustrative example of the synthesis of β-3'-fluoro unsaturated L-nucleosides from L-xylose, and in particular β-3'-fluoro unsaturated L-cytosine (2a) and β-3'-fluoro unsaturated L-thymidine (2b), according to the present invention.

FIG. 9 is a nonlimiting illustrative example of the synthesis of β-L-2',3'-dideoxy-3'-fluoro-4'-thionucleosides, according to the present invention.

FIG. 10 is a nonlimiting illustrative example of the synthesis of β-D-2',3'-dideoxy-2'-fluoro-4'-thionucleosides, according to the present invention.

FIG. 11 is a nonlimiting illustrative example of the synthesis of β-L-2',3'-dideoxy-2'-fluoro4'-thionucleosides, according to the present invention.

FIG. 12 is a nonlimiting illustrative example of the synthesis of β-D-2',3'-dideoxy-3'-fluoro-4'-thionucleosides, according to the present invention.

FIG. 13 is a nonlimiting illustrative example of the synthesis of β-L-2',3'-dideoxy-3'-fluoro-4'-thionucleosides, according to the present invention.

FIG. 14 is a nonlimiting illustrative example of the synthesis of β-D-2',3'-dideoxy-2'-fluoro-4'-thionucleosides, according to the present invention.

DETAILED DESCRIPTION OF THE INVENTION

Figure 1:
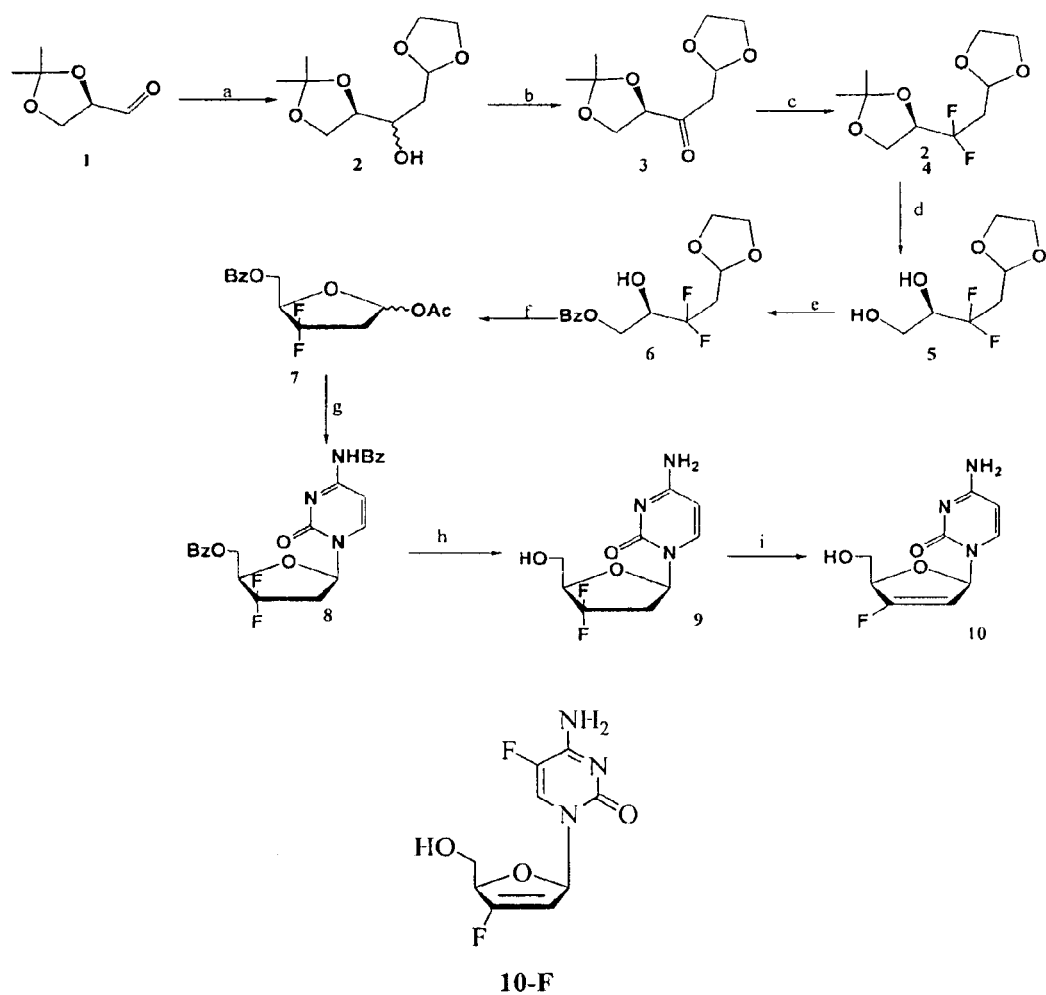
FIG. 1 is a nonlimiting illustrative example of the synthesis of β-3'-fluoro-2',3'-unsaturated D-cytosine from D-glyceraldehyde, according to the present invention.

The invention as disclosed herein is method and composition for the treatment of HIV, hepatitis B or C, or abnormal cellular proliferation, in humans or other host animals, that includes administering an effective amount of a β-D- or β-L-2'-halonucleoside, a pharmaceutically acceptable derivative, including a compound which has been alkylated or acylated at the 5'-position or on the purine or pyrimidine, or a pharmaceutically acceptable salt thereof, optionally in a pharmaceutically acceptable carrier. The compounds of this invention either possess antiviral (i.e., anti-HIV-1, anti-HIV-2, anti-hepatitis B virus) activity or antiproliferative activity, or are metabolized to a compound that exhibits such activity. The invention as disclosed herein also includes the process for the preparation of such β-D- or β-L-2'-halonucleosides, as well as the process for the preparation of a β-D- or β-L-2'-halo-4'-thionucleoside.

In summary, the present invention includes the following features:

(a) β-L and β-D-halonucleosides (I)–(VIII), as described herein, and pharmaceutically acceptable derivatives and salts thereof;

(b) synthesis of the β-L and β-D-halonucleosides (I)–(VIII), as described herein, and pharmaceutically acceptable derivatives and salts thereof;

(c) β-L and β-D-halonucleosides (I)–(VIII) as described herein, and pharmaceutically acceptable derivatives and salts thereof for use in medical therapy, for example for the treatment or prophylaxis of an HIV, hepatitis B (or C) virus infection or for the treatment of abnormal cellular proliferation;

(d) pharmaceutical formulations comprising the β-D or β-L-halonucleoside (I)–(VIII), or its pharmaceutically acceptable derivative or salt thereof, together with a pharmaceutically acceptable carrier or diluent;

(e) pharmaceutical formulations comprising the β-D or β-L-halonucleoside (I)–(VIII), or its pharmaceutically acceptable derivative or salt thereof, together with another active ingredient, such as another antiviral agent or antiproliferative agent;

(f) methods to treat a host suffering from an HIV infection, hepatitis B virus infection or abnormal cellular proliferation, comprising administering an effective amount of a β-D or β-L-halonucleoside (I)–(VIII), or its pharmaceutically acceptable derivative or salt thereof;

(g) methods to treat a host suffering from an HIV infection, hepatitis B virus infection or abnormal cellular proliferation, comprising administering an effective amount of a β-D or β-L-halonucleoside (I)–(VIII), or its pharmaceutically acceptable derivative or salt thereof, in combination or alternation with another active ingredient, such as another antiviral agent or antiproliferative agent;

(h) use of a β-D or β-L-halonucleoside (I)–(VIII), or its pharmaceutically acceptable derivative or salt thereof, in medical therapy, for example for the treatment or prophylaxis of an HIV infection, an hepatitis B virus infection or an abnormal cellular proliferation;

(f) use of a β-D or β-L-halonucleoside (I)–(VIII), or its pharmaceutically acceptable derivative or salt thereof, as an antiviral;

(g) use of a β-D or β-L-halonucleoside (I)–(VIII), or its pharmaceutically acceptable derivative or salt thereof, as an antiproliferative;

(h) use of a β-D or β-L-halonucleoside (I)–(VIII), or it pharmaceutically acceptable derivative or salt thereof, in combination or alternation with another active ingredient, such as another antiviral or antiproliferative agent in medical therapy, for example for the treatment or prophylaxis of an HIV infection, an hepatitis B virus infection or abnormal cellular proliferation;

(i) use of a β-D or β-L-halonucleoside (I)–(VIII), or it pharmaceutically acceptable derivative or salt thereof, for treatment or prophylaxis of an HIV infection, an hepatitis B virus infection or abnormal cellular proliferation;

(j) use of a β-D or β-L-halonucleoside (I)–(VIII), or it pharmaceutically acceptable derivative or salt thereof, in the manufacture of a medicament for treatment or prophylaxis of an HIV infection, an hepatitis B virus infection or abnormal cellular proliferation; and (k) processes for the preparation of β-L and β-D-2'-halo-4'-thionucleosides, as described in more detail below.

I. Active Compound

In one embodiment of the invention, the β-D or β-L-3'-halonucleoside is of the formula (I):

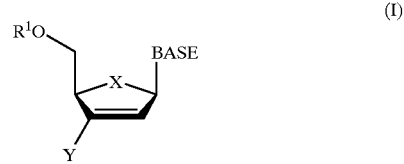

(I)

or its enantiomer, or its pharmaceutically acceptable salt or prodrug, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

X is O, S, $SO_2$ or $CH_2$;

Y is fluoro, chloro, bromo or iodo; and

BASE is a purine or pyrimidine base that may optionally be substituted.

In a particular sub-embodiment of the invention, the β-D or β-L-3'-halonucleoside is of the formula (II):

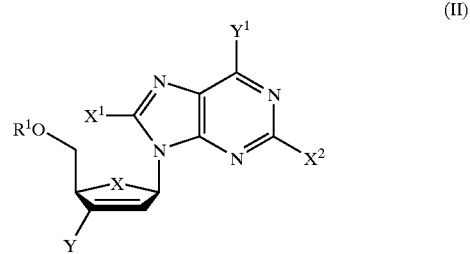

(II)

or its enantiomer, or its pharmaceutically acceptable salt or prodrug, wherein $R^1$, X and Y are as defined above;

$Y^1$ is $OR^2$, $NR^2R^3$ or $SR^2$;

$X^1$ and $X^2$ are independently selected from the group consisting of H, straight chained, branched or cyclic alkyl, CO-alkyl, CO-aryl, CO-alkoxyalkyl, halogen, $OR^4$, $NR^5$ or $SR^4$; and $R^2$, $R^3$, $R^4$ and $R^5$ are independently H, straight chained, branched or cyclic alkyl (especially cyclopropyl), dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In another sub-embodiment of the invention, the β-D or β-L-3'-halonucleoside is of the formula (III):

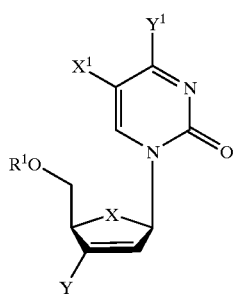

(III)

or its enantiomer, or its pharmaceutically acceptable salt or prodrug, wherein $R^1$, X, Y, $X^1$ and $Y^1$ are as defined above.

In a particular sub-embodiment, the β-D or β-L-3'-halonucleoside is of the formula (IV):

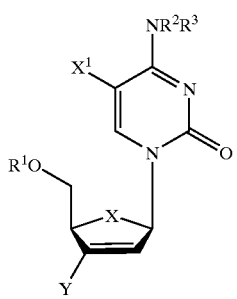

(IV)

or its enantiomer, or its pharmaceutically acceptable salt or prodrug, wherein $R^1$, X, Y, $X^1$ $R^2$ and $R^3$ are as defined above.

In a preferred embodiment, X is O for the compounds of the formula (I)–(IV).

In an alternatively preferred embodiment, X is S for the compounds of the formula (I)–(IV).

In a preferred embodiment, Y is F for the compounds of the formula (I)–(IV).

In one embodiment of the present invention, the compounds of the formula (I)–(IV) are in the β-D configuration. In an alternate embodiment of the present invention, the compounds of formula (I)–(IV) are in the β-L configuration.

In a second embodiment of the invention, the β-D or β-L-3'-halonucleoside is of the formula (V):

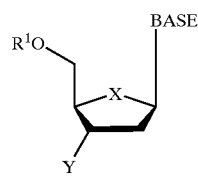

(V)

or its enantiomer, or its pharmaceutically acceptable salt or prodrug, wherein $R^1$, Y and BASE are as defined above.

In a particular sub-embodiment of the invention, the β-D or β-L-3'-halonucleoside is of the formula (VI):

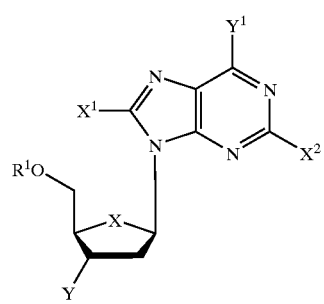

(VI)

or its enantiomer, or its pharmaceutically acceptable salt or prodrug, wherein $R^1$, Y, $X^1$, $X^2$ and $Y^1$ are as defined above.

In another sub-embodiment of the invention, the β-D or β-L-3'-halonucleoside is of the formula (VII):

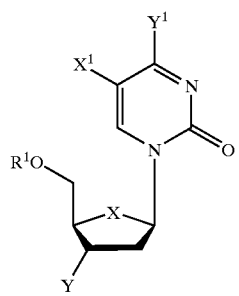

(VII)

or its enantiomer, or its pharmaceutically acceptable salt or prodrug, wherein $R^1$, X, Y, $X^1$ and $Y^1$ are as defined above.

In a particular sub-embodiment, the β-D or β-L-3'-halonucleoside is of the formula (VIII):

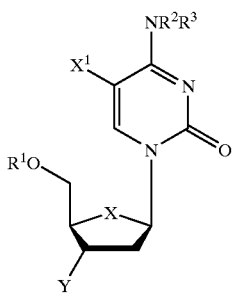

(VIII)

or its enantiomer, or its pharmaceutically acceptable salt or prodrug, wherein $R^1$, X, Y, $X^1$ $R^2$ and $R^3$ are as defined above.

In a preferred embodiment, X is O for the compounds of the formula (V)–(VIII).

In an alternatively preferred embodiment, X is S for the compounds of the formula (V)–(VIII).

In a preferred embodiment, Y is F for the compounds of the formula (V)–(VIII).

In one embodiment of the present invention, the compounds of the formula (V)–(VIII) are in the β-D configuration. In an alternate embodiment of the present invention, the compounds of formula (V)–(VIII) are in the β-L configuration.

In one important embodiment, the purine or pyrimidine base is provided in an alkylated (for example, lower alkyl, including cyclopropyl) or acylated (including but not limited to for example esterified or acetylated), form.

II. Definitions

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl,2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes chloro, bromo, iodo, and fluoro.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, 2-chloro-2-aminopurine, inosine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. Acyl can also include a natural or synthetic amino acid moiety.

As used herein, the term "substantially free of" or "substantially in the absence of" refers to a nucleoside composition that includes at least 95% to 98%, or more preferably, 99% to 100%, of the designated enantiomer of that nucleoside.

Similarly, the term "isolated" refers to a nucleoside composition that includes at least 85 or 90% by weight, preferably 95% to 98% by weight, and even more preferably 99% to 100% by weight, of the nucleoside, the remainder comprising other chemical species or enantiomers.

The term host, as used herein, refers to a unicellular or multicellular organism in which the virus can replicate, including cell lines and animals, and preferably a human, or a unicellular or multicellular organism in which the conditions of abnormal cellular proliferation can be mimicked. For example, in the case of HIV, HBV or HCV, the host is any unicellular or multicellular organism that can be carrying a part of the viral genome, whose replication or function can be altered by the compounds of the present invention. The term host specifically refers to infected cells, cells transfected with all or part of the viral genome and animals, in particular, primates (including chimpanzees) and humans. In most animal applications of the present invention, the host is a human patient. Veterinary applications, in certain indications, however, are clearly anticipated by the present invention (such as chimpanzees).

The term "pharmaceutically acceptable salt or prodrug" is used throughout the specification to describe any pharmaceutically acceptable form (such as an ester, phosphate ester, salt of an ester, acylation or alkylation product or a related derivative) of a nucleoside compound which, upon administration to a patient, provides the nucleoside compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against flavivirus or pestivirus, or are metabolized to a compound that exhibits such activity.

III. Pharmaceutically Acceptable Derivatives

The active compound can be administered as any derivative that upon administration to the recipient, is capable of providing directly or indirectly, the parent compound. Further, the modifications can affect the biological activity of the compound, in some cases increasing the activity over the parent compound. This can easily be assessed by preparing the derivative and testing its antiviral activity according to the methods described herein, or other method known to those skilled in the art.

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be administrated as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses.* 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hosteller, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4–6C cells by 3'-deoxythymidine diphosphate dimyristoylglycerol, a lipid prodrug of 3,-deoxythymidine." *Antimicrob. Agents Chemother.* 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent publications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Nonlimiting examples of nucleotide prodrugs are described in the following references: Ho, D. H. W. (1973) "Distribution of Kinase and deaminase of 1β-D-arabinofuranosylcytosine in tissues of man and muse." *Cancer Res.* 33, 2816–2820; Holy, A. (1993) Isopolar phosphorous-modified nucleotide analogues," In: De Clercq (Ed.), *Advances in Antiviral Drug Design*, Vol. I, JAI Press, pp. 179–231; Hong, C. I., Nechaev, A., and West, C. R. (1979a) "Synthesis and antitumor activity of 1-β-D-arabinofuranosylcytosine conjugates of cortisol and cortisone." *Bicohem. Biophys. Rs. Commun.* 88, 1223–1229; Hong, C. I., Nechaev, A., Kirisits, A. J. Buchheit, D. J. and West, C. R. (1980) "Nucleoside conjugates as potential antitumor agents. 3. Synthesis and antitumor activity of 1-(β-D-arabinofuranosyl) cytosine conjugates of corticosteriods and selected lipophilic alcohols." *J. Med. Chem.* 28, 171–177; Hosteller, K. Y., Stuhmniller, L. M., Lenting, H. B. M. van den Bosch, H. and Richman *J. Biol. Chem.* 265, 6112–6117; Hosteller, K. Y., Carson, D. A. and Richman, D. D. (1991); "Phosphatidylazidothymidine: mechanism of antiretroviral action in CEM cells." *J. Biol Chem.* 266, 11714–11717; Hosteller, K. Y., Korba, B. Sridhar, C., Gardener, M. (1994a) "Antiviral activity of phosphatidyl-dideoxycytidine in hepatitis B-infected cells and enhanced hepatic uptake in mice." *Antiviral Res.* 24, 59–67; Hosteller, K. Y., Richman, D. D., Sridhar. C. N. Feigner, P. L. Feigner, J., Ricci, J., Gardener, M. F. Selleseth, D. W. and Ellis, M. N. (1994b) "Phosphatidylazidothymidine and phosphatidyl-ddC: Assessment of uptake in mouse lymphoid tissues and antiviral activities in human immunodeficiency virus-infected cells and in rauscher leukemia virus-infected mice." *Antimicrobial Agents Chemother.* 38, 2792–2797; Hunston, R. N., Jones, A. A. McGuigan, C., Walker, R. T., Balzarini, J., and DeClercq, E. (1984) "Synthesis and biological properties of some cyclic phosphotriesters derived from 2'-deoxy-5-flourouridine." *J. Med. Chem.* 27, 440–444; Ji, Y. H., Moog, C., Schmitt, G., Bischoff, P. and Luu, B. (1990); "Monophosphoric acid esters of 7-β-hydroxycholesterol and of pyrimidine nucleoside as potential antitumor agents: synthesis and preliminary evaluation of antitumor activity." *J. Med. Chem.* 33 2264–2270; Jones, A. S., McGuigan, C., Walker, R. T., Balzarini, J. and DeClercq, E. (1984) "Synthesis, properties, and biological activity of some nucleoside cyclic phosphoramidates." *J. Chem. Soc. Perkin Trans. I*, 1471–1474; Juodka, B. A. and Smrt, J. (1974) "Synthesis of diribonucleoside phosph (P→N) amino acid derivatives." *Coll. Czech. Chem. Comm.* 39, 363–968; Kataoka, S., Imai, J., Yamaji, N., Kato, M., Saito, M., Kawada, T. and Imai, S. (1989) "Alkylated cAMP derivatives; selective synthesis and biological activities." *Nucleic Acids Res. Sym. Ser.* 21, 1–2; Kataoka, S., Uchida, "(cAMP) benzyl and methyl triesters." *Heterocycles* 32, 1351–1356; Kinchington, D., Harvey, J. J., O'Connor, T. J., Jones, B. C. N. M., Devine, K. G., Taylor-Robinson D., Jeffries, D. J. and McGuigan, C. (1992) "Comparison of antiviral effects of zidovudine phosphoramidate an dphosphorodiamidate derivates against HIV and ULV in vitro." *Antiviral Chem. Chemother.* 3, 107–112; Kodama, K., Morozumi, M., Saithoh, K. I., Kuninaka, H., Yosino, H. and Saneyoshi, M. (1989) "Antitumor activity and pharmacology of 1-β-D-arabinofuranosylcytosine-5'-stearylphosphate; an orally active derivative of 1-β-D-arabinofuranosylcytosine." *Jpn. J. Cancer Res.* 80, 679–685; Korty, M. and Engels, J. (1979) "The effects of adenosine- and guanosine 3',5' phosphoric and acid benzyl esters on guinea-pig ventricular myocardium." *Naunyn-Schmiedeberg's Arch. Pharmacol.* 310, 103–111; Kumar, A., Goe, P. L., Jones, A. S. Walker, R. T. Balzarini, J. and DeClercq, E. (1990) "Synthesis and biological evaluation of some cyclic phosphoramidate nucleoside derivatives." *J. Med. Chem,* 33, 2368–2375; LeBec, C., and Huynh-Dinh, T. (1991) "Synthesis of lipophilic phosphate triester derivatives of 5-fluorouridine an arabinocytidine as anticancer prodrugs." *Tetrahedron Lett.* 32, 6553–6556; Lichtenstein, J., Barner, H. D. and Cohen, S. S. (1960) "The metabolism of exogenously supplied nucleotides by *Escherichia coli.,*" *J. Biol. Chem.* 235, 457–465; Lucthy, J., Von Daeniken, A., Friederich, J. Manthey, B., Zweifel, J., Schlatter, C. and Benn, M. H. (1981) "Synthesis and toxicological properties of three naturally occurring cyanoepithioalkanes". *Mitt. Geg. Lebensmittelunters. Hyg.* 72, 131–133 (*Chem. Abstr.* 95, 127093); McGigan, C. Tollerfield, S. M. and Riley, P. a. (1989) "Synthesis and biological evaluation of some phosphate triester derivatives of the anti-viral drug Ara." *Nucleic Acids Res.* 17, 6065–6075; McGuigan, C., Devine, K. G., O'Connor, T. J., Galpin, S. A., Jeffries, D. J. and Kinchington, D. (1990a) "Synthesis and evaluation of some novel phosphoramidate derivatives of 3'-azido-3'-deoxythymidine (AZT) as anti-HIV compounds." *Antiviral Chem. Chemother.* 1 107–113; McGuigan, C., O'Connor, T. J., Nicholls, S. R. Nickson, C. and Kinchington, D. (1990b) "Synthesis and anti-HIV activity of some novel substituted dialkyl phosphate derivatives of AZT and ddCyd." *Antiviral Chem. Chemorher.* 1, 355–360; McGuigan, C., Nicholls, S. R., O'Connor, T. J., and Kinchington, D. (1990c) "Synthesis of some novel dialkyl phosphate derivative of 3'-modified nucleosides as potential anti-AIDS drugs." *Antiviral Chem. Chemother.* 1, 25–33; McGuigan, C., Devin, K. G., O'Connor, T. J., and Kinchington, D. (1991) "Synthesis and anti-HIV activity of some haloalkyl phosphoramidate derivatives of 3'-azido-3'-deoxythylmidine (AZT); potent activity of the trichloroethyl methoxyalaninyl compound." *Antiviral Res.* 15, 255–263; McGuigan, C., Pathirana, R. N., Balzarini, J. and DeClercq, E. (1993b) "Intracellular delivery of bioactive AZT nucleotides by aryl phosphate derivatives of AZT." *J. Med. Chem.* 36, 1048–1052.

Alkyl hydrogen phosphate derivatives of the anti-HIV agent AZT may be less toxic than the parent nucleoside analogue. *Antiviral Chem. Chemother.* 5, 271–277; Meyer, R. B., Jr., Shuman, D. A. and Robins, R. K. (1973) "Synthesis of purine nucleoside 3',5'-cyclic phosphoramidates." *Tetrahedron Lett.* 269–272; Nagyvary, J. Gohil, R. N., Kirchner, C. R. and Stevens, J. D. (1973) "Studies on neutral esters of cyclic AMP," *Biochem. Biophys. Res. Commun.* 55, 1072–1077; Namane, A. Gouyette, C., Fillion, M. P., Fillion, G. and Huynh-Dinh, T. (1992) "Improved brain delivery of AZT using a glycosyl phosphotriester prodrug." *J. Med Chem.* 35, 3039–3044; Nargeot, J. Nerbonne, J. M. Engels, J. and Leser, H. A. (1983) *Natl. Acad. Sci. U.S.A.* 80, 2395–2399; Nelson, K. A., Bentrude, W. G. Stser, W. N. and Hutchinson, J. P. (1987) "The question of chair-twist equilibria for the phosphate rings of nucleoside cyclic 3',5' monophosphates. $^1$HNMR and x-ray crystallographic study of the diastereomers of thymidine phenyl cyclic 3',5'-monophosphate." *J. Am. Chem. Soc.* 109, 4058–4064; Nerbonne, J. M., Richard, S., Nargeot, J. and Lester, H. A. (1984) "New photoactivatable cyclic nucleotides produce intracellular jumps in cyclic AMP and cyclic GMP concentrations." *Nature* 301, 74–76; Neumann, J. M., Herv, M., Debouzy, J. C., Guerra, F. I., Gouyette, C., Dupraz, B. and Huyny-Dinh, T. (1989) "Synthesis and transmembrane transport studies by NMR of a glucosyl phospholipid of thymidine." *J. Am. Chem. Soc.* 111, 4270–4277; Ohno, R., Tatsumi, N., Hirano, M., Imai, K. Mizoguchi, H., Nakamura, T., Kosaka, M., Takatuski, K., Yamaya, T., Toyama K., Yoshida, T., Masaoka, T., Hashimoto, S., Ohshima, T., Kimura, I., Yamada, K. and Kimura, J. (1991) "Treatment of myelodysplastic syndromes with orally administered 1-β-D-arabinouranosylcytosine-5' stearylphosphate." *Oncology* 48, 451–455. Palomino, E., Kessle, D. and Horwitz, J. P. (1989) "A. dihydropyridine carrier system for sustained delivery of 2', 3' dideoxynucleosides to the brain." *J. Med. Chem.* 32, 22–625; Perkins, R. M., Barney, S. Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. (1993) "Activity of BRLA7923 and its oral prodrug, SB203657A against a rauscher murine leukemia virus infection in mice." *Antiviral Res.* 20 (Suppl. I). 84; Piantadosi, C., Marasco, C. J., Jr., Norris-Natschke, S. L., Meyer, K. L., Gumus, F., Surles, J. R., Ishaq, K. S., Kucera, L. S. Iyer, N., Wallen, C. A., Piantadosi, S. and Modest, E. J. (1991) "Synthesis and evaluation of novel ether lipid nucleoside conjugates for anti-HIV-1 activity." *J. Med. Chem.* 34, 1408–1414; Pompon, A., Lefebvre, I., Imbach, J. L., Kahn, S. and Farquhar, D. (1994). "Decomposition pathways of the mono- and bis(pivaloyloxymethyl) esters of azidothymidine-5'-monophosphate in cell extract and in tissue culture medium; an application of the 'on-line ISRP-cleaning HPLC technique." *Antiviral Chem Chemother.* 5, 91–98; Postemark, T. (1974) "Cyclic AMP and cyclic GMP." *Annu. Rev. Pharmacol.* 14,23–33; Prisbe, E. J., Martin, J. C. M., McGhee, D. P. C., Barker, M. F., Smee, D. F. Duke, A. E., Matthews, T. R. and Verheyden, J. P. J. (1986) "Synthesis and antiherpes virus activity of phosphate an phosphonate derivatives of 9-[(1,3-dihydroxy-2-propoxy)methyl] guanine." *J. Med. Chem.* 29, 671–675; Pucch, F., Gosselin, G., Lefebvre, I., Pompon, a., Aubertin, A. M. Dirn, and Imbach, J. L. (1993) "Intracellular delivery of nucleoside monophosphate through a reductase-mediated activation process." *Antivral Res.* 22, 155–174; Pugaeva, V. P., Klochkeva, S. I., Mashbits, F. D. and Eizengart, R. S. (1969). "Toxicological assessment and health standard ratings for ethylene sulfide in the industrial atmosphere." *Gig. Trf. Prof. Zabol.* 14, 47–48 (*Chem. Abstr.* 72, 212); Robins, R. K. (1984) "The potential of nucleotide analogs as inhibitors of Retro viruses and tumors." *Pharm. Res.* 11–18; Rosowsky, A., Kim. S. H., Ross and J. Wick, M. M. (1982) "Lipophilic 5'-(alkylphosphate) esters of 1-β-D-arabinofuranosylcytosine and its N⁴-acyl and 2.2'-anhydro-3'0-acyl derivatives as potential prodrugs." *J. Med. Chem.* 25, 171–178; Ross, W. (1961) "Increased sensitivity of the walker turnout towards aromatic nitrogen mustards carrying basic side chains following glucose pretreatment." *Biochem. Pharm.* 8, 235–240; Ryu, E. K., Ross, R. J. Matsushita, T., MacCoss, M., Hong, C. I. and West, C. R. (1982). "Phospholipid-nucleoside conjugates. 3. Synthesis and preliminary biological evaluation of 1-β-D-arabinofuranosylcytosine 5' diphosphate [−], 2-diacylglycerols." *J. Med. Chem.* 25, 1322–1329; Saffhill, R. and Hume, W. J. (1986) "The degradation of 5-iododeoxyuridine and 5-bromoethoxyuridine by serum from different sources and its consequences for the use of these compounds for incorporation into DNA." *Chem. Biol. Interact.* 57, 347–355; Saneyoshi, M., Morozumi, M., Kodama, K., Machida, J., Kuninaka, A. and Yoshino, H. (1980) "Synthetic nucleosides and nucleotides. XVI. Synthesis and biological evaluations of a series of 1-β-D-arabinofuranosylcytosine 5'-alky or arylphosphates." *Chem Pharm. Bull.* 28, 2915–2923; Sastry, J. K., Nehete, P. N., Khan, S., Nowak, B. J., Plunkett, W., Arlinghaus, R. B. and Farquhar, D. (1992) "Membrane-permeable dideoxyuridine 5'-monophosphate analogue inhibits human immunodeficiency virus infection." *Mol. Pharmacol.* 41, 441–445; Shaw, J. P., Jones, R. J. Arimilli, M. N., Iouie, M. S., Lee, W. A. and Cundy, K. C. (1994) "Oral bioavailability of PMEA from PMEA prodrugs in male Sprague-Dawley rats." *9th Annual AAPS Meeting.* San Diego, Calif. (Abstract). Shuto, S., Ueda, S., Imamura, S., Fukukawa; K. Matsuda, A.; and Ueda, T. (1987) "A facile one-step synthesis of 5' phosphatidylnucleosides by an enzymatic two-phase reaction." *Tetrahedron Lett.* 28, 199–202; Shuto, S. Itoh, H., Ueda, S., Imamura, S., Kukukawa, K., Tsujino, M., Matsuda, A. and Ueda, T. (1988). *Pharm. Bull.* 36, 209–217. An example of a useful phosphate prodrug group is the S-acyl-2-thioethyl group, also referred to as "SATE".

IV. Combination and Alternation Therapy for HIV or HBV

It has been recognized that drug-resistant variants of HIV and HBV can emerge after prolonged treatment with an antiviral agent. Drug resistance most typically occurs by mutation of a gene that encodes for an enzyme used in viral replication, and most typically in the case of HIV, reverse transcriptase, protease, or DNA polymerase, and in the case of HBV, DNA polymerase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

The second antiviral agent for the treatment of HIV, in one embodiment, can be a reverse transcriptase inhibitor (a "RTI"), which can be either a synthetic nucleoside (a "NRTI") or a non-nucleoside compound (a "NNRTI"). In an alternative embodiment, in the case of HIV, the second (or third) antiviral agent can be a protease inhibitor. In other embodiments, the second (or third) compound can be a pyrophosphate analog, or a fusion binding inhibitor. A list compiling resistance data collected in vitro and in vivo for a number of antiviral compounds is found in Schinazi, et al, Mutations in retroviral genes associated with drug resistance, *International Antiviral News,* 1997.

Preferred compounds for combination or alternation therapy for the treatment of HBV include 3TC, FTC, L-FMAU, interferon, β-D-dioxolanyl-guanine (DXG), β-D-dioxolanyl-2,6-diaminopurine (DAPD), and β-D-dioxolanyl-6-chloropurine (ACP), famciclovir, penciclovir, BMS-200475, bis pom PMEA (adefovir, dipivoxil); lobucavir, ganciclovir, and ribavarin.

Preferred examples of antiviral agents that can be used in combination or alternation with the compounds disclosed herein for HIV therapy include cis-2-hydroxymethyl-5-(5-fluorocytosin-1-yl)-1,3-oxathiolane (FTC); the (−)-enantiomer of 2-hydroxymethyl-5-(cytosin-1-yl)-1,3-oxathiolane (3TC); carbovir, acyclovir, foscarnet, interferon, AZT, DDI, DDC, D4T, CS-87 (3'-azido-2',3'-dideoxyuridine), and β-D-dioxolane nucleosides such as β-D-dioxolanyl-guanine (DXG), β-D-dioxolanyl-2,6-diaminopurine (DAPD), and β-D-dioxolanyl-6-chloropurine (ACP), MKC-442 (6-benzyl-1-(ethoxymethyl)-5-isopropyl uracil.

Preferred protease inhibitors include crixivan (Merck), nelfinavir (Agouron), ritonavir (Abbott), saquinavir (Roche), DMP-266 (Sustiva) and DMP-450 (DuPont Merck).

A more comprehensive list of compounds that can be administered in combination or alternation with any of the disclosed nucleosides include (1S,4R)-4-[2-amino-6-cyclopropyl-amino)-9H-purin-9-yl]-2-cyclopentene-1-methanol succinate ("1592", a carbovir analog; GlaxoWellcome); 3TC: (−)-β-L-2',3'-dideoxy-3'-thiacytidine (GlaxoWellcome); a-APA R18893: a-nitro-anilino-phenylacetamide; A-77003; C2 symmetry-based protease inhibitor (Abbott); A-75925: C2 symmetry-based protease inhibitor (Abbott); AAP-BHAP: bishetero-arylpiperazine analog (Upjohn); ABT-538: C2 symmetry-based protease inhibitor (Abbott); AzddU:3'-azido-2',3'-dideoxyuridine; AZT: 3'-azido-3'-deoxythymidine (GlaxoWellcome); AZT-p-ddI: 3'-azido-3'-deoxythymidilyl-(5',5')-2',3'-dideoxyinosinic acid (Ivax); BHAP: bisheteroaryl-piperazine; BILA 1906: N-{1S-[[[3-[2S-{(1, 1-dimethylethyl)amino]carbonyl}-4R]-3pyridinylmethyl) thio]-1-piperidinyl]-2R-hydroxy-1S-(phenylmethyl)-propyl]amino]-carbonyl]-2-methylpropyl}-2-quinolinecarboxamide (Bio Mega/Boehringer-Ingelheim); BILA 2185: N-(1,1-dimethylethyl)-1-[2S-[[2-2,6-dimethyphenoxy)-1-oxoethyl]amino]-2R-hydroxy-4-phenylbutyl]4R-pyridinylthio)-2-piperidinecarboxamide (BioMega/Boehringer-Ingelheim); BM+51.0836: thiazolo-iso-indolinone derivative; BMS 186,318: aminodiol derivative HIV-1 protease inhibitor (Bristol-Myers-Squibb); d4API: 9-[2,5-dihydro-5-(phosphonomethoxy)-2-furanel] adenine (Gilead); d4C: 2',3'-didehydro-2',3'-dideoxycytidine; d4T: 2',3'-didehydro-3'-deoxythymidine (Bristol-Myers-Squibb); ddC; 2',3'-dideoxycytidine (Roche); ddI: 2',3'-dideoxyinosine (Bristol-Myers-Squibb); DMP-266: a 1,4-dihydro-2H-3,1-benzoxazin-2-one; DMP-450: {[4R-(4-a,5-a,6-b,7-b)]-hexahydro-5,6-bis(hydroxy)-1, 3-bis(3-amino)phenyl]-methyl)-4,7-bis-(phenylmethyl)-2H-1,3-diazepin-2-one}-bismesylate (Avid); DXG:(−)-β-D-dioxolane-guanosine (Triangle); EBU-dM:5-ethyl-1-ethoxymethyl-6-(3,5-dimethylbenzyl)-uracil; E-EBU: 5-ethyl-1-ethoxymethyl-6-benzyluracil; DS: dextran sulfate; E-EPSeU:1-(ethoxymethyl)-(6-phenylselenyl)-5-ethyluracil; E-EPU: 1-(ethoxymethyl)-(6-phenylthio)-5-ethyluracil; FTC: β-2',3'-dideoxy-5-fluoro-3'-thiacytidine (Triangle); HBY097:S-4-isopropoxy-carbonyl-6-methoxy- 3-(methylthio-methyl)-3,4-dihydroquinoxalin-2(1H)-thione; HEPT: 1-[(2-hydroxyethoxy)methyl]-6-(phenylthio) thymine; HIV-1:human immunodeficiency virus type 1; JM2763: 1,1'-(1,3-propanediyl)-bis-1,4,8,11-tetraaza-cyclotetradecane (Johnson Matthey); JM3100:1,1'-[1,4-phenylenebis-(methylene)]-bis-1,4,8,11-tetraazacyclotetradecane(Johnson Matthey); KNI-272: (2S, 3S)-3-amino-2-hydroxy-4-phenylbutyric acid-containing tripeptide; L-697,593;5-ethyl-6-methyl-3-(2-phthalimidoethyl)pyridin-2(1H)-one; L-735,524:hydroxy-aminopentane amide HIV-1 protease inhibitor (Merck); L-697, 661; 3-{[(4,7-dichloro-1,3-benzoxazol-2-yl)methyl] amino}-5-ethyl-6-methylpyridin-2(1 H)-one; L-FDDC: (-)-β-L-5-fluoro-2',3'-dideoxycytidine; L-FDOC:(-)-β-L-5-fluoro-dioxolane cytosine; MKC442:6-benzyl-1-ethoxymethyl-5-isopropyluracil (I-EBU; Triangle/Mitsubishi); Nevirapine: 11-cyclo-propyl-5,11-dihydro-4-methyl-6H-dipyridol-[3,2-b:2',3'-e]-diazepin-6-one (Boehringer-Ingelheim); NSC648400: 1-benzyloxymethyl-5-ethyl-6-(alpha-pyridylthio)uracil (E-BPTU); P9941: [2-pyridylacetyl-IIePheAla-y(CHOH)]₂ (Dupont Merck); PFA: phosphonoformate (foscamet; Astra); PMEA: 9-(2-phosphonylmethoxyethyl)adenine (Gilead); PMPA: (R)-9-(2-phosphonylmethoxypropyl)adenine (Gilead); Ro 31-8959: hydroxyethylarnine derivative HIV-1 protease inhibitor (Roche); RPI-312: peptidyl protease inhibitor, 1-[(3s)-3-(n-alpha-benzyloxycarbonyl)-1-asparginyl)-amino-2-hydroxy-4-phenylbutyryl]-n-tert-butyl-1-proline amide; 2720: 6-chloro-3,3-dimethyl-4-(isopropenyloxycarbonyl)-3,4-dihydro-quinoxalin-2-(1H)-thione; SC-52151: hydroxy-ethylurca isostere protease inhibitor (Searle); SC-55389A: hydroxyethyl-urea isostere protease inhibitor (Searle); TIBO R82150: (+)-(5S)-4,5,6,7-tetrahydro-5-methyl-6-(3-methyl-2-butenyl)imidazo[4,5,1jk][1,4]-benzodiazepin-2(1H)-thione (Janssen); TIBO 82913: (+)-(5S)-4,5,6,7,-tetrahydro-9-chloro-5-methyl-6-(3-methyl-2-butenyl)imidazo-[4,5,1jk]-[1,4]benzo-diazepin-2(1H)-thione (Janssen); TSAO-m3T:[2',5'-bis-O-(tert-butyldimethylsilyl)-3'-spiro-5'-(4'-amino-1',2'-oxathiole-2',2'-dioxide)]-β-D-pento-furanosyl-N3-methylthymine; U90152: 1-[3-[(1-methylethyl)-amino]-2-pyridinyl]-4-[[5-[(methylsulphonyl)-amino]-1H-indol-2yl]carbonyl]piperazine; UC: thiocarboxanilide derivatives (Uniroyal); UC-781: N-[4-chloro-3-(3-methyl-2-butenyloxy)phenyl]-2-methyl-3-furancarbothioamide; UC-82: N-[4-chloro-3-(3-methyl-2-butenyloxy)phenyl]-2-methyl-3-thiophenecarbothioamide; VB 11,328: hydroxyethyl-sulphonamide protease inhibitor (Vertex); VX-478: hydroxyethylsulphonamide protease inhibitor (Vertex); XM 323: cyclic urea protease inhibitor (Dupont Merck).

The active compound can also be administered in combination or alternation with ribavarin, interferon, interleukin or a stabilized prodrug of any of them. More broadly described, the compound can be administered in combination or alternation with any of the drugs listed below.

Table of Hepatitis C Drugs in Current Clinical Development

| Drug Name | Drug Category | Pharmaceutical Company |
| --- | --- | --- |
| PEGASYS pegylated interferon alfa-2a | Long acting interferon | Roche |
| INFERGEN interferon alfacon-1 | Interferon, Long acting interferon | InterMune |
| OMNIFERON natural interferon | Interferon, Long acting interferon | Viragen |
| ALBUFERON | Longer acting interferon | Human Genome Sciences |
| REBIF interferon beta-1a | Interferon | Ares-Serono |
| Omega Interferon | Interferon | BioMedicine |
| Oral Interferon alpha | Oral Interferon | Amarillo Biosciences |
| Interferon gamma-1b | Anti-fibrotic | InterMune |
| Interleukin-10 | Anti-fibrotic | Schering-Plough |
| IP-501 | Anti-fibrotic | Interneuron |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| HEPTAZYME | RNA inhibitor using Ribozymes | RPI |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody Therapeutic vaccine | NABI Innogenetics |
| LEVOVIRIN | Nucleoside Analogue | ICN |
| VIRAMIDINE | Nucleoside Analogue | ICN |
| ZADAXIN (thymosin alfa-1) | Immunomodulator | Sci Clone |
| CEPLENE histamine dihydrochloride | Immunomodulator | Maxim |
| VX 950/ LY 570310 | Protease Inhibitor | Vertex/Eli Lilly |
| ISIS 14803 | Antisense | Isis Pharmaceutical/ Elan |
| IDN-6556 | Caspase inhibitor | Idun Pharmaceuticals, Inc. http://www.idun.com |
| JTK 003 | Polymerase Inhibitor | AKROS Pharma |

V. Combination Therapy for the Treatment of Proliferative Conditions

In another embodiment, the compounds, when used as an antiproliferative, can be administered in combination with another compound that increases the effectiveness of the therapy, including but not limited to an antifolate, a 5-fluoropyrimidine (including 5-fluorouracil), a cytidine analogue such as β-L-1,3-dioxolanyl cytidine or β-L-1,3-dioxolanyl 5-fluorocytidine, antimetabolites (including purine antimetabolites, cytarabine, fudarabine, floxuridine, 6-mercaptopurine, methotrexate, and 6-thioguanine), hydroxyurea, mitotic inhibitors (including CPT-11, Etoposide (VP-21), taxol, and vinca alkaloids such as vincristine and vinblastine, an alkylating agent (including but not limited to busulfan, chlorambucil, cyclophosphamide, ifofamide, mechlorethamine, melphalan, and thiotepa), non-classical alkylating agents, platinum containing compounds, bleomycin, an anti-tumor antibiotic, an anthracycline such as doxorubicin and dannomycin, an anthracenedione, topoisomerase II inhibitors, hormonal agents (including but not limited to corticosteroids (dexamethasone, prednisone, and methylprednisone), androgens such as fluoxymesterone and methyltestosterone, estrogens such as diethylstilbesterol, antiestrogens such as tamoxifen, LHRH analogues such as leuprolide, antiandrogens such as flutamide, aminoglutethimide, megestrol acetate, and medroxyprogesterone), asparaginase, carmustine, lomustine, hexamethyl-melamine, dacarbazine, mitotane, streptozocin, cisplatin, carboplatin, levamasole, and leucovorin. The compounds of the present invention can also be used in combination with enzyme therapy agents and immune system modulators such as an interferon, interleukin, tumor necrosis factor, macrophage colony-stimulating factor and colony stimulating factor.

VI. Process for the Preparation of Active Compounds

A. Method for the preparation of β-3'-halo-2',3'-dideoxy-2', 3'-didehydro-nucleosides From Glyceraldehyde The key starting material for this process is an appropriately protected D- or L-glyceraldehyde. The D- or L-glyceraldehyde, or its sulfur analog can be purchased, which can then be protected using standard ketones. In one embodiment, the D- or L-glyceraldehyde, or its sulfur analog, is protected using acetone as taught in Greene, et al., *Protective Groups in Organic Synthesis*, John Wiley and Sons, Second Edition, 1991.

The protected glyceraldehyde, or its sulfur analog, can then be coupled with a nucleophilic acetaldehyde that is appropriately protected, for example an appropriately protected organometallic reagent, to give the alcohol, as shown below. The organometallic reagent can be derived from any viable metal, such as lithium, copper or magnesium, though most preferably magnesium. In a preferred embodiment, the appropriately protected nucleophilic acetaldehyde is (1,3-dioxolan-2-ylmethyl)-magnesium bromide.

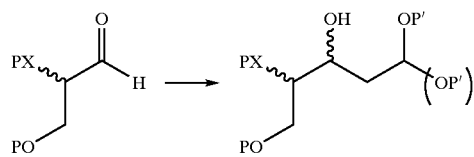

Any reaction solvent can be selected that can achieve the necessary temperature and that can solubilize the reaction components. Nonlimiting examples are any aprotic solvent including, but not limiting to, alkyl solvents such as hexane and cyclohexane, toluene, acetone, ethyl acetate, dithianes, THF, dioxane, acetonitrile, dichloromethane, dichloroethane, diethyl ether, pyridine, dimethylformamide (DMF), dimethylsulfoxide (DMSO), dimethylacetamide or any combination thereof, preferably anhydrous THF.

The coupling reaction can be carried out at any temperature that achieves the desired results, i.e., that is suitable for the reaction to proceed at an acceptable rate without promoting decomposition or excessive side products. Preferred temperatures are refluxing conditions using THF.

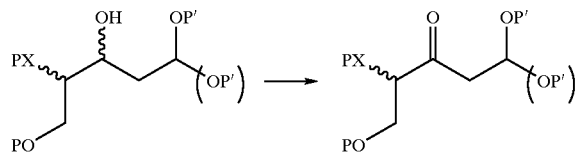

The coupled product, can then be oxidized to the appropriate ketone using any oxidation method to oxide secondary alcohols to ketones known to those skilled in the art. Examples of suitable oxidative methodologies include the chromate oxidations, manganate and permanganate oxidations, oxidation with Jones reagent, oxidation with Collins reagent, oxidation with Corey's reagent, Oppenauer oxidation and the Swern oxidation, though preferably using the mild conditions of the Swern oxidation.

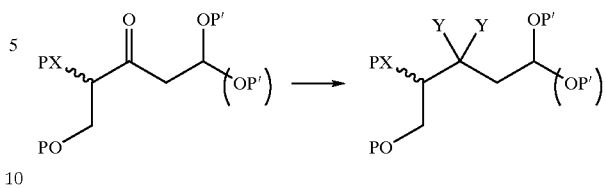

The ketone can be halogenated using any known halogenating agent in the art appropriate for dihalogenation. In a particular embodiment, the fluorinated product is desired, therefore, the fluorination can be achieved using (diethylamino)sulfur trifluoride (DAST). After halogenation, the compound can be selectively deprotected.

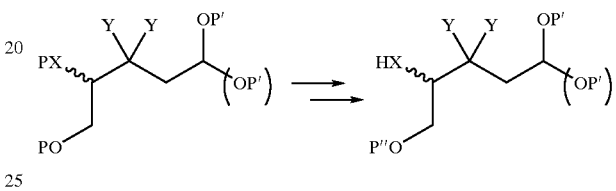

The selective deprotection can be achieved using any means known in the art, including those taught in Greene, et al., *Protective Groups in Organic Synthesis*, John Wiley and Sons, Second Edition, 1991. For instance, when X is O, the deprotected primary hydroxyl can then be selectively reprotected over the secondary hydroxyl using mild conditions as described in Greene, et al., *Protective Groups in Organic Synthesis*, John Wiley and Sons, Second Edition, 1991.

The selectively protected product can be cyclized under acidic conditions (i.e. deprotecting the aldehyde, and coupling with the secondary alcohol), optionally followed by activation of the resulting secondary alcohol. For example, a 1M solution of HCl, followed by a treatment of concentration sulfuric acid and acetic acid with acetic anhydride is sufficient to cyclize the compound and activate the resulting alcohol into an acetate.

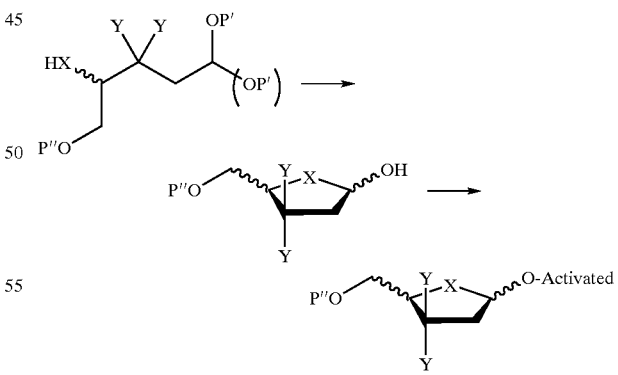

The activated cyclized product can then be coupled to the purine or pyrimidine base using any means known in the art, to obtain a protected β-D or β-L-3',3'-dihalonucleoside. For example, an activated purine or pyrimidine base, preferably via silylation of the base, is coupled to the ring using a Lewis acid, such as tin tetrachloride and titanium tetrachloride, or trimethylsilyl triflate.

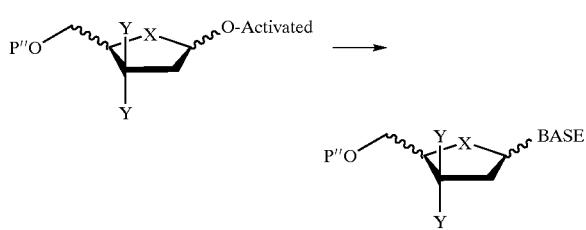

The β-D or β-L-3',3'-dihalonucleoside can then be optionally protected by any means known in the art, then one of the halogens can be eliminated by any means known in the art, or disclosed herein in the examples, to obtain the desired β-2',3'-dideoxy-2',3'-didehydro-halo-nucleoside. Finally, the 5'-hydroxyl can be deprotected by any means known in the art.

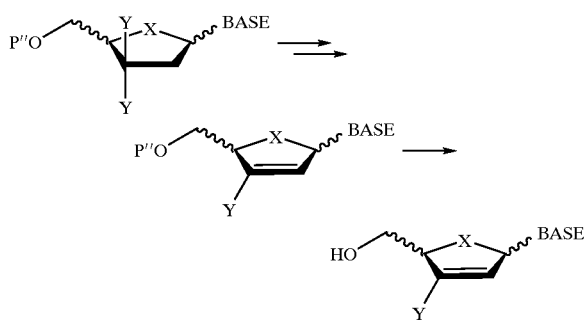

From a Sugar Ring

The key starting material for this process is an appropriately protected 5-carbon D- or L-sugar ring, or its sulfur analog. The D- or L-sugar, or its sulfur analog can be purchased as a pyranose or a furanose, preferably as a furanose. However, if the sugar is a pyranose, the 4' and 5' can be selectively protected to give the furanose, as taught in Ma et al., *J. Med. Chem.* 1996, 39 (14), 2835 and Cooperwood et al. *Nucleosides Nucleotides* 2000, 19 (1&2), 219.

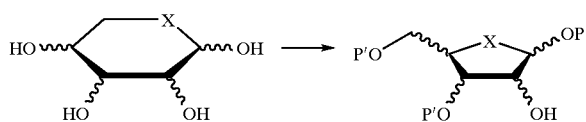

The protected furanose, or its sulfur analog, can then be activated to give an activated hydroxyl, which can then be eliminated.

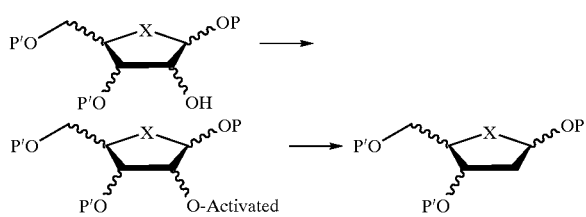

The dehydro product can then be selectively deprotected to give the free secondary hydroxyl, which can then be oxidized to the appropriate ketone using any oxidation method to oxide secondary alcohols to ketones known to those skilled in the art. Examples of suitable oxidative methodologies include the chromate oxidations, manganate and permanganate oxidations, oxidation with Jones reagent, oxidation with Collins reagent, oxidation with Corey's reagent, Oppenauer oxidation and the Swern oxidation, though preferably using chromic anhydride.

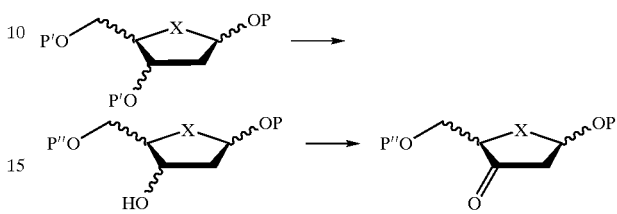

The ketone can be halogenated using any known halogenating agent in the art appropriate for dihalogenation. In a particular embodiment, the fluorinated product is desired, therefore, the fluorination can be achieved using DAST. After halogenation, the compound can be selectively deprotected and activated, preferably in one-pot.

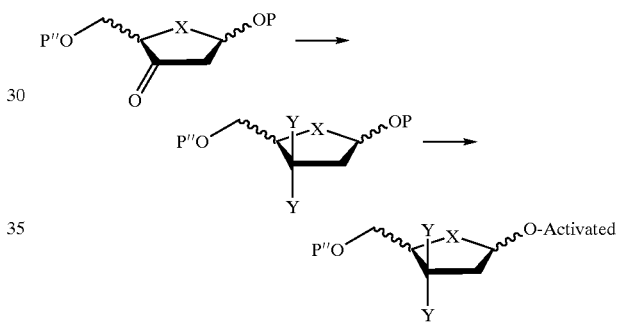

The activated cyclized product can then be coupled to the purine or pyrimidine base using any means known in the art, to obtain a protected β-D or β-L-3',3'-dihalonucleoside. For example, an activated purine or pyrimidine base, preferably via silylation of the base, is coupled to the ring using a Lewis acid, such as tin tetrachloride and titanium tetrachloride, or trimethylsilyl triflate.

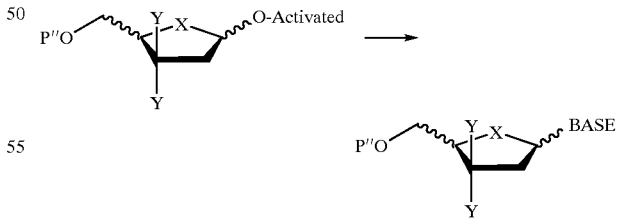

The β-D or β-L-3',3'-dihalonucleoside can then be optionally protected by any means known in the art, then one of the halogens can be eliminated by any means known in the art, or disclosed herein in the examples, to obtain the desired β-2',3'-dideoxy-2',3'-didehydro-halo-nucleoside. Finally, the 5'-hydroxyl can be deprotected by any means known in the art.

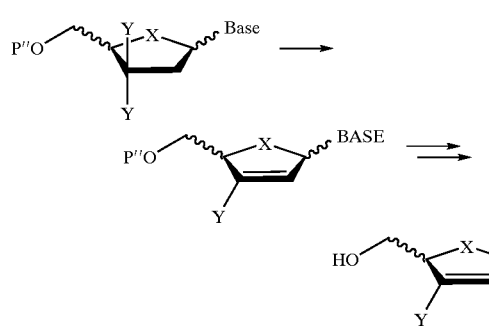

B. Method for the Preparation of β-3'-halo-nucleosides

From the Lactol

The key starting material for this process is an appropriately protected D- or L-lactol. The D- or L-lactol can be purchased or made by any means known in the art. In one embodiment, the thiolactol is desired, which can be made using the protocol set forth by Secrist III, J. A.; Tiwari, K. N.; Riordan, J. M.; Montgomery, J. A. Synthesis and biological activity of 2'-deoxy4-'thio pyrimidine nucleosides, *J. Med. Chem.* 1991, 34, 2361–2366; Tiwari, K. N.; Montgomery, J. A.; Secrist III, J. A. The synthesis and biological activity of 1-(2-deoxy-4-thio-a-L-threo-pentofuranosyl)thyrnine, *Nucleosides & Nucleotides,* 1993, 12(8), 841–846.

The lactol can then be activated and coupled to the to the purine or pyrimidine base using any means known in the art, to obtain a protected β-D or β-L-3',3'-dihalonucleoside. For example, an activated purine or pyrimidine base, preferably via silylation of the base, is coupled to the ring using a Lewis acid, such as tin tetrachloride and titanium tetrachloride, or trimethylsilyl triflate.

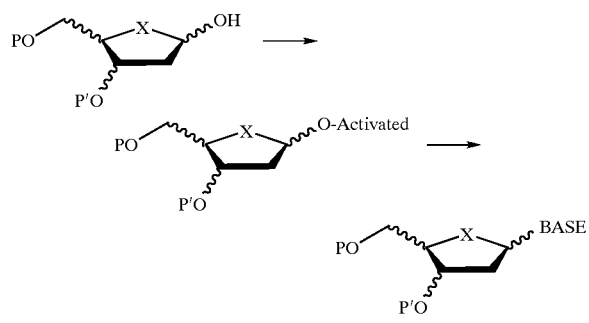

The β-D or β-L-nucleoside can then be optionally deprotected, and the secondary alcohol can be substituted with the appropriate halogen by any means known in the art or methodology set forth herein.

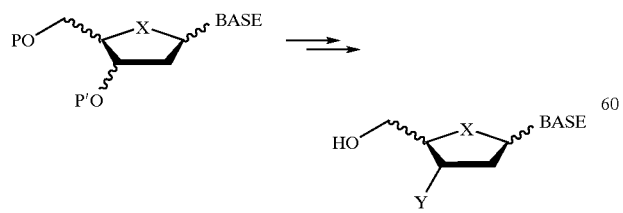

C. Method for the Preparation of β-2'-halo-2',3'-dideoxy-2',3'-didehydro-thionucleosides

From Glyceraldehyde

The key starting material for this process is an appropriately protected D- or L-glyceraldehyde. The D- or L-glyceraldehyde can be purchased, which can then be protected using standard ketones. In one embodiment, the D- or L-glyceraldehyde is protected using acetone as taught in Greene, et al., *Protective Groups in Organic Synthesis*, John Wiley and Sons, Second Edition, 1991.

The protected glyceraldehyde can then be coupled and cyclized by means well known in the art, or methods disclosed herein. For example, the cyclized compound can be made according to the procedure set for in Chong, Y.; Gumina, G.; Chu, C. K. *Tetrahedron Asymmetry.* 2000, 11, 4853–4875.

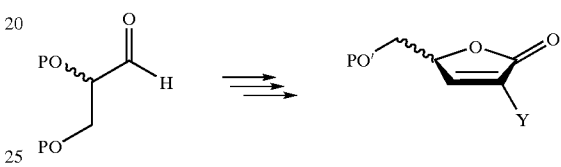

The cyclized product can then be selectively reduced, using any known reducing agent in the art to give the 2',3'-hydro product. For example, the lactone can be selectively reduced using palladium on carbon.

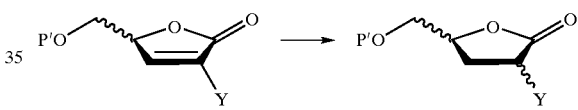

The reduced product can then be decyclized via a selective nucleophilic attack on the 4'-position of the lactone, for example, with iodine in the presence of triphenylphosphine and imidazole. The nucleophile can then be substituted with a nucleophilic sulfur by a simple substitution reaction known in the art, preferably with a sulfide such as KSAc.

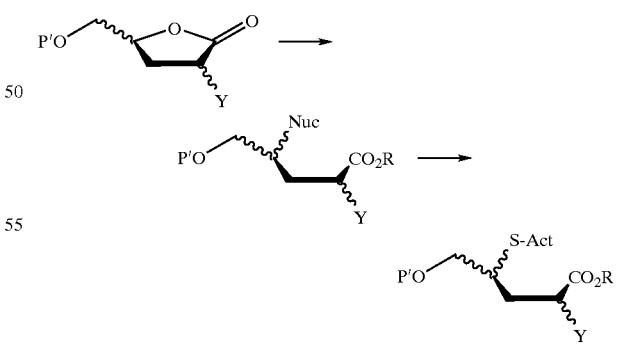

The resulting activated ester can then be reduced using any viable reducing agent known in the art, such as DIBAL-H, optionally activated, such as with an anhydride to give an acyl moiety (for example using acetic anhydride) and cyclized to give the thiolactone.

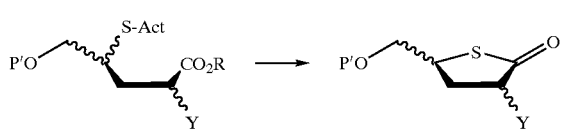

The thiolactone can then be enolized with a strong base, such as LiHMDS, and coupled to an electrophile (LG), which upon simple manipulation can be easily eliminated. Such moieties include phenylselenium and phenylsulfide.

The thiolactone can then be reduced with any known reducing agent known in the art, such as with DIBAL-H, optionally activated, such as with an anhydride to give an acyl moiety (for example using acetic anhydride) and coupled to the purine or pyrimidine base using any means known in the art, to obtain a protected β-D or β-L-3',3'-dihalonucleoside. For example, an activated purine or pyrimidine base, preferably via silylation of the base, is coupled to the ring using a Lewis acid, such as tin tetrachloride and titanium tetrachloride, or trimethylsilyl triflate.

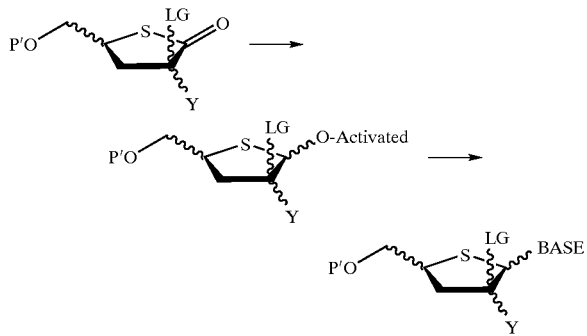

After coupling the thiolactone to the base, the LG is manipulated, i.e. in the case of phenylselenium is oxidized with an oxidizing agent, such as mCPBA, and eliminated to give the protected β-2'-halo-2',3'-dideoxy-2',3'-didehydro-thionucleosides, which can be optionally deprotected by any means known in the art.

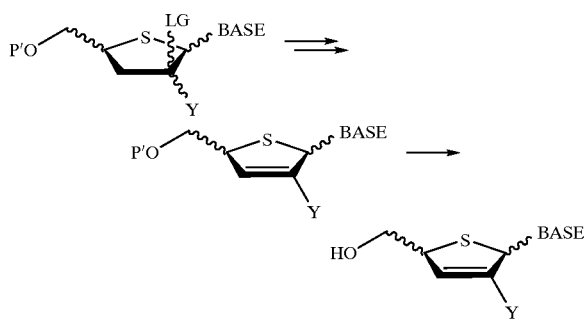

From Glutamic Acid

The key starting material for this process is an appropriately protected D- or L-Glutamic Acid. The D- or L-Glutamic Acid can be purchased, which can then be converted to the thio derivative by means well known in the art. Examples of such protocol are Cervinka, O.; Hub, L. Asymmetric reactions. XXVII. Absolute configurations of γ-butyrolactone-γ-carboxylic acid and γ-valerolactone-γ-carboxylic acid. *Collect. Czech. Chem. Commun.* 1968, 33, 2927–2932; Hanessian, S.; Murray, P. J. Stereochemical control of nature's biosynthetic pathways: A general strategy for the synthesis of polypropionate-derived structural units from a single chiral progenitor. *Tetrahedron* 1987, 43, 5055–5072; Secrist III, J. A.; Riggs, R. H.; Tiwari, K. N.; Montgomery, J. A. Synthesis and anti-HIV activity of 4'-thio-2',3'-dideoxynucleosides. *J. Med. Chem.* 1992, 35, 533–538.

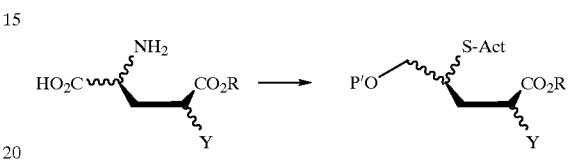

In a particular sub-embodiment of the invention, the process for the preparation of a β-D or β-L-2'-halo-4'-thionucleoside is for the preparation of a β-D or β-L-2'-halo-4'-thiopurine of the formula (X):

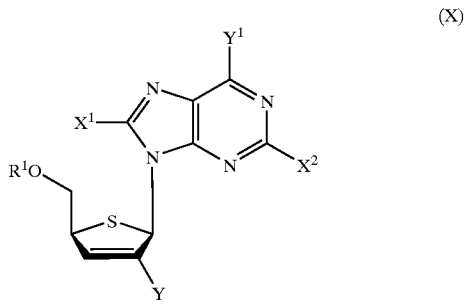

(X)

or its enantiomer, or its pharmaceutically acceptable salt or prodrug, wherein
$R^1$, Y, $X^1$, $X^2$ and $Y^1$ are as defined above.

In another sub-embodiment of the invention, the process for the preparation of a β-D or β-L-2'-halo-4'-thionucleoside is for the preparation of a β-D or β-L-2'-halo-4'-thiopyrimidine of the formula (XI):

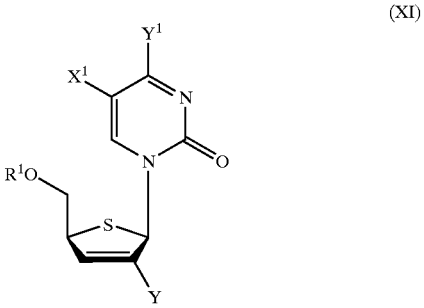

(XI)

or its enantiomer, or its pharmaceutically acceptable salt or prodrug, wherein
$R^1$, Y, $X^1$ and $Y^1$ are as defined above.

In a particular sub-embodiment, the process for the preparation of a β-D or β-L-2'-halo-4'-thionucleoside is for the preparation of a β-D or β-L-2'-halo-4'-thiocytidine of the formula (XII):

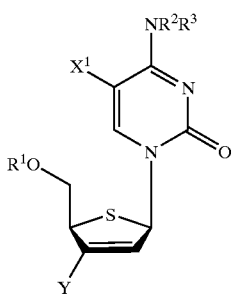

(XII)

or its enantiomer, or its pharmaceutically acceptable salt or prodrug, wherein
$R^1$, X, Y, $X^1$ $R^2$ and $R^3$ are as defined above.

In a preferred embodiment, Y is F for the compounds of the formula (IX)–(XII).

In an alternatively preferred embodiment, Y is F for the compounds of the formula (IX)–(XII).

The β-halonucleosides depicted above are in the β-D configuration, however, it should be understood that the β-halonucleosides can be either in the β-L or β-D configuration.

In one embodiment of the present invention, the compounds of the formula (IX)–(XII) are in the β-D configuration. In an alternate embodiment of the present invention, the compounds of formula (IX)–(XII) are in the β-L configuration.

The following working examples provide a further understanding of the method of the present invention. These examples are of illustrative purpose, and are not meant to limit the scope of the invention. Equivalent, similar, or suitable solvents, reagents or reaction conditions may be substituted for those particular solvents, reagents, or reaction conditions described herein without departing from the general scope of the method of synthesis.

EXAMPLES

Melting points were determined on a Mel-temp II apparatus and are uncorrected. NMR spectra were recorded on a Bruker 400 AMX spectrometer at 400 MHz for $^1$H NMR and 100 MHz for $^{13}$C NMR with TMS as internal standard. Chemical shifts (δ) are reported in parts per million (ppm), and. signals are reported as s (singlet), d (doublet), t (triplet), q (quartet), m (multiplet), or bs (broad singlet). IR spectra were measured on a Nicolet 510P FT-IR spectrometer. Mass spectra were recorded on a Micromass Autospec high-resolution mass spectrometer. TLC were performed on Uniplates (silica gel) purchased from Analtech Co. Column chromatography was performed using either silica gel-60 (220–440 mesh) for flash chromatography or silica gel G (TLC grade, >440 mesh) for vacuum flash column chromatography. UV spectra were obtained on a Beckman DU 650 spectrophotometer. Elemental analysis was performed by Atlantic Microlab, Inc., Norcross, Ga., or Galbraith Laboratories, Inc., Knoxville, Tenn. HPLC was performed with a Waters HPLC system (Millipore Corporation, Milford, Mass.) equipped with a Model 600 controller, a Model 996 photodiode array detector and a Model 717 plus autosampler. Millennium 2010 software was used for system control, data acquisition and processing. A chiralyser polarimetric detector, Perkin-Elmer Model 241MC polarimeter (Wilton, Conn.), was used for the determination of optical rotations.

Example 1

1-[(S)-2,2-Dimethyl-(1,3)-dioxolan-4-yl]-4-(1,3-dioxolan-2-yl)-2-ol (2, FIG. 1)

To a solution of (1,3-dioxolan-2ylmethyl)-magnesium bromide (0.5 M in THF, 325 mL, 162.5 mmol) at 60° C. was added a solution of D-glyceraldehyde (19.1 g, 147 mmol) in THF (100 mL) dropwise for 45 minutes. The resulting solution was stirred for another hour and then moved to an ice/water bath, followed by treatment with saturated ammonium chloride aqueous solution. The reaction mixture was extracted thoroughly by diethyl ether. The organic layer was dried over MgSO4. After removal of solvent, the residue was purified by flash silica gel column (35% EtOAc/Hexanes) to yield the alcohol 2 (yellow oil, 30.1 g, 94%). $^1$H NMR (CDCl$_3$) δ 1.339, 1.356, 1.401, 1.429 (s, 6H), 1.75–1.90 (m, 2H), 2.834 (d, J=3.28 Hz, D$_2$O exchangeable 0.57H), 3.062 (br s, D$_2$O exchangeable, 0.43H), 3.755–4.113 (m, 8H), 5.070 (m, 1H), MS (FAB) m/z 218 (M$^+$)

Example 2

1-[(S)-2,2-Dimethyl-(1,3)-dioxolan-4-yl]-4-(1,3-dioxolan-2-yl)-2-ol (3, FIG. 1)

To a solution of DMSO (8.58 mL) in dry CH$_2$Cl$_2$ was added dropwise (ClCO)$_2$ (5.25 mL) at −78° C. After 5 minutes, 2 (12.0 g, 54.9 mmol) in CH$_2$Cl$_2$ was added dropwise to the solution in 5 minutes. After another 15 minutes, triethyl amine (38.2 mL) was added to the resulting solution. The reaction solution was then warmed up. After standard work-up, the residue was purified by flash silica gel column (20% EtOAc/Hexanes) to yield 3 (yellow oil, 11.4 g, 95%). $^1$H NMR (CDCl$_3$) δ 1.354 (S, 3H), 1.453 (S, 3H), 2.953 (m, 2H), 3.83 (m, 2H), 3.95 (m, 2H), 4.027 (m, 1H), 4.154 (m, 1H), 4.417 (m, 1H), 5.268 (m, 1H), MS (FAB) m/z 216 (M$^+$)

Example 3

1-[(S)-2,2-Dimethyl-(1,3)-dioxolan-4-yl]-2-difluoro-4-(1,3-dioxolan-2-yl)pentane (4, FIG. 1)

To a solution of DAST (15 mL) in dry CH$_2$Cl$_2$ at 0° C. was added dropwise 3 (8.5 g, 39.4 mmol) in CH$_2$Cl$_2$. The resulting solution was stirred for 24 hours at room temperature. The reaction mixture was then poured into a saturated sodium bicarbonate solution at 0° C. After standard work-up, the residue was purified by flash silica gel column (10% EtOAc/Hexanes) to yield 4 (yellow oil, 4.8 g, 51.3%). $^1$H NMR (CDCl$_3$) δ 1.340 (s, 3H), 1.424 (s, 3H), 2.23–2.41 (m, 2H), 3.85 (m, 2H), 3.97 (m, 2H), 4.09 (m, 2H), 4.24–4.33 (m, 1H), 5.121 (t, 1H), MS (FAB) m/z 238 (M$^+$)

Example 4

3-difluoro-5-(1,3-dioxolan-2-yl)-2S-1,2-diol (5, FIG. 1)

To a solution of 4 (4.8 g, 20.2 mmol) in 1,4-dioxane at 0° C. was added 2.5% HCl aqueous solution. The resulting solution was stirred at room temperature overnight and then neutralized by sodium bicarbonate. After standard work-up, the residue was purified by flash silica gel column (60% EtOAc/Hexanes) to yield 5 (colorless oil, 3.6 g, 90%) $^1$H NMR (CDCl$_3$) δ 2.30–2.52 (m, 2H), 3.577 (d, J=5.88 Hz, D$_2$O exchangeable, 1H), 3.83–4.10 (m, 7H), 5.090 (q, 1H), MS (FAB) m/z 198 (M$^+$)

Example 5

1-Benzoxy-3-difluoro-5-(1,3-dioxolan-2-yl)-2S-ol (6, FIG. 1)

To a solution of 5 (3.1 g) in dry pyridine (5 mL) was added dropwise benzoyl chloride (1.82 mL) at 0° C. The resulting solution was stirred at room temperature for 1 hour. After removal of pyridine, the residue was dissolved in $CH_2Cl_2$, washed by saturated $NaHCO_3$ aqueous solution, dried over $MgSO_4$. After concentration, the residue was purified by flash silica gel column (30% EtOAc/Hexanes) to yield 6 (colorless oil, 4.0 g, 85%). $^1H$ NMR ($CDCl_3$) δ 2.43 (m, 2H), 3.84 (m, 2H), 3.95 (m, 2H), 4.03 (m, 1H), 4.19 (m, 1H), 4.48 (m, 1H), 4.59 (m, 1H), 5.08 (m, 1H), 7.38 (m, 2H), 7.51 (m, 1H), 8.01 (m, 1H), MS (FAB) m/z 302 ($M^+$)

Example 6

1-Acetyl-5-O-benzoyl-2,3-dideoxy-3,3-difluoro-D-ribofuranose (7, FIG. 1)

To a solution of 6 (1.6 g, 5.3 mmol) in methanol (15 mL) was added HCl/diethyl ether solution (1.0 M, 15 mL). The resulting solution was stirred and refluxed for 1 hour. After cooled down, the reaction solution was neutralized with $NaHCO_3$. After standard work-up, the residue was used for next step. Concentrated sulfuric acid (40 μL, 0.75 mmol) was added to an ice/cold solution of obtained residue and acetic anhydride (3 mL; 32.0 mmol) in glacial acetic acid (15 mL). The resulting solution was stirred at room temperature for 30 minutes. The reaction mixture was then poured into an ice-cold saturated solution of sodium bicarbonate (100 mL) and extracted with dichloromethane (3×100 mL). After standard work-up, the residue was purified by flash silica gel column (10% EtOAc/Hexanes) to yield anomeric mixture (2:1) 7 (yellow oil, 1.5 g, 95%). $^1H$ NMR ($CDCl_3$, 400 MHz) δ 2.02, 2.10 (s, 3H), 2.53–2.65 (m, 1H), 2.74–2.88 (m, 1H), 4.46–4.66 (m, 3H), 6.442, 6.399 (d, J=5.85, 5.76 Hz, 1H), 7.38–7.51 (m, 2H), 7.57 (m, 1H), 7.98–8.12 (m, 2H), MS (FAB) m/z 301 ($MH^+$).

Example 7

$N^4$-Benzoyl-1-(5-O-benzoyl-2,3-dideoxy-3,3-difluoro-β-L-ribofuranosyl)cytosine (8, FIG. 1)

A mixture of $N^4$-benzoylcytosine (900 mg, 4.20 mmol) and ammonium sulfate (28 mg, 0.212 mmol) in 1,1,1,3,3,3-hexamethyldisilazane (HMDS) (30 mL) was refluxed for 4 hours, then the solvent was removed in vacuo at 30–35° C. To the residual oil, a solution of 7 (630 mg, 2.1 mmol) in anhydrous acetonitrile (15 mL) was added followed, upon cooling to 0° C., by trimethylsilyl trifluoromethanesulfonate (TMSOTf, 0.60 mL, 3.2 mmol). The resulting mixture was stirred at room temperature for 3 hours, then poured into an ice/cold saturated solution of sodium bicarbonate (25 mL). The organic phase was separated, washed with brine (5 mL), dried over $MgSO_4$, filtered and concentrated to a crude that was purified by flash silica gel column (50% EtOAc/Hexanes) to give 8 (white solid, 350 mg, 36%). mp 166–167° C. (dec.); $[α]^{24}_D$ 80.50° (c 0.50, $CHCl_3$); UV (MeOH) $λ_{max}$ 259.5, 301.0; $^1H$ NMR ($CDCl_3$) δ 2.57 (m, J=15.6, 10.5, 5.3 Hz, 1H, $H_{2'β}$), 3.26 (m, J=15.6, 12.8, 7.0 Hz, 1H, $H_{2'α}$), 4.57 (ddd, J=18.0, 9.7, 4.8 Hz 1H, $H_{4'}$), 4.71 (dd, J=12.5, 5.5 Hz 1H, $H_{5'b}$), 4.75 (dd, J=12.5, 4.3 Hz, 1H, $H_{5'a}$), 6.30 (t, J=6.1 Hz, 1H, $H_{1'}$), 7.65–7.44 (m, 7 H), 8.10–7.88 (m, 5H), 8.81 (bs, 1H); HRMS (FAB) obsd, m/z 456.1377, calcd for $C_{23}H_{20}F_2N_3O_5$, m/z 456.1371 ($MH^+$). Anal. Calcd for $C_{23}H_{19}F_2N_3O_5$: C, 60.66; H, 4.21; N, 9.23. Found: C, 60.50, H, 4.19; N, 9.00.

Example 8

1-(2,3-Dideoxy-3,3-difluoro-β-L-ribofuranosyl)cytosine (9, FIG. 1)

A mixture of 8 (140 mg, 0.30 mmol) in saturated ammonia/methanol solution (10 mL) was stirred at room temperature for 4 hours, and then concentrated to dryness under reduced pressure. The residue was purified by flash silica gel column (10% methanol/chloroform) to give 9 (white solid, 80 mg, 100%). mp 194–196° C. (dec.); $[α]^{24}_D$ 45.56° (c 1.0, MeOH); UV (MeOH) $λ_{max}$ 276.5 (ε 18160) (pH 2), 268.0 (ε 13280) (pH 7), 268.5 (ε 13580) (pH 11); $^1H$ NMR ($CD_3OD$) δ 2.51 (m, 1H, $H_{2'}$), 2.90 (m, 1H, $H_{2'}$), 3.83 (m, 2H, $H_{5'}$), 4.17 (m, 1H, $H_{4'}$), 5.93 (d, J=7.3 Hz, 1H, $H_5$), 6.27 (t, J=6.8 Hz 1H, $H_{1'}$), 7.97 (d, J=7.3 Hz, 1H, $H_{6'}$); HRMS (FAB) obsd, m/z 248.0841, calcd for $C_9H_{12}F_2N_3O_3$, m/z 248.0847 ($MH^+$). Anal. Calcd for $C_9H_{11}F_2N_3O_3 \cdot 0.1$ $H_2O$: C, 43.41; H, 4.53; N, 16.88. Found: C, 43.45; H, 4.50; N, 16.54.

Example 9

1-(2,3-Dideoxy-3-fluoro-β-L-glycero-pent-2-eno-furanosyl)cytosine (10, FIG. 1)

A mixture of 9 (90 mg, 0.36 mmol) and sodium methoxide (150 mg, 1.1 mmol) in anhydrous DMF (3 mL) was stirred at room temperature overnight, then neutralized by Dowex 50 wx8 ($H^+$). After filtration and concentration, the crude solid was purified by silica gel column (10% methanol/chloroform) to yield 10 (white solid, 54 mg, 60%). mp 182–183° C. (dec.); $[α]^{22}_D$ −5.34° (c 0.39, MeOH); UV (MeOH) $λ_{max}$ 276.0 (ε 11990) (pH 2), 267.5 (ε 8010) (pH 7), 264.5 (ε 8060) (pH 11); $^1H$ NMR ($CD_3OD$) δ 3.766, 3.771 (m, 2H, H5'), 4.733 (m, 1H, $H_{4'}$), 5.438 (m, 1H, $H_{2'}$), 5.887 (d, J=7.5 Hz, 1H, $H_5$), 6.975 (m, 1H, $H_{1'}$), 8.137 (d, J=7.5 Hz, 1H, $H_{6'}$), HRMS (FAB) obsd, m/z 228.0776, calcd for $C_9H_{11}FN_3O_3$, m/z 228.0784 (MH+). Anal. Calcd for $C_9H_{10}FN_3O_3$: C, 47.58; H, 4.44; N, 18.50. Found: C, 47.34; H, 4.45; N, 18.27.

Example 10

5-O-Benzoyl-1,2-O-isopropylidene-α-L-ribofuranose (11, FIG. 2a)

See Ma et al., J. Med. Chem. 1996, 39(14), 2835 and Cooperwood et al., Nucleosides Nucleotides 2000, 19(1&2), 219–236.

Example 11

5-O-Benzoyl-3-O-benzyl-1,2-O-isopropylidene-α-L-ribofuranose (12, FIG. 2a)

A solution of 11 (20.00 g, 67.96 mmol) in anhydrous THF (120 mL) was slowly added to a suspension of sodium hydride (60% dispersion in mineral oil, 4.00 g, 100 mmol) at 0° C., and the mixture was stirred at room temperature for 1 hour. To the resulting suspension tetrabutylammonium iodide (2.50 g, 6.77 mmol) was added followed, upon re-cooling to 0° C., by benzyl bromide (9.0 mL, 75.67 mmol). The reaction was stirred in the dark at room temperature for 9 hours, then cooled to 0° C. and carefully quenched (being cautious of foaming) with ice-cold water (100 mL), then extracted with ethyl acetate (3×350 mL). The combined organic extracts were washed with brine (100 mL), dried over magnesium sulfate ($MgSO_4$), filtered and concentrated to dryness under reduced pressure. The resulting crude 12 (dark yellow oil, 34.40 g, 132% of the theoretical yield) was used in the following step without further purification.

12. Yellow oil: $^1H$ NMR ($CDCl_3$, 400 MHz) δ 7.93 (m, 2H), 7.56 (m, 1H), 7.43–7.21 (m 7H), 5.78 (d, 1H, $H_1$, J=3.7 Hz), 4.81 (d, 1H, J=12.1 Hz), 4.66–4.62 (m, 2H, $H_2$, $H_4$), 4.57 (d, 1H, J=12.1 Hz), 4.39–4.33 (m, 2H, $H_5$), 3.79 (dd, 1H, $H_3$, J=8.9, 4.3 Hz), 1.63 (s, 3H), 1.39 (s, 3H); $^{13}$C NMR ($CDCl_3$, 100 MHz) δ 166.11, 137.08, 132.97, 129.65, 128.45, 128.21, 128.05, 127.97, 113.06, 104.09, 77.22, 76.92, 76.31, 72.11, 62.87, 26.72, 26.43; MS (FAB) m/z 385 ($MH^+$).

Example 12

5-O-Benzoyl-3-O-benzyl-1-methyl-β-L-ribofuranose (13, FIG. 2a)

To an ice-cooled solution of crude 12 (33.24 g) in methanol (700 mL) was added a 4.0 M solution of HCl in dioxane (350 mL), and the mixture was stirred at room temperature for 90 minutes, then quenched with saturated sodium bicarbonate solution (200 mL) followed by solid sodium bicarbonate (125 g). The volatiles were evaporated under reduced pressure to ca. 250 mL and the aqueous residue was extracted with ethyl acetate (3×500 mL). The combined organic extracts were dried over $MgSO_4$, filtered and concentrated under reduced pressure to a crude that was purified by vacuum TLC-grade silica gel column chromatography (hexanes to ethyl 1:3 acetate/hexanes) to give 21.46 g (91% from 11) of 13 as a yellow oil.

13. Yellow oil: $^1$H NMR ($CDCl_3$, 400 MHz) δ 8.04 (m, 2H), 7.57 (m, 1H), 7.44 (m, 2H), 7.38–7.26 (m, 5H), 4:90 (s, 1H, $H_1$), 4.63 (d, 1H, J=11.6 Hz), 4.58 (d, 1H, J=11.6 Hz), 4.50 (dd, 1H, J=11.1, 3.2 Hz), 4.38–4.29 (m, 2H, $H_5$), 4.24 (m, 1H), 4.08 (m, 1H), 3.30 (s, 3H); $^{13}$C NMR ($CDCl_3$, 100 MHz) δ 166.28, 136.71, 133.08, 129.82, 129.66, 128.66, 128.40, 128.34, 128.01, 108.27, 79.06, 78.98, 73.06, 72.94, 64.98, 55.00; HRMS (FAB) obsd, m/z 359.1517, calcd for $C_{20}H_{23}O_6$, m/z 359.1495 ($MH^+$). Anal Calcd for $C_{20}H_{22}O_6$: C, 67.03; H, 6.19. Found: C, 66.87; H, 6.22.

Example 13

5-O-Benzoyl-3-O-benzyl-2-deoxy-1-methyl-β-L-ribofuranose (14, FIG. 2a)

Phenyl chlorothionoformate (9.3 mL, 67.24 mmol) was added to a solution of 13 and 4-(dimethylamino)pyridine (16.32 g, 133.58 mmol) in anhydrous toluene (700 mL), and the resulting bright yellow slurry was stirred at 90° C. for 3 hours. The reaction mixture was then cooled to 0° C. and the yellow solid was filtered off and washed with small portions of anhydrous toluene. To the orange filtrate was added 2,2'-azobisisobutyronitrile (AIBN, 0.92 g, 5.60 mmol), then, upon refluxing, a solution of tributyltin hydride (37.4 mL, 139.04 mmol) and AIBN (0.92 g, 5.60 mmol) in anhydrous toluene was added over 30 minutes. The reaction was refluxed for 30 minutes more, to give a colorless cloudy mixture that was concentrated to dryness under reduced pressure. This crude was purified by vacuum column TLC-grade silica gel chromatography (1:9 hexanes to ethyl acetate/hexanes) to give 14.14 g (74%) of 14 as a colorless oil.

14. Colorless oil: $[\alpha]^{22}_D$ 45.11° (c 5.58, $CHCl_3$); $^1$H NMR ($CDCl_3$, 400 Mz) δ 8.05 (m, 2H), 7.57 (m, 1H), 7.44 (m, 2H), 7.32–7.26 (m, 5H), 5.12 (dd, 1H, $H_1$, J=5.3, 1.3 Hz), 4.53 (s, 2H), 4.46–4.33 (m, 3H, $H_3$, $H_4$), 4.30 (td, 1H, $H_3$, J=6.6, 3.8 Hz), 3.32 (s, 3H), 2.33 (ddd, 1H, $H_{2\beta}$, J=13.2, 6.9, 1.3), 2.16 (ddd, 1H, $H_{2\alpha}$, J=13.2, 6.5, 5.3), $^{13}$C NMR ($CDCl_3$, 100 MHz) δ 166.30, 137.61, 133.04, 129.93, 129.67, 128.44, 128.35, 127.82, 127.67, 105.41, 81.60, 79.32, 71.88, 65.62, 54.93, 39.38; HRMS (FAB) obsd, m/z 343.1543, calcd for $C_{20}H_{23}O_5$, m/z 343.1545 ($MH^+$). Anal. Calcd for $C_{20}H_{22}O_5$: C, 70.16; H, 6.48. Found: C, 69.90; H, 6.42.

Example 14

5-O-Benzoyl-2-deoxy-1-methyl-β-L-ribofuranose (15, FIG. 2a)

A mixture of 14 (4.27 g, 12.47 mmol) and 10% Pd/C (2.65 g, 2.49 mmol) in absolute ethanol (200 mL) was hydrogenated at room temperature and 50 psi of $H_2$ for 72 hours. The resulting mixture was filtered over Celite, washed with ethanol, and concentrated in vacuo to a crude, which was purified by silica gel flash column chromatography (1:2 ethyl acetate/hexanes) to give 1.88 g (60%) of 15 as a light yellow oil.

15. Yellow oil: $[\alpha]^{23}_D$ 65.850 (c 5.23, $CHCl_3$); $^1$H NMR ($CDCl_3$, 400 MHz) δ 8.07 (m, 2H), 7.57 (m, 1H), 7.46–7.41 (m, 2H), 5.10 (dd, 1H, $H_1$, J=5.2, 1.3 Hz), 4.56 (m, 1H, $H_3$), 4.48 (dd, 1H, $H_{5a}$, J=11.6, 4.9 Hz), 4.38 (dd, 1H, $H_{5b}$, J=11.6, 5.7 Hz), 4.20 (dd, 1H, $H_4$, J=10.2, 5.1 Hz), 3.31 (s, 3H), 2.76 (m, exchangeable, 3'-OH), 2.31 (ddd, 1H, $H_{2\beta}$, J=13.3, 6.8, 1.3), 2.12 (ddd, 1H, $H_{2\alpha}$, J=13.3, 6.8, 5.2); $^{13}$C NMR ($CDCl_3$, 100 MHz) δ 166.59, 133.07, 129.66, 129.58, 128.28, 104.97, 83.53, 71.93, 65.25, 54.85, 41.39; HRMS (FAB) obsd, m/z 253.1083, calcd for $C_{13}H_{17}O_5$, m/z 253.1076 ($MH^+$). Anal. Calcd for $C_{13}H_{16}O_5$: C, 61.90; H, 6.39. Found: C, 61.57; H, 6.38.

Example 15

Methyl 5-O-benzoyl-2-deoxy-β-L-glycero-pentofuranosid-3-ulose (16, FIG. 2a)

Chromic anhydride (2.73 g, 27.30 mmol) was added to a stirred mixture of anhydrous pyridine (4.5 mL, 55.64 mmol) and anhydrous dichloromethane (50 mL) at room temperature, and stirring was continued at room temperature for 15 minutes. A solution of 15 (1.72 g, 6.82 mmol) in anhydrous dichloromethane (20 mL) was then added, followed immediately by acetic anhydride (2.6 mL, 27.51 mmol). After 15 minutes, the dark brown solution was treated with ethyl acetate (400 mL) and the resulting mixture was filtered through a TLC-grade silica gel pad, which was washed with ethyl acetate (one portion of 500 mL). The filtrate was concentrated under reduced pressure, co-evaporated with toluene (3×100 mL), and solvents were removed in vacuo to give 1.50 g (88%) of 16 as an orange oil.

16. Orange oil: $[\alpha]^{23}_D$ 64.89° (c 1.25, $CHCl_3$); $^1$H NMR ($CDCl_3$, 400 MHz) δ 8.08 (m, 2H), 7.57 (m, 1H), 7.46–7.42 (m, 2H), 5.37 (d, 1H, $H_1$, J=5.6 Hz), 4.66 (dd, 1H, $H_{5a}$, J=11.7, 3.2 Hz), 4.46 (dd, 1H, $H_{5b}$, J=11.7, 6.1 Hz), 4.40 (dd, 1H, $H_4$, J=6.1, 3.2 Hz), 3.40 (s, 3H), 2.82, (dd, 1H, $H_{2\alpha}$, J=18.3, 5.6), 2.12 (d, 1H, $H_{2\beta}$, J=18.3); $^{13}$C NMR ($CDCl_3$, 100 MHz) δ 210.70, 166.17, 133.11, 129.73, 129.69, 128.33, 102.36, 77.63, 64.55, 55.07, 43.54; HRMS (FAB) obsd, m/z 251.0920, calcd for $C_{13}H_{15}O_5$, m/z 251.0919 ($MH^+$). Anal. Calcd for $C_{13}H_{14}O_5 \cdot 0.07$Tol: C, 63.12; H, 5.72. Found: C, 63.51; H, 5.37.

Example 16

5-O-Benzoyl-2,3-dideoxy-3,3-difluoro-1-methyl-β-L-ribofuranose (17, FIG. 2a)

(Diethylamino)sulfur trifluoride (3.0 mL, 22.71 mmol) was added to a solution of 16 (1.40 g, 5.59 mmol) in anhydrous dichloromethane (25 mL) and the reaction mixture was refluxed for 36 hours. The resulting solution was then carefully poured into an ice-cooled saturated solution of sodium bicarbonate (50 mL) and extracted with diethyl ether (4×100 mL). The combined organic extracts were washed with brine (50 mL), dried over MgSO$_4$, filtered and concentrated to a crude oil that is purified by silica gel flash column chromatography (1:9 ethyl acetate/hexanes) to give 1.01 g (66%) of 17 as a yellow oil.

17. Yellow oil: $[\alpha]^{23}_D$ 40.78° (c 4.28, CHCl$_3$); $^1$H NMR (CDCl$_3$, 400 MHz) δ 8.08 (m, 2H), 7.57 (m, 1H), 7.45 (m, 2H), 5.15 (dt, 1H, H$_1$, J=5.7, 1.7 Hz), 4.63–4.41 (m, 3H, H$_4$, H$_5$), 3.40 (s, 3H), 2.67 (tdd, 1H, H$_{2\alpha}$, J=16.6, 15.0, 5.7 Hz), 2.49 (tdd, 1H, H$_{2\beta}$, J=15.0, 9.0, 2.0 Hz); $^{13}$C NM (CDCl$_3$, 100 MHz) δ 166.05, 133.14, 129.71, 128.38, 128.32 (t, J$_{C-F}$=252.8 Hz), 103.70 (dd, J$_{C-F}$=7.1, 4.2 Hz), 79.46 (dd, J$_{C-F}$=32.1, 24.9 Hz), 62.94 (dd, J$_{C-F}$=7.5, 4.5 Hz), 55.38, 42.26 (t, J$_{C-F}$=24.3 Hz); HRMS (FAB) obsd, m/z 273.0950, calcd for C$_{13}$H$_{15}$F$_2$O$_4$, m/z 273.0938 (MH$^+$). Anal. Calcd for C$_{13}$H$_{14}$F$_2$O$_4$: C, 57.35; H, 5.18. Found: C, 57.64; H, 5.30.

Example 17

1-Acetyl-5-O-benzoyl-2,3-dideoxy-3,3-difluoro-β-L-ribofuranose (18, FIG. 2a)

Concentrated sulfuric acid (80 μL, 1.50 mmol) was added to an ice-cold solution of 17 (200 mg, 0.73 mmol) and acetic anhydride (300 μL, 3.20 mmol) in glacial acetic acid, and the reaction was stirred at 0° C. for 5 minutes, then at room temperature for 10 minutes more. The resulting mixture is poured into an ice-cold saturated solution of sodium bicarbonate (100 mL) and extracted with dichloromethane (3×100 mL). The combined organic extracts were washed with water (30 mL), brine (30 mL), dried over MgSO$_4$, filtered, concentrated and co-evaporated with toluene (3×10 mL) to give 210 mg (95%) of 5:3 epimeric mixture 18 as a crude yellow oil which was used in the following reaction without further purification.

18. Yellow oil: $^1$H NMR (CDCl$_3$, 400 MHz) δ 8.06–8.02 (m, 4H), 7.57 (m, 2H), 7.47–7.43 (m, 4H), 6.45 [d, 1H, H$_1$ (major isomer), J=5.3 Hz], 6.41 [d, 1H, H$_1$ (minor isomer), J=5.9 Hz], 4.65–4.49 (m, 6H, H$_4$, H$_5$), 2.11 (s, 3H), 2.04 (s, 3H); $^{13}$C NMR (CDCl$_3$, 100 MHz) (major isomer) δ 169.72, 165.91, 133.28, 129.68, 128.43, 127.50 (dd, J$_{C-F}$=254.9, 251.6 Hz), 95.34 (dd, J$_{C-F}$=7.7, 4.5 Hz), 79.10 (dd, J$_{C-F}$=33.0, 24.7 Hz), 61.01 (dd, J$_{C-F}$=7.7, 2.4 Hz), 41.91 (t, J$_{C-F}$=25.1 Hz) 21.03; (minor isomer) δ 169.62, 165.91, 133.27, 129.73, 128.41, 127.35 (dd, J$_{C-F}$=255.1, 251.3 Hz), 95.83(dd, J$_{C-F}$=7.6, 3.8 Hz), 80.31 (dd, J$_{C-F}$=32.0, 25.0 Hz), 62.12 (dd, J$_{C-F}$=7.8, 3.5 Hz), 41.27 (t, J$_{C-F}$=24.8 Hz) 21.00; MS (FAB) m/z 301 (MH$^+$).

Example 18

N$^4$-Benzoyl-1-(5-O-benzoyl-2,3-dideoxy-3,3-difluoro-β-L-ribofuranosyl)cytosine (19, FIG. 2a) and N$^4$-benzoyl-1-(5-O-benzoyl-2,3-dideoxy-3,3-difluoro-α-L-ribofuranosyl)cytosine (20, FIG. 2a)

A mixture of N$^4$-benzoylcytosine (225 mg, 1.05 mmol) and ammonium sulfate (7 mg, 0.053 mmol) in 1,1,1,3,3,3-hexamethyldisilazane (HMDS) was refluxed for 4 hours, then the solvent was removed in vacuo at 30–35° C. To the residual oil, a solution of 18 (210 mg, 0.70 mmol) in anhydrous acetonitrile (10 mL) was added followed, upon cooling to 0° C., by trimethylsilyl trifluoromethanesulfonate (TMSOTf, 0.19 mL, 1.05 mmol). The resulting mixture was stirred at room temperature overnight, then diluted to 50 mL with dichloromethane and poured into an ice-cold saturated solution of sodium bicarbonate (25 mL). The organic phase was separated, washed with brine (5 mL), dried over MgSO$_4$, filtered and concentrated to a crude that was purified by flash column chromatography (3:97 methanol/chloroform) to give 80 mg of 20 (25%) as the first eluted product and 100 mg of 19 (31%) as the second eluted product. Both isomers are colorless oils, which become white solids upon trituration with diethyl ether and a drop of methanol.

19. White solid: mp 166–167° C. (dec.); $[\alpha]^{24}_D$ –89.75° (c 0.31, CHCl$_3$); UV (MeOH) 80 $_{max}$ 259.5, 301.0; $^1$H NMR (CDCl$_3$, 400 MHz) δ 8.81 (bs, 1H), 8.10–7.88 (m, 5H), 7.65–7.44 (m, 7H), 6.30 (t, 1H, H$_{1'}$, J=6.1 Hz), 4.75 (dd, 1H, H$_{5'a}$, J=12.5,4.3 Hz), 4.71 (dd, 1H, H$_{5'b}$, J=12.5, 5.5 Hz), 4.57 (ddd, 1H, H$_{4'}$, J=18.0, 9.7, 4.8 Hz), 3.26 (dtd, 1H, H$_{2'\alpha}$, J=15.6, 12.8, 7.0 Hz), 2.57 (m, 1H, H$_{2'\beta}$, J=15.6, 10.5, 5.3 Hz); $^{13}$C NMR (CDCl$_3$, 100 MHz) δ 166.48, 165.91, 162.58, 154.55, 143.35, 133.59, 133.31, 129.63, 129.07, 128.60, 127.53, 125.71 (t, J$_{C-F}$=253.6 Hz),96.90, 84.39 (dd, J$_{C-F}$=6.6, 3.6 Hz), 79.80 (dd, J$_{C-F}$=31.5, 25.1 Hz), 60.77 (d, J$_{C-F}$=4.8 Hz), 41.69 (t, J$_{C-F}$=23.7 Hz); HRMS (FAB) obsd, m/z 456.1377, calcd for C$_{23}$H$_{20}$F$_2$N$_3$O$_5$, m/z 456.1371 (MH$^+$).

20. White solid: mp 176–178° C. (dec.); $[\alpha]^{24}_D$ 42.61° (c 1.19, CHCl$_3$); UV (MeOH) λ$_{max}$ 259.0; $^1$H NMR (CDCl$_3$, 400 MHz) δ 8.89 (bs, 1H), 8.06–7.89 (m, 5H), 7.65–7.47 (m, 7 H), 6.29 (dd, 1H, H$_{1'}$, J=7.3, 3.2 Hz), 4.82 (m, 1H, H$_{4'}$),4.69 (dd, 1H, H$_{5'a}$, J=12.4, 3.8 Hz), 4.57 (dd, 1H, H$_{5'b}$, J=12.4, 4.6 Hz), 3.21 (dddd, 1H, H$_{2'\beta}$, J=15.4, 12.8, 7.3, 5.4 Hz), 2.82 (dtd, 1H, H$_{2'\alpha}$, J=15.4, 7.5, 3.2 Hz); $^{13}$C NMR (CDCl$_3$, 100 MHz) δ 166.54, 165.80, 162.77, 154.62, 143.48, 133.51, 133.19, 129.58, 128.94, 128.60, 127.58, 126.51 (dd, J$_{C-F}$=255.7, 249.3 Hz), 96.71, 86.83 (dd, J$_{C-F}$=8.1, 2.0 Hz), 80.78 (dd, J$_{C-F}$=31.7, 25.2 Hz), 61.47 (t, J$_{C-F}$=5.3 Hz), 41.14 (t, J$_{C-F}$=24.0 Hz); HRMS (FAB) obsd, m/z 456.1374, calcd for C$_{23}$H$_{20}$F$_2$N$_3$O$_5$, m/z 456.1371 (MH$^+$).

Example 19

N$^4$-Benzoyl-1-(5-O-benzoyl-2,3-dideoxy-3,3-difluoro-α/β-L-ribofuranosyl)thymine (25, FIG. 2b)

Alternatively, a mixture of 17 (170 mg, 0.62 mmol), thymine (160 mg, 1.27 mmol) and N,O-bis-trimethylsilyl trifluoroacetamide (0.83 mL, 3.12 mmol) in anhydrous acetonitrile (10 mL) was stirred at room temperature for 3h. The resulting clear solution was treated with TMSOTf (0.17 mL, 0.94 mmol) at 0° C., then allowed to reach room temperature and stirred for 72 hours. The resulting mixture was diluted to 100 mL with dichloromethane and poured into an ice-cold saturated solution of sodium bicarbonate (50 mL). The organic phase was separated, washed with water (20 mL) and brine (20 mL), then dried over MgSO$_4$, filtered and concentrated to a crude that was purified by flash column chromatography (1:49 methanol/chloroform) to give 120 mg of 25 (53%) as a yellow oil.

25. Yellow oil: UV (MeOH) λ$_{max}$ 263.5; $^1$H NMR (CDCl$_3$, 400 MHz) δ 9.60 [bs, 1H (major isomer)], 9.55 (bs, 1H (minor isomer)], 8.04 (m, 4H), 7.59 (m, 2H), 7.49 (m, 4H), 7.22 [d, 1H, H$_6$ (minor isomer), J=1.2 Hz], 7.18 [d, 1H, H$_6$ (major isomer), J=1.2 Hz), 6.42 [t, 1H, H$_{1'}$ (minor isomer), J=7.0 Hz], 6.33 (dd, 1H, H$_{1'}$ (major isomer), J=7.5, 5.0 Hz), 4.81–4.73 (m, 2H, H$_{4'}$), 4.62–4.53 (m, 4H, H$_{5'}$), 3.10–2.94 (m, 2H, H$_{2'}$), 2.83–2.76 (m, 1H, H$_{2'}$), 2.57–2.43 (m, 1H, H2'); $^{13}$C NMR (CDCl$_3$, 100 MHz) (major isomer) δ 165.87, 163.78, 150.25, 135.05, 133.47, 126.67 (dd, J$_{C-F}$=255.7, 251.1 Hz), 111.71, 84.84 (t, J$_{C-F}$=5.9 Hz), 80.15 (dd, J$_{C-F}$=31.3, 24.5 Hz), 61.51 (dd, J$_{C-F}$=6.7, 4.1 Hz), 40.34

(t, $J_{C-F}$=24.3 Hz), 12.59; (minor isomer) δ 165.84, 163.45, 150.25, 133.82, 133.59, 125.91 (dd, $J_{C-F}$=255.1, 252.3 Hz), 112.39, 81.18 (t, $J_{CF}$=5.9 Hz), 79.11 (dd, $J_{C-F}$=31.6, 24.6 Hz), 60.88 (dd, $J_{C-F}$=6.1, 3.1 Hz), 40.47 (t, $J_{CF}$=23.9 Hz), 12.32; HRMS (FAB) obsd, m/z 367.1122, calcd for $C_{17}H_{17}F_2N_2O_5$, m/z 367.1106 (MH+). Anal. Calcd for $C_{17}H_{16}F2N_2O_5$·0.03 $CHCl_3$: C, 55.30; H, 4.37; N, 7.57. Found: C, 54.92; H, 4.40; N, 7.37.

Example 20

1-(2,3-Dideoxy-3,3-difluoro-β-L-ribofuranosyl) cytosine (21, FIG. 2a) and 1-(2,3-dideoxy-3,3-difluoro-α-L-ribofuranosyl)cytosine (22, FIG. 2a)

A mixture of 19 (70 mg, 0.15 mmol) or 20 (40 mg, 0.09 mmol) in saturated ammonia/methanol solution (10 or 5 mL, respectively) was stirred at room temperature for 4 h, and then concentrated to dryness under reduced pressure. The residue was purified by preparative TLC (1:9 methanol/chlorofonrn) to give 38 mg of 21 (100%) or 20 mg of 22 (100%) as white solids.

21. White solid: mp 194–196° C. (dec.); $[\alpha]^{24}_D$ −51.89° (c 1.15, MeOH); UV (MeOH) $\lambda_{max}$ 276.5 (ε 18160) (pH 2), 268.0 (ε 13280) (pH 7), 268.5 (ε 13580) (pH 11); $^1$H NMR ($CD_3OD$, 400 MHz) δ 7.97 (d, 1H, $H_6$, J=7.3 Hz), 6.27 (t, 1H, $H_{1'}$, J=6.8 Hz), 5.93 (d, 1H, $H_5$, J=7.3 Hz), 4.17 (m, 1H, $H_{4'}$), 3.83 (m, 2H, $H_{5'}$), 2.90 (m, 1H, $H_{2'}$), 2.51 (m, 1H, $H_{2'}$); $^{13}$C NMR (DMSO-$d_6$, 100 MHz) δ 168.19, 158.46, 142.62, 128.71 (dd, $J_{C-F}$=255.1, 247.4 Hz), 97.04, 84.73 (dd, $J_{C-F}$=6.7, 4.9 Hz), 83.74 (dd, $J_{C-F}$=29.5, 25.0 Hz), 60.73 (t, $J_{C-F}$=4.8 Hz), 42.14 (t, $J_{C-F}$=23.4 Hz), 12.29; HRMS (FAB) obsd, m/z 248.0850, calcd for $C_9H_{12}F_2N_3O_3$, m/z 248.0847 (MH+). Anal. Calcd for $C_9H_{11}F_2N_3O_3$·0.1 $H_2O$: C, 43.41; H, 4.53; N, 16.88. Found: C, 43.63; H, 4.50; N, 16.48.

22. White solid: $[\alpha]^{25}_D$ 28.23° (c 0.27, MeOH); UV (MeOH) $\lambda_{max}$ 277.5 (ε 15010) (pH 2), 269.0 (ε 10130) (pH 7), 269.0 (ε 10150) (pH 11); $^1$H NMR ($CD_3OD$, 400 MHz) δ 7.69 (d, 1H, $H_6$, J=7.5 Hz), 6.21 (dd, 1H, $H_{1'}$, J=7.4, 3.6 Hz), 5.90 (d, 1H, $H_5$, J=7.5 Hz), 4.49 (m, 1H, $H_{4'}$), 3.79 (dd, 1H, $H_{5'}$, J=12.5, 3.6 Hz), 3.74 (ddd, 1H, $H_{5'}$, J=12.5, 4.0, 1.5 Hz), 3.01 (m, 1H, $H_{2'}$), 2.63 (m, 1H, $H_{2'}$); $^{13}$C NNR ($CD_3OD$, 100 MHz) δ 168.37, 158.54, 142.57, 129.28 (dd, $J_{C-F}$=254.3, 247.2 Hz), 96.48, 87.75 (dd, $J_{C-F}$=8.7, 3.6 Hz), 84.93 (dd, $J_{C-F}$=29.3, 25.3 Hz), 61.24 (t, $J_{C-F}$=5.4 Hz), 42.63 (t, $J_{C-F}$=23.9 Hz), 12.29; HRMS (FAB) obsd, m/z 248.0829, calcd for $C_9H_{12}F_2N_3O_3$, m/z 248.0847 (MH+).

1-(2,3-Dideoxy-3,3-difluoro-β-L-ribofuranosyl)thymine (26, FIG. 2b) and 1-(2,3-dideoxy-3,3-difluoro-α-L-ribofuranosyl)thymine (27, FIG. 2b) were obtained analogously to compounds 21–22.

26. White solid: mp 140° C. (dec.); UV (MeOH) $\lambda_{max}$ 264.0 (ε 11700) (pH 2), 263.5 (ε 12170) (pH 7), 264.0 (ε 8660) (pH 11); $^1$H NMR (DMSO-$d_6$, 400 MHz) δ 11.43 (bs, 1H), 7.64 (s, 1H, $H_6$), 6.21 (t, 1H, $H_{1'}$, J=7.2), 5.25 (t, 1H, 5'-OH), 4.11 (m, 1H, $H_{4'}$), 3.67 (m, 2H, $H_{5'}$), 2.83 (m, 1H, $H_{2'}$), 2.65(m, 1H, $H_{2'}$), 1.78 (s, 3H); $^{13}$C NMR (DMSO-$d_6$, 100 MHz) δ 163.59, 150.36, 135.40, 127.26 (dd, $J_{C-F}$=255.8, 246.7 Hz), 110.20, 80.97 (dd, $J_{C-F}$=28.5, 24.4 Hz), 80.32 (dd, $J_{C-F}$=7.1, 4.1 Hz), 58.50, 38.54 (t, $J_{C-F}$=23.6 Hz), 12.29; HRMS (FAB) obsd, m/z 263.0849, calcd for $C_{10}H_{13}F_2N_2O_4$, m/z 263.0843 (MH+). Anal. Calcd for $C_{10}H_{12}F_2N_2O_4$·0.14 $Et_2O$: C, 46.53; H, 4.95; N, 10.28. Found: C, 46.28; H, 4.90; N, 9.88.

27. White solid: mp 145–148° C. (dec.); [α]...$_D$ −26.50° (c 0.15, $CHCl_3$); UV (MeOH) $\lambda_{max}$ 265.5 (ε 12820) (pH 2), 263.5 (ε 12590) (pH 7), 264.0 (ε 10030) (pH 11); $^1$H NMR (DMSO-$d_6$, 400MHz) δ 11.41 (bs, 1H), 7.52 (s, 1H, $H_6$), 6.21 (t, 1H, $H_{1'}$, J=6.4), 5.13 (t, 1H, 5'-OH), 4.50 (m, 1H, $H_{4'}$), 3.59 (m, 2H, $H_{5'}$), 2.97–2.73 (m, 2H, $H_{2'}$), 1.78 (s, 3H); $^{13}$C NMR (DMSO-$d_6$, 100 MHz) δ 163.77, 150.38, 136.32, 127.77 (dd, $J_{C-F}$=252.3, 249.2 Hz), 109.82, 83.47 (t, $J_{C-F}$= 6.0 Hz), 81.75 (dd, $J_{CF}$=28.5, 24.3 Hz), 58.76, 38.57 (t, $J_{C-F}$=23.6 Hz), 12.17; HRMS (FAB) obsd, m/z 263.0835, calcd for $C_{10}H_{13}F_2N_2O_4$, m/z 263.0843 (MH+). Anal. Calcd for $C_{10}H_{12}F_2N_2O_4$·0.5 MeOH: C, 45.33; H, 5.07; N, 10.07. Found: C, 45.49; H, 4.96; N, 9.76.

Example 21

1-(2,3-Didcoxy-3-fluoro-β-L-glycero-pent-2-eno-furanosyl)cytosine (23, FIG. 2a)

A mixture of 21 (30 mg, 0.12 mmol) and sodium methoxide (50 mg, 0.37 mmol) in anhydrous DMF (5 mL) was stirred at room temperature overnight, then quenched with 1 mL of a saturated aqueous solution of ammonium chloride. Evaporation of volatiles in vacuo gave a crude solid that was purified by a very short silica gel flash column chromatography (chloroform to 1:15 methanol/chloroform) to yield 15 mg (54%) of 23 as a white solid.

23. White solid: mp 182–183° C. (dec.); $[\alpha]^{22}_D$ 6.67(c 0.54, MeOH); UV (MeOH) $\lambda_{max}$ 276.0 (ε 11990) (pH 2), 267.5 (ε 8010) (pH 7), 264.5 (ε 8060) (pH 11); $^1$H NMR ($CD_3OD$, 400 MHz) δ 8.14 (d, 1H, $H_6$, J=7.5 Hz), 7.01 (m, 1H, $H_{1'}$), 5.90 (d, 1H, $H_5$ J=7.5 Hz), 5.46 (m, 1H, $H_{2'}$), 4.76 (m, 1H, $H_{4'}$), 3.80 (m, 1H, H5'), 3.79 (m, 1H, H5'); $^{13}$C NMR (CD3OD, 100 MHz) δ 168.31, 163.40 (d, $J_{C-F}$=284.8 Hz), 159.05, 144.05, 102.34 (d, $J_{C-F}$=9.7 Hz), 95.68, 88.42 (d, $J_{C-F}$=14.9 Hz), 81.96 (d, $J_{C-F}$=24.7 Hz), 61.82 (d, $J_{C-F}$=2.2 Hz); HRMS (FAB) obsd, m/z 228.0778, calcd for $C_9H_{11}FN_3O_3$, m/z 228.0784 (MH+). Anal. Calcd for $C_9H_{10}FN_3O_3$: C, 47.58; H, 4.44; N, 18.50. Found: C, 47.47; H, 4.44; N, 18.17.

1-(2,3-dideoxy-3-fluoro-β-L-glycero-pent-2-eno-furanosyl)thymine (28, FIG. 2b) was obtained analogously to compound 23.

28. White solid: mp 146–148° C. (dec.); $[\alpha]^{22}_D$ 32.19° (c 0.20, $CHCl_3$); UV (MeOH) $\lambda_{max}$ 264.0 (ε 10080) (pH 2), 264.5 (ε 10130) (pH 7), 264.5 (ε 7710) (pH 11); $^1$H NMR ($CDCl_3$, 400 MHz) δ 8.94 (bs, 1H), 7.70 (s, 1H, $H_6$), 7.05 (s, 1H, $H_{1'}$), 5.26 (s, 1H, $H_{2'}$), 4.73 (s, 1H, $H_{4'}$), 3.94 (m, 2H, $H_{5'}$), 3.30 (bs, 1H, 5'-OH), 1.86 (s, 3H); $^{13}$C NMR ($CDCl_3$, 100 MHz) δ 164.01, 161.54 (d, $J_{C-F}$=287.8 Hz), 150.50, 136.85, 110.83, 99.64 (d, $J_{C-F}$=10.2 Hz), 85.65 (d, $J_{C-F}$=14.8 Hz), 79.98 (d, $J_{C-F}$=24.5 Hz), 60.56 (d, $J_{C-F}$=1.8 Hz), 12.28; HRMS (FAB) obsd, m/z 243.0789, calcd for $C_{10}H_{12}FN_2O_4$, m/z 243.0781 (MH+). Anal. Calcd for $C_{10}H_{11}FN_2O_4$: C, 49.59; H, 4.58; N, 11.57. Found: C, 49.33; H, 4.30; N, 11.78.

Example 22

Figure 3A:
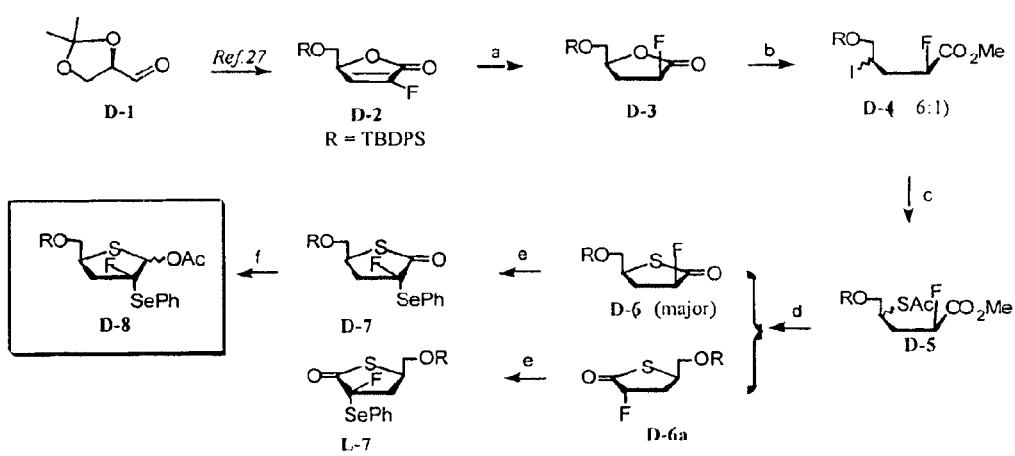
FIG. 3 are nonlimiting illustrative examples of the synthesis of pyrimidine (3a) and purine (3b) β-D-2',3'-didehydro-2',3'-dideoxy-2'-fluoro-4'-thionucleosides, according to the present invention.

(S)-(−)-4-tert-butyldiphenylsilyloxymethyl-2-fluoro-2-buten-4-olide (D-2, FIG. 3a)

The detailed procedure for the preparation of this compound is described in the literature; A divergent synthesis of D- and L-carbocyclic 4'-fluoro-2',3'-dideoxynucleosides as potential antiviral agents. Chong, Y.; Gumina, G.; Chu, C. K. Tetrahedron Asymmetry. 2000, 11, 4853–4875.

Example 23

Figure 4A:
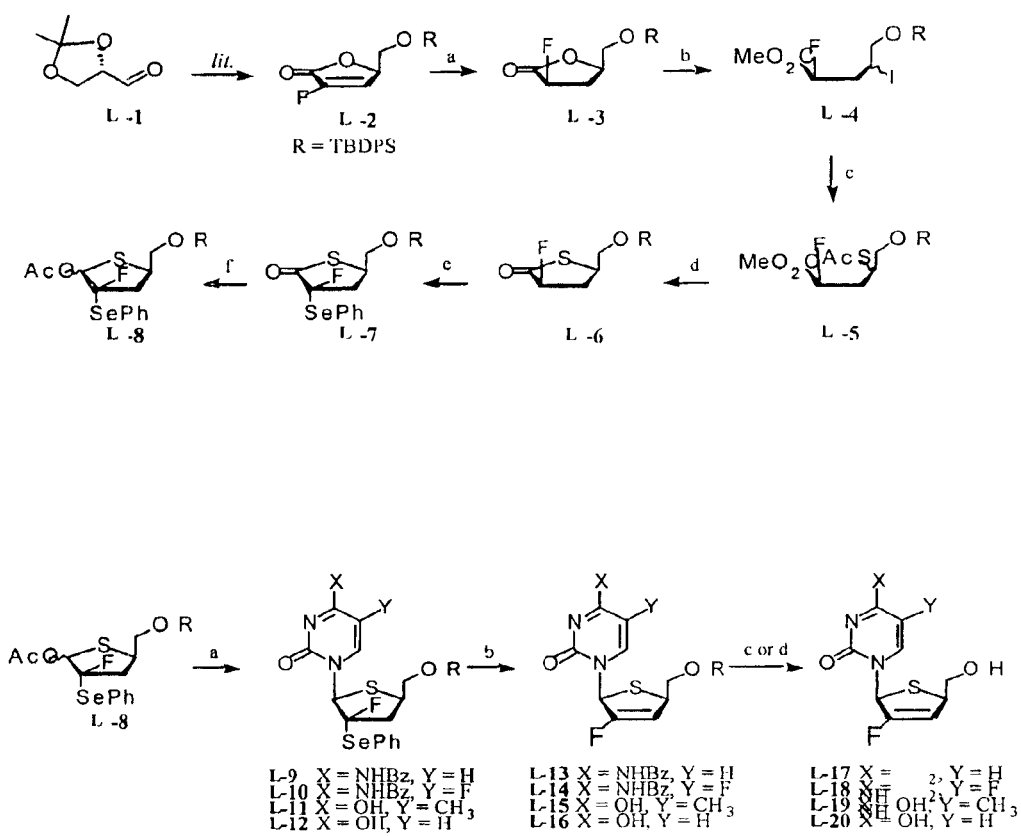
FIG. 4 are nonlimiting illustrative examples of the synthesis of pyrimidine (4a) and purine (4b) β-L-2',3'-didehydro-2',3'-dideoxy-2'-fluoro-4'-thionucleosides, according to the present invention.

(R)-(+)-4-tert-butyldiphenylsilyloxymethyl-2-fluoro-2-buten-4-olide (L-2, FIG. 4a)

The detailed procedure for the preparation of this compound is described in the literature; Synthesis and anti-HIV and anti-HBV activities of 2'-fluoro-2',3'-unsaturated L-nucleosides. Lee, K.; Choi, Y.; Gullen E.; Schlueter-Wirtz, S.; Schinazi, R. F.; Cheng, Y. C.; Chu, C. K. *J. Med. Chem.* 1999, 42, 1320–1328.

Example 24

(2S,4S)-(+)-4-tert-butyldiphenylsilyloxymethyl-2-fluoro-γ-butyrolactone (D-3, FIG. 3a)

To a solution of lactone D-2 (14.8 g, 39.9 mmol) in 200 mL of EtOAc, was added 2.0 g of Pd/C (5% w/w) under H$_2$ atmosphere for 3 hours. After filtration of the reaction mixture through a celite pad, the filtrate was concentrated, purified by silica gel column chromatography with 5% EtOAc in hexanes to give compound D-3 (13.9 g, 37.5 mmol, 94% yield) as a white solid. mp 87~89° C.; $[\alpha]^{24}_D$ 15.5° (c 0.85, CHCl$_3$); $^1$H NMR (CDCl$_3$) δ 7.70~7.35 (m, 10H), 5.26 (dt, J=51.2, 8.8 Hz, 1H), 4.54~4.47 (m, 1H), 3.93 (dd, J=11.4, 2.3 Hz, 1H), 3.71 (dd, J=11.4, 3.6 Hz, 1H), 2.65 (ddt, J=13.1, 8.4, 6.6 Hz, 1H), 2.54 (ddt, J=24.2, 13.2, 9.0 Hz, 1H), 1.04 (s, 9H); $^{13}$C NMR (CDCl$_3$) δ 171.30 (d, J=21.3 Hz), 135.59, 135.30, 132.52, 132.20, 129.76, 129.35, 127.82, 127.63, 89.30 (d, J=191.0 Hz), 76.24 (d, J=6.1 Hz), 63.73, 30.14 (d, J=20.0 Hz), 26.58, 19.12; Anal. Calcd for C$_{21}$H$_{25}$FO$_3$Si: C, 67.71; H,6.76. Found: C, 67.70; H, 6.79.

Example 25

(2R,4R)-(−)-4-tert-butyldiphenylsilyloxymethyl-2-fluoro-γ-butyrolactone (L-3, FIG. 4a)

A solution of compound L-2 (25 g, 67.5 mmol) in 500 mL of EtOAc was treated with 2.5 g of palladium on carbon (5% wlw) under H$_2$ atmosphere for 3 hours. After filtration through a celite pad, the filtrate was concentrated and purified by silica gel column chromatography with 7% EtOAc in hexanes to give compound L-3 (23.8 g, 64.1 mmol, 95% yield) as a white solid. mp 88~89° C.; $[a]^{24}_D$ −15.3° (c 0.835, CHCl$_3$); $^1$H NMR (CDCl$_3$) δ 7.69~7.38 (m, 10H), 5.27 (dt, J=51.4, 8.9 Hz, 1H), 4.54~4.47 (m, 1H), 3.92 (dd, J=11.7, 2.4 Hz, 1H), 3.74 (dd, J=11.7, 3.7 Hz, 1H), 2.67 (ddt, J=13.2, 8.6, 6.6 Hz, 1H), 2.54 (ddt, J=24.4, 13.2, 9.0 Hz, 1H), 1.06 (s, 9H); $^{13}$C NMR (CDCl$_3$) δ 171.19 (d, J=21.3 Hz), 135.62, 135.51, 132.73, 132.40, 129.97, 129.95, 127.97, 127.84, 89.82 (d, J=193.0 Hz), 76.31 (d, J=6.1 Hz), 63.94, 30.26 (d, J=20.0 Hz), 26.64, 19.21; FABMS m/z 373 (M+H)$^+$; Anal. Calcd for C$_{21}$H$_{25}$FO$_3$Si: C, 67.71; H, 6.76. Found: C, 67.71; H, 6.78.

Example 26

(2S,4S/R)-5-tert-butyldiphenylsilyloxy-2-fluoro-4-iodopentanoic acid methyl ester (D-4, FIG. 3a) and (2R,4R/S)-5-tert-butyldiphenylsilyloxy-2-fluoro-4-iodopentanoic acid methyl ester (L-4, FIG. 4a)

A mixture of compound D-3 (7.49 g, 20.1 mmol) in 5% aqueous EtOH was treated with solid NaOH (0.885 g, 22.1 mmol) at room temperature for 2 hours. The resulting mixture was concentrated and co-evaporated two times with 250 mL of toluene to dryness. The crude carboxylate sodium salt was dissolved in 15 mL of DMSO and treated with dimethyl sulfate (2.29 mL, 24.2 mmol) at 0° C. After addition, the ice-bath was removed. The reaction mixture was stirred for 1 hour and then, poured to ice-cooled water (500 mL) and extracted with ethyl ether (3×200 mL). The combined organic layer was washed with water (3×200 mL), dried over MgSO$_4$, and concentrated to dryness. The crude methyl ester was treated with I$_2$ (7.65 g, 30.1 mmol), imidazole (4.11 g, 60.4 mmol), and Ph$_3$P (10.55 g, 40.2 mmol) in toluene (300 mL) at 60° C. for 4 hours. Aqueous NaHCO$_3$ (200 mL) was added to the resulting mixture and iodine was added portion-wise until the iodine color persisted to remove remaining Ph$_3$P. Aqueous Na$_2$S$_2$O$_3$ was added dropwise until the iodine color disappeared to remove the remaining iodine. The resulting mixture was poured to a separatory funnel, diluted with 300 mL of toluene, washed with brine, dried over MgSO$_4$, filtered, concentrated, and purified by silica gel column chromatography with 7% EtOAc in hexanes to give compounds D-4 (7.52 g, 14.6 mmol, 73% yield) as pale yellow oil. $^1$H NMR (CDCl$_3$) for major δ 7.71~7.33 (m, 10H), 5.08 (ddd, J=47.9, 7.2, 5.0 Hz, 1H), 4.31~4.17 (m, 1H), 3.96~3.76 (m, 2H), 3.79 (s, 3H) 2.75~2.08 (m, 2H), 1.10 (s, 9H), for minor δ 7.71~7.33 (m, 10H), 5.16 (ddd, J=48.2, 10.3, 2.1 Hz, 1H), 4.31~4.17 (m, 1H), 3.96~3.76 (m 2H), 3.81 (s, 3H), 2.75~2.08 (m, 2H), 1.08 (s, 9H); HRMS (FAB) obsd, m/z 515.0945, calcd for C$_{22}$H$_{29}$FIO$_3$Si, m/z 515.0915 (M+H)$^+$; Anal. Calcd for C$_{22}$H$_{28}$FIO$_3$Si0.2C$_6$H$_{14}$: C, 52.41; H, 5.84; I, 23.87. Found: C, 52.30; H, 5.55; I, 23.83.

The $^1$H NMR of the crude compound D-3 showed no contamination by the epimer at C2.

Scheme 1. Epimerization at C4 during iodination$^a$.

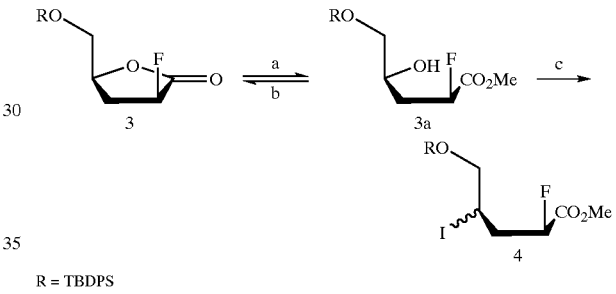

R = TBDPS

R=TBDPS
$^a$Keys: (a) i) NaOH, EtOH, ii) dimethyl sulfate, DMSO, (b) pyridine, rt, c) I$_2$, Ph$_3$P, imidazole, toluene In order to confirm which carbon center has epimerized, the hydroxyl methylester D-3a was subjected to re-closure of the ring to give the starting 2-fluorobutenolide D-3 under basic conditions (Scheme 1). The spectroscopic data ($^1$H and $^{13}$C NMR) of this compound matched that of the starting compound, which suggested that there was no significant epimerization during saponification followed by methylation. Iodination under several different reaction conditions, however, confirmed that high temperature and longer reaction time resulted in partial epimerization at C4. Treatment of the hydroxyl methylester D-3a under Mitsunobu conditions at 60° C. for 4 hours was found to be the optimum conditions to minimize the epimerization. The epimeric mixture of iodoester 4 was subjected to nucleophilic attack by potassium thioacetate in DMF to give an epimeric mixture of thioacetates D-5. DIBAL-mediated reduction of the thioacetates followed by Moffat-type oxidation provided the corresponding thiolactone D-6 and D-6a, in 54% yield. At this stage, the two epimers could be separated by column chromatography on silica gel. During the ensuing phenylselenylation, the C2 position was sp$^2$-hybridized by trapping the enolate as silylenolether. The phenylselenyl group approached the least hindered α face of the silylenolether to give the corresponding enantiomers D-7 and L-7 (FIG. 3a). The optical rotation values of these two compounds were matched with opposite signs {for D-7; $[\alpha]^{24}_D$ 54.0° (c 0.606, CHCl$_3$) and for L-7; [α]$^{24}_D$ −56.40 (c 0.542, CHCl$_3$)), which finally confirmed the epimerization at C4 during iodination under Mitsunobu conditions. The epimerized product L-7, therefore, can be recycled as the key intermediate for the synthesis of L-antipodes.

A similar procedure was followed using compound L-3 (12.2 g, 32.6 mmol) treated with solid NaOH (1.44 g, 36.0 mmol) to give compounds L-4 (13.7 g, 26.6 mmol, 82% yield) as pale yellow oil. $^1$H NMR (CDCl$_3$) for major δ 7.75~7.35 (m, 10H), 5.10 (ddd, J=48.4, 7.5, 5.2 Hz, 1H), 4.33~4.18 (m, 1H), 3.95~3.78 (m 2H), 3.82 (s, 3H) 2.80~2.40 (m, 2H), 1.10 (s, 9H), for minor δ 7.75~7.35 (m, 10H), 5.18 (ddd, J=49.2, 10.8, 2.3 Hz, 1H), 4.33~4.18 (m, 1H), 3.95~3.78 (m 2H), 3.83 (s, 3H), 2.45~2.10 (m, 2H), 1.09 (s, 9H); HRMS (FAB) obsd, m/z 515.0972, calcd for C$_{22}$H$_{29}$FIO$_3$Si, m/z 515.0915 (M+H)$^+$; Anal. Calcd for C$_{22}$H$_{28}$FIO$_3$Si.0.05C$_6$H$_{14}$: C, 51.63; H, 5.58; I, 24.46. Found: C, 51.84; H, 5.53; I, 24.52.

Example 27

(2S,4R/S)-4-acetylsulfanyl-5-tert-butyldiphenylsilyloxy-2-fluoropentanoic acid methyl ester (D-5, FIG. 3a) and (2R,4S/R)-4-acetylsulfanyl-5-tert-butyldiphenylsilyloxy-2-fluoropentanoic acid methyl ester (L-5, FIG. 4a)

A solution of compounds D-4 (11.72 g, 22.8 mmol) in 12 mL of DMF was treated with solid KSAc (5.2 g, 45.7 mmol) at room temperature for 8 hours. The resulting mixture was diluted with EtOAc (500 mL), washed with water (2×200 mL), dried over MgSO$_4$, filtered, concentrated and purified by column chromatography with 10% EtOAc in hexanes to give products D-5 (9.2 g, 19.9 mmol, 87% yield) as a red-brown oil. $^1$H NMR (CDCl$_3$) for major 87.61~7.32 (m, 10H), 5.22~4.88 (m, 1H), 3.89~3.65 (m, 3H), 3.78 (s, 3H), 2.41~2.07 (m, 2H), 2.29 (s, 3H), 1.05 (s, 9H), for major δ 7.61~7.32 (m, 10H), 5.22~4.88 (m, 1H), 3.89~3.65 (m, 3H), 3.78 (s, 3H), 2.41~2.07 (m, 2H), 2.27 (s, 3H), 1.06 (s, 9H); HRMS (FAB) obsd, m/z 463.1770, calcd for C$_{24}$H$_{32}$FO$_4$SSi, m/z 463.1775 (M+H)$^+$; Anal. Calcd for C$_{24}$H$_{31}$FO$_4$SSi: C, 62.31; H, 6.75; S, 6.93. Found: C, 62.03; H, 6.63; S, 6.98.

A similar procedure was followed using compound L-4 (13.7 g, 26.6 mmol) in 20 mL of DMF was treated with solid KSAc (6.08 g, 53.2 mmol) to give products L-5 (11.14 g, 24.1 mmol, 91% yield) as a red-brown oil. $^1$H NMR (CDCl3) for major δ 7.67~7.35 (m, 10H), 5.12~4.92 (m, 1H), 3.93~3.68 (m, 3H), 3.81 (s, 3H), 2.44~2.10 (m, 2H), 2.32 (s, 3H), 1.057 (s, 9H), for major δ 7.67~7.35 (m, 10H), 5.12~4.92 (m, 1H), 3.93~3.68 (m, 3H), 3.81 (s, 3H), 2.44~2.10 (m, 2H), 2.30 (s, 3H), 1.062 (s, 9H); HRMS (FAB) obsd, m/z 463.1789, calcd for C$_{24}$H$_{32}$FO$_4$SSi, m/z 463.1775 (M+H)$^+$; Anal. Calcd for C$_{24}$H$_{31}$FO$_4$SSi: C, 62.31; H, 6.75; S, 6.93. Found: C, 62.36; H, 6.69; S, 7.04.

Example 28

(2S,4S)-(+)-4-tert-butyldiphenylsilyloxymethyl-2-fluoro-γ-thiobutyrolactone (D-6, FIG. 3a) and (2R,4R-(−)-4-tert-butyldiphenylsilyloxymethyl-2-fluoro-γ-thiobutyro-lactone (L-6, FIG. 4a)

A solution of compounds D-5 (9.2 g, 19.9 mmol) in toluene (200 mL) was treated with 43.7 mL of 1M DIBAL-H in hexane at −78° C. for 1 hour. The reaction was quenched with 9.6 mL of MeOH and warmed up to room temperature for 1 hour and aqueous NaHCO$_3$ (19 mL) and EtOAc (200 mL) were added to the mixture. The resulting mixture was filtered and the filtrate was concentrated to dryness. The crude thiolactol was treated with Ac$_2$O (19 mL) and DMSO (20 mL) at room temperature for 24 hours. The reaction mixture was poured to a separatory funnel containing ice-cooled water (300 mL) and extracted with ethyl ether (3×300 mL). The combined organic layer was washed with water (3×300 mL), dried over MgSO$_4$, filtered, concentrated and purified by silica gel column chromatography with 5% Et$_2$O in hexanes to give the product D-6 (4.2 g, 10.8 mmol, 54% yield) and D-6a (0.7 g, 1.8 mmol, 9% yield) as a yellow oil. For D-6: [α]$^{25}_D$ 28.2° (c 1.08, CHCl$_3$); $^1$H NMR (CDCl$_3$) δ 7.68~7.37 (m, 10H), 5.07 (ddd, J=50.5, 10.2, 6.9 MHz, 1H), 3.96~3.78 (m, 3H), 2.70~2.62 (m, 1H), 2.18~2.05 (m, 1H), 1.07 (s, 9H); $^{13}$C NMR (CDCl$_3$) δ 200.69 (d, J=18.0 MHz), 135.53, 132.68, 132.60, 130.01, 127.86, 93.27 (d, J=197.0 MHz), 66.64, 43.98 (d, J=7.0 MHz), 32.61 (d, J=19.4 MHz), 26.69, 19.23; Anal. Calcd for C$_{21}$H$_{25}$FO$_2$SSi: C, 64.91; H, 6.48; S, 8.25. Found: C, 64.88; H, 6.51; S, 8.15. For D-6a: [α]$^{27}_D$ −46.7° (c 0.5, CHCl$_3$); $^1$H NMR (CDCl$_3$) δ 7.66~7.40 (m, 10H), 5.18 (dt, J=44.4, 7.0 Hz, 1H), 4.02 (quint, J=5.0 Hz) 3.86 (dd, J=10.8, 5.0 Hz, 1H), 3.84 (dd, J=10.8, 5.0 Hz, 1H), 2.88~2.78 (m, 2H), 1.07 (s, 9H); Anal. (C$_{21}$H$_{25}$FO$_2$SSi) C, H, S.

Similarly, (2R,4R)-(−)-4-tert-butyldiphenylsilyloxymethyl-2-fluoro-γ-thiobutyro-lactone (L-6, FIG. 4a), was made. A solution of compounds L-5 (11.1 g, 24.1 mmol) in toluene (200 mL) was treated with 53 mL of 1M DIBAL-H in hexane at −78° C. for 1 hour. The reaction was quenched with 12 mL of MeOH and warmed up to room temperature for 1 hour and aqueous NaHCO$_3$ (23 mL) and EtOAc (200 mL) were added to the mixture. The resulting mixture was filtered and the filtrate was concentrated to dryness. The crude thiolactol was treated with Ac$_2$O (34 mL) and DMSO (35 mL) at room temperature for 24 hours. The reaction mixture was poured to a separatory funnel containing ice-cooled water (300 mL) and extracted with ethyl ether (3×300 mL). The combined organic layer was washed with water (3×300 mL), dried over MgSO$_4$, filtered, concentrated and purified by silica gel column chromatography with 5% Et$_2$O in hexanes to give the product L-6 (5.08 g, 13.1 mmol, 54% yield) as a yellow oil: [α]$^{25}_D$ −29.4° (c 1.18, CHCl$_3$); $^1$H NMR (CDCl$_3$) δ 7.68~7.37 (m, 10H), 5.07 (ddd, J=50.5, 10.2, 6.9 MHz, 1H), 3.96~3.78 (m, 3H), 2.72~2.62 (m, 1H), 2.18~2.07 (m, 1H), 1.07 (s, 9H); $^{13}$C NMR (CDCl$_3$) δ 200.70 (d, J=17.4 MHz), 135.50, 132.66, 132.58, 129.99, 127.85, 93.26 (d, J=196.9 MHz), 66.61, 43.97 (d, J=7.1 MHz), 32.58 (d, J=19.6 MHz), 26.68, 19.21; Anal. Calcd for C$_{21}$H$_{25}$FO$_2$SSi: C, 64.91; H, 6.48; S, 8.25. Found: C, 65.15; H, 6.58; S, 8.12.

Example 29

(2R,4S)-(+)-4-ter-butyldiphenylsilyloxymethyl-2-fluoro-2-phenylselenyl-γ-thio-butyro-lactone (D-7, FIG. 3a) and (2S,4R)-(−)-4-tert-butyldiphenylsilyloxymethyl-2-fluoro-2-phenylselenyl-γ-thiobutyro-lactone (L-7, FIG. 4a)

To a solution of compound D-6 (4.74 g, 12.2 mmol) in THF (60 mL), 14.7 mL of 1M LiHMDS in THF was added slowly at −78° C., and the reaction mixture was stirred at the same temperature for 1 hour. TMSCl (2.01 mL, 15.9 mmol) was added dropwise to the reaction mixture and the mixture was allowed to warm to room temperature. The resulting mixture was stirred at room temperature for 30 minutes and cooled to −78° C. A solution of PhScBr (4.37 g, 18.3 mmol) in THF (20 mL) was rapidly added and the mixture was stirred at −78° C. for 1 hour. The mixture was diluted with ethyl ether (300 mL), washed with water (4×100 mL), dried over MgSO$_4$, filtered, concentrated and purified by silica gel column chromatography with 3% Et$_2$O in hexanes to give desired product D-7 (4.77 g, 8.76 mmol, 72% yield) as a pale yellow syrup. [α]$^{24}_D$ 54.0° (c 0.606, CHCl$_3$); $^1$H NMR (CDCl$_3$) δ 7.68~7.35 (m, 15H), 3.96~3.89 (m, 1H), 3.87 (dd. J=10.2, 5.1 Hz, 1H), 3.80 (dd, J=10.1, 7.1 Hz, 1H), 2.49 (dd, J=13.4, 4.0 Hz, 1H), 2.22 (td, J=13.5, 10.5 Hz, 1H), 1.06 (s, 9H); $^{13}$C NMR (CDCl$_3$) δ 196.32 (d, J=23.1 Hz), 137.01, 135.52, 132.63, 132.50, 130.02, 129.99, 129.38, 127.87, 124.78, 105.12 (d, J=260.6 Hz), 65.66, 44.58 (d, J=2.9 Hz), 39.13 (d, J=21.4 Hz), 26.69, 19.20; Anal. Calcd for C$_{27}$H$_{29}$FO$_2$SSeSi: C, 59.65; H, 5.38; S, 5.90. Found: C, 60.10; H, 5.46; S, 5.85.

Similarly, to a solution of compound L-6 (5.08 g, 13.1 mmol) in THF (60 mL), 15.7 mL of 1M LiHMDS in THF was added slowly at −78° C., and the reaction mixture was stirred at the same temperature for 1 hour. TMSCl (2.16 mL, 17 mmol) was added dropwise to the reaction mixture and the mixture was allowed to warm to room temperature. The resulting mixture was stirred at room temperature for 30 minutes and cooed to −78° C. A solution of PhSeBr (4.69 g, 19.6 mmol) in THF (20 mL) was rapidly added and the mixture was stirred at −78° C. for 1 hour. The mixture was diluted with ethyl ether (300 mL), washed with water (4×100 mL), dried over MgSO$_4$, filtered, concentrated and purified by silica gel column chromatography with 3% Et$_2$O in hexanes to give desired product L-7 (5.28 g, 9.69 mmol, 74% yield) as a pale yellow syrup. [α]$^{24}_D$ −56.4° (c 0.542, CHCl$_3$); $^1$H NMR (CDCl$_3$) δ 7.70~7.35 (m, 15H), 3.97~3.77 (m, 3H), 2.49 (dd, J=13.3, 4.5 Hz, 1H), 2.22 (td, J=14.4, 10.5 Hz, 1H), 1.05 (s, 9H); $^{13}$C NMR (CDCl$_3$) δ 196.34 (d, J=22.7 Hz), 137.03, 135.53, 132.63, 132.50, 130.03, 129.39, 127.87, 124.79, 105.13 (d, J=260.6 Hz), 65.67, 44.59 (d, J=2.9 Hz), 39.13 (d, J=21.4 Hz), 26.70, 19.21; HRMS (FAB) obsd, m/z 545.0873, calcd for C$_{27}$H$_{30}$FO$_2$SSeSi, m/z 545.0885 (M+H)$^+$; Anal. Calcd for C$_{27}$H$_{29}$FO$_2$SSeSi.0.15CHCl$_3$: C, 58.07; H, 5.23; S, 5.70. Found: C, 57.88; H, 5.36; S, 5.76.

Alternatively, L-6 was prepared from D-6a in the same manner on 9.69 mmol scale. D-7a was obtained in 74% yield as a pale yellow syrup: [α]$^{24}_D$ −56.4° (c 0.542, CHCl$_3$); $^1$H NMR (CDCl$_3$) δ 7.70~7.35 (m, 15H), 3.97~3.77 (m, 3H), 2.49 (dd, J=13.3, 4.5 Hz, 1H), 2.22 (td, J=14.4, 10.5 Hz, 1H), 1.05 (s, 9H); $^{13}$C NMR (CDCl$_3$) δ 196.34 (d, J=22.7 Hz), 137.03, 135.53, 132.63, 132.50, 130.03, 129.39, 127.87, 124.79, 105.13 (d, J=260.6 Hz), 65.67, 44.59 (d, J=2.9 Hz), 39.13 (d, J=21.4 Hz), 26.70, 19.21; HRMS (FAB) obsd, m/z 545.0873, calcd for C$_{27}$H$_{30}$FO$_2$SSeSi, m/z 545.0885 (M+H)$^+$; Anal. (C$_{27}$H$_{29}$FO$_2$SSeSi.0.15CHCl$_3$) C, H, S.

Example 30

(1R/S,2R,4S)-1-O-acetyl-5-O-(tert-butyldiphenylisilyl)-2,3-dideoxy-2-fluoro-2-phenyl-selenyl-4-thio-β-D-ribofuranoside (D-8, FIG. 3a)

A solution of compounds D-7 (4.77 g, 8.76 mmol) in toluene (100 mL) was treated with 17.5 mL of 1M DIBAL-H in hexane at −78° C. for 1 hour. The reaction was quenched with 4 mL of MeOH and warmed up to room temperature for 1 hour and aqueous NaHCO$_3$ (8 mL) and EtOAc (100 mL) were added to the mixture. The resulting mixture was filtered, and the filtrate was concentrated to dryness. A solution of the crude thiolactol in CH$_2$Cl$_2$ (100 ML) was treated with Ac$_2$O (2.48 mL, 26.3 mmol), TEA (3.66 mL, 26.3 mmol) and catalytic amount of 4-DMAP at room temperature for 3 hours. The resulting mixture was concentrated and purified by silica gel column chromatography with 3% Et$_2$O in hexanes to give the acetate D-8 (4.4 g, 7.48 mmol, 85% yield) as a pale yellow oil. $^1$H NMR (CDCl$_3$) δ 7.70~7.32 (m, 15H), 6.03, 5.99 (d & s, J=7.6 Hz, 1H), 3.76~3.60 (m, 3H), 2.60~2.53 (m, 1H), 2.41~2.31 (m, 1H) 2.13, 2.01 (2s, 3H), 1.04, 0.99 (2s, 9H); Anal. Calcd for C$_{29}$H$_{28}$FO$_3$SSeSi: C, 59.27; H, 5.66; S, 5.46. Found: C, 59.61; H, 5.72; S, 5.57.

Example 31

(1S/R,2S,4R)-1-O-acetyl-5-O-(tert-butyldiphenylsilyl)-2,3-dideoxy-2-fluoro-2-phenyl-selenyl-4-thio-β-L-ribofuranoside (L-8, FIG. 4a)

A solution of compound L-7 (4.98 g, 9.14 mmol) in toluene (100 mL) was treated with 18.3 mL of 1M DIBAL-H in hexane at −78° C. for 1 hour. The reaction was quenched with 4 mL of MeOH and warmed up to room temperature for 1 hour and aqueous NaHCO$_3$ (8 mL) and EtOAc (100 mL) were added to the mixture. The resulting mixture was filtered, and the filtrate was concentrated to dryness. A solution of the crude thiolactol in CH$_2$Cl$_2$ (100 mL) was treated with Ac$_2$O (2.6 mL, 28 mmol), TEA (3.8 mL, 28 mmol) and catalytic amount of 4-DMAP at room temperature for 3 hours. The resulting mixture was concentrated and purified by silica gel column chromatography with 3% Et$_2$O in hexanes to give the acetate L-8 (4.48 g, 7.61 mmol, 83% yield) as a pale yellow oil. $^1$H NMR (CDCl$_3$) δ 7.70~7.32 (m, 15H), 6.03, 5.99 (d & s, J=7.6 Hz, 1H), 3.76~3.60 (m, 3H), 2.60~2.53 (m, 1H), 2.41~2.31 (m, 1H) 2.13, 2.01 (2s, 3H), 1.04, 0.99 (2s, 9H); Anal. Calcd for C$_{29}$H$_{28}$FO$_3$SSeSi: C, 59.27; H, 5.66; S, 5.46. Found: C, 59.24; H, 5.68; S, 5.42.

Example 32

(+)-N$^4$-Benzoyl-1-[(1S,2S,4R)-5-O-(tert-butyldiphenylsilyl)-2,3-dideoxy-2-fluoro-2-phenyl-selenyl-4-thio-β-D-ribofuranosyl]cytosine (D-9, FIG. 3a)

A mixture of N$^4$-benzoylcytosine (0.505 g, 2.35 mmol) in HMDS (15 mL) and CH$_3$CN (15 mL) was refluxed for 5 hours. After removing solvent using vacuum pump, a solution of the acetate D-8 (0.460 g, 0.786 mmol) in 15 mL of CH$_3$CN was added to the reaction flask containing the silylated N$^4$-benzoylcytosine, then TMSOTf (0.28 mL, 1.4 mmol) was added dropwise at room temperature. After 16 hours, the reaction was quenched with 1 mL of saturated NaHCO$_3$ and the resulting mixture was concentrated. The crude mixture was diluted with 100 mL of CH$_2$Cl$_2$, washed with aqueous NaHCO$_3$, dried over MgSO$_4$, filtered and concentrated. The crude product was purified by silica gel column chromatography with 30% EtOAc in hexanes to give cytosine derivative D-9 (0.269 g, 0.362 mmol, 46% yield) as a foam. The condensation gave the β-anomer exclusively by virtue of the bulky α-phenylselenyl group (Chu, C. K.; Babu, J. R.; Beach, W.; Ahn, S. K.; Huang, H.; Jeong, L. S.; Lee, S. J. A highly stereoselective glycosylation of 2-(phenylselenyl)-2,3-dideoxyribose derivative with thymine: Synthesis of 3'-deoxy-2',3'-didehydrothymidine and 3'-deoxythymidine. J. Org. Chem. 1990, 55, 1418–1420). [α]$^{24}_D$ 179.9° (c 0.50, CH$_2$Cl$_2$); UV(MeOH) λ$_{max}$ 308 nm, $^1$H NMR (CDCl$_3$) δ 8.82 (br s, 1H), 8.12 (d, J=6.5 Hz, 1H), 7.92 (d, J=7.3 Hz, 2H), 7.69~7.27 (m, 19H), 6.91 (d, J=15.6 Hz, 1H), 3.87~3.72 (m, 2H), 3.68~3.58 (m, 1H), 2.62~2.47 (m, 2H), 1.02 (s, 9H); $^{13}$C NMR (CDCl$_3$) δ 161.94, 155.42, 147.17, 136.96, 135.60, 135.54, 133.21, 132.83, 129.96, 129.92, 129.41, 129.20, 129.03, 127.78, 127.60, 125.73, 106.39 (d, J=248.8 Hz), 96.87, 66.74 (d, J=17.6 Hz), 66.29, 47.21, 42.39 (d, J=22.2 Hz), 26.73, 19.15; Anal. Calcd for $C_{38}H_{38}FN_3O_3SSeSi$: C, 61.44; H, 5.16; N, 5.66; S, 4.32. Found: C, 61.52; H, 5.42; N, 5.47; S, 4.21.

A similar procedure for condensation of the acetate D-8 with various pyrimidines can be performed to obtain the various other (+)-$N^4$-Benzoyl-1-[(1S,2S,4R)-5-O-(tert-butyldi-phenylsilyl)-2,3-dideoxy-2-fluoro-2-phenyl-selenyl-4-thio-β-D-ribofuranosyl]pyrimidines.

For instance, (+)-$N^4$-Benzoyl-1-[(1S,2S,4R)-5-O-(tert-butyldiphenylsilyl)-2,3-dideoxy-2-fluoro-2-phenylselenyl-4-thio-β-D-ribofuranosyl]-5-fluorocytosine (D-10, FIG. 3a) was made using the general procedure for condensation reaction of the acetate D-8 with pyrimidines. The compound D-10 was obtained on 0.850-mmol scale in 52% yield. $[\alpha]^{24}_D$ 202.6° (c 0.410, $CH_2Cl_2$); UV($CH_2Cl_2$) $\lambda_{max}$ 332.5 nm; $^1$H NMR (CDCl$_3$) δ 12.70 (br s, 1H), 8.33 (d, J=7.5 Hz, 2H), 7.87 (dd, J=5.9, 1.7 Hz, 1H), 7.72~7.28 (m, 18H), 6.73 (d, J=16.3 Hz, 1H), 3.92~3.76 (m, 2H), 3.67~3.58 (dt J=11.5, 6.8 Hz, 1H), 2.63~2.46 (m, 2H), 1.07 (s, 9H); $^{13}$C NMR (CDCl$_3$) δ 151.88 (d J=19.2 Hz), 147.15, 139.01 (d, J=237.9 Hz), 136.78, 135.90, 135.49, 135.47, 133.00, 132.71, 130.01, 129.96, 129.91, 129.51, 129.18, 128.24, 127.76, 126.85 (d, J=34.4 Hz), 124.74, 105.60 (d, J=247.5 Hz), 67.01 (d, J=18.6), 66.43, 47.19, 41.64 (d, J=21.0 Hz), 26.68, 19.09.

In addition, the thymine analog (D-11, FIG. 3a) was made using the general procedure for condensation reaction of the acetate D-8 with pyrimidines. The compound D-11 was obtained on 0.850-mmol scale in 45% yield. $[\alpha]^{25}_D$ 137.8° (c 0.42, $CH_2Cl_2$); UV($CH_2Cl_2$) $\lambda_{max}$ ($CH_2Cl_2$) 266.0 nm; $^1$H NMR (CDCl$_3$) δ 9.13 (br s, 1H), 7.74~7.25 (m, 16H), 6.72 (d, J=18.1 Hz, 1H), 3.87~3.73 (m, 2H), 3.67~3.57 (m, 1H), 2.62~2.44 (m, 2H), 1.83 (s, 3H), 1.07 (s, 9H); $^{13}$C NMR (CDCl$_3$) δ 163.25, 150.93, 137.22 (d, J=6.1 Hz), 136.88, 135.48, 132.94, 132.90, 129.87, 129.46, 129.15, 127.74, 125.16, 110.67, 106.15 (d, J=247.03 Hz), 66.76, 65.85 (d, J=18.3 Hz), 46.79, 42.04 (d, J=21.0 Hz), 26.70, 19.17, 12.59.

Similarly, the uracil analog (D-12, FIG. 3a) was made using the general procedure for condensation reaction of the acetate D-8 with pyrimidines. The compound D-12 was obtained on 0.766-mmol scale in 53% yield. $[\alpha]^{23}_D$ 136.5° (c 0.36, $CH_2Cl_2$); UV($CH_2Cl_2$) $\lambda_{max}$ 262.5 nm; $^1$H NMR (CDCl$_3$) δ 9.26 (br s, 1H), 7.72 (dd, J=8.2, 2.0 Hz, 1H), 7.68~7.30 (m, 15H), 6.63 (d, J=14.7 Hz, 1H), 5.56 (dd, J=8.2, 1.9 Hz, 1H), 3.87~3.72 (m, 2H), 3.62~3.58 (ps quin, J=6.2 Hz, 1H), 2.55~2.41 (m, 2H), 1.03 (s, 9H); $^{13}$C NMR (CDCl$_3$) δ 162.77, 150.77, 141.80 (d, J=5.0 hz), 136.94, 135.58, 135.51, 132.80, 132.77, 129.93, 129.61, 129.26, 127.79, 125.12, 106.24 (d, J=248.7 Hz), 102.31, 66.06, 65.99 (d, J=14.6 Hz), 46.86, 41.58 (d, J=21.8 Hz), 26.75, 19.18.

The synthesis of purine analogues needed more careful treatments. The key intermediate D-8 was condensed with 6-chloropurine and 2-fluoro-6-chloropurine to give the corresponding nucleosides D-21 and D-22 in 65% and 66% yield, respectively. To achieve a clean and high-yield conversion, the temperature of the reaction mixture had to be carefully controlled in such a manner that, after addition of TMSOTf at 0° C., the reaction mixture was stirred for 6 hours at room temperature and then for 2 hours at 60° C. The 6-chloropurine derivative D-21 was syn-eliminated by successive treatment with mCPBA and pyridine to give an inseparable mixture of 2',3'-unsaturated nucleoside D-23 and its $\Delta^{1,2}$-isomer D-24 in 81% yield (3:1 determined by $^1$H NMR). Amination of the mixture of D-23 and D-24 by treatment with methanolic ammonia at 100° C. in a steel bomb gave the adenosine analogue, which was deprotected by TBAF in THF to give 2'-fluoro4'-thio-2',3'-unsaturated adenosine 24 in 61% yield. The $\Delta^{1,2}$-isomer D-24, however, did not survive under reaction conditions and silica gel column chromatography due to its instability. The 2-fluoro-6-chloropurine derivative D-22 was also treated with mCPBA followed by pyridine to give an inseparable mixture of the syn-eliminated product D-25 and its $\Delta^{1,2}$-isomer D-26 in 71% yield. Dry ammonia gas was bubbled into a solution of D-25 and D-26 in ethylene glycol dimethyl ether (DME) at room temperature for 16 hours to give the 2-amino-6-chloropurine derivative D-29 and 2-fluoro-6-aminopurine derivative D-30 in 45% and 25% yield, respectively, which were readily separated by silica gel column chromatography. The $\Delta^{1,2}$-isomer D-26 was not stable enough to survive the reaction and purification conditions.

Example 33

(−)-$N^4$-Benzoyl-1-[(1S,2S,4R)-5-O-(tert-butyldiphenylsilyl)-2,3-dideoxy-2-fluoro-2-phenylselenyl-4-thio-β-L-ribofuranosyl]cytosine (L-9, FIG. 4a)

A mixture of $N^4$-benzoylcytosine (0.548 g, 2.55 mmol) in HMDS (15 mL) and $CH_3CN$ (15 mL) was rejluxed for 5 hours. After removing solvent using vacuum pump, a solution of the acetate L-8 (0.500 g, 0.849 mmol) in 15 mL of $CH_3CN$ was added to the reaction flask containing the silylated $N^4$-benzoylcytosine, and then TMSOTf (0.31 mL, 1.7 mmol) was added dropwise at room temperature. After 16 hours, the reaction was quenched with 1 mL of saturated NaHCO$_3$ and the resulting mixture was concentrated to one fifth of volume. The crude mixture was diluted with 100 mL of $CH_2Cl_2$, washed with aqueous NaHCO$_3$, dried over MgSO$_4$, filtered and concentrated. The crude product was purified by silica gel column chromatography with 30% EtOAc in hexanes to give cytosine derivative L-9 (0.300 g, 0.404 mmol, 48% yield) as a foam. $[\alpha]^{24}_D$ −168.38° (c 0.486, $CH_2Cl_2$); UV(MeOH) $\lambda_{max}$ 308 nm; $^1$H NMR (CDCl$_3$) δ 8.82 (br s, 1H), 8.12 (d, J=6.5 Hz, 1H), 7.92 (d, J=7.3 Hz, 2H), 7.69~7.27 (m, 19H), 6.91 (d, J=15.6 Hz, 1H), 3.87~3.72 (m, 2H), 3.68~3.58 (m, 1H), 2.62~2.47 (m, 2H), 1.02 (s, 9H); $^{13}$C NMR (CDCl$_3$) δ 161.94, 155.42, 147.17, 136.96, 135.60, 135.54, 133.21, 132.83, 129.96, 129.92, 129.41, 129.20, 129.03, 127.78, 127.60, 125.73, 106.39 (d, J=248.8 Hz), 96.87, 66.74 (d, J=17.6 Hz), 66.29, 47.21, 42.39 (d, J=22.2 Hz), 26.73, 19.15; Anal. Calcd for $C_{38}H_{38}FN_3O_3SSeSi \cdot 0.2Et_2O$: C, 61.51; H, 5.32; N, 5.55; S, 4.23. Found: C, 61.88; H, 5.55; N, 5.56; S, 4.21.

(−)-$N^4$-Benzoyl-1-[(1S,2S,4R)-5-O-(tert-butyldiphenylsilyl)-2,3-dideoxy-2-fluoro-2-phenylselenyl-4-thio-β-L-ribofuranosyl]-5-fluorocytosine (L-10, FIG. 4a) was made using the general procedure for condensation reaction of the acetate L-8 with pyrimidines. The compound L-10 was obtained on 0.849-mmol scale in 59% yield: $[\alpha]^{24}_D$ −209.1° (c 0.693, $CH_2Cl_2$); UV($CH_2Cl_2$) $\lambda_{max}$ 332.5 nm; $^1$H NMR (CDCl$_3$) δ 12.70 (br s, 1H), 8.33 (d, J=7.5 Hz, 2H), 7.87 (dd, J=5.9, 1.7 Hz, 1H), 7.72~7.28 (m, 18H), 6.73 (d, J=16.3 Hz, 1H), 3.92~3.76 (m, 2H), 3.67~3.58 (dt J=11.5, 6.8 Hz, 1H), 2.63~2.46 (m, 2H), 1.07 (s, 9H); $^{13}$C NMR (CDCl$_3$) δ 151.88 (d J=19.2 Hz), 147.15, 139.01 (d, J=237.9 Hz), 136.78, 135.90, 135.49, 135.47, 133.00, 132.71, 130.01, 129.96, 129.91, 129.51, 129.18, 128.24, 127.76, 126.85 (d, J=34.4 Hz), 124.74, 105.60 (d, J=247.5

Hz), 67.01 (d, J=18.6), 66.43, 47.19, 41.64 (d, J=21.0 Hz), 26.68, 19.09; FABMS m/z 762 (M+H)$^+$; Anal. Calcd for $C_{38}H_{37}F_2N_3O_3SSeSi$: C, 59.99; H, 4.90; N 5.52; S, 4.21. Found: C, 59.97; H, 5.05; N, 5.44; S, 4.23.

This general procedure for condensation reaction of the acetate L-8 is applicable for condensation with various pyrimidines.

(−)-1-[(1S,2S,4R)-5-O-(tert-butyldiphenylsilyl)-2,3-dideoxy-2-fluoro-2-phenyl-selenyl-4-thio-β-L-ribofuranosyl]thymine (L-11, FIG. 4a) was made using the general procedure for condensation reaction of the acetate L-8 with pyrimidines. The compound L-11 was obtained on 0.849-mmol scale in 38% yield: $[\alpha]^{26}_D$ −130.6° (c 0.464, $CH_2Cl_2$); UV($CH_2Cl_2$) $\lambda_{max\ (CH2Cl2)}$ 266.0 nm; $^1H$ NMR ($CDCl_3$) δ 9.13 (br s, 1H), 7.74~7.25 (m, 16H), 6.72 (d, J=18.1 Hz, 1H), 3.87~3.73 (m, 2H), 3.67~3.57 (m, 1H), 2.62~2.44 (m, 2H), 1.83 (s, 3H), 1.07 (s, 9H); $^{13}C$ NMR ($CDCl_3$) δ 163.25, 150.93, 137.22 (d, J=6.1 Hz), 136.88, 135.48, 132.94, 132.90, 129.87, 129.46, 129.15, 127.74, 125.16, 110.67, 106.15 (d, J=247.03 Hz), 66.76, 65.85 (d, J=18.3 Hz), 46.79, 42.04 (d, J=21.0 Hz), 26.70, 19.17, 12.59; FABMS m/z 655 (M+H)$^+$; Anal. Calcd for $C_{32}H_{35}FN_2O_3SSeSi\cdot0.1CH_2Cl_2$: C, 58.22; H, 5.36; N, 4.23; S, 4.84. Found: C, 58.05; H, 5.46; N, 4.20; S, 4.98.

(−)-1-[(1S,2S,4R)-5-O-(tert-butyldiphenylsilyl)-2,3-dideoxy-2-fluoro-2-phenyl-selenyl-4-thio-β-L-ribofuranosyl]uracil (L-12, FIG. 4a) was made using the general procedure for condensation reaction of the acetate L-8 with pyrimidines. The compound L-12 was obtained on 0.849-mmol scale in 48% yield: $[\alpha]^{23}_D$ −129.2° (c 0.578, $CH_2Cl_2$); UV($CH_2Cl_2$) $\lambda_{max}$ 262.5 nm; $^1H$ NMR ($CDCl_3$) δ 9.26 (br s, 1H), 7.72 (dd, J=8.2, 2.0 Hz, 1H), 7.68~7.30 (m, 15H), 6.63 (d, J=14.7 Hz, 1H), 5.56 (dd, J=8.2, 1.9 Hz, 1H), 3.87~3.72 (m, 2H), 3.62~3.58 (ps quin, J=6.2 Hz, 1H), 2.55~2.41 (m, 2H), 1.03 (s, 9H); $^{13}C$ NMR ($CDCl_3$) δ 162.77, 150.77, 141.80 (d, J=5.0 hz), 136.94, 135.58, 135.51, 132.80, 132.77, 129.93, 129.61, 129.26, 127.79, 125.12, 106.24 (d, J=248.7 Hz), 102.31, 66.06, 65.99 (d, J=14.6 Hz), 46.86, 41.58 (d, J=21.8 Hz), 26.75, 19.18; Anal. Calcd for $C_{31}H_{33}FN_2O_3SSeSi$: C, 58.20; H, 5.20; N, 4.38; S, 5.01. Found: C, 58.18; H, 5.33; N, 4.33; S, 4.95.

Example 34

(−)-N$^4$-Benzoyl-1-[(1S,4R)-5-O-(tert-butyldiphenylsilyl)-2,3-dideoxy-2,3-didehydro-2-fluoro-4-thio-β-D-ribofuranosyl]cytosine (D-13, FIG. 3a)

To a solution of compound D-9 (0.229 g, 0.310 mmol) in 5 mL of $CH_2Cl_2$, a solution of mCPBA (57~86%, 69 mg) in 5 mL of $CH_2Cl_2$ was added at −78° C. and the mixture was stirred at −78° C. for 30 minutes. Pyridine (0.07 mL, 0.9 mmol) was then added and the resulting mixture was stirred at room temperature for 2 hours. The reaction mixture was diluted with 50 mL of $CH_2Cl_2$, washed with aqueous $NaHCO_3$, dried over $MgSO_4$, filtered, and concentrated. The crude product was purified by silica gel column chromatography with 40% EtOAc in hexanes to give eliminated product D-13 (0.107 g, 0.225 mmol, 72% yield) as a foam. $[\alpha]^{25}_D$ −140.2° (c 0.366, $CH_2Cl_2$); UV(MeOH) $\lambda_{max}$ 308 nm; $^1H$ NMR ($CDCl_3$) δ 8.95 (brs, 1H), 7.91 (d, J=7.5 Hz, 2H), 7.69~7.38 (m, 15H), 7.03 (s, 1H), 5.82 (s, 1H), 4.23~4.15 (m, 1H), 3.83 (dd, J=10.4, 6.1 Hz, 1H), 3.78 (dd, J=10.4, 6.3 Hz, 1H), 1.10 (s, 9H); $^{13}C$ NMR ($CDCl_3$) δ 171.09, 166.78, 162.14, 155.06, 155.04 (d, J=280.8 Hz), 144.49, 135.58, 135.50, 133.19, 132.96, 132.76, 132.43, 130.11, 128.97, 127.89, 127.58, 111.29 (d, J=16.6 Hz), 98.40, 67.75, 61.91 (d, J=23.6 Hz), 46.83 (d, J=7.2 Hz), 26.82, 19.24; Anal. Calcd for $C_{32}H_{32}FN_3O_3SSi$: C, 65.88; H, 5.66; N, 7.07; S, 5.39. Found: C, 66.01; H, 5.88; N, 6.82; S, 5.20.

General procedure for syn-elimination reaction using mCPBA to give 2′,3′-unsaturated nucleosides.

A similar procedure for syn-elimination reaction using mCPBA can be performed to obtain the various other 2′,3′-unsaturated nucleosides.

For instance, (−)-N$^4$-Benzoyl-1-[(1S,4R)-5-O-(tert-butyldiphenylsilyl)-2,3-di-deoxy-2,3-didehydro-2-fluoro-4-thio-β-D-ribofuranosyl]-5-fluorocytosine (D-14, FIG. 3a) was made using the general procedure for syn-elimination reaction using mCPBA. The compound D-14 was obtained on 0.465-mmol scale in 69% yield. $[\alpha]^{25}_D$ −150.5° (c 0.345, $CH_2Cl_2$); UV($CH_2Cl_2$) λmax 331.0 nm; $^1H$ NMR ($CDCl_3$) δ 12.80 (br s, 1H), 8.30 (d, J=7.3 Hz, 2H), 7.72~7.38 (m, 14H), 6.95 (s, 1H), 5.80 (s, 1H), 4.23~4.15 (m, 1H), 3.84 (dd, J=10.5, 6.2 Hz, 1H), 3.79 (dd, J=10.2, 6.6 Hz, 1H), 1.10 (s, 9H); $^{13}C$ NMR ($CDCl_3$) δ 152.88 (d, J=281.3 Hz), 152.08 (d, J=19.1 Hz), 147.13, 140.42 (d, J=241.0 Hz), 135.86, 135.59, 135.50, 133.17, 132.59, 132.39, 130.18, 130.15, 130.11, 128.33, 127.93, 124.05 (d, J=36.2 Hz), 111.24 (d, J=16.5 Hz), 67.77, 61.85 (d, J=23.54 hz), 47.05 (d, J=7.1 Hz), 26.79, 19.23.

In addition, (−)-1-[(1S,4R)-5-O-(tert-butyldiphenylsilyl)-2,3-dideoxy-2,3-dide-hydro-2-fluoro-4-thio-β-D-ribofuranosyl]thymine (D-15, FIG. 3a) was made using the general procedure for syn-elimination reaction using mCPBA. The compound D-15 was obtained on 0.375-mmol scale in 69% yield: $[\alpha]^{26}_D$ −43.2° (c 0.34, $CH_2Cl_2$); UV($CH_2Cl_2$) $\lambda_{max}$ 266.0 nm; $^1H$ NMR ($CDCl_3$) δ 9.45 (br s, 1H), 7.72~7.35 (m, 10H), 7.02 (s, 1H), 6.96 (s, 1H), 5.81 (s, 1H), 4.22~4.13 (m, 1H), 3.85 (dd, J=10.5, 6.5 Hz, 1H), 3.77 (dd, J=10.2, 7.0 Hz, 1H), 1.74 (s, 3H), 1.08 (s, 9H); $^{13}C$ NMR ($CDCl_3$) δ 163.47, 154.97 (d, J=281.2 Hz), 150.78, 135.52, 135.43, 134.52, 132.79, 132.51, 130.03, 127.84, 112.65, 110.45 (d, J=16.8 Hz), 68.23, 60.49 (d, J=23.7 Hz), 46.74 (d, J=7.1 Hz), 26.74, 19.23, 12.54.

Similarly, (−)-1-[(1S,4R)-5-O-(tert-butyldiphenylsilyl)-2,3-dideoxy-2,3-dide-hydro-2-fluoro-4-thio-β-D-ribofuranosyl]uracil (D-16, FIG. 3a) was made using the general procedure for syn-elimination reaction using mCPBA. The compound D-16 was obtained on 0.391-mmol scale in 58% yield. $[\alpha]^{25}_D$ −72.1° (c 0.35, $CH_2Cl_2$); UV($CH_2Cl_2$) $\lambda_{max}$ 262.5 nm; $^1H$ NMR ($CDCl_3$) δ 9.34 (br s, 1H), 7.70~7.35 (m, 11H), 6.93 (s, 1H), 5.75 (s, 1H), 5.44 (dd, J=8.1, 1.2 Hz, 1H), 4.22~4.14 (m, 1H), 3.85 (dd, J=10.6, 5.9 Hz, 1H), 3.81 (dd, J=10.5, 5.6 Hz, 1H), 1.09 (s, 9H); $^{13}C$ NMR ($CDCl_3$) δ 162.78, 154.79 (d, J=280.9 Hz), 150.59, 139.55, 135.59, 135.49, 132.79, 132.37, 130.13, 130.10, 127.92, 127.90, 110.70 (d, J=16.9 Hz), 104.01, 67.33, 60.74 (d, J=23.7 Hz), 46.88 (d, J=7.2 Hz), 26.87, 19.31.

9-[(1R,4S)-5-O-(tert-butyldiphenylsilyl)-2,3-dideoxy-2,3-didehydro-2-fluoro-4-thio-β-D-ribofuranosyl]-6-chloropurine (D-23, FIG. 3b) and 9-[(4S)-5-O-(tert-butyldiphenylsilyl)-2,3-dideoxy-1,2-didehydro-2-fluoro-4-thio-β-D-ribofuranosyl]-6-chloropurine (D-24, FIG. 3b) were also made using the general procedure for syn-elimination reactions. A mixture of compounds D-23 and D-24 (3:1) were obtained on 1.48-mmol scale in 86% yield as a pale yellow foam. UV($CH_2Cl_2$) $\lambda_{max}$ 264.5 nm; $^1H$ NMR ($CDCl_3$), for major D-23: δ 8.69 (s, 1H), 8.12 (s, 1H), 7.69~7.35 (m, 10H), 6.87 (s, 1H), 5.87 (s, 1H), 4.33~4.25 (m, 1H), 3.96 (dd, J=10.2, 6.8 Hz, 1H), 3.86 (ps t, J=8.8 Hz, 1H), 1.08 (s, 9H); for minor D-24 δ 8.82 (s, 1H), 8.19 (s, 1H), 7.69~7.35 (m, 10H) 4.05~3.78 (m, 3H), 3.25 (ddd, J=16.6, 9.2, 3.1 Hz, 1H), 3.03 (dd, J=16.6, 5.2 Hz, 1H), 1.08 (s, 9H); Anal. Calcd for $C_{26}H_{26}ClFN_4OSSi$: C, 59.47; H, 4.99; N, 10.67; S, 6.11. Found: C, 59.58; H, 5.03; N, 10.41; S, 6.09.

Similarly, 9-[(1R,4S)-5-O-(tert-butyldiphenylsilyl)-2,3-dideoxy-2,3-didehydro-2-fluoro-4-thio-β-D-ribofuranosyl]-6-chloro-2-fluoropurine (D-25, FIG. 3b) and 9-[(4S)-5-O-(tert-butyldiphenylsilyl)-2,3-dideoxy-1,2-didehydro-2-fluoro-4-thio-β-D-ribofuranosyl]-6-chloro-2-fluoropurine (D-26, FIG. 3b) were made using the general procedure for syn-elimination reactions. A mixture of compounds D-25 and D-26 were obtained on 1.14-mmol scale in 71% yield as a pale yellow foam. UV($CH_2Cl_2$) $\lambda_{max}$ 266.0 nm; $^1$H NMR ($CDCl_3$) for major D-25: δ 8.08 (s, 1H), 7.69~7.36 (m, 10H), 6.68 (s, 1H), 6.75 (s, 1H), 5.86 (s, 1H), 4.32~4.23 (m, 1H), 3.94 (dd, J=10.2, 6.0 Hz, 1H), 3.87~3.83 (m, 1H), 1.08 (s, 9H), for minor D-26 δ 8.12 (s, 1H), 7.75~7.31 (m, 10H) 4.04~3.80 (m, 3H), 3.24 (ddd, J=16.3, 9.3, 3.1 Hz, 1H), 3.01 (ddd, J=16.8, 5.1, 0.6 Hz, 1H), 1.08 (s, 9H).

Example 35

(+)-$N^4$-Benzoyl-1-[(1S,4R)-5-O-(tert-butyldiphenylsilyl)-2,3-dideoxy-2,3-didehydro-2-fluoro-4-thio-β-L-ribofuranosyl]cytosine (L-13, FIG. 4a)

To a solution of compound L-9 (0.169 g, 0.228 mmol) in 5 mL of $CH_2Cl_2$, a solution of mCPBA (57~86%, 69 mg) in 5 mL of $CH_2Cl_2$ was added at −78° C. and the mixture was stirred at −78° C. for 30 minutes. Pyridine (0.07 mL, 0.9 mmol) was then added and the resulting mixture was stirred at room temperature for 2 hours. The reaction mixture was diluted with 50 mL of $CH_2Cl_2$, washed with aqueous $NaHCO_3$, dried over $MgSO_4$, filtered, and concentrated. The crude product was purified by silica gel column chromatography with 30% EtOAc in hexanes to give eliminated product L-13 (0.107 g, 0.183 mmol, 80% yield) as a foam. $[\alpha]^{24}_D$ 128.81° (c 0.515, $CH_2Cl_2$); UV(MeOH) $\lambda_{max}$ 308 nm; $^1$H NMR ($CDCl_3$) δ 8.95 (brs, 1H), 7.91 (d, J=7.5 Hz, 2H), 7.69~7.38 (m, 15H), 7.03 (s, 1H), 5.82 (s, 1H), 4.23~4.15 (m, 1H), 3.83 (dd, J=10.4, 6.1 Hz, 1H), 3.78 (dd, J=10.4, 6.3 Hz, 1H), 1.10 (s, 9H); $^{13}$C NMR ($CDCl_3$) δ 171.09, 166.78, 162.14, 155.06, 155.04 (d, J=280.8 Hz), 144.49, 135.58, 135.50, 133.19, 132.96, 132.76, 132.43, 130.11, 128.97, 127.89, 127.58, 111.29 (d, J=16.6 Hz), 98.40, 67.75, 61.91 (d, J=23.6 Hz), 46.83 (d, J=7.2 Hz), 26.82, 19.24; Anal. Calcd for $C_{32}H_{32}FN_3O_3SSi.0.1C_6H_{14}$: C, 65.88; H, 5.66; N, 7.07; S, 5.39. Found: C, 66.01; H, 5.88; N, 6.82; S, 5.20.

This general procedure for syn-elimination reaction using mCPBA can be used to give various 2',3'-unsaturated nucleosides.

(+)-$N^4$-Benzoyl-1-[(1S,4R)-5-O-(tert-butyldiphenylsilyl)-2,3-dideoxy-2,3-didehydro-2-fluoro-4-thio-β-L-ribofuranosyl]-5-fluorocytosine (L-14, FIG. 4a) was made using the general procedure for syn-elimination reaction. The compound L-14 was obtained on 0.493-mmol scale in 73% yield: $[\alpha]^{26}_D$ 152.58° (c 0.485, $CH_2Cl_2$); UV($CH_2Cl_2$) $\lambda_{max}$ 331.0 nm; $^1$H NMR ($CDCl_3$) δ 12.80 (br s, 1H), 8.30 (d, J=7.3 Hz, 2H), 7.72~7.38 (m, 14H), 6.95 (s, 1H), 5.80 (s, 1H), 4.23~4.15 (m, 1H), 3.84 (dd, J=10.5, 6.2 Hz, 1H), 3.79 (dd, J=10.2, 6.6 Hz, 1H), 1.10 (s, 9H); $^{13}$C NMR ($CDCl_3$) δ 152.88 (d, J=281.3 Hz), 152.08 (d, J=19.1 Hz), 147.13, 140.42 (d, J=241.0 Hz), 135.86, 135.59, 135.50, 133.17, 132.59, 132.39, 130.18, 130.15, 130.11, 128.33, 127.93, 124.05 (d, J=36.2 Hz), 111.24 (d, J=16.5 Hz), 67.77, 61.85 (d, J=23.54 hz), 47.05 (d, J=7.1 Hz), 26.79, 19.23; FABMS m/z 604 (M+H)$^+$; Anal. Calcd for $C_{32}H_{31}FN_3O_3SSi$: C, 63.66; H, 5.18; N, 6.96; S, 5.31. Found: C, 63.69; H, 5.30; N, 6.78; S, 5.26.

(+)-1-[(1S,4R)-5-O-(tert-butyldiphenylsilyl)-2,3-dideoxy-2,3-didehydro-2-fluoro-4-thio-β-L-ribofuranosyl] thymine (L-15, FIG. 4a) was made using the general procedure for syn-elimination reaction. The compound L-15 was obtained on 0.326-mmol scale in 76% yield: $[\alpha]^{26}_D$ 50.7° (c 0.530, $CH_2Cl_2$); UV($CH_2Cl_2$) $\lambda_{max}$ 266.0 nm; $^1$H NMR ($CDCl_3$) δ 9.45 (br s, 1H), 7.72~7.35 (m, 10H), 7.02 (s, 1H), 6.96 (s, 1H), 5.81 (s, 1H), 4.22~4.13 (m, 1H), 3.85 (dd, J=10.5, 6.5 Hz, 1H), 3.77 (dd, J=10.2, 7.0 Hz, 1H), 1.74 (s, 3H), 1.08 (s, 9H); $^{13}$C NMR ($CDCl_3$) δ 163.47, 154.97 (d, J=281.2 Hz), 150.78, 135.52, 135.43, 134.52, 132.79, 132.51, 130.03, 127.84, 112.65, 110.45 (d, J=16.8 Hz), 68.23, 60.49 (d, J=23.7 Hz), 46.74 (d, J=7.1 Hz), 26.74, 19.23, 12.54; HRMS (FAB) obsd, m/z 497.1725, calcd for $C_{26}H_{30}FN_2O_3SSi$, m/z 497.1730 (M+H)$^+$; Anal. Calcd for $C_{26}H_{29}FN_2O_3SSi.0.1CHCl_3$: C, 61.64; H, 5.65; N, 5.38; S, 6.30. Found: C, 61.34; H, 5.82; N, 5.36; S, 6.13.

(+)-1-[(1S,4R)-5-O-(tert-butyldiphenylsilyl)-2,3-dideoxy-2,3-didehydro-2-fluoro-4-thio-β-L-ribofuranosyl] uracil (L-16, FIG. 4a) was made using the general procedure for syn-elimination reaction. The compound L-16 was obtained on 0.411-mmol scale in 68% yield: $[\alpha]^{26}_D$ 77.7° (c 0.492, $CH_2Cl_2$); UV($CH_2Cl_2$) $\lambda_{max}$ 262.5 nm; $^1$H NMR ($CDCl_3$) δ 9.34 (br s, 1H), 7.70~7.35 (m, 11H), 6.93 (s, 1H), 5.75 (s, 1H), 5.44 (dd, J=8.1, 1.2 Hz, 1H), 4.22~4.14 (m, 1H), 3.85 (dd, J=10.6, 5.9 Hz, 1H), 3.81 (dd, J=10.5, 5.6 Hz, 1H), 1.09 (s, 9H); $^{13}$C NMR ($CDCl_3$) δ 162.78, 154.79 (d, J=280.9 Hz), 150.59, 139.55, 135.59, 135.49, 132.79, 132.37, 130.13, 130.10, 127.92, 127.90, 110.70 (d, J=16.9 Hz), 104.01, 67.33, 60.74 (d, J=23.7 Hz), 46.88 (d, J=7.2 Hz), 26.87, 19.31; HRMS (FAB) obsd, m/z 483.1572, calcd for $C_{25}H_{28}FN_2O_3SSi$, m/z 483.1574 (M+H)$^+$; Anal. Calcd for $C_{25}H_{27}FN_2O_3SSi$: C, 62.21; H, 5.64; N, 5.80; S, 6.64. Found: C, 62.41; H, 5.68; N, 5.71; S, 6.52.

9-[(1S,4R)-5-O-(tert-butyldiphenylsilyl)-2,3-dideoxy-2,3-didehydro-2-fluoro-4-thio-β-L-ribofuranosyl]-6-chloropurine (L-23, FIG. 4b) and 9-[(4R)-5-O-(tert-butyldiphenylsilyl)-2,3-dideoxy-1,2-didehydro-2-fluoro-4-thio-β-L-ribofuranosyl]-6-chloropurine (L-24, FIG. 4b) were also made using the general procedure for syn-elimination reaction. A mixture of title compounds L-23 and L-24 (3:1) were obtained on 1.10-mmol scale in 81% yield as a pale yellow foam. UV($CH_2Cl_2$) $\lambda_{max}$ 264.5 nm; $^1$H NMR ($CDCl_3$) for major L-23: δ 8.69 (s, 1H), 8.12 (s, 1H), 7.67 (t, J=14.4 Hz, 4H), 7.50~7.36 (m, 6H), 6.87 (s, 1H), 5.87 (s, 1H), 4.33~4.24 (m, 1H), 3.96 (dd, J=10.2, 6.8 Hz, 1H), 3.86 (dd, J=10.0, 7.5 Hz, 1H), 1.08 (s, 9H); for minor L-24: δ 8.81 (s, 1H), 8.18 (s, 1H), 7.70~7.35 (m, 10H) 4.03~3.83 (m, 3H), 3.25 (ddd, J=16.8, 9.3, 3.3 Hz, 1H), 3.03 (ddd, J=16.6, 5.7, 1.2 Hz, 1H), 1.08 (s, 9H); Anal. Calcd for $C_{26}H_{26}ClFN_4OSSi.0.4C_6H_{14}$: C, 60.96; H, 5.69; N, 10.01; S, 5.73. Found: C, 60.96; H, 5.50; N, 10.13; S, 5.93.

9-[(1S,4R)-5-O-(tert-butyldiphenysilyl)-2,3-dideoxy-2,3-didehydro-2-fluoro4-thio-β-L-ribofuranosyl]-6-chloro-2-fluoropurine (L-25, FIG. 4b) and 9-[(4R)-5-O-(tert-butyldiphenylsilyl)-2,3-dideoxy-1,2-didehydro-2-fluoro-4-thio-β-L-ribofuranosyl]-6-chloro-2-fluoropurine (L-26, FIG. 4b) were made using the general procedure for syn-elimination reaction. A mixture of compounds L-25 and L-26 were obtained on 1.12-mmol scale in 71% yield as a pale yellow foam: UV($CH_2Cl_2$) $\lambda_{max}$ 266.0 nm; $^1$H NMR ($CDCl_3$) for major L-25: δ 8.01 (s, 1H), 7.63~7.28 (m, 10H), 6.68 (s, 1H), 5.79 (s, 1H), 4.25~4.18 (m, 1H), 3.86 (td, J=10.2, 6.5 Hz, 1H), 3.82~3.77 (m, 1H), 1.01 (s, 9H), for minor L-26 δ 8.12 (s, 1H), 7.75~7.31 (m, 10H) 4.04~3.80 (m, 3H), 3.24 (ddd, J=16.3, 9.3,3.1 Hz, 1H), 3.01 (ddd, J=16.8, 5.1, 0.6 Hz, 1H), 1.08 (s, 9H); Anal. Calcd for $C_{26}H_{25}ClF_2N_4OSSi$: C, 57.50; H, 4.64; N, 10.32; S, 5.90. Found: C, 57.42; H, 5.02; N, 9.93; S, 5.65.

Example 36

(−)-1-[(1S,4R)-2,3-dideoxy-2,3-didehydro-2-fluoro4-thio-β-D-ribofuranosyl]-cytosine (D-17, FIG. 3a)

A solution of the protected cytidine D-13 (0.135 g, 0.225 mmol) in 15 mL of THF was treated with 0.31 mL of 1M TBAF in THF for 2 hours. The mixture was concentrated, and filtered through a short pad of silica gel. After the filtrate was concentrated, without further purification, the crude product was treated with methanolic ammonia at room temperature for 30 hours. After removal of solvent, the residue was purified by silica gel column chromatography with 5% MeOH in $CH_2Cl_2$ to give cytidine analog D-17 (0.048 g, 0.186 mmol, 84% yield) as a white solid: mp 89–91° C. (dec.); $[\alpha]^{24}_D$ −171.3° (c 0.44, MeOH); $UV(H_2O)$ $\lambda_{max}$ 279.5 nm (ε 19,900, pH 2). 272.0 nm (ε 15,900, pH 7), 272.5 nm (ε 16,200, pH 11); $^1H$ NMR (DMSO-$d_6$) δ 7.83 (d, J=7.4 Hz, 1H), 7.33, 7.37 (2 br s, 2H), 6.85 (s, 1H), 5.94 (s, 1H), 5.84 (d, J=7.5 Hz, 1H), 5.28 (t, J=5.4 Hz, 1H, $D_2O$ exchangeable), 4.02 (m, 1H), 3.59~3.62 (m, 2H); Anal. Calcd for $C_9H_{10}FN_3O_2S.0.6H2O.0.5MeOH$: C, 42.36; H, 4.74; N, 15.94; S, 12.16. Found: C, 42.07; H, 4.45; N, 15.62; S, 12.06.

A similar procedure for the two successive deprotections of protected unsaturated nucleosides can be used of the other (−)-1-[(1S,4R)-2,3-dideoxy-2,3-didehydro-2-fluoro-4-thio-β- D-ribofuranosyl]nucleosides.

For example, (−)-1-[(1S,4R)-2,3-dideoxy-2,3-didehydro-2-fluoro-4-thio-β-D-ribofuranosyl]-5-fluorocytosine (D-18, FIG. 3a) was made using the general procedure for two successive deprotections from D-14. The compound D-18 was obtained on 0.296-mmol scale in 90% yield: mp 187~189° C.; $[\alpha]^{25}_D$ −208.3° (c 0.42, MeOH); $UV(H_2O)$ $\lambda_{max}$ 286.0 nm (ε 8,600, pH 2). 282.0 nm (ε 7,500, pH 7), 282.0 nm (ε 6,900, pH 11); $^1H$ NMR (MeOH-$d_4$) δ 8.39 (d, J=6.6 Hz, 1H), 6.92 (s, 1H), 5.84 (s, 1H), 4.17 (s, 1H), 3.84 (dd, J=11.8, 3.7 Hz, 1H), 3.68 (br d, J=10.6, 1H).

Similarly, (−)-1-[(1S,4R)-2,3-dideoxy-2,3-didehydro-2-fluoro-4-thio-β-D-ribofuranosyl]-thymine (D-19, FIG. 3a) was made using the general procedure for two successive deprotections from D-15. The compound D-19 was obtained on 0.235 mmol scale in 88% yield as a white solid: mp 174~176° C.; $[\alpha]^{25}_D$ −46.5° (c 0.29, MeOH); $UV(H_2O)$ $\lambda_{max}$ 268.5 nm (ε 5,700, pH 2). 268.5 nm (ε 5,500, pH 7), 269.0 nm (ε 4,500, pH 11); $^1H$ NMR (MeOH-$d_4$) δ 8.03 (s, 1H), 6.87 (ps t, J=1.0, 1H), 5.86 (s, 1H), 4.17 (m, 1H), 3.84 (dd, J=11.9, 4.0 Hz, 1H), 3.77 (ddd, J=11.9, 3.7, 1.7 Hz, 1H), 1.88 (d, J=1.2, 3H).

(−)-1-[(1S,4R)-2,3-dideoxy-2,3-didehydro-2-fluoro-4-thio-β-D-ribofuranosyl]-uracil (D-20, FIG. 3a) was made using the general procedure for desilylation reaction from D-16. The compound D-20 was obtained on 0.193-mmol scale in 89% yield: mp 184~185° C.; $[\alpha]^{25}_D$ −136.4° (c 0.47, MeOH); $UV(H_2O)$ $\lambda_{max}$ 263.0 nm (ε 9,100, pH 2). 263.0 nm (ε 9,700, pH 7), 263.5 nm (ε 7,800, pH 11); $^1H$ NMR (MeOH-$d_4$) δ 8.11 (dd, J=8.1, 0.8 Hz, 1H), 6.87 (s, 1H), 5.89 (s, 1H), 5.77 (d, J=8.1 Hz, 1H), 4.19~4.13 (m, 1H), 3.80 (dd, J=11.7, 4.5 Hz, 1H), 3.71 (ddd, J=11.7, 4.1, 1.4Hz, 1H).

Similarly, the purine, (+)-9-[(1R,4S)-2,3-dideoxy-2,3-didehydro-2-fluoro-4-thio-β-D-ribofuranosyl]-2-fluoroadenosine (D-33, FIG. 3b) was made using the general procedure of desilylation. The compound D-33 was obtained on 0.22-mmol scale in 70% yield: mp>300° C.; $[\alpha]^{26}_D$ 17.1° (c 0.15, MeOH); $UV(H_2O)$ $\lambda_{max}$ 261.0 nm (ε 12,700, pH 2). 261.0 nm (ε 12,900, pH 7), 260.5 nm (ε 13,100, pH 11); $^1H$ NMR (MeOH-$d_4$) δ 8.44 (s, 1H), 6.77 (s, 1H), 5.92 (s, 1H), 4.27~4.22 (m, 1H), 3.89 (dd, J=11.7, 4.9 Hz, 1H), 3.82 (ddd, J=12.0, 4.6, 1.2 Hz, 1H); Anal. Calcd for $C_{10}H_9F_2N_5OS.0.4Et_2O$: C, 44.24; H, 4.16; N,22.24; S, 10.18. Found: C, 44.28; H, 3.97; N, 22.39; S, 10.29.

Alternatively, a similar procedure can be used for analogous desilylations of tert-butyldiphenyl ethers by using TBAF.

Example 37

(+)-1-[(1S,4R)-2,3-dideoxy-2,3-didehydro-2-fluoro-4-thio-β-L-ribofuranosyl]-cytosine (L-17, FIG. 4a)

A solution of the unsaturated cytidine L-13 (0.180 g, 0.307 mmol) in 15 mL of THF was treated with 0.37 mL of 1M TBAF in THF for 2 hours. The mixture was concentrated, and filtered through a short pad of silica gel. The filtrate was concentrated and, without further purification, the crude product was treated with methanolic ammonia at room temperature for 30 hours. After removal of solvent, the residue was purified by silica gel column chromatography with 5% MeOH in $CHCl_3$ to give cytidine analog L-17 (0.066 g, 0.27 mmol, 88% yield) as a white solid: mp 89–91° C. (dec.); $[\alpha]^{24}_D$ 205.3° (c 0.140, MeOH); $UV(H_2O)$ $\lambda_{max}$ 279.5 nm (ε 19,900, pH 2). 272.0 nm (ε 15,900, pH 7), 272.5 nm (ε 16,200, pH 11); $^1H$ NMR (DMSO-$d_6$) δ 7.83 (d, J=7.4 Hz, 1H), 7.33, 7.37 (2 br s, 2H), 6.85 (s, 1H), 5.94 (s, 1H), 5.84 (d, J=7.5 Hz, 1H), 5.28 (t, J=5.4 Hz, 1H, $D_2O$ exchangeable), 4.02 (m, 1H), 3.59~3.62 (m, 2H); Anal. Calcd for $C_9H_{10}FN_3O_2S.0.32CH_2Cl_2$: C, 41.39; H, 3.97; N, 15.54; S, 11.86. Found: C, 41.15; H, 4.10; N, 15.55; S, 11.82.

The general procedure for successive deprotections of protected unsaturated nucleoside can be used to prepare analogous deprotected unsaturated nucleosides.

(+)-1-[(1S,4R)-2,3-dideoxy-2,3-didehydro-2-fluoro-4-thio-β-L-ribofuranosyl]-5-fluoro-cytosine (L-18, FIG. 4a) was made using the general procedure for successive deprotections. The compound L-18 was obtained on 0.346-mmol scale in 88% yield: mp 189~190° C.; $[\alpha]^{24}_D$ 169.2° (c 0.159, MeOH); $UV(H_2O)$ $\lambda_{max}$ 286.0 nm (ε 8,600, pH 2). 282.0 nm (ε 7,500, pH 7), 282.0 nm (ε 6,900, pH 11); $^1H$ NMR (MeOH-$d_4$) δ 8.39 (d, J=6.6 Hz, 1H), 6.92 (s, 1H), 5.84 (s, 1H), 4.17 (s, 1H), 3.84 (dd, J=11.8, 3.7 Hz, 1H), 3.68 (br d, J=10.6, 1H); Anal. Calcd for $C_9H_{10}FN_3O_2S$: C, 41.38; H, 3.47; N, 16.08; S, 12.27. Found: C, 41.45; H, 3.60; N, 15.95; S, 12.14.

Similarly, (+)-1-[(1S,4R)-2,3-dideoxy-2,3-didehydro-2-fluoro-4-thio-β-L-ribofuranosyl]-thymine (L-19, FIG. 4a) was made using the general procedure of desilylation. The compound L-29 was obtained on 0.248 mmol scale in 91% yield as a white solid: mp 174~176° C.; $[\alpha]^{24}_D$ 50.4° (c 0.180, MeOH); $UV(H_2O)$ $\lambda_{max}$ 268.5 nm (ε 5,700, pH 2). 268.5 nm (ε 5,500, pH 7), 269.0 nm (ε 4,500, pH 11); $^1H$ NMR (MeOH-$d_4$) δ 8.03 (s, 1H), 6.87 (ps t, J=1.0, 1H), 5.86 (s, 1H), 4.17 (m, 1H), 3.84 (dd, J=11.9, 4.0 Hz, 1H), 3.77 (ddd, J=11.9, 3.7, 1.7 Hz, 1H), 1.88 (d, J=1.2, 3H); Anal. Calcd for $C_{10}H_{11}FN_2O_3S.0.35Et_2O$: C, 48.18; H, 5.14; N, 9.86; S, 11.28. Found: C, 48.49; H, 4.88; N, 10.07; S, 11.59.

(+)-1-[(1S,4R)-2,3-dideoxy-2,3-didehydro-2-fluoro-4-thio-β-L-ribofuranosyl]-uracil (L-20, FIG. 4a) was made using the general procedure for desilylation reaction. The compound L-20 was obtained on 0.280-mmol scale in 92% yield: mp 184~185° C.; $[\alpha]^{24}_D$ 132.9° (c 0.103, MeOH); UV(H$_2$O) λmax 263.0 nm (ε 9,100, pH 2). 263.0 nm (ε 9,700, pH 7), 263.5 nm (ε 7,800, pH 11); $^1$H NMR (MeOH-d$_4$) δ 8.11 (dd, J=8.1, 0.8 Hz, 1H), 6.87 (s, 1H), 5.89 (s, 1H), 5.77 (d, J=8.1 Hz, 1H), 4.19~4.13 (m, 1H), 3.80 (dd, J=11.7, 4.5 Hz, 1H), 3.71 (ddd, J=11.7, 4.1, 1.4 Hz, 1H); Anal. Calcd for C$_9$H$_9$FN$_2$O$_3$S.0.03CHCl$_3$: C, 43.76; H, 3.67; N, 11.30; S, 12.94. Found: C, 43.77; H, 3.91; N, 11.13; S, 12.62.

A similar procedure can be used for analogous desilylations of tert-butyldiphenyl ethers by using TBAF.

Example 38

(+)-9-[(1R,2R,4S)-5-O-(tert-butyldiphenylsilyl)-2,3-dideoxy-2-fluoro-2-phenyl-selenyl-4-thio-β-L-ribofuranosyl]-6-chloropurine (D-21, FIG. 4a)

A mixture of 6-chloropurine (0.947 g, 6.12 mmol) and ammonium sulfate (0.135 g, 1.02 mmol) in 60 mL of HMDS was refluxed for 5 hours. HMDS was evaporated to give yellow solid. To this flask containing the silylated 6-chloropurine, a solution of the acetate D-8 (1.2 g, 2.04 mmol) in 1,2-dichloroethane (30 mL) was added. The resulting slurry was cooled to −25° C. and TMSOTf (0.74 mL, 4.08 mmol) was added dropwise at −25° C. The reaction mixture was stirred for 3 hours at −25~−10° C., for 8 hours at room temperature, and for 5 hours at 40° C. The resulting mixture was diluted with 300 mL of CH$_2$Cl$_2$, washed with aqueous NaHCO$_3$, dried over MgSO$_4$, filtered and concentrated. The crude product was purified by silica gel column chromatography with 11% EtOAc in hexanes to give compound D-21 (1.01 g, 1.48 mmol, 73% yield) as a pale yellow foam. $[\alpha]^{22}_D$ 75.4° (c 1.08, CHCl$_3$); UV(CH$_2$Cl$_2$) $\lambda_{max}$ 264.5 nm; $^1$H NMR (CDCl$_3$) δ 8.69 (s, 1H), 8.31 (d, J=2.9 Hz, 1H), 7.70~7.13 (m, 15H), 6.63 (d, J=14.7 Hz, 1H), 3.96 (ps t, J=8.2 Hz, 1H), 3.88 (ps td, J=7.6, 1.8 Hz, 1H), 3.80~3.73 (m, 1H), 2.75~2.63 (m, 1H), 2.60 (td, J=14.7, 7.8 Hz, 1H), 1.05 (s, 9H); $^{13}$C NMR (CDCl$_3$) δ 151.84, 150.87, 144.98 (d, J=5.7 Hz), 136.32, 135.60, 135.53, 132.85, 132.76, 131.21, 130.02, 129.96, 129.44, 128.99, 128.79, 127.82, 124.34, 105.10 (d, J=248.1 Hz), 66.64, 65.68 (d, J=20.3 Hz), 47.33, 41.68 (d, J=20.7 Hz), 26.74, 19.17; Anal. Calcd for C$_{32}$H$_{32}$ClFN$_4$OSSeSi.0.5EtOAc: C, 56.23; H, 5.00; N, 7.71; S, 4.42. Found: C, 56.66; H, 5.26; N, 7.40; S, 4.51.

A similar procedure for the condensation reaction of the acetate D-8 can be done with the other purines.

For example, (+)-9-[(1R,2R,4S)-5-O-(tert-butyldiphenylsilyl)-2,3-dideoxy-2-fluoro-2-phenylselenyl-4-thio-β-D-ribofuranosyl]-6-chloro-2-fluoropurine (D-22, FIG. 3b) was made using the same general procedure for condensation reaction of the acetate D-8. The compound D-22 was obtained on 1.70-mmol scale in 67% yield. $[\alpha]^{23}_D$ 81.0° (c 1.37, CHCl$_3$); UV(CHCl$_3$) $\lambda_{max}$ 270.0 nm; $^1$H NMR (CDCl$_3$) δ 8.27 (d, J=2.9 Hz 1H), 7.70~7.14 (m, 15H), 6.45 (d, J=14.0 Hz, 1H), 3.97 (dd, J=9.7, 7.3 Hz, 1H), 3.89 (ps td, J=7.6, 1.2 Hz, 1H), 3.80~3.72 (m, 1H), 2.76~2.63 (m, 1H), 2.60 (td, J=14.8, 7.9 Hz, 1H), 1.06 (s, 9H); $^{13}$C NMR (CDCl$_3$) δ 157.00 (d, J=220.8 Hz), 153.53 (d, J=17.1 Hz), 152.4 (d, J=17.3 Hz), 145.53, 136.26, 135.59, 135.52, 132.80, 132.70, 130.03, 129.97, 129.79 (d, J=4.9 Hz), 129.49, 129.00, 127.83, 124.19, 104.99 (d, J=248.5 Hz), 66.53, 65.90 (d, J=20.7 Hz), 47.36, 41.48 (d, J=20.7 Hz), 26.75, 19.17; Anal. Calcd for C$_{32}$H$_{31}$ClF$_2$N$_4$OSSeSi.0.2Hexane: C, 55.58; H, 4.75; N, 7.81; S, 4.47. Found: C, 55.55; H, 4.68; N, 7.74; S, 4.36.

Example 39

Figure 4B:
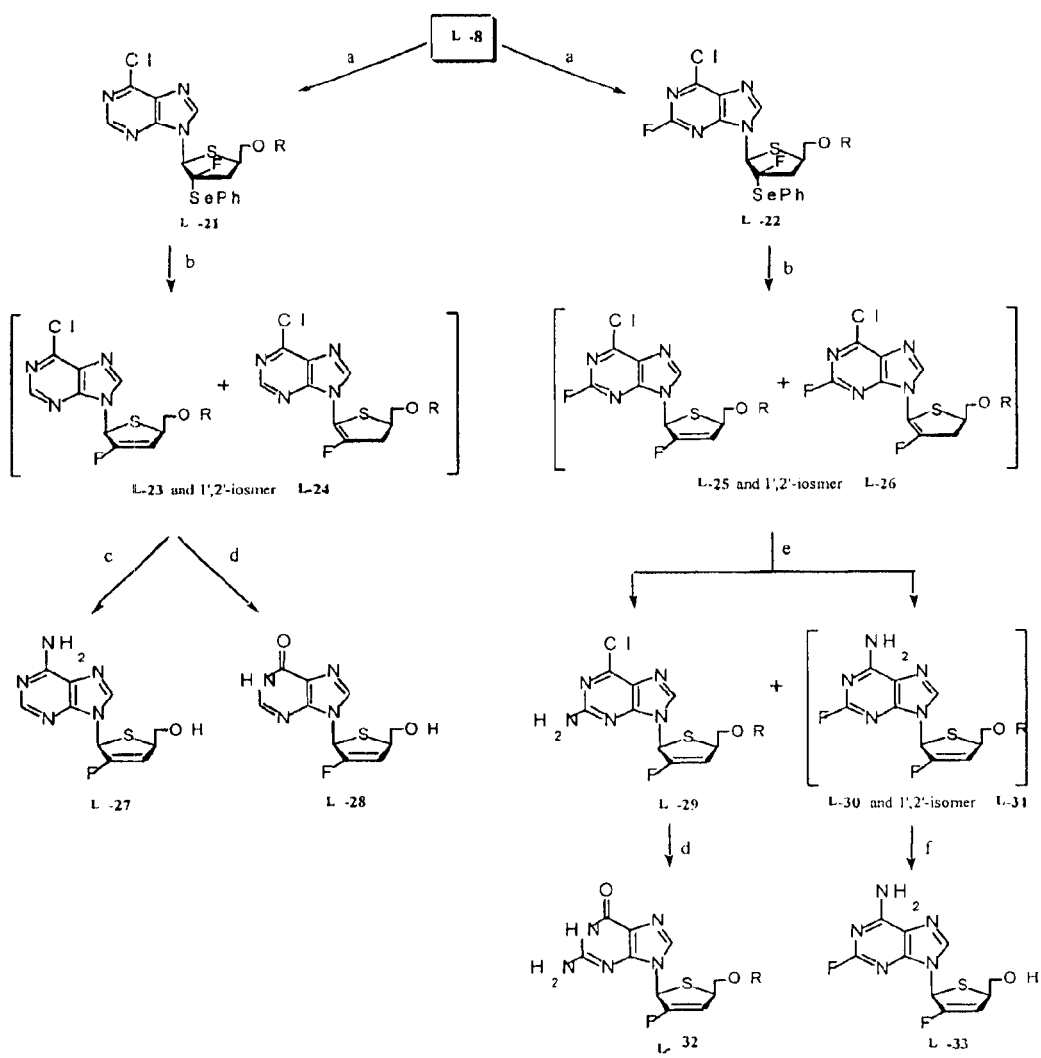

(−)-9-[(1S,2S,4R)-5-O-(tert-butyldiphenylsilyl)-2,3-dideoxy-2-fluoro-2-phenylselenyl-4-thio-β-L-ribofuranosyl]-6-chloropurine (L-21, FIG. 4b)

A mixture of 6-chloropurine (0.789 g, 5.10 mmol) and ammonium sulfate (0.112 g, 0.85 mmol) in 30 mL of HMDS was refluxed for 5 hours. HMDS was evaporated to give yellow solid. To this flask containing the silylated 6-chloropurine, a solution of the acetate L-8 (1.0 g, 1.70 mmol) in 1,2-dichloroethane (30 mL) was added. The resulting slurry was cooled to −25° C. and TMSOTf (0.62 mL, 3.40 mmol) was added dropwise at −25° C. The reaction mixture was stirred for 3 hours at −25~−10° C., for 8 hours at room temperature, and for 5 hours at 40° C. The resulting mixture was diluted with 300 mL of CH$_2$Cl$_2$, washed with aqueous NaHCO$_3$, dried over MgSO$_4$, filtered and concentrated. The crude product was purified by silica gel column chromatography with 11% EtOAc in hexanes to give compound L-21 (0.754 g, 1.10 mmol, 65% yield) as a pale yellow foam. $[\alpha]^{24}_D$ −90.0° (c 1.287, CHCl$_3$); UV(CH$_2$Cl$_2$) $\lambda_{max}$ 264.5 nm; $^1$H NMR (CDCl$_3$) δ 8.60 (s, 1H), 8.23 (d, J=1.7 Hz, 1H), 7.63~7.01 (m, 15H), 6.55 (d, J=14.7 Hz, 1H), 3.88 (ps t, J=8.5 Hz, 1H), 3.80 (ps t, J=8.7 Hz, 1H), 3.72~3.62 (m, 1H), 2.67~2.46 (m, 2H), 0.96 (s, 9H); $^{13}$C NMR (CDCl$_3$) δ 151.76, 151.73, 150.77, 144.92 (d, J=5.7 Hz), 136.24, 135.53, 135.46, 132.77, 132.68, 131.13, 129.95, 129.89, 129.35, 128.91, 127.75, 124.26, 105.04 (d, J=248.1 Hz), 66.56, 65.60 (d, J=20.4 Hz), 47.30, 41.59 (d, J=20.9 Hz), 26.69, 19.10; Anal. Calcd for C$_{32}$H$_{32}$ClFN$_4$OSSeSi: C, 56.34; H, 4.73; N, 8.21; S, 4.70. Found: C, 56.00; H, 4.81; N, 8.04; S, 4.73.

A similar procedure for the condensation reaction of the acetate L-8 can be done with the other purines.

(−)-9-[(1S,2S,4R)-5-O-(tert-butyldiphenylsilyl)-2,3-dideoxy-2-fluoro-2-phenylselenyl-4-thio-β-L-ribofuranosyl]-6-chloro-2-fluoropurine (L-22, FIG. 4b) was made using the general procedure for condensation reaction of the acetate L-8 with purines. The compound L-22 was obtained on 1.70-mmol scale in 66% yield. $[\alpha]^{24}_D$ −86.5° (c 1.44, CHCl$_3$); UV(CHCl$_3$) $\lambda_{max}$ 266.0 nm; $^1$H NMR (CDCl$_3$) δ 8.20 (s, 1H), 7.62~7.06 (m, 15H), 6.37 (d, J=13.9 Hz, 1H), 3.89 (dd, J=9.7, 6.9 Hz, 1H), 3.80 (td, J=7.8, 1.3 Hz, 1H), 3.72~3.64 (m, 1H), 2.68~2.57 (m, 1H), 2.52 (td, J=12.9, 7.7 Hz, 1H), 0.98 (s, 9H); $^{13}$C NMR (CDCl$_3$) δ 157.03 (d, J=220.8 Hz), 153.55 (d, J=16.7 Hz), 152.44 (d, J=17.3 Hz), 145.53, 136.28, 135.61, 135.54, 132.82, 132.72, 130.05, 129.99, 129.80 (d, J=4.6 Hz), 129.51, 129.03, 127.84, 124.20, 105.00 (d, J=248.3 Hz), 66.56, 65.92 (d, J=21.1 Hz), 47.38, 41.51 (d, J=20.9 Hz), 26.76, 19.19; Anal. Calcd for C$_{32}$H$_{31}$ClF$_2$N$_4$OSSeSi: C, 54.89; H, 4.46; N, 8.00; S, 4.58. Found: C, 54.81; H, 4.64; N, 7.81; S, 4.63.

Example 40

Figure 3B:
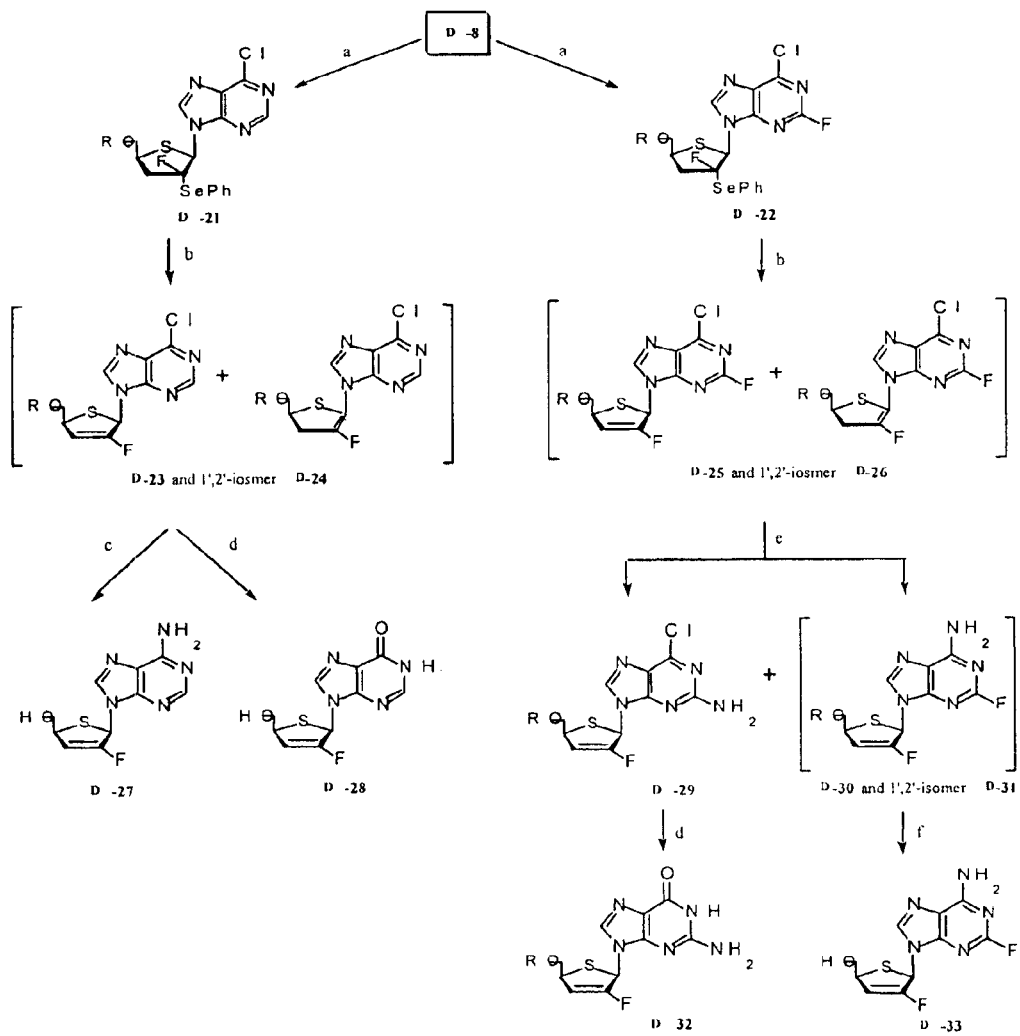

(−)-9-[(1R,4S)-2,3-dideoxy-2,3-didehydro-2-fluoro-4-thio-β-D-ribofuranosyl]-adenine (D-27, FIG. 3b)

A mixture of compound D-23 and compound D-24 (0.342 g, 0.65 mmol) was treated with methanolic ammonia at 80° C. for 12 hours using steel bomb. Solvent was evaporated and the residue was dried under vacuum for 3 hours. A solution of the dried crude product in 30 mL of THF was treated with 0.3 mL of 1M TBAF in THF at room temperature for 3 hours. The resulting mixture was concentrated and purified by preparative TLC chromatography with 5~10% MeOH in CH$_2$Cl$_2$ to give the desired compound D-27 (0.099 g, 0.37 mmol 57% yield) as a white solid. mp 190~191° C.; $[\alpha]^{25}{}_D$ −33.7° (c 0.164, 7:1 CH$_2$Cl$_2$:MeOH); UV(H$_2$O) $\lambda_{max}$ 257.5 nm ($\epsilon$ 9,600, pH 2). 259.0 nm ($\epsilon$ 9,500, pH 7), 259.0 nm ($\epsilon$ 9,800, pH 11); $^1$H NMR (MeOH-d$_4$) δ 8.52 (s, 1H), 8.20 (s, 1H), 6.88 (s, 1H), 5.93 (s, 1H), 4.31~4.24 (m, 1H), 3.90 (dd, J=11.6, 4.4 Hz, 1H), 3.81 (ddd, J=11.5, 4.1, 1.2 Hz, 1H); $^{13}$C NMR (MeOH-d$_4$) δ 157.43, 156.31 (d, J=277.9 Hz), 153.98, 150.51, 141.22, 120.10, 111.65 (d, J=17.1 Hz), 65.63, 60.38 (d, J=24.7 Hz), 49.73 (d, J=7.7 Hz); Anal. Calcd for C$_{10}$H$_{10}$FN$_5$OS.0.06Et$_2$O: C, 45.26; H, 3.93; N, 25.77; S, 11.80. Found: C, 45.33; H, 4.07; N, 25.38; S, 11.59.

Example 41

(−)-9-[(1S,4R)-2,3-dideoxy-2,3-didehydro-2-fluoro-4-thio-β-L-ribofuranosyl]adenine (L-27, FIG. 4b)

A mixture of compound L-23 and compound L-24 (0.241 g, 0.46 mmol) was treated with methanolic ammonia at 80° C. for 12 hours using steel bomb. Solvent was evaporated and the residue was dried under vacuum for 3 hours. A solution of the dried crude product in 30 mL of THF was treated with 0.5 mL of 1M TBAF in THF at room temperature for 3 hours. The resulting mixture was concentrated and purified by preparative TLC chromatography with 5~10% MeOH in CH$_2$Cl$_2$ to give the desired compound L-27 (0.075 g, 0.28 mmol 61% yield) as a white solid: mp 192~194° C.; $[\alpha]^{26}{}_D$ −38.1° (c 0.165, MeOH); UV(H$_2$O) $\lambda_{max}$ 258.0 nm ($\epsilon$ 9,500, pH 2). 259.0 nm ($\epsilon$ 8,900, pH 7), 259.5 nm ($\epsilon$ 8,600, pH 11); $^1$H NMR (MeOH-d$_4$) δ 8.52 (s, 1H), 8.20 (s, 1H), 6.89 (s, 1H), 5.93 (s, 1H), 4.28 (s, 1H), 3.90 (dd, J=11.5, 4.2 Hz, 1H), 3.81 (dd, J=11.4, 3.2 Hz, 1H); $^{13}$C NMR (MeOH-d$_4$) δ 157.46, 156.31 (d, J=278.2 Hz), 154.01, 150.51, 141.21, 120.10, 111.64 (d, J=17.0 Hz), 65.65, 60.38 (d, J=24.6 Hz), 49.81 (d, J=9.1 Hz); HRMS (FAB) obsd, m/z 268.0669, calcd for C$_{10}$H$_{11}$FN$_5$OS, m/z 268.0668 (M+H)$^+$; Anal. Calcd for C$_{10}$H$_{10}$FN$_5$OS.0.3CH$_3$OH: C, 44.68; H, 4.08; N, 25.29; S, 11.58. Found: C, 44.49; H, 4.03; N, 25.46; S, 11.33.

Example 42

(+)-9-[(1R,4S)-2,3-dideoxy-2,3-didehydro-2-fluoro-4-thio-β-D-ribofuranosyl]-hypoxanthine (D-28, FIG. 3b)

A mixture of compound D-23 and compound D-24 (0.323 g, 0.62 mmol) in anhydrous MeOH (20 mL) was treated with 2-mercaptoethanol (0.17 mL, 2.46 mmol) and NaOMe (0.136 g, 2.52 mmol) at 60° C. for 24 hours. The resulting mixture was quenched with 0.1 mL of glacial AcOH, concentrated, and filtered through a short pad of silica gel with 4% MeOH in CH$_2$Cl$_2$. The filtrate was concentrated to dryness. The crude product was treated with 0.68 mL of 1M TBAF in THF at room temperature for 3 hours. The reaction mixture was concentrated, and purified by preparative TLC chromatography with 7% MeOH in CH$_2$Cl$_2$ to give the desired compound D)-28 (0.135 g, 0.50 mmol, 81% yield) as a white solid: mp 143~145° C. (dec.); $[\alpha]^{27}{}_D$ 21.5° (c 0.132, 7:1, CH$_2$Cl$_2$:MeOH); UV(H$_2$O) $\lambda_{max}$ 247.5 nm ($\epsilon$ 10,200, pH 2). 248.0 nm ($\epsilon$ 10,000, pH 7), 253.5 nm ($\epsilon$ 10,700, pH 11); $^1$H NMR (MeOH-d$_4$) δ 8.51 (s, 1H), 8.07 (s, 1H), 6.90 (s, 1H), 5.93 (s, 1H), 4.28~4.23 (m, 1H), 3.88 (dd, J=11.7, 4.7 Hz, 1H), 3.80 (dd, J=10.5, 4.0 Hz, 1H); $^{13}$C NMR (MeOH-d$_4$) δ 158.85, 156.22 (d, J=248.4 Hz), 150.04, 147.13, 140.66, 125.29, 111.77 (d, J=17.0 Hz), 65.50, 60.51 (d, J=24.8 Hz), 49.83 (d, J=7.3 Hz); Anal. Calcd for C$_{10}$H$_9$FN$_4$O$_2$S.0.17CH$_2$Cl$_2$: C, 43.21; H, 3.33; N, 19.82; S, 11.34. Found: C, 43.26; H, 3.61; N, 19.61; S, 11.01.

Example 43

(−)-9-[(1S,4R)-2,3-dideoxy-2,3-didehydro-2-fluoro-4-thio-β-L-ribofuranosyl]-hypoxanthine (L-28, FIG. 4b)

A mixture of compound L-23 and compound L-24 (0.216 g, 0.41 mmol) in anhydrous MeOH (20 mL) was treated with 2-mercaptoethanol (0.12 mL, 1.65 mmol) and NaOMe (0.091 g, 1.69 mmol) at 60° C. for 24 hours. The resulting mixture was quenched with 0.1 mL of glacial AcOH, concentrated, and filtered through a short pad of silica gel with 4% MeOH in CH$_2$Cl$_2$. The filtrate was concentrated to dryness. The crude product was treated with 0.84 mL of 1M TBAF in THF at room temperature for 3 hours. The reaction mixture was concentrated, and purified by preparative TLC chromatography with 7% MeOH in CH$_2$Cl$_2$ to give the desired compound L-28 (0.050 g, 0.19 mmol, 46% yield) as a white solid. mp 143~145° C. (dec.); $[\alpha]^{23}{}_D$ −23.7° (c 0.324 7:1, CH$_2$Cl$_2$:MeOH); UV(H$_2$O) $\lambda_{max}$ 246.5 nm ($\epsilon$ 12,000, pH 2). 248.0 nm ($\epsilon$ 10,600, pH 7), 253.5 nm ($\epsilon$ 10,900, pH 11); $^1$H NMR (MeOH-d$_4$) δ 8.51 (s, 1H), 8.07 (s, 1H), 6.90 (s, 1H), 5.93 (s, 1H), 4.26 (s, 1H), 3.88 (dd, J=11.6, 4.7 Hz, 1H), 3.80 (dd, J=10.7, 3.2 Hz, 1H); $^{13}$C NMR (MeOH-d$_4$) δ 158.86, 156.22 (d, J=278.3 Hz), 150.03, 147.13, 140.65, 125.28, 111.76 (d, J=17.1 Hz), 65.48, 60.51 (d, J=24.5 Hz), 49.82 (d, J=7.9 Hz); HRMS (FAB) obsd, m/z 269.0517, calcd for C$_{10}$H$_9$FN$_4$O$_2$S, m/z 269.0509 (M+H)$^+$; Anal. Calcd for C$_{10}$H$_9$FN$_4$O$_2$S.0.63MeOH: C, 44.26; H, 4.03; N, 19.42; S, 11.12. Found. C, 43.86; H, 3.65; N, 19.45; S, 11.09.

In the same way, (+)-9-[(1S,4R)-2,3-dideoxy-2,3-didehydro-2-fluoro-4-thio-β-L-ribofuranosyl]-guanosine (L-32, FIG. 4b) was made using the procedure for the preparation of compound L-28. The compound L-32 was obtained on 0.16-mmol scale in 61% yield: mp 210° C. (dec.); $[\alpha]^{25}{}_D$ 75.2° (c 0.15, DMSO); UV(H$_2$O) $\lambda_{max}$ 256.0 nm ($\epsilon$ 11,100, pH 2). 255.0 nm ($\epsilon$ 12,500, pH 7), 266.0 nm ($\epsilon$ 10,700, pH 11); $^1$H NMR (MeOH-d$_4$) δ 7.98 (s, 1H), 6.61 (s, 1H), 5.83 (s, 1H), 4.22~4.14 (m, 1H), 3.84~3.74 (m, 2H); $^{13}$C NMR (DMSO-d$_6$) δ 160.12, 157.49 (d, J=278.1 Hz), 157.44, 154.47, 138.61, 119.83, 114.34 (d, J=17.0 Hz), 67.90, 61.00 (d, J=24.5 Hz), 51.73 (d, J=7.6 Hz), 44.06 (d, J=9.1 Hz).

Example 44

(−)-2-amino-9-[(1R,4S)-5-O-(tert-butyldiphenylsilyl)-2,3-dideoxy-2,3-didehydro-2-fluoro-4-thio-β-D-ribofuranosyl]-6-chloropurine (D-29, FIG. 3b), 6-amino-9-[(1R,4S)-5-O-(tert-butyldiphenylsilyl)-2,3-dideoxy-2,3-didehydro-2-fluoro-4-thio-β-D-ribofuranosyl]-2-fluoropurine (D-30, FIG. 3b) and 6-amino-9-[(4S)-5-O-(tert-butyldiphenylsilyl)-2,3-dideoxy-1,2-didehydro-2-fluoro-4-thio-β-D-ribofuranosyl]-2-fluoropurine (D-31, FIG. 3b)

Dry ammonia gas was bubbled into a stirred solution of a mixture of compounds D-25 and D-26 (0.430 g, 0.79 mmol) in 1,2-dimethoxyethane (25 mL) at room temperature for 5 hours. The solvent was removed under reduced pressure, and the residue was purified by preparative TLC chromatography with 20% EtOAc in hexanes to give pure compound D-29 (0.190 g, 0.352 mmol, 45% yield) and a mixture of compound D-30 and compound D-31 (0.116 g, 0.22 mmol, 28% yield). For compound D-29: $[\alpha]^{24}_D$ −70.4° (c 0.40, $CH_2Cl_2$); $UV(CH_2Cl_2)$ $\lambda_{max}$ 303.5 nm; $^1H$ NMR ($CDCl_3$) δ 7;74 (s, 1H), 7.68~7.36 (m, 10H), 6.65 (s, 1H), 5.82 (s, 1H), 5.37 (s, 1H), 4.25~4.19 (m, 1H), 3.90 (dd, J=10.1, 7.0 Hz, 1H), 3.81 (dd, J=9.8, 7.4 Hz, 1H), 1.07 (s, 9H); $^{13}C$ NMR ($CDCl_3$) δ 159.11, 154.78 (d, J=281.2 Hz), 153.48, 151.49, 139.92, 135.57, 135.48, 132.76, 132.48, 130.12, 130.09, 127.91, 127.88, 125.30, 109.95 (d, J=16.5 Hz), 68.01, 58.33 (d, J=24.0 Hz), 47.46 (d, J=7.1 Hz), 26.76, 19.19; Anal. Calcd for $C_{26}H_{27}ClFN_5OSSi.0.6CH_2Cl_2.0.5EtOAc$: C, 54.08; H, 5.11; N, 11.03; S, 5.05. Found: C, 53.73; H, 4.99; N, 10.98; S, 5.12: a mixture of compounds D-30 and D-31; $UV(CHCl_3)$ $\lambda_{max}$ 261.0 nm; $^1H$ NMR ($CDCl_3$) for major D-30: δ 7.77 (s, 1H), 7.73~7.38 (m, 10H), 6.71 (s, 1H), 6.41, 6.40 (2s, 2H), 5.82 (s, 1H), 4.27~4.19 (m, 1H), 3.93~3.82 (m, 2H), 1.08 (s, 9H); for minor D-31: δ 7.82 (s, 1H), 7.73~7.38 (m, 10H) 4.00~3.75 (m, 3H), 3.20 (ddd, J=16.5, 9.2, 3.1 Hz, 1H), 2.99 (ddd, J=16.5, 4.9, 1.1 Hz, 1H), 1.08 (s, 9H).

Example 45

(+)-2-amino-9-[(1S,4R)-5-O-(tert-butyldiphenylsilyl)-2,3-dideoxy-2,3-didehydro-2-fluoro-4-thio-β-L-ribofuranosyl]-6-chloropurine (L-29, FIG. 4b), 6-amino-9-[(1S,4R)-5-O-(tert-butyldiphenylsilyl)-2,3-dideoxy-2,3-didehydro-2-fluoro-4-thio-β-L-ribofuranosyl]-2-fluoro-purine (L-30, FIG. 4b) and 6-amino-9-[(4R)-5-O-(tert-butyldiphenylsilyl)-2,3-dideoxy-1,2-didehydro-2-fluoro-4-thio-β-L-ribofuranosyl]-2-fluoropurine (L-31, FIG. 4b)

Dry ammonia gas was bubbled into a stirred solution of a mixture of compounds L-25 and L-26 (0.430 g, 0.79 mmol) in 1,2-dimethoxyethane (25 mL) at room temperature for 5 hours. The solvent was removed under reduced pressure, and the residue was purified by. preparative TLC chromatography with 20% EtOAc in hexanes to give pure compound L-29 (0.190 g, 0.352 mmol, 45% yield) and a mixture of compound L-30 and compound L-31 (0.106 g, 0.20 mmol, 25% yield). For compound L-29: $[\alpha]^{24}_D$ 74.0° (c 0.236, $CH_2Cl_2$); $UV(CH_2Cl_2)$ $\lambda_{max}$ 300.0 nm; $^1H$ NMR ($CDCl_3$) δ 7.74 (s, 1H), 7.70~7.37 (m, 10H), 6.65 (s, 1H), 5.83 (s, 1H), 5.18 (s, 2H), 4.26~4.22 (m, 1H), 3.90 (dd, J=10.1, 7.2 Hz, 1H), 3.81 (dd, J=9.8, 7.3 Hz, 1H), 1.07 (s, 9H); $^{13}C$ NMR ($CDCl_3$) δ 159.11, 154.78 (d, J=281.2 Hz), 153.48, 151.49, 139.92, 135.57, 135.48, 132.76, 132.48, 130.12, 130.09, 127.91, 127.88, 125.30, 109.95 (d, J=16.5 Hz), 68.01, 58.33 (d, J=24.0 Hz), 47.46 (d, J=7.1 Hz), 26.76, 19.19; Anal. Calcd for $C_{26}H_{27}ClFN_5OSSi.0.3EtOAc$: C, 57.66; H, 5.24; N, 12.36; S, 5.66. Found: C, 57.87; H, 5.35; N, 12.41; S, 5.62: a mixture of compounds L-30 and L-31; $UV(CHCl_3)$ $\lambda_{max}$ 261.0 nm; $^1H$ NMR ($CDCl_3$) for major L-30: δ 7.80 (s, 1H), 7.74~7.31 (m, 10H), 6.95 (br s, 2H), 6.72 (s, 1H), 5.83 (s, 1H), 4.29~4.19 (m, 1H), 3.94 (dd, J=10.2, 6.6 Hz, 1H), 3.87 (dd, J=10.1, 7.1 Hz, 1H), 1.08 (s, 9H); for minor L-31: δ 7.84 (s, 1H), 7.74~7.31 (m, 10H), 6.95 (br s, 2H), 4.02~3.79 (m, 3H), 3.20 (ddd, J=16.5, 9.2, 3.1 Hz, 1H), 3.00 (dd, J=16.7, 4.6 Hz, 1H), 1.08 (s, 9H).

Example 46

(−)-9-[(1R,4S)-2,3-dideoxy-2,3-didehydro-2-fluoro-4-thio-β-D-ribofuranosyl]-guanosine (D-32, FIG. 3b)

See the procedure for the preparation of compound D-28. The title compound D-32 was obtained on 0.29-mmol scale in 61% yield: mp 210° C. (dec.); $[\alpha]^{25}_D$ −73.7° (c 0.152, DMSO); $UV(H_2O)$ $\lambda_{max}$ 254.0 nm (ε 11,600, pH 2). 255.0 nm (ε 12,400, pH 7), 265.0 nm (ε 12,500, pH 11); $^1H$ NMR (MeOH-$d_4$) δ 8.14 (s, 1H), 6.73 (s, 1H), 5.93 (s, 1H), 4.27~4.23 (m, 1H), 3.86 (dd, J=11.3, 4.6 Hz, 1H), 3.81 (ddd, J=11.5, 4.6, 1.1 Hz, 1H); $^{13}C$ NMR (DMSO-$d_6$) δ 160.12, 157.49 (d, J=278.1 Hz), 157.44, 154.47, 138.61, 119.83, 114.34 (d, J=17.0 Hz), 67.90, 60.99 (d, J=24.5 Hz), 51.73 (d, J=7.6 Hz), 44.06 (d, J=9.1 Hz); Anal. Calcd for $C_{10}H_{10}FN_5O_2S.0.11CHCl_3$: C, 40.97; H, 3.44; N, 23.63; S, 10.82. Found: C, 41.35; H, 3.62; N, 23.32; S, 11.09.

Example 47

(−)-9-[(1S,4R)-2,3-dideoxy-2,3-didehydro-2-fluoro-4-thio-β-L-ribofuranosyl]-2-fluoro-adenosine (L-33, FIG. 4b)

See the general procedure of desilylation. The title compound L-33 was obtained on 0.20-mmol scale in 70% yield: mp>300° C.; $[\alpha]^{26}_D$ −17.8° (c 0.200, MeOH); $UV(H_2O)$ $\lambda_{max}$ 260.5 nm (ε 12,700, pH 2). 260.5 nm (ε 12,700, pH 7), 261.5 nm (ε 12,200, pH 11); $^1H$ NMR (MeOH-$d_4$) δ 8.44 (s, 1H), 6.77 (s, 1H), 5.92 (s, 1H), 4.28~4.21 (m, 1H), 3.89 (dd, J=11.6, 4.7 Hz, 1H), 3.85~3.79 (m, 1H); $^{13}C$ NMR (DMSO-$d_6$) δ 160.12; Anal. Calcd for $C_{10}H_9F_2N_5OS.0.24Et_2O$: C, 43.44; H, 3.79; N, 23.11; S, 10.58. Found: C, 43.30; H, 3.78; N, 23.47; S, 10.28.

Example 48

Figure 5:
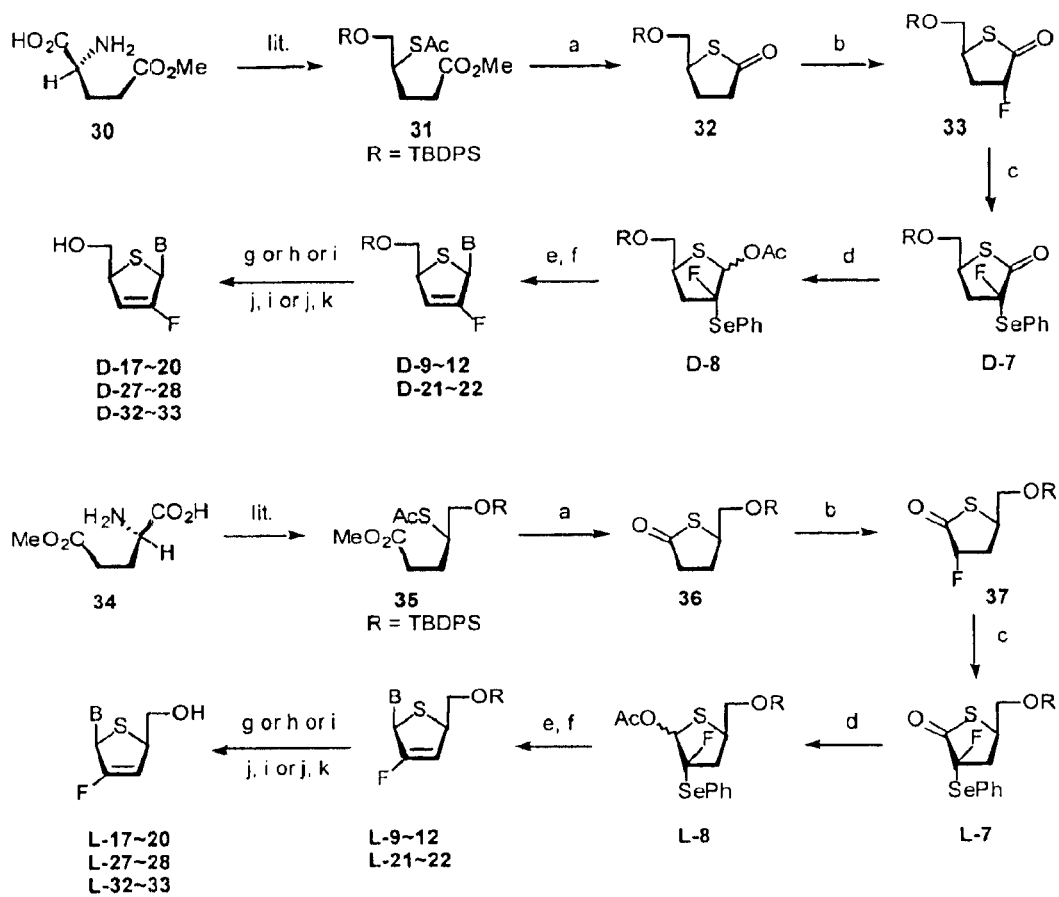
FIG. 5 is a nonlimiting illustrative example of the synthesis of β-D- and β-L-2',3'-didehydro-2',3'-dideoxy-2'-fluoro-4'-thionucleosides from L- and D-glutamic acid, respectively, according to the present invention.

4(S)-(Acetylthio)-5-[(tert-butyldiphenylsilyl)oxy] pentanoic acid methyl ester (31, FIG. 5)

The title compound was prepared from L-glutarnic acid according to the following literatures: Cervinka, O.; Hub, L. Asymmetric reactions. XXVII. Absolute configurations of γ-butyrolactone-γ-carboxylic acid and γ-valerolactone-γ-carboxylic acid. *Collect. Czech. Chem. Commun.* 1968, 33, 2927–2932; Hanessian, S.; Murray, P. J. Stereochemical control of nature's biosynthetic pathways: A general strategy for the synthesis of polypropionate-derived structural units from a single chiral progenitor. *Tetrahedron* 1987, 43, 5055–5072; Secrist III, J. A.; Riggs, R. H.; Tiwari, K. N.; Montgomery, J. A. Synthesis and anti-HIV activity of 4'-thio-2',3'-dideoxynucleosides. *J. Med. Chem.* 1992, 35, 533–538.

The L-analogue (compound 35) was prepared from D-glutamic acid using the same procedures as for the D-analogue (see FIG. 5).

Example 49

4(S)-tert-Butyldipbenylsilyloxymethyl-γ-thiobutyrolactone (32, FIG. 5).

A solution of compound 31 (6 g, 13.5 mmol) in toluene (100 mL) was treated with 29.4 mL of 1 M DIBAL-H in hexane at −78° C. for 1 hour. The reaction was quenched with 7.2 mL of MeOH and warmed up to room temperature for 1 hour and aqueous $NaHCO_3$ (15 mL) and EtOAc (90 mL) were added to the mixture. The resulting mixture was filtered and the filtrate was concentrated to dryness. The crude thiolactol was treated with $Ac_2O$ (12.75 mL) and DMSO (13.5 mL) at room temperature for 24 hours. The reaction mixture was poured to a separatory funnel containing ice-cooled water (100 mL) and extracted with ethyl ether (3×120 mL). The combined organic layer was washed with water (3×100 mL), dried over $Na_2SO_4$, filtered, concentrated and purified by silica gel column chromatography with 5% Et₂O in hexanes to give the product 32 (2.69 g, 57% yield) as a yellow oil. $^1$H NMR (CDCl₃) δ 7.68–7.65, 7.47–7.39 (2m, 10H), 3.81–3.50 (m, 3H), 2.22–2.13 (m, 2H), 2.03–1.97(m, 2H), 1.06 (s, 9H).

The L-analogue (compound 36) was prepared from 35 using the same procedures as for the D-analogue (see FIG. 5).

Example 50

4(S)-tert-butyldiphenylsilyloxymethyl-2-phenylselenyl-γ-thiobutyrolactone (33, FIG. 5)

To a solution of compound 32 (2.223 g, 6 mmol) in THF (30 mL) was added N-fluorodibenzenesulfonimide (NFSi, 1.893 g, 6 mmol). The solution was cooled to −78° C., and LiHMDS (1M solution in THF, 7.2 mL, 7.2 mmol) was added dropwise over a period of 1 hour. After being stirred at −78° C. for 2 hours, the solution was allowed to warm to room temperature and stirred for 1 hour. The reaction was quenched with saturated NH₄Cl (1 mL), and the mixture was poured onto a mixture of EtOAc and saturated NaHCO₃. The organic layer was washed with saturated NaHCO₃ and brine, and dried over Na₂SO₄. After removal of the solvent, the residue was purified by flash chromatography on silica gel column eluting with 5% Et₂O in hexanes to give the product 33 (1.35 g, 58% yield) as a yellow oil. $^1$H NMR (CDCl₃) δ 7.62–7.36 (m, 10H), 5.07 (m, 1H), 3.95–3.77 (m, 3H), 2.70–2.61 (m, 1H), 2.18–2.05 (m, 1H), 1.06 (s, 9H).

The L-analogue (compound 37) was prepared from 36 using the same procedures as for the D-analogue (see FIG. 5).

Example 51

(2R,4S)-(+)-4-tet-butyldiphenylsilyloxymethyl-2-fluoro-2-phenylselenyl-γ-thio-butyro-lactone (D-7, FIG. 5)

To a solution of compound 33 (1.166 g, 3 mmol) in THF (15 mL), 3.6 mL of 1 M LiHMDS in THF was added slowly at −78° C., and the reaction mixture was stirred at −78° C. for 1 hour. TMSCl (0.49 mL, 3.9 mmol) was added dropwise to the reaction mixture and the mixture was allowed to warm to room temperature. The resulting mixture was stirred at room temperature for 30 minutes and cooled to −78° C. A solution of PhSeBr (1.07 g, 4.5 mmol) in THF (6 mL) was rapidly added and the mixture was stirred at −78° C. for 1 hour. The mixture was diluted with ethyl ether (120 mL), washed with water (4×30 mL), dried over Na₂SO₄, filtered, concentrated and purified by silica gel column chromatography with 3% Et₂O in hexanes to give desired product D-7 (1.16 g, 71% yield) as a pale yellow syrup. $^1$H NMR (CDCl₃) δ 7.68–7.35 (m, 15H), 3.96–3.89 (m, 1H), 3.87 (dd, J=10.2 & 5.1 Hz, 1H), 3.80 (dd, J=10.1 & 7.1 Hz, 1H), 2.49 (dd, J=13.4 & 4.0 Hz, 1H), 2.22 (td, J=13.5 & 10.5 Hz, 1H), 1.06 (s, 9H).

The L-analogue (compound L-7) was prepared from 37 using the same procedures as for the D-analogue (see FIG. 5).

The final target compounds (D-17~20, D-27~28, D-32~33, and L-17~20, L-27~28, L-32~33) were synthesized from D-7 and L-7 using the same procedures as described in the previous part.

Example 52

Figure 8:
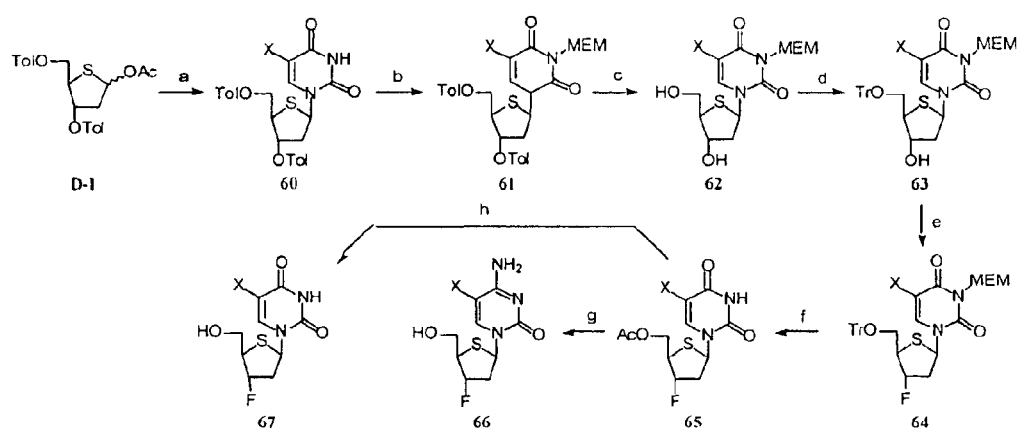
FIG. 8 is a nonlimiting illustrative example of the synthesis of β-D-2',3'-dideoxy-3'-fluoro-4'-thionucleosides, according to the present invention.
Figure 15:
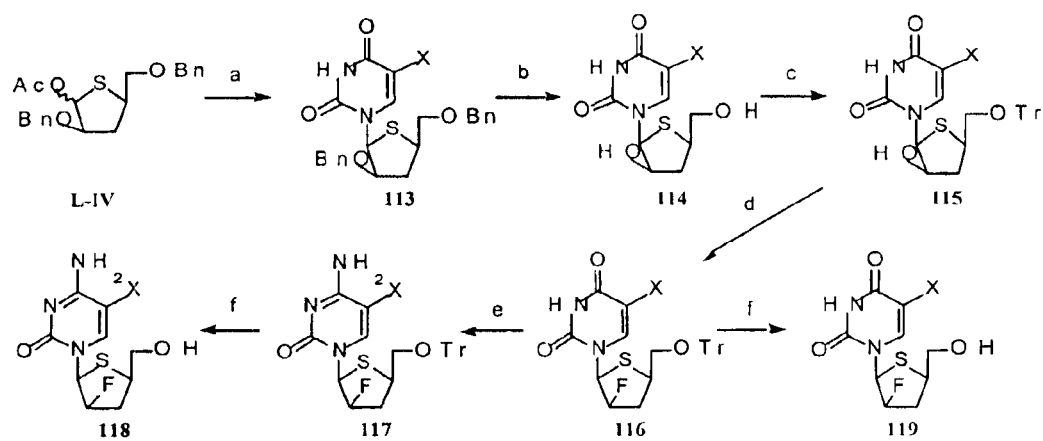
FIG. 15 is a nonlimiting illustrative example of the synthesis of β-L-2',3'-dideoxy-2'-fluoro4'-thionucleosides, according to the present invention.

1-O-Acetyl-2-deoxy-4-thio-3,5-di-O-p-toluoyl-D-erythro-pentofuranoside (D-I, FIG. 8)

Figure 6:
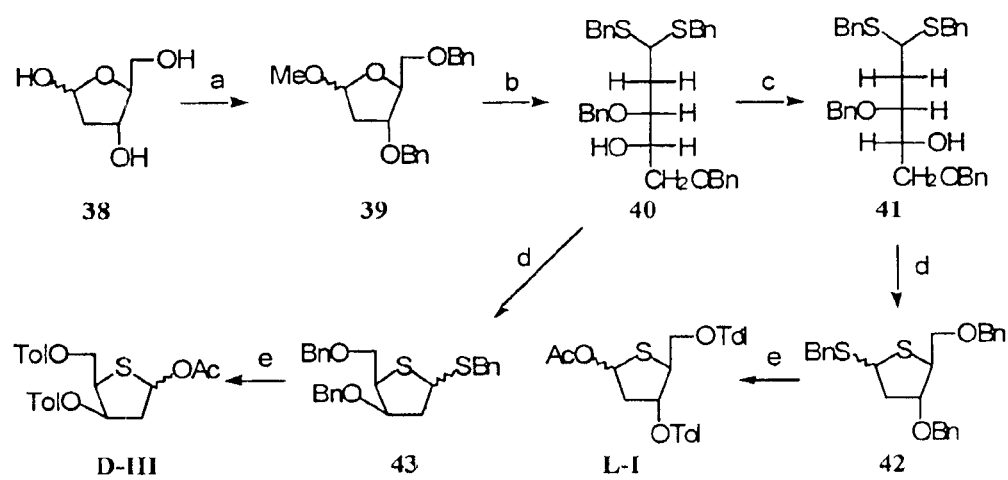
FIG. 6 is a nonlimiting illustrative example of the synthesis of 2-deoxy-4-thio-sugars, according to the present invention.
Figure 7:
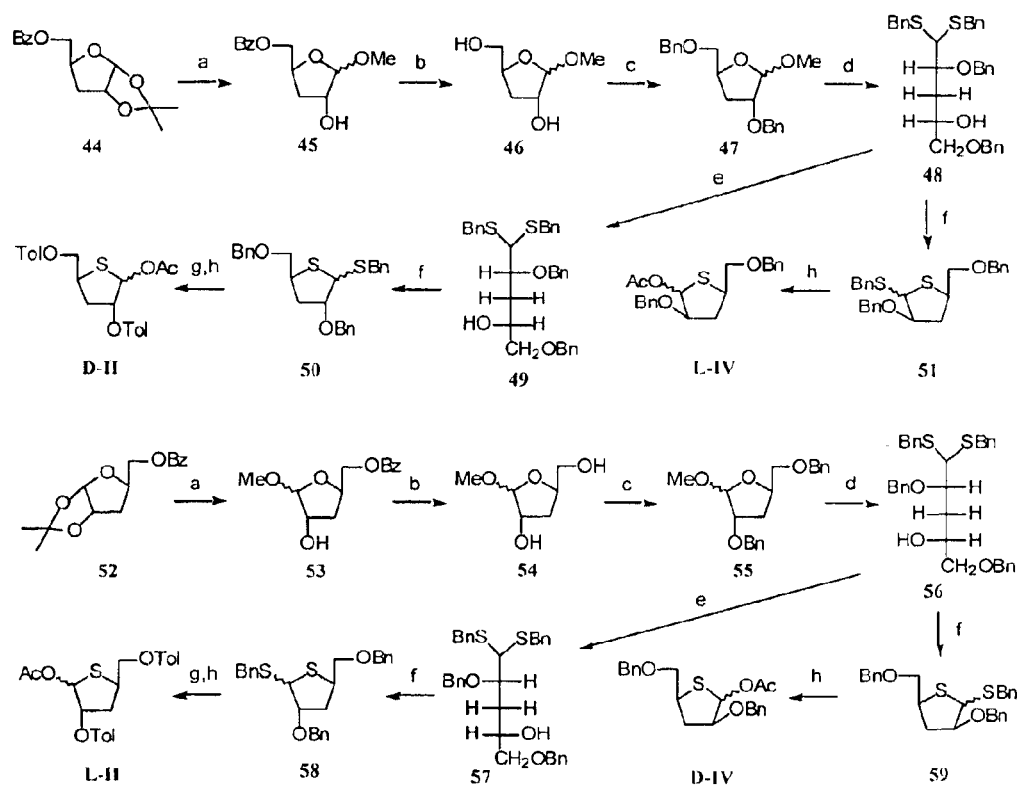
FIG. 7 are nonlimiting illustrative examples of the synthesis of 3-deoxy-4-thio-sugars, according to the present invention.

1-O-Acetyl-2-deoxy-4-thio-3,5-di-O-p-toluoyl-D-erythro-pentofuranoside (D-I, FIG. 8), as well as 1-O-acetyl-2-deoxy-4-thio-3,5-di-O-p-toluoyl-L-threo-pentofuranoside (L-III, FIG. 13) and thiolactol acetates D-II, D-III, D-IV, L-I, L-II and L-IV (FIGS. 6 and 7) were prepared according to following literature references: Sccrist III, J. A.; Tiwari, K. N.; Riordan, J. M.; Montgomery, J. A. Synthesis and biological activity of 2'-deoxy-4-'thio pyrimidine nucleosides, *J. Med. Chem.* 1991, 34, 2361–2366; Tiwari, K. N.; Montgomery, J. A.; Secrist III, J. A. The synthesis and biological activity of 1-(2-deoxy-4-thio-a-L-threo-pentofuranosyl)-thymine, *Nucleosides & Nucleotides,* 1993, 12(8), 841–846.

Example 53

1-(2-Deoxy-4-thio-3,5-di-O-toluoyl-β-D-erythro-pentofuranosyl)-5-fluorouracil (60, X=F, FIG. 8)

A suspension of 5-fluorouracil (975 mg, 7.5 mmol) and ammonium sulfate (10 mg) in HMDS (40 mL) was heated at reflux under nitrogen atmosphere for 2 hours. The excess of HMDS was evaporated in vacuo. To the residue was added the solution of D-I (2.14 g, 5 mmol) in anhydrous CH₃CN (25 mL). The resulting mixture was cooled to 0° C., and TMSOTf (1.361 g, 6 mmol) was added. The reaction mixture was stirred at 0° C. for 20 minutes, then at room temperature for 2 hours. Then the mixture was diluted with CH₂Cl₂, washed with saturated NaHCO₃, dried over Na₂SO₄, filtered and concentrated to dryness. The residue was purified by flash chromatography on silica gel eluting with CH₂Cl₂MeOH (99:1), and recrystallized from CH₂Cl₂/hexane to give the title compound 60, where X is fluorine (872 mg, 35%), as a solid. $^1$H NMR (CDCl₃) δ 7.98 (d, 1H, H-6), 7.96–7.25 (m, 8H, aromatic), 6.69 (dd, 1H, H-1'), 5.76 (m, 1H, H-3'), 4.68 (m, 2H, H-5'), 4.05 (m, 1H, H-4'), 2.75, 2.41 (2m, 2H, H-2'), 2.42 (s, 6H, 2 CH₃).

Compounds 60, where X is methyl, 68, 76, 84, 92, 99, 106 and 113 (see FIGS. 8, 9, 10, 11, 12, 13, 14 and 15 respectively) were prepared utilizing similar procedure as above described for 60, where X is fluorine.

Example 54

1-[2-Deoxy-N³-(2-methoxyethoxymethyl)-4-thio-3,5-di-O-toluoyl-β-D-erythro-pentofuranosyl]-5-fluorouracil (61, X=F, FIG. 8)

To a solution of 60, where X is fluorine (748 mg, 1.5 mmol), in dry THF (8 mL) was added Et₃N (455 mg, 4.5 mmol), followed by MEMCl (280 mg, 2.25 mmol). The mixture was heated at reflux for 2 hours, and then evaporated to dryness. The residue was dissolved in CH₂Cl₂, washed with water, dried, concentrated in vacuo, and purified by column chromatography (hexane/EtOAc, 9:1) to give the title compound 61, where X is fluorine (651 mg, 74%), as a solid. $^1$H NMR (CDCl₃) δ 7.99 (d, 1H, H-6), 7.96–7.25 (m, 8H, aromatic), 6.69 (dd, 1H, H-1'), 5.76 (m, 1H, H-3'), 4.66 (m, 2H, H-5'), 4.05 (m, H, H-4'), 3.82–3.51 (m, 4H, OCH₂CH₂O), 3.31 (s, 3H, OCH₃), 2.75, 2.41 (2m, 2H, H-2'), 2.42 (s, 6H, 2 CH₃).

Compounds 61, where X is methyl, 69, 77 and 85 (see FIGS. 8, 9, 10 and 11, respectively) were prepared utilizing similar procedure as above described for 61, where X is fluorine.

Example 55

1-[2-Deoxy-N³-(2-methoxyethoxymethyl)-4-thio-β-D-erythro-pentofuranosyl]-5-fluorouracil (62, X=F, FIG. 8)

To a solution of 61, where X is fluorine (587 mg, 1 mmol), in anhydrous MeOH (10 mL) at room temperature NaOMe (1 M solution in MeOH, 3 mL, 3 mmol) was added, and the reaction mixture was stirred at room temperature for 1 hour. The mixture was neutralized by addition of Dowex 50 W and filtered. The resin was washed with MeOH, and the combined filtrate was concentrated. The residue was purified by flash chromatography on silica gel eluting with $CH_2Cl_2$/MeOH (4:1) to give the title compound 62, where X is fluorine (322 mg, 92%), as a solid. $^1H$ NMR (DMSO-$d_6$) δ 8.16 (d, 1H, H-6), 6.24 (dd, 1H, H-1'), 5.30–5.21 (m, 2H, OH-3' and OH-5'), 4.36 (m, 1H, H-3'), 3.51–3.81 (m, 6H, $OCH_2CH_2O$ and H-5'), 3.33 (s, 3H, $OCH_3$), 3.31 (m, 1H, H-4'), 2.23 (m, 2H, H-2').

Compounds 62, where X is methyl, 70, 78, 86, 93 and 100 (see FIGS. 8, 9, 10, 11, 12 and 13 respectively) were prepared utilizing similar procedure as above described for 62, where X is fluorine.

Example 56

1-[2-Deoxy-$N^3$-(2-methoxyethoxymethyl)-4-thio-5-O-trityl-β-D-erythro-pentofurunosyl]-5-fluorouracil (63, X=F, FIG. 8)

A mixture of 62, where X is fluorine (701 mg, 2 mmol), and triphenylmethyl chloride (669 mg, 2.4 mmol) in anhydrous pyridine (10 mL) was heated at reflux for 3 hours. Then the mixture was cooled to room temperature, and slowly poured into ice-water with stirring. The precipitate was filtered off, washed with water, dried under vacuum, and crystallized from acetone/hexane to give the title compound 63, where X is fluorine (1.02 g, 86%), as a solid. $^1H$ NMR (DMSO-$d_6$) δ 8.12 (d, 1H, H-6), 7.40–7.23 (m, trityl), 6.24 (dd, 1H, H-1'), 5.25–5.21 (m, 1H, OH-3'), 4.35 (m, 1H, H-3'), 3.81–3.50 (m, 6H, $OCH_2CH_2O$ and H-5'), 3.32 (s, 3H, $OCH_3$), 3.30 (m, 1H, H-4'), 2.23 (m, 2H, H-2').

Compounds 63, where X is methyl, 71, 79, 87, 94, 101, 108 and 115 (see FIGS. 8, 9, 10, 11, 12, 13, 14 and 15 respectively) were prepared utilizing similar procedure as above described for 63, where X is fluorine.

Example 57

1-[2,3-Dideoxy-3-fluoro-$N^3$-(2-methoxyethoxymethyl)-4-thio-5-O-trityl-β-D-erythro-pentofuranosyl]-5-fluorouracil (64, X=F, FIG. 8)

To a solution of 63, where X is fluorine (889 mg, 1.5 mmol), in anhydrous $CH_2Cl_2$ (10 mL) at −78° C. was added (diethylamino)sulfur trifluoride (764 mg, 4.5 mmol) and the mixture was stirred at −78° C. for 1 hour under nitrogen atmosphere. KF (261 mg, 4.5 mmol) was added to the reaction mixture at −78° C. and the reaction mixture was allowed to warm to room temperature. After stirring at room temperature for 1 hour, saturated aqueous $NaHCO_3$ and $CHCl_3$ were added. The organic phase was washed with saturated $NaHCO_3$, dried over $Na_2SO_4$, and evaporated in vacuo. The residue was purified by flash chromatography on silica gel eluting with $CH_2Cl_2$/MeOH (99:1) to give the title compound 64, where X is fluorine (776 mg, 87%). $^1H$ NMR (DMSO-$d_6$) δ 8.10 (d, 1H, H-6), 7.37–7.26 (m, trityl), 6.26 (dd, 1H, H-1'), 5.34 (dd, 1H, H-3'), 3.81–3.50 (m, 6H, $OCH_2CH_2O$ and H-5'), 3.48 (m, 1H, H-4'), 3.32 (s, 3H, $OCH_3$), 2.45 (m, 2H, H-2').

Compounds 64, where X is methyl, 72, 80 and 88 (see FIGS. 8, 9, 10 and 11 respectively) were prepared utilizing similar procedure as above described for 64, where X is fluorine.

Example 58

1-[5-O-Acetyl-2,3-dideoxy-3-fluoro-4-thio-β-D-erythro-pentofuranosyl]-5-fluoro-uracil (65, X=F, FIG. 8)

To a solution of 64, where X is fluorine (714 mg, 1.2 mmol), in $Ac_2O$ (5 mL) at 0° C. was added $BF_3$-$Et_2O$ (511 mg, 3.6 mmol) followed by LiBr (313 mg, 3.6 mmol). The mixture was stirred at room temperature under nitrogen atmosphere for 3 days and then evaporated to dryness. The residue was extracted with $CHCl_3$, and the extract was washed with water, dried, and evaporated in vacuo. The residue was purified by flash chromatography on silica gel eluting with hexane/EtOAc (4:1) to give the title compound 65, where X is fluorine (242 mg, 66%), as a pale yellow solid. $^1H$ NMR (DMSO-$d_6$) δ 8.13 (d, 1H, H-6), 6.32 (dd, 1H, H-1'), 5.36 (dd, 1H, H-3'), 4.43 (m, 2H, H-5'), 3.49 (m, 1H, H-4'), 2.45 (m, 2H, H-2'), 2.06 (s, 3H, $CH_3$).

Compounds 65, where X is methyl, 73, 81 and 89 (see FIGS. 8, 9, 10 and 11 respectively) were prepared utilizing similar procedure as above described for 65, where X is fluorine.

Example 59

1-[2,3-Dideoxy-3-fluoro-4-thio-β-D-erythro-pentofuranosyl]-5-fluorocytosine (66, X=F, FIG. 8)

To a solution of 65, where X is fluorine (166 mg, 0.54 mmol), in anhydrous $CH_3CN$ (10 mL) and $Et_3N$ (0.4 mL) at 0° C. was added TIPSCl (343 mg, 1.1 mmol) and DMAP(66 mg, 0.54 mmol). The reaction mixture was stirred at room temperature under nitrogen atmosphere for 1 day, and then $NH_4OH$ (28%, 5 mL) was added. After stirring at room temperature for 24 hours, the solvent was removed by evaporation, and the residue was purified by flash chromatography on silica gel eluting with $CH_2Cl_2$/MeOH (95:5) to give the title compound 66, where X is fluorine (81 mg, 57%), as a pale yellow solid. $^1H$ NMR (DMSO-$d_6$) δ 8.18 (d, 1H, H-6), 7.80, 7.60 (2br, 2H, $NH_2$), 6.28 (d, 1H, H-1'), 5.36 (dd, 1H, H-3'), 5.19 (t, 1H, OH-5'), 3.63 (m, 1H, H-4'), 3.60–3.48 (m, 2H, H-5'), 2.40 (m, 2H, H-2').

Compounds 66, where X is methyl, 74, 82, 90, 96, 103, 110 and 117 (see FIGS. 8, 9, 10, 11, 12, 13, 14 and 15 respectively) were prepared utilizing similar procedure as above described for 66, where X is fluorine.

Example 60

1-[2,3-Dideoxy-3-fluoro-4-thio-β-D-erytro-pentofuranosyl]-5-fluorouracil (67, X=F, FIG. 8)

A solution of 65, where X is fluorine (61 mg, 0.2 mmol), in 2 M $NH_3$-MeOH (6 mL) was kept in a stoppered flask at room temperature overnight. Evaporation of the solvent and column chromatography ($CH_2Cl_2$/MeOH, 95:5) gave the title compound 67, where X is fluorine (49 mg, 94%), as a white solid. $^1H$ NMR (DMSO-$d_6$) δ 11.76 (br, 1H, NH), 8.26 (d, 1H, H-6), 6.34 (d, 1H, H-1'), 5.36 (dd, 1H, H-3'), 5.17 (t, 1H, OH-5'), 3.65 (m, 1H, H-4'), 3.61–3.47 (m, 2H, H-5'), 2.42 (m, 2H, H-2').

Compounds 67, where X is methyl, 75, 83 and 91 (see FIGS. 8, 9, 10 and 11 respectively) were prepared utilizing similar procedure as above described for 67, where X is fluorine.

Example 61

1-[2,3-Dideoxy-3-fluoro-4-thio-β-D-threo-pentofuranosyl]-5-fluorocytosine (97, X=F, FIG. 12)

A solution of 96, where X is fluorine (101 mg, 0.2 mmol), in. 80% AcOH (5 mL) was heated at 90° C. for 1 hour.

Evaporation followed by co-evaporation with toluene and flash chromatography on silica gel column (CH$_2$Cl$_2$/MeOH 95:5) gave the title compound 97, where X is fluorine (28 mg, 53%), as a white solid. $^1$H NMR (DMSO-d$_6$) δ 7.85 (d, 1H, H-6), 7.82, 7.61 (2br, 2H, NH$_2$), 6.16 (d, 1H, H-1'), 5.35 (dd, 1H, H-3'), 5.19 (t, 1H, OH-5'), 3.64 (m, 1H, H-4'), 3.62–3.50 (m, 2H, H-5'), 2.58, 2.26 (2m, 2H, H-2').

Compounds 97, where X is methyl, 98, 104, 105, 111, 112, 118 and 119 (see FIGS. 12, 13, 14 and 15) were prepared utilizing similar procedure as above described for 97, where X is fluorine.

Example 62

1-(3-Deoxy-4-thio-β-D-threo-pentofuranosyl)-5-fluorouracil (107, X=F, FIG. 14)

To a solution of 106, where X is fluorine (664 mg, 1.5 mmol), in anhydrous CH$_2$Cl$_2$ (10 mL) at −78° C. was added slowly BBr$_3$ (1 M solution in CH$_2$Cl$_2$, 7.5 mL) and the reaction mixture was stirred at −78° C. under nitrogen atmosphere for 4 hours. The reaction was quenched by addition of MeOH (5 mL), and neutralized by pyridine. After removal of the solvent by evaporation, the residue was purified by flash chromatography on silica gel eluting with CH$_2$Cl$_2$/MeOH (4:1) to give the title compound 107, where X is fluorine (303 mg, 77%). $^1$H NMR (DMSO-d$_6$) δ 8.20 (d, 1H, H-6), 6.24 (dd, 1H, H-1'), 5.65 (br, 1H, OH-2'), 5.19 (t, 1H, OH-5'), 4.01 (m, 1H, H-2'), 3.70–3.58 (m, 2H, H-5'), 3.20 (m, 1H, H-4'), 2.23 (m, 1H, H-3'), 1.76 (m, 1H, H-3').

Compound 107, where X is methyl, and 114 (see FIGS. 14 and 15) was prepared utilizing similar procedure as above described for 107, where X is fluorine.

Elemental Analysis Data D-Enantiomers

| Cmpd No | Formula | Calc for C | Calc for H | Calc for N | Calc for S | Found for C | Found for H | Found for N | Found for S |
|---|---|---|---|---|---|---|---|---|---|
| D-3 | C$_{21}$H$_{25}$FO$_3$Si | 67.71 | 6.76 | —[a] | —[a] | 67.70 | 6.79 | —[a] | —[a] |
| D-4 | C$_{22}$H$_{28}$FIO$_3$Si0.2C$_6$H$_{14}$ | 52.41 | 5.84 | —[a] | —[a] | 52.30 | 5.55 | —[a] | —[a] |
| D-5 | C$_{24}$H$_{31}$FO$_4$SSi | 62.31 | 6.75 | —[a] | 6.93 | 62.03 | 6.63 | —[a] | 6.98 |
| D-6 | C$_{21}$H$_{25}$FO$_2$SSi | 64.01 | 6.48 | —[a] | 8.25 | 64.88 | 6.51 | —[a] | 8.15 |
| D-6a | C$_{21}$H$_{25}$FO$_2$SSi | 64.01 | 6.48 | —[a] | 8.25 | 65.15 | 6.58 | —[a] | 8.12 |
| D-7 | C$_{27}$H$_{29}$FO$_2$SSeSi | 59.65 | 5.38 | —[a] | 5.90 | 60.10 | 5.46 | —[a] | 5.85 |
| L-7 | C$_{27}$H$_{29}$FO$_2$SSeSi0.15SCHCl$_3$ | 58.07 | 5.23 | —[a] | 5.70 | 57.88 | 5.36 | —[a] | 5.76 |
| D-8 | C$_{29}$H$_{28}$FO$_3$SSeSi | 59.27 | 5.66 | —[a] | 5.46 | 59.61 | 5.72 | —[a] | 5.57 |
| D-9 | C$_{38}$H$_{38}$FN$_3$O$_3$SSeSi | 61.44 | 5.16 | 5.66 | 4.32 | 61.52 | 5.42 | 5.47 | 4.21 |
| D-10 | C$_{38}$H$_{37}$F$_2$N$_3$O$_3$SSeSi | 59.99 | 4.90 | 5.52 | 4.21 | 59.96 | 5.07 | 5.42 | 4.23 |
| D-11 | C$_{32}$H$_{35}$FN$_2$O$_3$SSeSi0.4H$_2$O | 58.15 | 5.47 | 4.23 | 4.85 | 58.03 | 5.49 | 4.21 | 4.95 |
| D-12 | C$_{31}$H$_{33}$FN$_2$O$_3$SSeSi | 58.20 | 5.20 | 4.38 | 5.01 | 58.17 | 5.35 | 4.32 | 4.93 |
| D-13 | C$_{32}$H$_{32}$FN$_3$O$_3$SSi | 65.88 | 5.66 | 7.07 | 5.39 | 66.04 | 5.85 | 6.81 | 5.17 |
| D-14 | C$_{32}$H$_{31}$F$_2$N$_3$O$_3$SSi | 63.66 | 5.18 | 6.96 | 5.31 | 63.71 | 5.32 | 6.76 | 5.27 |
| D-15 | C$_{26}$H$_{29}$FN$_2$O$_3$SSi0.6H$_2$O | 61.54 | 6.00 | 5.50 | 6.30 | 61.31 | 5.87 | 5.34 | 6.11 |
| D-16 | C$_{25}$H$_{27}$FN$_2$O$_3$SSi | 62.21 | 5.64 | 5.80 | 6.64 | 62.38 | 5.65 | 5.69 | 6.48 |
| D-17 | C$_9$H$_{10}$FN$_3$O$_2$S0.2H$_2$O | 43.79 | 4.25 | 17.02 | 12.99 | 43.87 | 4.31 | 16.92 | 12.86 |
| D-18 | C$_9$H$_9$F$_2$N$_3$O$_2$S | 41.38 | 3.47 | 16.08 | 12.27 | 41.29 | 3.52 | 15.99 | 12.18 |
| D-19 | C$_{10}$H$_{11}$FN$_2$O$_3$S0.1Et$_2$O | 47.02 | 4.55 | 10.54 | 12.07 | 47.02 | 4.56 | 10.48 | 11.89 |
| D-20 | C$_9$H$_9$FN$_2$O$_3$S0.3CH$_3$OH | 44.00 | 4.05 | 11.04 | 12.63 | 44.01 | 3.89 | 11.22 | 12.76 |
| D-21 | C$_{32}$H$_{32}$ClFN$_4$OSSeSi | 56.34 | 4.73 | 8.21 | 4.70 | 56.69 | 5.12 | 7.95 | 4.51 |
| D-22 | C$_{32}$H$_{31}$ClF$_2$N$_4$OSSeSi0.2C$_6$H$_{14}$ | 55.58 | 4.75 | 7.81 | 4.47 | 55.55 | 4.68 | 7.74 | 4.36 |
| D-23 | C$_{26}$H$_{26}$ClFN$_4$OSSi | 59.47 | 4.99 | 10.67 | 6.11 | 59.58 | 5.03 | 10.41 | 6.09 |
| D-25 | C$_{26}$H$_{25}$ClF$_2$N$_4$OSSi | 57.50 | 4.64 | 10.32 | 5.90 | 57.18 | 4.50 | 10.13 | 5.68 |
| D-27 | C$_{10}$H$_{10}$FN$_5$OS | 44.94 | 3.77 | 26.20 | 12.00 | 45.23 | 4.07 | 25.98 | 11.79 |
| D-28 | C$_{10}$H$_9$FN$_4$O$_2$S | 44.77 | 3.38 | 20.88 | 11.95 | 44.53 | 3.67 | 21.15 | 11.91 |
| D-29 | C$_{26}$H$_{27}$ClFN$_5$OSSi | 57.82 | 5.04 | 12.97 | 5.94 | 57.73 | 4.99 | 12.98 | 5.82 |
| D-32 | C$_{10}$H$_{10}$FN$_5$O$_2$S | 42.40 | 3.56 | 24.72 | 11.32 | 42.27 | 3.74 | 24.56 | 11.09 |
| D-33 | C$_{10}$H$_9$F$_2$N$_5$OS | 42.10 | 3.18 | 24.55 | 11.24 | 42.28 | 3.37 | 24.39 | 11.19 |

[a]Not applicable.

Elemental Analysis Data-L-Enantiomers

| Cmpd No | Formula | Calc for C | Calc for H | Calc for N | Calc for S | Found for C | Found for H | Found for N | Found for S |
|---|---|---|---|---|---|---|---|---|---|
| L-3 | C$_{21}$H$_{25}$FO$_3$Si | 67.71 | 6.76 | —[a] | —[a] | 67.71 | 6.78 | —[a] | —[a] |
| L-4 | C$_{22}$H$_{28}$FIO$_3$Si0.05C$_6$H$_{14}$ | 51.63 | 5.58 | —[a] | —[a] | 51.84 | 5.53 | —[a] | —[a] |
| L-5 | C$_{24}$H$_{31}$FO$_4$SSi | 62.31 | 6.75 | —[a] | 6.93 | 62.36 | 6.69 | —[a] | 7.04 |
| L-6 | C$_{21}$H$_{25}$FO$_2$SSi | 64.91 | 6.48 | —[a] | 8.25 | 65.15 | 6.58 | —[a] | 8.12 |
| L-6a | C$_{21}$H$_{25}$FO$_2$SSi | 64.91 | 6.48 | —[a] | 8.25 | 64.94 | 6.42 | —[a] | 8.16 |
| L-7 | C$_{27}$H$_{29}$FO$_2$SSeSi0.15CHCl$_3$ | 58.07 | 5.23 | —[a] | 5.70 | 57.88 | 5.36 | —[a] | 5.76 |
| L-8 | C$_{29}$H$_{28}$FO$_3$SSeSi | 59.27 | 5.66 | —[a] | 5.46 | 59.24 | 5.68 | —[a] | 5.42 |
| L-9 | C$_{38}$H$_{38}$FN$_3$O$_3$SSeSi0.2Et$_2$O | 61.51 | 5.32 | 5.55 | 4.23 | 61.88 | 5.55 | 5.56 | 4.21 |
| L-10 | C$_{38}$H$_{37}$F$_2$N$_3$O$_3$SSeSi | 59.99 | 4.90 | 5.52 | 4.21 | 59.97 | 5.05 | 5.44 | 4.23 |
| L-11 | C$_{32}$H$_{35}$FN$_2$O$_3$SSeSi | 58.79 | 5.40 | 4.29 | 4.90 | 58.85 | 5.46 | 4.20 | 4.98 |
| L-12 | C$_{31}$H$_{33}$FN$_2$O$_3$SSeSi | 58.20 | 5.20 | 4.38 | 5.01 | 58.18 | 5.33 | 4.33 | 4.95 |
| L-13 | C$_{32}$H$_{32}$FN$_3$O$_3$SSi0.1C$_6$H$_{14}$ | 65.88 | 5.66 | 7.07 | 5.39 | 66.01 | 5.88 | 6.82 | 5.20 |
| L-14 | C$_{32}$H$_{31}$F$_2$N$_3$O$_3$SSi | 63.66 | 5.18 | 6.96 | 5.31 | 63.69 | 5.30 | 6.78 | 5.26 |
| L-15 | C$_{26}$H$_{29}$FN$_2$O$_3$SSi | 62.87 | 5.89 | 5.64 | 6.46 | 62.54 | 5.82 | 5.36 | 6.13 |

-continued

| | | | | | | | | |
|---|---|---|---|---|---|---|---|---|
| L-16 | $C_{25}H_{27}FN_2O_3SSi$ | 62.21 | 5.64 | 5.80 | 6.64 | 62.41 | 5.68 | 5.71 | 6.52 |
| L-17 | $C_9H_{10}FN_3O_2S$ | 44.44 | 4.14 | 17.27 | 13.18 | 44.26 | 3.92 | 16.96 | 13.03 |
| L-18 | $C_9H_9F_2N_3O_2S$ | 41.38 | 3.47 | 16.08 | 12.27 | 41.45 | 3.60 | 15.95 | 12.14 |
| L-19 | $C_{10}H_{11}FN_2O_3S0.35Et_2O$ | 48.18 | 5.14 | 9.86 | 11.28 | 48.49 | 4.88 | 10.07 | 11.59 |
| L-20 | $C_9H_9FN_2O_3S$ | 44.26 | 3.71 | 11.47 | 13.13 | 44.22 | 3.81 | 11.15 | 12.84 |
| L-21 | $C_{32}H_{32}ClFN_3OSSeSi$ | 56.34 | 4.73 | 8.21 | 4.70 | 56.00 | 4.81 | 8.04 | 4.73 |
| L-22 | $C_{32}H_{31}ClF_2N_4OSSeSi$ | 54.89 | 4.46 | 8.00 | 4.58 | 54.81 | 4.64 | 7.81 | 4.63 |
| L-23 | $C_{26}H_{26}ClFN_4OSSi$ | 59.47 | 4.99 | 10.67 | 6.11 | 59.56 | 5.30 | 10.33 | 5.93 |
| L-25 | $C_{26}H_{25}ClF_2N_4OSSi$ | 57.50 | 4.64 | 10.32 | 5.90 | 57.42 | 5.02 | 9.93 | 5.65 |
| L-29 | $C_{26}H_{27}ClFN_5OSSi0.3EtOAc$ | 57.66 | 5.24 | 12.36 | 5.66 | 57.87 | 5.35 | 12.41 | 5.62 |
| L-27 | $C_{10}H_{10}FN_5OS$ | 44.94 | 3.77 | 26.20 | 12.00 | 44.83 | 3.88 | 25.83 | 11.85 |
| L-28 | $C_{10}H_9FN_4O_2S$ | 44.77 | 3.38 | 20.88 | 11.95 | 44.86 | 3.65 | 20.75 | 11.89 |
| L-32 | $C_{10}H_{10}FN_5O_2S0.2H_2O$ | 41.87 | 3.65 | 24.41 | 11.18 | 42.17 | 3.35 | 24.37 | 11.16 |
| L-33 | $C_{10}H_9F_2N_5OS$ | 42.10 | 3.18 | 24.55 | 11.24 | 41.99 | 3.16 | 24.36 | 11.28 |

[a]Not Applicable $^1$H NMR Data[a] DENANTIOMERS

| Cpd | H-1' | H-3' | H-4' | H-5' | Other protons |
|---|---|---|---|---|---|
| D-9 | 6.91(d, J=15.6Hz) | 2.62–2.47 (m) | 3.68–3.58 (m) | 3.87–3.72 (m) | 8.82(brs, 1H), 8.12(d, J=6.5Hz, 1H), 7.92(d, J=7.3Hz, 2H), 7.69–7.27(m, 19H), 1.02(s, 9H) |
| D-10 | 6.73(d, J=16.3Hz) | 2.63–2.46 (m) | 3.67–3.58 (m) | 3.92–3.76 (m) | 12.70(brs, 1H), 8.33(d, J=7.5Hz, 2H), 7.87(dd, J=5.9, 1.7Hz, 1H), 7.72–7.28(m, 18H), 1.07(s, 9H) |
| D-11 | 6.63(d, J=14.7Hz) | 2.55–2.41 (m) | 3.62–3.58 (m) | 3.87–3.72 (m) | 9.26(brs, 1H), 7.72(dd, J=8.2, 2.0Hz, 1H), 7.68–7.30(m, 15H), 5.56(dd, J=8.2, 1.9Hz, 1H), 1.03(s, 9H) |
| D-12 | 6.72(d, J=18.1Hz) | 2.62–2.44 (m) | 3.67–3.57 (m) | 3.87–3.73 (m) | 9.13(brs, 1H), 7.74–7.25(m, 16H), 1.83(s, 3H), 1.07(s, 9H) |
| D-13 | 7.03 (s) | 5.82 (s) | 4.23–4.15 (m) | 3.83(dd, J=10.4, 6.1Hz) 3.78(dd, J=10.4, 6.3Hz) | 8.95(brs, 1H), 7.91(d, J=7.5Hz, 2H), 7.69–7.38(m, 15H), 1.10(s, 9H) |
| D-14 | 6.95 (s) | 5.80 (s) | 4.23–4.15 (m) | 3.84(dd, J=10.5, 6.2Hz) 3.79(dd, J=10.2, 6.6Hz) | 12.80(brs, 1H), 8.30(d, J=7.3Hz, 2H), 7.72–7.38(m, 14H), 1.10(s, 9H) |
| D-15 | 6.93 (s) | 5.75 (s) | 4.22–4.14 (m) | 3.85(dd, J=10.6, 5.9Hz) 3.81(dd, J=10.5, 5.6Hz) | 9.34(brs, 1H), 7.70–7.35(m, 11H), 5.44 (dd, J=8.1, 1.2Hz, 1H), 1.09(s, 9H) |
| D-16 | 3.96 (s) | 5.81 (s) | 4.22–4.13 (m) | 3.85(dd, J=10.5, 6.5Hz) 3.77(dd, J=10.2, 7.0Hz) | 9.45(brs, 1H), 7.72–7.35(m, 10H), 7.02(s, 1H), 1.74(s, 3H), 1.08(s, 9H) |
| D-17 | 6.93 (s) | 5.89–5.85 (m) | 4.17–4.12 (m) | 3.78(dd, J=11.7, 4.6Hz) 3.69(ddd, J=11.6, 4.3, 1.2Hz) | 8.05(dd, J=7.5, 1.0Hz, 1H), 5.97(d, J=7.5Hz, 1H) |
| D-18 | 6.92 (s) | 5.84 (s) | 4.17 (s) | 3.84(dd, J=11.8, 3.7Hz) 3.68(brd, J=10.6Hz) | 8.39(d, J=6.6Hz, 1H) |
| D-19 | 6.87 (s) | 5.89 (s) | 4.19–4.13 (m) | 3.80(dd, J=11.7, 4.5Hz) 3.71(ddd, J=11.7, 4.1, 1.4Hz) | 8.11(dd, J=8.1, 0.8Hz, 1H), 5.77(d, J=8.1Hz, 1H) |
| D-20 | 6.87(t, J=1.0Hz) | 5.86 (s) | 4.17 (s) | 3.84(dd, J=11.9, 4.0Hz) 3.77(ddd, J=11.9, 3.7, 1.7Hz) | 8.03(s, 1H), 1.88(d, J=1.2Hz, 3H) |
| D-21 | 6.63(d, J=14.7Hz) | 2.75~2.63 (m) | 3.80–3.73 (m) | 3.96(t, J=8.2Hz) 3.88(td, J=7.6, 1.8Hz) | 8.69(s, 1H), 8.31(d, J=2.9Hz, 1H), 7.70~7.13(m, 15H), 1.05(s, 9H) |
| D-22 | 6.45(d, J=14.0Hz) | 2.76~2.63 (m) 2.60(td, J=14.8, 7.9Hz) | 3.80–3.72 (m) | 3.97(dd, J=9.7, 7.3Hz) 3.89(pstd, J=7.6, 1.2Hz) | 8.27(d, J=2.9Hz, 1H), 7.70~7.14(m, 15H), 1.06(s, 9H) |
| D-23 | 6.87 (s) | 5.87 (s) | 4.33–4.25 (m) | 3.96(dd, J=10.2, 6.8Hz) 3.86(t, J=8.8Hz) | 8.69(s, 1H), 8,12(s, 1H), 7.69~7.35(m, 10H), 1.08(s, 9H) |
| D-24 | — | 3.25(ddd, J=16.6, 9.2, 3.1Hz) 3.03(dd, J=16.6, 5.2Hz) | 4.05~3.78(m, 3H) | | 8.82(s, 1H), 8,19(s, 1H), 7.69~7.35(m, 10H), 1.08(s, 9H) |
| D-25 | 6.68 (s) | 5.86 (s) | 4.32~4.23 (m) | 3.94(dd, J=10.2, 6.0Hz) 3.87~3.83(m) | 8.08(s, 1H), 7.69~7.36(m, 10H), 1.08(s, 9H) |
| D-26 | — | 3.24(ddd, J=16.3, 9.3, 3.1Hz) 3.01(ddd, J=16.8, 5.1, 0.6Hz) | 4.04~3.80 (m, 3H) | | 8.12(s, 1H), 7.75~7.31(m, 10H), 1.08(s, 9H) |
| D-27 | 6.88 (s) | 5.93 (s) | 4.31~4.24 (m) | 3.90(dd, J=11.6, 4.4Hz) 3.81(ddd, J=11.5, 4.1, 1.2Hz) | 8.52(s, 1H), 8.20(s, 1H) |

-continued

| Cmpd | | | | | |
|---|---|---|---|---|---|
| D-28 | 6.90 (s) | 5.93 (s) | 4.28–4.23 (m) | 3.88(dd, J=11.7, 4.7Hz) 3.80(dd, J=10.5, 4.0Hz) | 8.51(s, 1H), 8.07(s, 1H) |
| D-29 | 6.65 (s) | 5.82 (s) | 4.25~4.19 (m) | 3.90(dd, J=10.1, 7.0Hz) 3.81(dd, J=9.8, 7.4Hz) | 7.74(s, 1H), 7.68~7.36(m, 10H), 5.37(s, 1H), 1.07(s, 9H) |
| D-30 | 6.71(s) | 5.82 (s) | 4.27~4.19 (m) | 3.93~3.82 (m) | 7.77(s, 1H), 7.73~7.38(m, 10H), 6.40(brs, 2H), 1.08(s, 9H) |
| D-32 | 6.73 (s) | 5.93 (s) | 4.27~4.23 (m) | 3.86(dd, J=11.3, 4.6Hz) 3.81(ddd, J=11.5, 4.6, 1.1Hz) | 8.14(s, 1H) |
| D-33 | 6.77 (s) | 5.92 (s) | 4.27–4.22 (m) | 3.89(dd, J=11.7, 4.9Hz) 3.82(ddd, J=12.0, 4.6, 1.2Hz) | 8.44(s, 1H) |

[a]CD$_3$OD; ppm; s, singlet; d, doublet; dd, double doublet; t, triplet; brs, broad singlet; m, multiplet; td, triple doublet; ddd, double double doublet.

TABLE 1

$^1$H NMR Data L-Enantiomers

| Cmpd | H-1' | H-3' | H-4' | H-5' | Other protons |
|---|---|---|---|---|---|
| L-9[a] | 6.91(d, J=15.6Hz) | 2.62–2.47 (m) | 3.68–3.58 (m) | 3.87–3.72 (m) | 8.82(brs, 1H), 8.12(d, J=6.5Hz, 1H), 7.92(d, J=7.3Hz, 2H), 7.69–7.27(m, 19H), 1.02(s, 9H) |
| L-10[a] | 6.73(d, J=16.3Hz) | 2.63–2.46 (m) | 3.67–3.58 (m) | 3.92–3.76 (m) | 12.70(brs, 1H), 8,33(d, J=7.5Hz, 2H), 7.87(dd, J=5.9, 1.7Hz, 1H), 7.72–7.28(m, 18H), 1.07(s, 9H) |
| L-11[a] | 6.72(d, J=18.1Hz) | 2.62–2.44 (m) | 3.67–3.57 (m) | 3.87~3.73 (m) | 9.13(brs, 1H), 7.74–7.25(m, 16H), 1.83(s, 3H), 1.07(s, 9H) |
| L-12[a] | 6.63(d, J=14.7Hz) | 2.55–2.41 (m) | 3.62–3.58 (m) | 3.87–3.72 (m) | 9.26(brs, 1H), 7.72(dd, J=8.2, 2.0Hz, 1H), 7.68–7.30(m, 15H), 5.56(dd, J=8.2, 1.9Hz, 1H), 1.03(s, 9H) |
| L-13[a] | 7.03 (s) | 5.82 (s) | 4.23–4.15 (m) | 3.83(dd, J=10.4, 6.1Hz) 3.78(dd, J=10.4, 6.3Hz) | 8.95(brs, 1H), 7.91(d, J=7.5Hz, 2H), 7.69~7.38(m, 15H), 1.10(s, 9H) |
| L-14[a] | 6.95 (s) | 5.80 (s) | 4.23–4.15 (m) | 3.84(dd, J=10.5, 6.2Hz) 3.79(dd, J=10.2, 6.6Hz) | 12.80(brs, 1H), 8.30(d, J=7.3Hz, 2H), 7.72~7.38(m, 14H), 1.10(s, 9H) |
| L-15[a] | 6.96 (s) | 5.81 (s) | 4.22~4.13 (m) | 3.85(dd, J=10.5, 6.5Hz) 3.77(dd, J=10.2, 7.0Hz) | 9.45(brs, 1H), 7.72–7.35(m, 10H), 7.02(s, 1H), 1.74(s, 3H), 1.08(s, 9H) |
| L-16[a] | 6.93 (s) | 5.75 (s) | 4.22~4.14 (m) | 3.85(dd, J=10.6, 5.9Hz) 3.81(dd, J=10.5, 5.6Hz) | 9.34(brs, 1H), 7.70~7.35(m, 11H), 5.44(dd, J=8.1, 1.2Hz, 1H), 1.09(s, 9H) |
| L-17[b] | 6.93 (s) | 5.89–5.85 (m) | 4.17–4.12 (m) | 3.78(dd, J=11.7, 4.6Hz) 3.69(ddd, J=11.6, 4.3, 1.2Hz) | 8.05(dd, J=7.5, 1.0Hz, 1H), 5.97(d, J=7.5Hz, 1H) |
| L-18[b] | 6.92 (s) | 5.84 (s) | 4.17 (s) | 3.84(dd, J=11.8, 3.7Hz) 3.68(brd, J=10.6Hz) | 8.39(d, J=6.6Hz, 1H) |
| L-19[b] | 6.87 (s) | 5.86 (s) | 4.17 (s) | 3.84(dd, J=11.9, 4.0Hz) 3.77(ddd, J=11.9, 3.7, 1.7Hz) | 8.03(s, 1H), 1.88(d, J=1.2Hz, 3H) |
| L-20[b] | 6.87 (s) | 5.89 (s) | 4.19–4.13 (m) | 3.80(dd, J=11.7, 4.5Hz) 3.71(ddd, J=11.7, 4.1, 1.4Hz) | 8.11(dd, J=8.1, 0.8Hz, 1H), 5.77(d, J=8.1Hz, 1H) |
| L-21[a] | 6.55(d, J=14.7Hz) | 2.67~2.46 (m) | 3.72–3.62 (m) | 3.88(pst, J=8.5Hz) 3.80(pst, J=8.7Hz) | 8.60(s, 1H), 8.23(d, J=1.7Hz, 1H), 7.63~7.01(m, 15H), 0.96(s, 9H) |
| L-22[a] | 6.37(d, J=13.9Hz) | 2.68~2.57 (m) 2.52(td, J=12.9, 7.7Hz) | 3.72~3.64 (m) | 3.89(dd, J=9.7, 6.9Hz) 3.80(td, J=7.8, 1.3Hz) | 8.20(s, 1H), 7.62~7.06(m, 15H), 0.98(s, 9H) |
| L-23[a] | 6.87 (s) | 5.87 (s) | 4.33–4.24 (m) | 3.96(ddd, J=10.2, 6.8Hz) 3.86(dd, J=10.0, 7.5Hz) | 8.69(s, 1H), 8.12(s, 1H), 7.67(t, J=14.4Hz, 4H), 7.50–7.36(m, 6H), 1.08(s, 9H) |
| L-24[a] | na[c] | 3.25(ddd, J=16.8, 9.3, 3.3Hz, 1H), 3.03(ddd, J=16.6, 5.7, 1.2Hz, 1H), | 4.03~3.83 (m, 3H) | | 8.81(s, 1H), 8.18(s, 1H), 7.70~7.35(m, 10H), 1.08(s, 9H) |
| L-25[a] | 6.68 (s) | 5.79 (s) | 4.25~4.18 (m) | 3.86(td, J=10.2, 6.5Hz) 3.82~3.77 (m) | 8.01(s, 1H), 7.63~7.28(m, 10H), 1.01(s, 9H) |
| L-26[a] | na[c] | 3.24(ddd, J=16.3, 9.3, 3.1Hz, 1H) 3.01(ddd, J=16.8, 5.1, 0.6Hz, 1H) | 4.04~3.80 (m, 3H) | | 8.12(s, 1H), 7.75~7.31(m, 10H), 1.08(s, 9H) |
| L-27[b] | 6.89 (s) | 5.93 (s) | 4.28 (s) | 3.90(dd, J=11.5, 4.2Hz) 3.81(dd, J=11.4, 3.2Hz) | 8.52(s, 1H), 8.20(s, 1H) |

TABLE 1-continued

¹H NMR Data L-Enantiomers

| Cmpd | H-1' | H-3' | H-4' | H-5' | Other protons |
|---|---|---|---|---|---|
| L-28[b] | 6.90 (s) | 5.93 (s) | 4.26 (s) | 3.88(dd, J=11.6, 4.7Hz) 3.80(dd, J=10.7, 3.2Hz) | 8.51(s, 1H), 8.07(s, 1H) |
| L-29[a] | 6.65 (s) | 5.83 (s) | 4.26~4.22 (m) | 3.90(dd, J=10.1, 7.2Hz) 3.81(dd, J=9.8, 7.3Hz) | 7.74(s, 1H), 7.70~7.37(m, 10H), 5.18(s, 2H), 1.07(s, 9H) |
| L-30[a] | 6.72 (s) | 5.83 (s) | 4.29~4.19 (m) | 3.94(dd, J=10.2, 6.6Hz) 3.87(dd, J=10.1, 7.1Hz) | 7.80(s, 1H), 7.74~7.31(m, 10H), 6.95(brs, 2H), 1.08(s, 9H) |
| L-31[a] | na[c] | 3.20(ddd, J=16.5, 9.2, 3.1Hz, 1H), 3.00(dd, J=16.7, 4.6Hz, 1H) | 4.02~3.79 (m, 3H) | | 7.84(s, 1H), 7.74~7.31(m, 10H), 6.95(brs, 2H), 1.08(s, 9H) |
| L-32[b] | 6.61 (s) | 5.83 (s) | 4.22–4.14 (m) | 3.84–3.74 (m) | 7.98(s, 1H) |
| L-33[b] | 6.77 (s) | 5.92 (s) | 4.28–4.21 (m) | 3.89(dd, J=11.6, 4.7Hz) 3.85–3.79(m) | 8.44(s, 1H) |

[a]CDCl$_3$,
[b]CD$_3$OD,
[c]na: Not Applicable

VII. Biological Activity

Quantitative real-time PCR ("Q-RT-PCR") allows evaluation of candidate antiviral compounds and simultaneously scores the effect on host nucleic acids levels. These assays included (i) a HIV-1. genotype B viral load assay, (ii) a HBV viral load assay, (iii) a BVDV viral load assay, (iv) a human β-actin gene assay, (v) a mitochondrial COXII gene assay, and (vi) a rRNA gene assay.

The antiviral efficacy and cytotoxicity of β-D- and β-L-2',3'-didehydro-2',3'-dideoxy-2'-fluoro4'-thiocytidine. (D-17 and L-17, respectively), β-D- and β-L-2',3'-didehydro-2',3'-dideoxy-2'-fluoro-4'-thio-5-fluorocytidine (D-18 and L-18, respectively), β-D- and β-L-2',3'-didehydro-2',3'-dideoxy-3'-fluoro-cytidine (10 and 23, respectively) and β-D- and β-L-2',3'-didehydro-2',3.'-dideoxy-3'-fluoro-5-fluoro cytidine (10-F and 23-F, respectively) were evaluated. As control compounds, AZT (3'-azido-3'-deoxythymidine), 3TC [(−)-β-2',3'-dideoxy-3'-thiacytidine)], D-ddC (β-D-2',3'-dideoxycytidine), ribavirin (1-β-D-ribofuranosyl-1H-,1,2,4-triazole-3-carboxamide), (+)-BCH-189 [(+)-β-2',3'-dideoxy-3'-thiacytidine], FIAU (1-(2-deoxy-2-fluoro-1-β-D-arabinofuranosyl)-5-iodocytosine), D4T (β-D-2',3'-didehydro-3'-deoxythymidine), ACV [9-(2-hydroxyethoxymethyl)guanine] and D-D4FC (β-D-2',3'-didehydro-2'3'-dideoxy-5-fluorocytidine) were also evaluated.

All compounds were tested (i) against wild type (xxBRU) and 3TC-resistant (184V) HIV-1; (ii) for their ability to inhibit HBV production in the inducible HepAD38 cell line; and (iii) for their ability to inhibit BVDV production in acutely infected MDBK cells. Three quantitative PCR assays (Q-PCR) were designed (Taqman 7700 chemistry, PE BioSystems), for the HIV-1 genotype B, for HBV essentially as described (24), and for bovine viral diarrhea virus (BVDV). The latter virus is often used as surrogate model for the hepatitis C virus (HCV)(16, 21). Quantitative amplification assays (TaqMan RT-PCR) were designed for all viral (HBV, HIV, BVDV) and host targets (β-actin gene, mitochondrial COXII gene, rRNA gene) allowing precise quantification of cellular and viral DNA and/or RNA levels.

The design of viral load assays, especially for HIV-1, is generally complicated by the extremely variable nature of the viral genome (25, 30, 31). The primers and probes were designed based on regions that exhibited a limited amount of variability, showed excellent linearity over 6-log range and covered the genetic variability of viral strains routinely used in antiviral research laboratories. The broader applicability of the current selection of primers and probe for diagnostic purposes on clinical samples from different geographical origin will involve investigating specificity, sensitivity, reproducibility, optimization of the linear range for different genotypes/clades, and standardization with other commercially available tests, essentially as described for other applications (2, 13).

Several compounds demonstrated potent antiviral activity against the wild-type HIV-1 strain (range $EC_{90}$ values 0.16 to 5.16 μM), but a marked increase in $EC_{90}$ was noted for these compounds when tested against the 3TC-resistant HIV-1 (range $EC_{90}$ values 53 to >100 μM). The β-L-enantiomers of both classes of compounds were more potent than the corresponding β-D-enantiomers. One compound inhibited HBV production in AD38 cells ($EC_{90}$=1.0 μM). The compounds were essentially not cytotoxic ($IC_{50}$>87 μM) in human PBM cells and HepG2 cells. No effect on mitochondrial DNA levels was observed after a 7-day incubation with 10 μM of the nucleoside analogs. These studies demonstrate that modification of the sugar ring of cytosine nucleoside analogs with the 4'-thio instead of an oxygen results in compounds with potent inhibition of wild-type virus, but with reduced potency against 3TC-resistant virus.

Example 63

Toxicity Assays.

HepG2 and human PBM cells (5×104 per well) were seeded in 96-well plates in the presence of increasing concentrations of the test compound and incubated in a 37° C., 5% $CO_2$ incubator. After a three day-incubation for HepG2, or 5 days for human PBM cells, cell viability and mitochondrial activity were measured in a colorimetric assay using the MTS- or MTT dye method (Promega, Madison, Wis.). Eight compounds were tested in routine MTT or MTS toxicity assays and had $IC_{50}$ values higher than 87 μM in the cells evaluated (HepG2 and human PBM cells) (Table 1).

TABLE 1

Cytotoxicity of test compounds.

| | Cytotoxicity[a] | |
|---|---|---|
| | PBM $IC_{50}$ | HepG2 $IC_{50}$ |
| 10 | >100 | >100 |
| 10-F | >100 | >100 |
| 23 | 87 | >100 |
| 23-F | >100 | >100 |
| D-17 | >100 | >100 |
| D-18 | >100 | >100 |
| L-17 | >100 | >100 |
| L-18 | >100 | >100 |
| AZT | >100 | >100 |
| 3TC | >100 | >100 |
| D-D4FC | 80 | >100 |
| Ribavirin | >100 | 90 |

[a]values in $\mu M$

Example 64

HIV-1 Cell Culture

Human PBM cells (1×106 cells/T25 flask) were PHA stimulated for 2 or 3 days, and infected with either a wild type (LAI and xxBRU) or a 3TC-resistant (xxBRU 184V) HIV-1 strain at 100 TCID50, as previously described (27). The culture was kept for 5 days in presence of test compounds at serial 1-log dilutions. Subsequently, human PBM cells were removed from the culture supernatant by centrifugation (10 minutes, 400×g, 4° C.). This clarified supernatant was tested either in the RT-assay, or in the Q-RT-PCR assay.

Example 65

HIV-1 RT-Assay

Virus particles present in a 1 mL aliquot of culture supernatant were concentrated by high-speed centrifugation (2 hours, 20,000×g, 4° C.). The supernatant was then removed and the virus pellet was dispensed into a 100 µL virus solubilization buffer (VSB: 0.5% Triton X-100; 0.8 M NaCl, 0.5 mM phenylmethylsulfonyl, 20% glycerol, 50 mM Tris.HCl pH 7.8). A 10 µL aliquot of RT-VSB was mixed with 75 µL RT cocktail (60 mM Tris.HCl pH 7.8, 12 mM MgCl2, 6 mM DTT, 6 µg/mL poly (rA)n-oligo (dT)10–12, 1.2 mM dATP, and 80 µCi/mL 3H-TTP) and incubated for 2 hours at 37° C. Subsequently 100 µL of 10% TCA was added, and the total amount of incorporated 3H-TTP was determined.

Example 66

HIV-1 Q-RT-PCR Assay in Human PBM Cells

Viral RNA present in the culture supernatant was prepared using commercially available columns (QIAamp Viral RNA mini Kit, Qiagen, Valencia, Calif.). Viral RNA was detected in real-time by monitoring increases in fluorescence signal that resulted from degradation of a quenched fluorescent probe molecule following the hybridization of the probe to the arnplified viral DNA (TaqMan 7700 chemistry, Applied Biosystems, Foster City, Calif.). The TaqMan probe and primers were designed using the Primer Express software (Applied Biosystems); they cover highly conserved sequences complementary to an 81 base pair long fragment from the HIV-1 RT gene between codon 230 and 257 of the group MHIV-1 genome;

probe 5'-6FAM-TTTCTGGCAGCACTATAGGCTGTACTGTCCATT-TAMRA-3' (Sequence 1)

sense primer: 5'-TGGGTTATGAACTCCATCCTGAT-3' (Sequence 2); and antisense primer 5'-TGTCATTGACAGTCCAGCGTCT-3' (Sequence 3).

A total of 5 µL RNA was RT-amplified using reagents and conditions as described by the manufacturer (Applied Biosystems). The standard curve ranged from 1.41×102 copieslmL to over 1.41×108 copies/mL. Copy numbers were calibrated using the Roche Amplicor HIV-1 Monitor test™ (Roche Diagnostics, Branchburg, N.J.) on a 1-log dilution series of a clinical HIV-1 genotype B isolate (attenuated in vitro to obtain a high viral load). The 10–6 diluted sample became positive at threshold cycle (Ct=PCR cycle threshold where a sample becomes detectable)=35.52, which corresponded to 1,410 copies/mL in the Roche monitor HIV-1 version II assay. When validated over a dynamic range of 3 logs of virus, there was excellent correlation (r2~1) between the two methodologies. The Q-RT-PCR had a lower limit of detection of 141 copies/mL (Ct=38.85) and was linear over 6-logs of virus dilution. Therefore, the currently designed primer and probe set allowed reliable quantification of both clinical samples and HIV-1 in vitro preparations.

Figure 16:
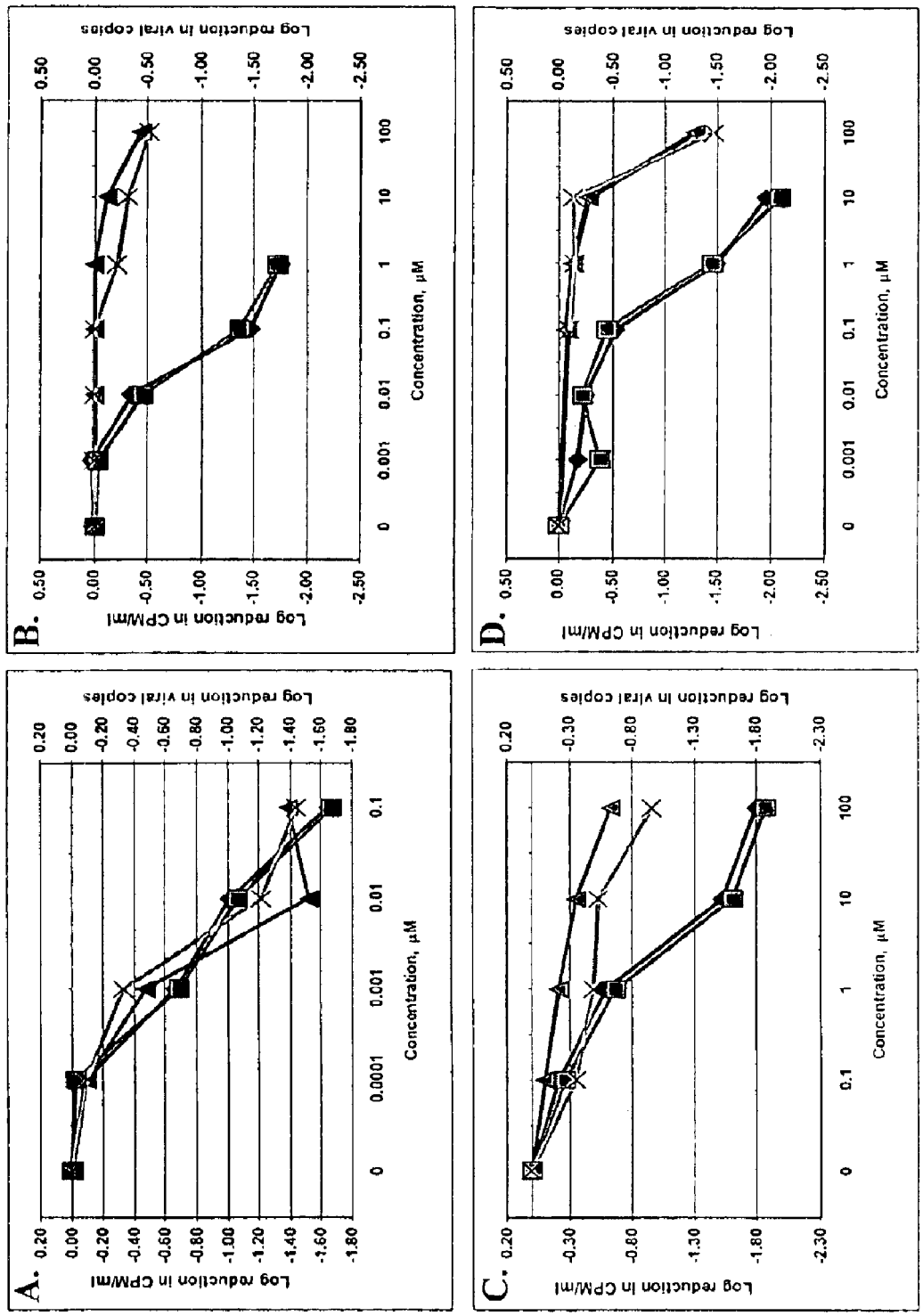
FIG. 16 are examples of dose-response curves for anti-HIV-1 activities of test compounds. Panel A: AZT; Panel B: 3TC; Panel C: compound L-17; Panel D: compound 23. (♦) RT assay xxBRU; (■) Q-RT-PCR xxBRU; (▲) RT assay xxBRU-184V; (X): Q-RT-PCR xxBRU-184V. CPM/mL: counts per min/mL.

The antiviral compounds were compared to AZT, 3TC, and D-D4FC against three HIV-1 strains (LAI, xxBRU, and a 3TC resistant xxBRU-184V) in a 5-day assay using PHA-stimulated human PBM cells. HIV-1 present in culture supernatant fluids was quantified by two different methodologies: i) the Q-RT-PCR with read-out in log copies/mL; and ii) the endogenous viral RT assay on cell supernatant with read-out in log counts per minute/mL (CPM/mL). Upon addition of antiviral compounds to the culture media, a dose-related decrease in virus production was observed. Some representative examples of these results are shown in FIG. 16. Although the two methodologies measured different parameters (viral RNA versus active RT enzyme), results were not markedly different from each other. The HIV-1 Q-RT-PCR results were compared with a previously established cell-based antiviral drug evaluation assay (endogenous HIV-1 RT polymerization activity in cell supematant)(27).

A summnary of the data, expressed as effective concentration to reduce the viral RNA, or the RT activity, by 90% ($EC_{90}$) for the three HIV-1 viral strains is given in Table 2.

TABLE 2

Anti-HIV-1 activity of nucleosides in acutely infected human PBM cells.

| | RT-Assay[a] | | | | Q-RT-PCR HIV-1 assay[a] | | | |
|---|---|---|---|---|---|---|---|---|
| | LAI $EC_{90}$ | xxBRU $EC_{90}$ | 184V $EC_{90}$ | FI[b] | LAI $EC_{90}$ | xxBRU $EC_{90}$ | 184V $EC_{90}$ | FI[b] |
| 10 | 25.3 | 35.5 | 572 | 16.1 | 50.6 | 35.4 | >100 | nr[c] |
| 10-F | 34.5 | 37.5 | 494 | 13.2 | 36.3 | 34.8 | >100 | nr[c] |
| 23 | 0.67 | 0.14 | 82.0 | 586 | 0.92 | 0.60 | 68.4 | 115 |
| 23-F | 0.12 | 0.14 | 67.0 | 479 | 0.09 | 0.16 | 53.0 | 333 |
| D-17 | 11.9 | 5.0 | 125 | 25.0 | 24.6 | 5.2 | 65.8 | 12.8 |
| D-18 | >100 | 119 | >100 | nr[c] | >100 | 73.9 | >100 | nr[c] |
| L-17 | 3.3 | 1.4 | 1,569 | 1,121 | 4.1 | 2.1 | >100 | >50 |
| L-18 | 2.6 | 1.1 | >100 | >100 | 4.3 | 0.94 | >100 | >100 |
| AZT | 0.02 | 0.01 | 0.002 | 0.29 | 0.03 | 0.01 | 0.01 | 1.00 |
| 3TC | 0.13 | 0.08 | 535 | 6,688 | 0.37 | 0.06 | >100 | >1,562 |
| D-D4FC | 0.18 | 0.08 | 0.15 | 1.9 | 0.38 | 0.22 | 0.21 | 0.97 |

[a]values in $\mu M$
[b]FI is the fold increase ($EC_{90}$ HIV-$1_{184V}$/$EC_{90}$ HIV-$1_{xxBRU}$)
[c]nr = not relevant Example 67

HBV Q-RT-PCR Assay in AD38 Cells

The HepAD38 cell line replicates HBV under conditions that can be regulated with tetracycline (12, 15). In the presence of this drug, the cell supernatant is virtually free of viral DNA, but upon the removal of tetracycline from the culture medium, these cells secrete virus-like particle into the supernatant (12). HepAD38 cells were seeded at 5×104 cells/well in a 96-well plate in seeding medium (DMEM/F12+10% FBS, 50 $\mu$g/mL penicillin, 50 $\mu$g/mL streptomycin, 100 $\mu$g/mL kanamycin, 400 $\mu$g/mL G418, and 0.3 $\mu$g/mL tetracycline) and incubated for 2 days at 37° C. in a 5% $CO_2$ humid atmosphere. The seeding media was removed, and cells were washed 3 times with PBS. Cells were then incubated with 200 $\mu$L assay medium (DMEM/F12+10% FBS+P/S/K) containing either no compound, test compound, or control drugs at 10 $\mu$M. After a 5-day incubation, the cell supernatant was collected and stored at −70° C. until HBV DNA was quantified. HBV DNA was extracted from supernatant using QiaAmp DNA blood Mini kit (Qiagen) and nucleic acids eluted in 200 $\mu$L. Viral DNA was detected in Q-PCR. The TaqMan probe and primers were designed using the Primer Express software (Applied Biosystems) and cover highly conserved sequences complementary to the DNA sequences present in HBsAg (24). A total of 5 $\mu$L DNA was amplified using reagents and conditions as described by the manufacturer (Applied Biosystems). The standard curve showed a dynamic range of at least 6 logs, and ranged from 2×102 copies/mL to over 2×108 copies/mL (not shown).

Figure 17:
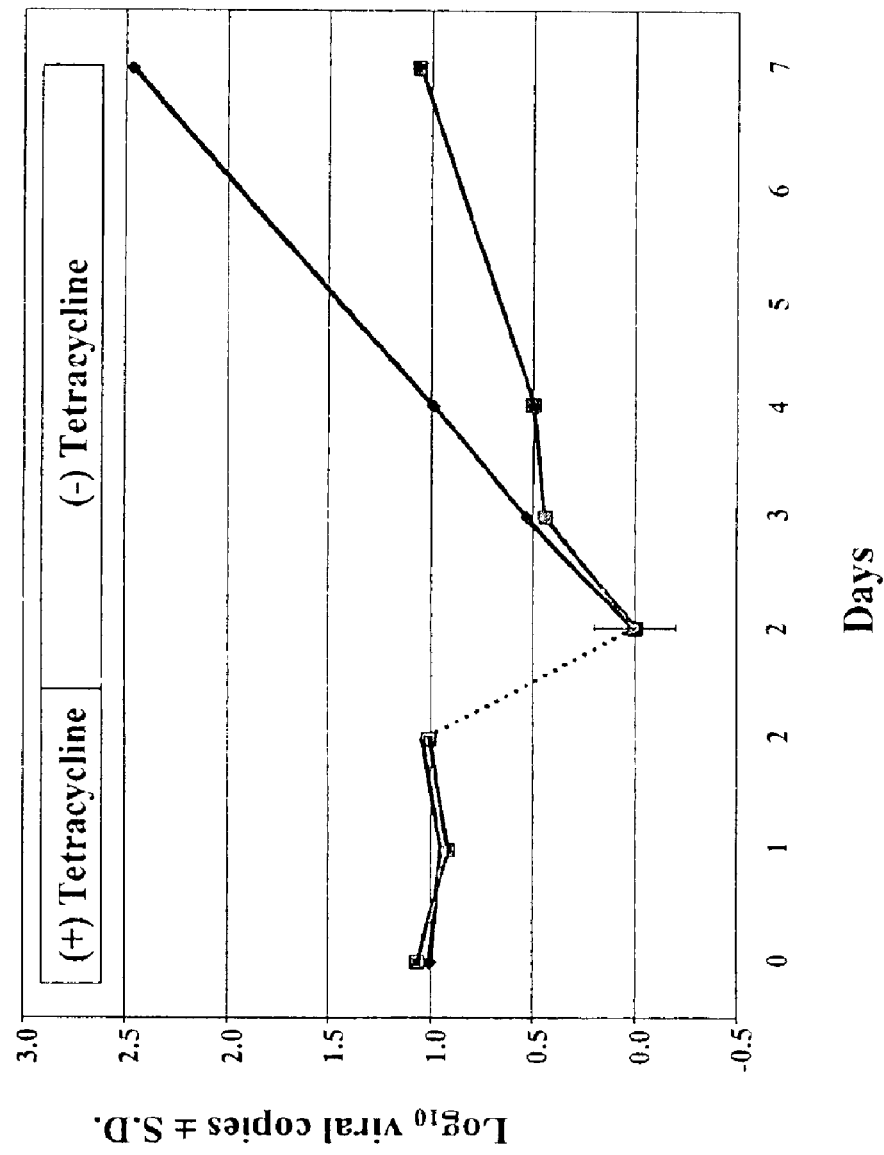
FIG. 17 is a non-limiting illustrative example of the time course of HBV induction in HepAD38 cells. (■) HBV DNA levels in medium from untreated cells; (♦) HBV DNA levels in medium from 3TC (10 $\mu$M) treated cells. The differences in viral load are expressed as changes from the day 2 time-point (after removal of tetracycline from medium). The dotted line represents two sampling points on the same day.

The time course of viral induction of HBV in HepAD38 cells was investigated (FIG. 17). Following a 2-day HBV suppression (using tetracycline containing medium), and a 5-day incubation of these cells with or without 3TC at 10 $\mu$M, the following observations were made: (i) immediately after seeding, viral DNA was detected in cell supernatant, but the quantity did not change over the three sampling points (day 0, day 1 and day 2 in seeding media). This indicates the presence of HBV DNA sequences in the supernatant representing material from cell debris, (ii) tetracycline completely shut down HBV DNA expression; (iii) 5 days post induction, there is an increase of approximately 2.5 logs of HBV DNA in the cell supernatant; and (iv) 10 $\mu$M 3TC prevented the release of viral DNA in the supernatant by almost 1.5 log.

$EC_{90}$ values for the 8 candidate compounds against HBV were determined in AD38 cells. As expected, 3TC showed a potent inhibition, ($EC_{90}$=2.9 $\mu$M), while compound 23 had comparable activity ($EC_{90}$=1.0 $\mu$M). All other compounds were considered inactive (Table 3) since the $EC_{90}$ was >100 $\mu$M.

Many studies on the anti-HBV activity of test compounds have employed the HepG2.2.15 cell system using a quantitative HBV Southern blot technology (1, 14). When the HepG2.2.15 system was employed using the Q-PCR technology, it was found that there was a very narrow dynamic range with a maximal reduction of 0.6 logs for 10 $\mu$M 3TC. Therefore, the AD38 system (12, 15) was evaluated in a Q-PCR technology (FIG. 17) and a dynamic range of virus production of approximately 2.5 logs of HBV DNA in the cell supernatant was observed. In addition, 5 days of exposure to 10 $\mu$M 3TC reduced the release of viral DNA in the supernatant by almost 1.5 log. Compared to HepG2.2.15 technology, the Q-PCR approach in AD38 cells gave a broader dynamic range, shorter incubation time, and no radioactive detection was required. The 8 candidate compounds and 3TC were tested in AD38 cells, and as expected, 3TC showed a potent reduction in the amount of HBV DNA in cell supernatant ($EC_{90}$=3 $\mu$M). The only test compound that was able to reduce HBV DNA in the cell supernatant was compound 23 ($EC_{90}$=1 $\mu$M). However, this compound was found 586-fold less potent against a 3TC-resistant HIV-1 (Table 2), and hence, it is anticipated that compound 23 will be less potent against 3TC-resistant HIV as well. Since it is an L-nucleoside (29), these data indicate that the β-L-2',3'-didehydro-2',3'-dideoxy-3'-fluoro sugar configuration has similar activity and resistance profile as compounds with the β-L-2',3'-dideoxy-3'-thia configuration. Interestingly, the addition of a fluorine atom at the 5 position of cytidine (compound 23-F) resulted in an almost inactive compound for HBV ($EC_{90}$=68 $\mu$M), while the analog with the β-L-2',3'-dideoxy-3'-thia configuration [(−)-FTC, emtricitabine] showed a potent inhibition of HBV with an EC50 value of 0.24 $\mu$M (22).

Example 68

BVDV Q-RT-PCR Assay in MDBK Cells

Madin-Darby Bovine Kidney (MDBK) cells were maintained in DMEM/F12 supplemented with 10% heat-inactivated horse serum at 37° C. in a humidified, 5% $CO_2$ atmosphere. Cells were seeded in 96-well plates at 5×10^3 cells/well and incubated for 1 hour. BVDV (strain NADL) was used to infect the cells in monolayer at MOI 0.02. After 45 minutes of infection, the viral inoculum was removed and the cells were washed twice. Media or media containing test compound was added to these cells, followed by 24 hour incubation. Cell supernatant fluids were collected, clarified by centrifugation (2 minutes, 3,000 g, room temperature) and viral RNA was prepared (QIAamp Viral RNA mini Kit, Qiagen). Viral RNA was detected in real-time RT-PCR. Primers and probe were designed for the BVDV NS5B region using the Primer Express software (Applied Biosystems);

probe: 5'-6FAM-AAATCCTCCTAACAAGCGGGTTCCAGG-TAMRA-3' (Sequence 4);

sense primer: 5'-AGCCTTCAGTTTCTTGCTGATGT-3' (Sequence 5); and antisense primer: 5'-TGTTGCGAAAGGACCAACAG-3' (Sequence 6).

A standard curve with a linear range of at least 6-log was obtained (data not shown). Ribavirin (Schering-Plough, Raritan, N.J.) was used as positive control in these experiments. Ribavirin showed potent inhibition ($EC_{90}$=5 μM), but none of the test compounds prevented release of virus from the infected cells ($EC_{90}$>200 μM, Table 3).

TABLE 3

Cytotoxicity and anti-HBV and anti-BVDV activities of test compounds.

| | Cytotoxicity[a] | | HBV assay[a] | BVDV assay[a] |
|---|---|---|---|---|
| | PBM $IC_{50}$ | HepG2 $IC_{50}$ | Q-PCR $EC_{90}$ | Q-PCR $EC_{90}$ |
| 10 | >100 | >100 | 100 | >200 |
| 10-F | >100 | >100 | >100 | >200 |
| 23 | 87 | >100 | 1.0 | >200 |
| 23-F | >100 | >100 | 68 | >200 |
| D-17 | >100 | >100 | >100 | >200 |
| D-18 | >100 | >100 | >100 | >200 |
| L-17 | >100 | >100 | >100 | >200 |
| L-18 | >100 | >100 | >100 | >200 |
| AZT | >100 | >100 | ND[b] | >200 |
| 3TC | >100 | >100 | 3.0 | >200 |
| D-D4FC | 80 | >100 | ND[b] | >200 |
| Ribavirin | >100 | 90 | >100 | 5.0 |

[a]values in μM
[b]ND = not determined

Example 69

Q-RT-PCR Assay for Mitochondrial DNA and rRNA Gene

The Q-RT-PCR technology was also used to evaluate potential mitochondrial γ-DNA polymerase inhibition by the compounds of the present invention in relevant human cells. Nucleoside analogs useful in the treatment of viral or proliferative disorders can exhibit toxicity in patients resembling inherited mitochondrial diseases (i.e. hepatic steatosis, lactic acidosis, myopathy, nephrotoxicity, peripheral neuropathy, multiple symmetric lipomatosis, and pancreatitis) (3, 18). Since active nucleoside compounds in the triphosphate form lack a 3'-OH, thereby stopping virus replication by chain termination, there is a concern that these nucleoside analogues are also substrates for the human DNA polymerase γ, resulting in inhibition of mitochondrial DNA replication and subsequently toxic side effects (11, 19). In an attempt to provide direct quantifiable data on mitochondrial DNA levels intracellular, a Q-PCR technology was designed and relative quantification of COXII DNA levels were calculated using the comparative Ct method. D-ddC and (+)-BCH-189 served as controls and were confirmed to reduce rnitochondrial COXII DNA levels (7). Also, in agreement with previous observations, no changes in normalized mitochondrial DNA levels were observed after FIAU and D4T treatment (6, 8, 23). None of the test compounds showed any significant reduction in the COXII DNA levels. However, the Q-PCR technology described herein does not predict potential incorporation of the inhibitor into mitochondrial DNA, as well as other mitochondrial aberrations such as mitochondrial morphology changes (loss of cristae), lactic acid production, and lipid droplet formation.

Low passage number HepG2 cells, obtained from American Tissue Culture Collection (ATCC, Manassas, Va.) were seeded at 5,000 cells/well in collagen-coated 96-well plates. Test compounds were added to the media to obtain a final concentration of 10 μM. On culture day 7, cellular nucleic acids were prepared by using commercially available columns (RNeasy 96 kit, Qiagen). These kits co-purify RNA and DNA, and hence total nucleic acids were eluted from columns in 140 μL water. The mitochondrial cytochrome C oxidase subunit II (COXII) gene and the β-actin or rRNA gene were amplified from 5 μL with a multiplex Q-PCR protocol using the suitable primers and probes for both target and reference (designed using the Primer Express software, Applied Biosystems);

for COXII.

sense primer 5'-TGCCCGCCATCATCCTA-3' (Sequence 7);

probe 5'-TET-TCCTCATCGCCCTCCCATCCC-TAMRA-3' (Sequence 8); and antisense probe 5'-CGTCTGTTATGTAAAGGATGCGT-3' (Sequence 9);

for exon 3 of β-actin (GenBank E01094):

sense primer 5'-GCGCGGCTACAGCTTCA-3' (Sequence 10);

probe 5'-6FAM-CACCACGGCCGAGCGGGA-TAMRA-3' (Sequnece 11); and antisense probe 5'-TCTCCTTAATGTCACGCACGAT-3' (Sequence 12).

The rRNA gene primers and probes were purchased from Applied Biosystems. Standard curves using 1-log diluted total HepG2 DNA were linear over more than 5 logs. In addition, efficiencies of target (COXII DNA) and reference (β-actin DNA or rRNA) amplification were approximately equal, because the slope of the ΔCt line (Ct β-actin minus Ct mitochondrial) was less than 0.1 (not shown). Since equal amplification efficiencies were obtained for both genes, the comparative cycle threshold (Ct) method was used to investigate potential inhibition of the mitochondrial DNA polymerase γ. The comparative Ct method uses arithmetic formulas in which the amount of target (COXII gene) is normalized to an endogenous reference (β-actin gene or rRNA gene) and is relative to a calibrator (no drug control at day 7). The arithmetic formula for this approach is given by 2-ΔΔCt (User bulletin # 2, Applied Biosystems).

In order to study the consequences of possible inhibitory effects of these compounds on host DNA polymerases, nuclear and rnitochondrial DNA levels were quantified and compared to no-treatment controls. Cells were incubated for 7 days with 10 µM of each compound, followed by total nucleic acid extractions and multiplex Q-PCR of the rRNA gene and the mitochondrial COXII gene. Nucleic acids from cells exposed to the control compounds were also amplified in multiplex for mitDNA and the β-actin gene. The results are presented in Table 4 using the comparative Ct method.

Q-RT-PCR assay gave results comparable to the endogenous RT assay eliminating the need for radioactive experiment. This study also indicates that the modifications in the sugar ring of cytosine nucleoside analogs with a 4'-thio instead of one oxygen (especially compounds L-17 and L-18 results in compounds with reduced potency against 3TC-resistant virus.

TABLE 4

Relative quantitation of gene products using the comparative Ct method in HepG2 cells treated with various antiviral agents.

| | Average ΔCt ± SD[a] | | | Average ΔΔCt ± SD[b] | | | $COXII_{NrDNA}$ (range) | $COXII_{Nβ\text{-actin DNA}}$ (range) |
|---|---|---|---|---|---|---|---|---|
| Cmpd. | COXII DNA | rDNA | β-actin DNA | COXII-rDNA | COXII-β-actin | rDNA-β-actin | relative to control[c] | relative to control[c] |
| Control | 0 ± 0.42 | 0 ≅ 0.98 | 0 ± 0.65 | 0 ± 0.87 | 0 ± 0.57 | 0 ± 0.87 | 1 (0.59–1.69) | 1 (0.68–1.48) |
| D-ddC | 2.27 ± 0.26[d] | 0.18 ± 0.53 | −0.62 ± 0.21[d] | 2.09 ± 0.65[d] | 2.9 ± 0.23[d] | 0.81 ± 0.59 | 0.23 (0.15–0.37) | 0.13 (0.1I–0.16) |
| AZT | 0.25 ± 0.13 | 0.86 ± 0.55 | 0.10 ± 0.38 | −0.61 ± 0.56 | 0.16 ± 0.44 | 0.76 ± 0.87 | 1.52 (1.03–2.24) | 0.90 (0.66–1.22) |
| 3TC | 0.08 ± 0.33 | 0.47 ± 0.51 | 0.11 ± 0.23 | −0.39 ± 0.50 | −0.02 ± 0.43 | 0.36 ± 0.66 | 1.31 (0.92–1.88) | 1.02 (0.75–1.37) |
| (+)-BCH-189 | 2.16 ± 0.32[d] | −0.14 ± 0.61 | −0.36 ± 0.31 | 2.3 ± 0.66[d] | 2.53 ± 0.36[d] | 0.23 ± 0.39 | 0.20 (0.13–0.32) | 0.17 (0.14–0.22) |
| D-FIAU | 0.09 ± 0.17 | ND[e] | 0.23 ± 0.01 | ND[e] | −0.14 ± 0.12 | ND[e] | ND[e] | 1.10 (1.01–1.20) |
| D-D4T | 0.29 ± 0.01 | ND[e] | 0.05 ± 0.06 | ND[e] | 0.23 ± 0.04 | ND[e] | ND[e] | 0.85 (0.79–0.88) |
| ACV | −0.37 ± 0.08 | ND[e] | 0.17 ± 0.01 | ND[e] | −0.54 ± 0.06 | ND[e] | ND[e] | 1.45 (1.34–1.52) |
| 10 | −0.29 ± 0.19 | −0.08 ± 0.50 | ND[e] | −0.21 ± 0.51 | ND[e] | ND[e] | 1.16 (0.81–1.64) | ND[e] |
| 10-F | −0.49 ± 0.31 | −0.44 ± 0.31 | ND[e] | −0.05 ± 0.37 | ND[e] | ND[e] | 1.04 (1.34–0.80) | ND[e] |
| 23 | −0.16 ± 0.17 | −0.51 ± 0.35 | ND[e] | 0.36 ± 0.41 | ND[e] | ND[e] | 0.78 (0.59–1.04) | ND[e] |
| 23-F | −0.3 ± 0.46 | 0.19 ± 0.56 | ND[e] | −0.49 ± 0.60 | ND[e] | ND[e] | 1.40 (0.93–2.13) | ND[e] |
| D-17 | −0.14 ± 0.10 | 0.81 ± 0.60 | ND[e] | −0.96 ± 0.56 | ND[e] | ND[e] | 1.94 (1.31–2.87) | ND[e] |
| D-18 | −0.39 ± 0.43 | −0.45 ± 0.60 | ND[e] | 0.06 ± 0.29 | ND[e] | ND[e] | 0.96 (0.78–1.17) | ND[e] |
| L-17 | −0.05 ± 0.16 | 0.49 ± 0.77 | ND[e] | −0.55 ± 0.75 | ND[e] | ND[e] | 1.46 (0.87–2.47) | ND[e] |
| L-18 | −0.06 ± 0.24 | 0.10 ± 0.44 | ND[e] | −0.16 ± 0.56 | ND[e] | ND[e] | 1.12 (0.76–1.64) | ND[e] |

[a]value obtained by subtracting average Ct vaiue (n = datapoints) from the average controi Ct value (n = 18 datapoints)
[b]value obtained by subtraction of average ΔCts from indicated parameters
[c]normalized COXII DNA levels relative to control as given by the expression 2-ΔΔCt, range is between ΔΔCt + SD and ΔΔCt − SD
[d]significantly different from control; p-values from a two-tailed distribution two-sample unequal variance T-test; significance at 0.005.
[e]ND = not determined The values given are averages of 3 different cell populations, amplified in duplicate. Standard deviations (SD) of duplicate samples were tight (range 0.01 to 0.3 ΔCt values, not shown), but after combining the results of different cell populations, the SD increased (range 0.10 to 0.98 ΔCt values).

A significant reduction in COXII DNA was observed for D-ddC and (+)-BCH-189 (2.27 and 2.16 ΔCt, respectively), while no significant decrease in COXII DNA was observed for any of the test compounds. In the rRNA testing, there were no significant differences observed in ΔCt values of test compounds compared to controls. In the β-actin testing, a minor but significant increase (−0.62 ΔCt) in the D-ddC treated cultures was noted, but this increase is most likely attributed to a PCR-primer effect.

After normalization and relative to the no-treatment control, D-ddC and (+)-BCH-189 significantly reduced the total amount of COXTII DNA by more than 2 ΔΔCt, while none of the 8 new test compounds showed any significant COXII DNA reduction.

The following general conclusion on this series of nucleoside analogues can be made; (i) the β-L-enantiomers are more potent than the corresponding β-D-enantiomers; (ii) compounds are less potent against 3TC-resistant HIV-1, indicating cross-resistance with 3TC-selected 184V viral strains; (iii) the antiviral activity of D-D4FC is strongly reduced by introducing a fluorine moiety at the 3' position; (iv) the 5-fluorocytosine modification did not improve the activity, and did not change the toxicity pattern significantly ($IC_{50}$>87 µM for all compounds), and (v) the one-step Example 70

Adenosine Deaminase (ADA) Kinetics Study

In an attempt to understand metabolic stability of the adenosine analogue D-27, adenosine deaminase (ADA) binding efficiencies and deamination kinetics studies were performed (Marquez, V. E.; Tseng, C. K. -H.; Mitsuya, H.; Aoki, S.; Kelley, J. A.; Ford, H. Jr.; Roth, J. S.; Broder, S.; Johns, D. G.; Driscoll, J. S. Acid-stable 2'-fluoro purine dideoxynucleosides as active agents against HIV. *J. Med. Chem.* 1990, 33, 978–985). Assays were performed at 25° C. in phosphate buffer solution (pH 7.4) with substrate concentrations in the range of 15–100 µM and with 0.15 unit of adenosine deaminase (EC.3.5.4.4. from calf intestinal mucosa). The assays were monitored with a UV spectrometer at 265 nm. Initially, the qualitative assays were performed with D-β-2'-F-4'-S-d4A 24 (200 µM) in the presence of 0.24 unit of adenosine deaminase for 120 minutes to determine whether it is a substrate of this enzyme. The concentration ($c_t$) of each substrate at a certain time (t) was calculated from the absorbance ($A_t$) at that time (t), where it was assumed that the total change of absorbance ($A_0-A_\infty$) was directly related to the disappearance of the substrate.[35] Initial hydrolysis rates for each substrate concentration were measured manually through graphical curve fitting of the concentration versus time data for reaction of each substrate. From Lineweaver-Burke plot of these initial rates, $V_{max}$ (maximum velocity) and $K_M$ (Michaelis constant) were obtained for each substrate and $k_{cat}$ was also calculated with 0.15 unit of the enzyme (M.W. 33,000) in 2 mL of buffer solution. The $t_{1/2}$ of D-β-2'-F-4'-S-d4A 24 and adenosine were also measured at 20 μM with 0.15 unit of the enzyme.

As shown in Table 5, the adenine derivative D-27 was found to be tightly bound ($K_M$=18.3 μM) to the mammalian adenosine deaminase (from calf intestinal mucosa, EC.3.5.4.4), but the turnover number ($k_{cat}$=0.94 s$^{-1}$) was very low, which indicates that even though the adenine derivative D-27 can strongly bind to ADA, it can barely be catalyzed by ADA to the corresponding inosine derivative. Compared with other substrates of ADA, β-D-2'-F4'-Sd4A D-27 has very low $K_M$ and $k_{cat}$ values, and the catalytic efficiency ($k_{cat}/K_M$) is as low as that of β-FddA (Ford, H. Jr.; Dai, F.; Mu, L.; Siddiqui, M. A.; Nicklaus, M. C.; Anderson, L.; Marquez, V. E.; Barchi, J. J. Jr. Adenosine deaminase prefers a distinct sugar ring conformation for binding and catalysis: Kinetic and structural studies. *Biochemistry*, 2000, 39, 2581–2592). From a therapeutic point of view, this metabolic stability of adenosine analogue D-27 has important implications because adenosine deaminase is one of the major deactivating enzymes of the purine catabolism pathway (Kredich, N. M.; Hershfeld, M. S. In *The Metabolic and Molecular Basis of Inherited Disease*; Scriver, C. R.; Beaudet, A. L.; Sly, W. S.; Valle, D., Eds.; McGraw-Hill: N.Y., 1989; pp 1045–1075).

TABLE 5

Kinetic Constants for Adenosine Analogues as Substrates of ADA.[a]

| Compound | $K_M$ (μM) | $k_{cat}$ (s$^{-1}$) | $k_{cat}/K_M$ (μM$^{-1}$s$^{-1}$) | t½ (min) |
|---|---|---|---|---|
| D-2'-F-4'-Sd4A (D-27) | 18.3 | 0.94 | 0.05 | 33 |
| D-2'-F-d4A[28] | 23.0 | NA[b] | NA[b] | 42 |
| Adenosine | 24.5 | 76.4 | 3.1 | 0.5 |

[a]Kinetic data were obtained spectrophotometrically at 25° C. by following the decrease in absorbance at 265 nm.
[b]Not Available.

Example 71

Cytotoxicity Assays

The cytotoxicity of the synthesized nucleosides, cytidine (D-17), 5-fluorocytidine (D-18), adenosine (D-27) and 2-fluoroadenosine (D-33) were assessed in human PBM, CEM and Vero cells. The 2-fluoroadenosine analogue (D-33) showed antiviral potency as well as high cytotoxicity ($IC_{50}$ 1.5, 1.1 and 7.6 μM for PBM, CEM and Vero, respectively) whereas no other compound showed cytotoxicity up to 100 μM.

The compounds were evaluated for their potential toxic effects on uninfected PHA-stimulated human PBM cells, in CEM (T-lymphoblastoid cell line obtained from American Type Culture Collection, Rockville, Md.) and Vero (African green monkey kidney) cells. PBM cells were obtained from whole blood of healthy seronegative donors (HIV-1 and hepatitis B virus) by single-step Ficoll-Hypaque discontinuous gradient centrifugation. Log phase Vero, CEM and PHA-stimulated human PBM cells were seeded at a density of 5×10$^3$, 2.5×10$^3$ and 5×10$^4$ cells/well respectively. All of the cells were plated in 96-well cell culture plates containing ten-fold serial dilutions of the test drug. The cultures were incubated for 3, 4 and 5 days for Vero, CEM, and PBM cells, respectively in a humidified 5% CO$_2$-air at 37° C. At the end of incubation, MTT tetrazolium dye solution (Cell titer 96®, Promega, Madison, Wis.) was added to each well and incubated overnight. The reaction was stopped with stop solubilization solution (Promega, Madison, Wis.). The plates were incubated for 5 hours to ensure that the formazan crystals were dissolved. The plates were read at a wavelength of 570 nm using an ELISA plate reader (Bio-tek instruments, Inc., Winooski, Vt., Model # EL 312e). The 50% inhibition concentration ($IC_{50}$) was determined from the concentration-response curve using the median effect method.Error! Bookmark not defined.

Example 72

HIV Assay in PBM Cells

The antiviral activity of the synthesized compounds were evaluated against HIV-1 in human peripheral blood mononuclear (PBM) cells, among which cytidine (D-17), 5-fluorocytidine (D-18), adenosine (D-27) and 2-fluoroadenosine (D-33) showed moderate to potent anti-HIV activities ($EC_{50}$ 1.3, 11.6, 8.1 and 1.2 μM, respectively). Similarly, the synthesized pyrimidine (L-17 to L-20) and purine (L-27, L-28, L-32 and L-33) nucleosides were evaluated.

Human peripheral blood mononuclear (PBM) cells (obtained from Atlanta Red Cross) were isolated by Ficoll-Hypaque discontinuous gradient centrifugation from healthy seronegative donors. Cells were stimulated with phytohemagglutinin A (Difco, Sparks, Md.) for 2–3 days prior to use. HIV-1$_{LA}$I obtained from the Centers for Disease Control and Prevention (Atlanta, Ga.) was used as the standard reference virus for the antiviral assays. The molecular infectious clones HIV-1$_{xxBru}$ and HIV-1$_{M184Vpin}$ were obtained from Dr. John Mellors (University of Pittsburgh). Infections were done in bulk for one hour, either with 100 TCID$_{50}$/1× 10$^7$ cells for a flask (T25) assay or with 200 TCID$_{50}$/6×10$^5$ cells/well for a 24 well plate assay. Cells were added to a plate or flask containing a ten-fold serial dilution of the test compound. Assay medium was RPMI-1640 supplemented with heat inactivated 16% fetal bovine serum, 1.6 mM L-glutamine, 80 IU/ml penicillin, 80 μg/ml streptomycin, 0.0008% DEAE-Dextran, 0.045% sodium bicarbonate, and 26 IU/ml recombinant interleukin-2 (Chiron Corp, Emeryville, Calif.). AZT was used as a positive control for the assay. Untreated and uninfected PBM cells were grown in parallel at equivalent cell concentrations as controls. The cell cultures were maintained in a humidified 5% CO$_2$-air at 37° C. for 5 days and supernatants were collected for reverse transcriptase (RT) activity.

Supernatants were centrifuged at 12,000 rpm for 2 hours to pellet the virus. The pellet was solubilized with vortexing in 100 μl virus solubilization buffer (VSB) containing 0.5% Triton X-100, 0.8 M NaCl, 0.5 mM phenylmethylsulfonyl fluoride, 20% glycerol, and 0.05 M Tris, pH 7.8. Ten μL of each sample were added to 75 μL RT reaction mixture (0.06 M Tris, pH 7.8, 0.012 M MgCl$_2$, 0.006 M dithiothreitol, 0.006 mg/ml poly (rA)$_n$, oligo (dT)$_{12-18}$, 96 μg/ml dATP, and 1 μM of 0.08 mCi/ml $^3$H-thymidine triphosphate (Moravek Biochemicals, Brea, Calif.) and incubated at 37° C. for 2 hours. The reaction was stopped by the addition of 100 μL 10% trichloroacetic acid containing 0.05% sodium pyrophosphate. The acid insoluble product was harvested onto filter paper using a Packard Harvester (Meriden, Conn.), and the RT activity was read on a Packard Direct Beta Counter (Meriden, Conn.). The RT results were expressed in counts per minute (CPM) per milliliter. The antiviral 50% effective concentration ($EC_{50}$) and 90% effective concentration ($EC_{90}$) were determined from the concentration-response curve using the median effect method (Belen'kii, S. M.; Schinazi, R. S. Multiple drug effect analysis with confidence interval. *Antiviral. Res.* 1994, 25, 1–11).

The synthesized pyrimidine (D-17 to D-20) and purine (D-27, D-28, D-32 and D-33) nucleosides were evaluated against HIV-1 in human PBM cells in vitro, and AZT was included as a positive control. Among the tested nucleosides, two pyrimidine nucleosides, cytidine D-17 ($EC_{50}$ 1.3 μM) and 5-fluorocytidine D-18 ($EC_{50}$ 11.6 μM), and all purine nucleosides synthesized, adenosine D-27 ($EC_{50}$ 8.1 μM), inosine D-28 ($EC_{50}$ 43.6 μM), guanosine D-32 ($EC5_0$ 80.5 μM) and 2-fluoroadenosine D-33 ($EC_{50}$ 1.2 μM), showed moderate to potent antiviral activities. The 2-fluoroadenosine analogue D-33 showed antiviral potency as well as high cytotoxicity ($IC_{50}$ 1.5, 1.1 and 7.6 μM for PBM, CEM and Vero, respectively) whereas no other compound showed cytotoxicity up to 100 μM. Compared with the β-D-2'-Fd4N nucleosides,[11(b)] there was a general trend of antiviral activities throughout the series, where cytidine, 5-fluorocytidine and adenosine analogues were most potent and almost all purine nucleosides showed moderate to potent activities. However, the β-D-2'-Fd4N nucleosides[11(b)] were consistently more potent than their 4'-thio congeners, which suggests that the two types of nucleosides may have similar structural features and may be recognized in the same fashion at the kinase level, but the way they interact with the viral polymerase (HIV-1 reverse transcriptase) must be somewhat different (vide infra for molecular modeling studies). The results are summarized in Table 6.

TABLE 6

Anti-HIV activity and cytotoxicity of D-2',3'-didehydro-2',3'-dideoxy-2'-fluoro-4'-thionucleosides

| Compound | Activity ($EC_{50}$, μM) | Cytotoxicity ($IC_{50}$, μM) | | |
|---|---|---|---|---|
| | HIV-1 | PBM | CEM | Vero |
| D-17 | 1.3 | >100 | >100 | >100 |
| D-18 | 11.6 | >100 | >100 | >100 |
| D-19 | 92.3 | >100 | >100 | 53.0 |
| D-20 | >100 | >100 | >100 | >100 |
| D-27 | 8.1 | >100 | >100 | >100 |
| D-28 | 43.6 | >100 | >100 | >100 |
| D-32 | 80.5 | >100 | >100 | >100 |
| D-33 | 1.2 | 1.5 | 1.1 | 7.6 |
| AZT | 0.004 | >100 | 14.3 | 28.0 |

Similarly, the synthesized pyrimidine (L-17 to L-20) and purine (L-27, L-28, L-32 and L-33) nucleosides were evaluated for their anti-HIV activity and cytotoxicity in vitro, and results are summarized in Table 7. Among these nucleosides, two pyrimidine nucleosides, cytidine L-17 ($EC_{50}$ 0.12 μM) and 5-fluorocytidine L-18 ($EC_{50}$ 0.15 μM) showed the most potent anti-HIV-1 activity, and the purine nucleosides, adenosine L-27 ($EC_{50}$ 1.7 μM), inosine L-28 ($EC_{50}$ 15,5 μM), guanosine L-32 ($EC_{50}$ 43.5 μM) and 2-fluoroadenosine L-33 ($EC_{50}$ 11.5 μM), also showed moderate antiviral activity whereas significant cytotoxicity was observed in 2-fluoroadenosine L-33 ($IC_{50}$ 13.0, 10.4 and 66.1 μM for PBM, CEM and Vero cells, respectively). However, all other synthesized nucleosides showed no significant cytotoxicity. Despite the replacement of an oxygen atom (β-L-2'F-d4N) by a sulfur atom (β-L-2'F-4'S-d4N), the anti-HIV activity was generally maintained.

TABLE 7

Activity of L-2',3'-didehydro-2',3'-dideoxy-2'-fluoro-4'-thionucleosides

| Compound | Anti-HIV-1 Activity ($EC_{50}$, μM) | Cytotoxicity ($IC_{50}$, μM) | | |
|---|---|---|---|---|
| | | PBM | CEM | Vero |
| L-17 | 0.12 | >100 | >100 | >100 |
| L-18 | 0.15 | >100 | >100 | >100 |
| L-19 | >100 | >100 | >100 | >100 |
| L-20 | >100 | >100 | >100 | >100 |
| L-27 | 1.7 | >100 | >100 | >100 |
| L-28 | 15.5 | >100 | >100 | >100 |
| L-32 | 11.5 | 13.0 | 10.4 | 66.1 |
| L-33 | 43.5 | >100 | 41.5 | 66.4 |
| AZT | 0.004 | >100 | 29.0 | 14.3 |

Example 73

Antiviral Activity Against Lamivudine-Resistant (HIV-1$_{M184V}$) Mutant Strain

Lamivudine (3TC, (-)-β-2',3'-dideoxy-3'-thiacytidine) is an important component of the highly active antiretroviral therapy (HAART), and is the most commonly used nucleoside in combination therapy for HIV-1 infection (Carpenter, C. C. J.; Fischl, M. A.; Hammer, S. M.; Hirsch, M. S.; Jacobsen, D. M.; Katzenstein, D. A.; Montaner, J. S. G.; Richman, D. D.; Saag, M. S.; Schooley, R. T.; Thompson, M. A.; Vella, S.; Yeni, P. G.; Volberding, P. A. Antiretroviral therapy for HIV infection in 1998: updated recommendations of the International AIDS Society-USA Panel. *JAMA*, 1998,.280, 78–86). 3TC monotherapy results in the selection of 3TC-resistant viral variant, resulting in prompt rebound in plasma viral load (Kavlick, M. F.; Shirasaka, T.; Kojima, E.; Pluda, J. M.; Hiu, F.; Yarchoan, R.; Mitsuya, H. Genotypic and phenotypic characterization of HIV-1 isolated from patients receiving (-)-2',3'-dideoxy-3'-thiacytidine. *Antivir. Res.* 1995, 28, 133–146). A single mutation at residue 184 (M184V) in the catalytic domain of HIV-1 RT bring about a high-level of resistance to 3TC, causing the 50% inhibitory concentration of 3TC to be increased at least 1,000-fold (Schinazi, R. F.; Lloyd, Jr. R. M.; Nguyen, M. -H.; Cannon, D. L.; McMillan, A.; Ilksoy, N.; Chu, C. K.; Liotta, D. C.; Bazni, H. Z.; Mellors, J. W. Characterizatin of human immunodeficiency viruses resistant to oxthiolane-cytosine nucleosides. *Antimicrob Agents Chemother.* 1993, 37, 875–881; Tisdale, M.; Kemp, S. D.; Parry, N. R.; Larder, B. A. Rapid in vitro selection of human immunodeficiency virus type 1 resistant to 3'-thiacytidine inhibitors due to a mutation in the YMDD region of reverse transcnptase. *Proc. Natl. Acad. Sci. USA* 1993, 90, 5653–5656), contributing to the failure of anti-AIDS combination therapy. Therefore, there is an urgent need to discover new drug candidates active against the M184V mutant HIV-1 RT. The cytosine (D-17) and 5-fluorocytosine analogues (D-18), along with two positive controls, AZT and 3TC, were evaluated against the lamivudine-resistant mutant strain (HHV-1$_{M184V}$) in human PBM cells in vitro (Table 8). The antiviral activity of an L-enantiomer, namely the cytosine analogue (L-17), was also evaluated, along with other 2',3'-unsaturated nucleosides such as β-D-2'F-d4FC (Lee, K.; Choi, Y.; Gumina, G.; Zhou, W.; Schinazi, R. F.; Chu, C. K. Structure-activity relationships of 2'-fluoro-2',3'-unsaturated D-nucleosides as anti-HIV-1 agents. *J. Med. Chem.* 2002, 45, 1313–1320), β-D-2'F-4'S-d4C (Chong, Y.; Choo, H.; Choi, Y.; Schinazi, R. F.; Chu, C. K. Stereoselective synthesis and antiviral activities of D-2',3'-didehydro-2',3'-dideoxy-2'-fluoro-4'-thionucleosides. *J. Med. Chem. Submitted for publication*) and β-L-2'F-d4C (Lee, K.; Choi, Y.; Gullen, E.; Schlueter-Wirtz, S.; Schinazi, R. F.; Cheng, Y. -C.; Chu, C. K. Synthesis and anti-HIV and anti-HBV activities of 2'-fluoro-2',3'-unsaturated L-nucleosides. *J. Med. Chem.* 1999, 42, 1320–1328) (Table 8).

TABLE 8

Activity of selected nucleosides against lamivudine-resistant virus (HIV-1$_{M184V}$) in human PBM cells.

| Compound | xxBRU (EC$_{90}$, μM) | M184V (EC$_{90}$, μM) | FI[a] |
|---|---|---|---|
| D-17 | 5.0 | ≈125 | 25 |
| L-17 | 1.4 | >100 | >100 |
| β-D-2'-F-d4FC[b] | 9.9 | 34.7 | 3.5 |
| AZT | 0.01 | 0.003 | 0.3 |
| 3TC | 0.08 | 535 | 6,688 |

[a]FI is the fold increase (EC$_{90}$ HIV-1$_{M184V}$/EC$_{90}$ HIV-1$_{xxBRU}$)
[b]Ref. 11(b): Lee et al. J. Med. Chem. 2002, 45, 1313~1320

Example 74

Molecular Modeling

Conformational analysis: The initial conformations of D-β-2'-F-d4C and D-β-2'-F-4'-S-d4C (D-17) were constructed by builder module in Spartan 5.1.1 (Wavefunctions, Inc. Irvine, Calif.), and all calculations were performed on a Silicon Graphics O2 workstation. The initial conformations were cleaned up and geometry-optimized through quantum mechanical ab initio calculations using RHF/3-21G* basis in Spartan 5.1.1.

Binding affinity study to HIV-1 reverse transcriptase: All molecular modeling of the enzyme-substrate complexes was. carried out using Sybyl 6.7 (Tripos Associates, St. Louis, Mo.) on a Silicon Graphics Octane2 workstation. The enzyme site of the enzyme-ligand complex was constructed based on the X-ray structure of the covalently trapped catalytic complex of HIV-1 RT with TTP and primer-template duplex (PDB entry 1rtd).[29] A model of the NRTI binding site was constructed which consisted of residues between Lys1 and Pro243 in the p66 subunit, and a 7:4 (template-primer) duplex. The geometry-optimized structures of each inhibitor, obtained from the geometry optimization study, were used as the initial Cartesian coordinates. The heterocyclic moiety of n+1$^{th}$ nucleotide in template overhang was modified to the base complementary to the incoming NRTIs. Thus, the adenine moiety which was in the original X-ray structure (1rtd)[29] was modified to guanine. The inhibitor triphosphates were manually docked to the active site of the enzyme by adjusting the torsional angles to those found in the X-ray structure.[29] Gästeiger-Hückel charge was given to the enzyme-ligand complex with formal charges (+2) to two Mg atoms in the active site. Then, Kollman-All-Atom charges were loaded to enzyme site from the biopolymer module in Sybyl. Fluorine parameters were obtained from the literature (See the website: http://www.amber.uscf.edu/amber/Questions/fluorine.html, Cornell, W. D.; Cieplak, P.; Bayly, C. I.; Gould, I. R.; Merz, K. M.; Ferguson, D. M.; Spellmeyer, D. C.; Fox, T.; Caldwell, J. W.; Kollman, P. A. A 2nd generation force-field for the simulation of proteins, nucleic acids, and organic-molecules. *J. Am. Chem. Soc.* 1995, 117, 5179–5197; Dunitz, J. D.; Taylor, R. Orgainc fluorine hardly ever accepts hydrogen bonds. *Chem. Eur. J.* 1997, 3, 89–98) and MM2 parameters and put to the parameter files. In order to eliminate local strains resulting from merging inhibitors and/or point mutations, residues inside 6 Å from the merged inhibitors and mutated residues were annealed until energy change from one iteration to the next was less than 0.05 kcal/mol. The annealed enzyme-inhibitor complexes were minimized by using Kollman-All-Atom Force Field until iteration number reached 5,000.

Figure 18:
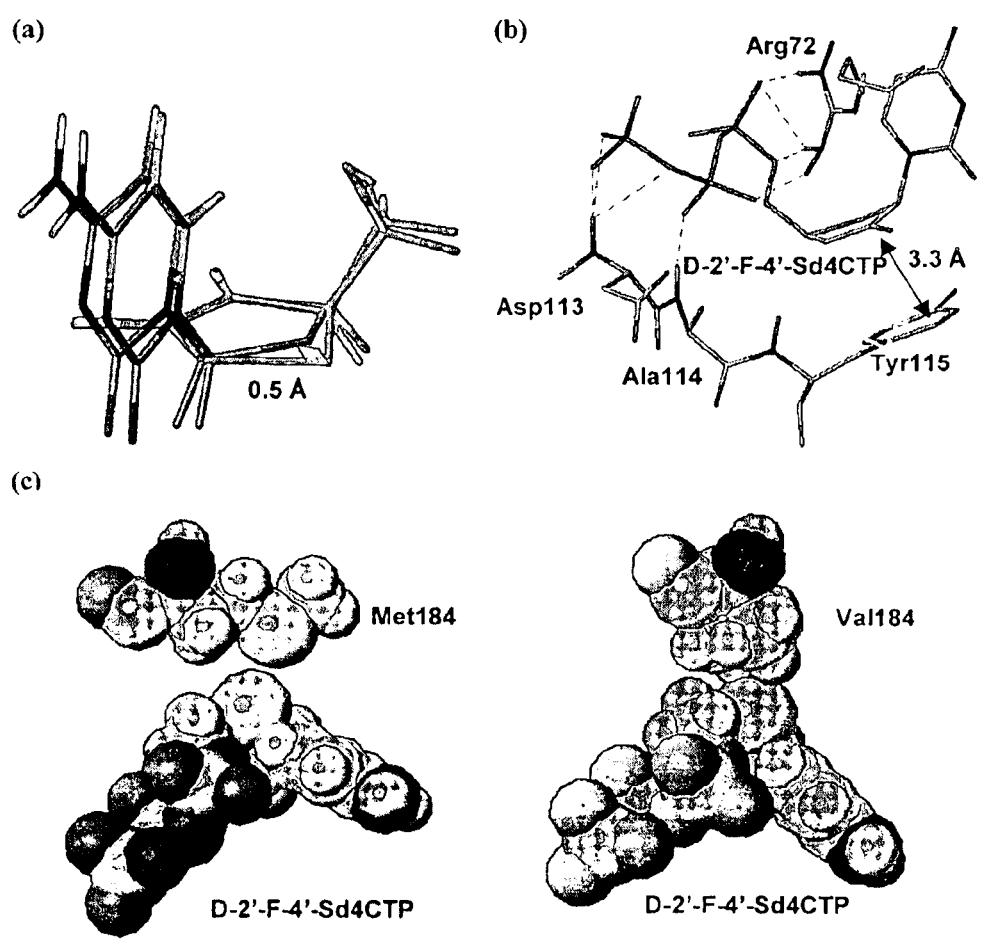
FIG. 18 is a non-limiting example of the molecular modeling for β-D-2'-halo nucleosides. (a) Superimposed, geometry-optimized structures of D-2'-F-4'-Sd4C; (17) and D-2'-Fd4C; (b) Binding mode of D-2'-F-4'-Sd4C (17) to the active site of HIV-1 RT; (c) Energy minimized structure of D-2'-F-4'-Sd4C (17), complexed with the wild-type HIV-1 RT (left) and M184V mutant RT (right).

Since there is no crystal structure available for kinases, molecular modeling studies were based on the polymerase level. The molecular modeling studies of the triphosphates of several nucleoside reverse transcriptase inhibitors (NRTIs) was done according to the crystal structure of HIV-1 RT, complexed with thymidine triphosphate and DNA duplex based on Huang et al. (Structure of a covalently trapped catalytic complex of HIV-1 reverse transcriptase: Implications for drug resistance. *Science*, 1998, 282, 1669–1675). The conformations of β-D-2'-Fd4N and the corresponding 4'-thio congeners were compared. A quantum mechanical calculation (RHF/3-21G*) was performed on cytidine analogues (β-D-2'-Fd4C$^{11(b)}$ and β-D-2'-F-4'-Sd4C (D-17), and the geometry-optimized structures were compared (FIG. 18-a). The two structures were superimposable except for the 4'-positions; the strain inside the 4'-thio sugar ring caused by the longer C—S bond length resulted in moving the 4'-sulfur atom by 0.5 Å down to the plane formed by C1', C2', C3' and C4'. Another reason for this out-of-plane moving the 4'-sulfur atom is that, unlike 4'-oxygen, the 4'-sulfur atom cannot form a hydrogen bond with 5'-OH due to the lack of the gauche effect. However, the critically important configurations of the N1 and C5' atoms of a nucleoside are in good accordance, which may imply the similar tolerance to the two types of nucleosides by the kinases. On the other hand, when the triphosphates of β-D-2'-Fd$_4$C$^{11(b)}$ and β-D-2'-F-4'-Sd4C (D-17) bind to the active site of HIV-1 reverse transcriptase, the isosteric replacement of 4'-oxygen with 4'-sulfur atom exerts effects on the interaction between the nucleoside triphosphates and the active site residues, particularly Tyr115 and Met184 (FIGS. 18-b and 18-c). The energy-minimized structures of β-D-2'-Fd4C and β-D-2'-F-4'-Sd4C (D-17) bound to HIV-1 RT shows that nucleoside inhibitors are located in a well-defined binding pocket formed by Arg72, Met184 and 3'-OH pocket residues (Asp113, Tyr115, Phe116 and Gln151) (FIG. 18-b) (Lee, K.; Chu, C. K. Molecular modeling approach to understanding the mode of action of L-nucleosides as antiviral agents. *Antimicrob. Agents Chemother.* 2001, 45, 138–144). The role of Arg72 is notable because, as it moves into the binding pocket, it stabilizes the bound nucleotide through hydrogen bonding with the triphosphate moiety as well as nonspecific hydrophobic interaction with the heterocyclic moiety of the nucleoside triphosphate (FIG. 18-b). An additional characteristic binding mode of these d4-nucleotides is the possible π—π interaction between C2'–C3' fluorovinyl moiety of the nucleotide and the aromatic ring of nearby Tyr115, which could be one reason for the high antiviral activity of 2',3'-unsaturated nucleosides (FIG. 18-b) (Takagi, R.; Nakamura, M.; Hashizume, M.; Kojima, S.; Ohkata, K. Stereoselective cyclopropanation of 3-aryl-2-phosphonoacrylates induced by the (−)-8-phenylmenthyl group as a chiral auxiliary. *Tetrahedron lett.* 2001, 42, 5891–5895). Fluorine substitution at C2' position would make the C2'–C3' double bond electron poor and, thus, increase the π—π interaction with the electron-rich aromatic ring of Tyr115. In spite of almost the same binding mode of β-D-2'-Fd4C and β-D-2'-F-4'-Sd4C (D-17), the decreased antiviral activity of β-D-2'-F-4'-Sd4C can be explained by the decrease in π—π interaction. The replacement of electronegative oxygen by sulfur depolarizes charges inside the sugar ring in β-D-2'-F4'-Sd4C (D-17), which may result in reduced π—π interaction between the fluorovinyl moiety and aromatic ring of Tyr115. Because of its out-of-plane location and large van der Waals radius, the 4'-sulfur atom in the β-D-2'-F-4'-Sd4N sugar moiety is in close contact to Met184 (FIG. 18-c). As a result, the mutation of Met184 to Val184, which has a bulky side chain, results in a significant steric hindrance between the 4'-sulfur atom in the β-D-2'-F-4'-Sd4N sugar moiety and the side chain of Val184, which might be one of the reasons for the high cross-resistance of HIV-$1_{M184V}$ to β-D-2'-F-4'-Sd4C (D-17) and β-D-2'-F4'-Sd4FC (D-18) (Table 9, FIG. 18-c).

The isosteric replacement of 4'-oxygen in β-D-2'-Fd4 nucleosides with 4'-sulfur caused substantial changes in the binding mode of β-D-2'-F-4'-Sd4 to the active site of HIV-1 RT, resulting in reduced in vitro anti-HIV-1 activity. The lamivudine-resistant mutant strain (HIV-$1_{M184V}$) showed significant cross-resistance to the β-D-2'-F-4'-Sd4 nucleosides, which could be explained by the larger van der Waals radius as well as the close proximity to Met184 of the 4'-sulfur atom.

Figure 19:
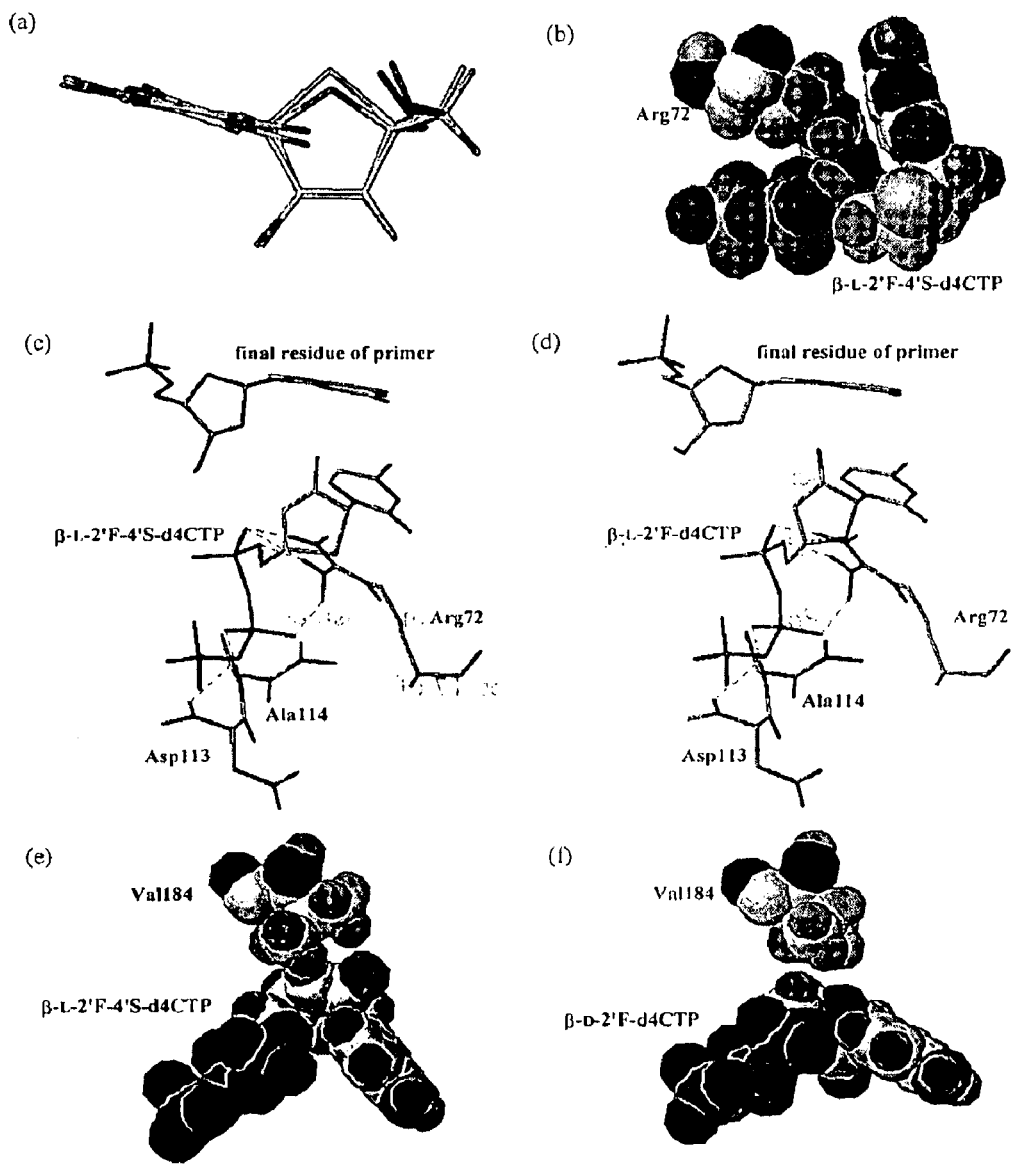
FIG. 19 is non-limiting example of the molecular modeling for β-L-2'-halo nucleosides. (a) Superimposed, geometry-optimized structures of β-L-2'F-d4C and β-L-2'F-4'S-d4C; (b) The CPK structure showing interaction of β-L-2'F-4'S-d4CTP with Arg72; (c) The minimized structure of β-L-2'F4'S-d4CTP after docking to the active site of HIV-1 reverse transcriptase; (d) The minimized structure of β-L-2'F-d4CTP after docking to the active site of HIV-1 reverse transcriptase; (e) β-L-2'F-4'S-d4CTP/RT complex after mutation from M184 to V184 showing a steric hindrance between the sugar moiety of β-L-2'F-4'S-d4CTP and the side chain of V184; and (f) β-D-2'F-d4CTP/RT complex after mutation showing no steric hindrance.

Similarly, molecular modeling studies were conducted on the representative L-cytidine analogs (β-L-2'F-d4C and β-L-2'F-4'S-d4C L-17). Again, the two geometry-optimized structures were nicely superimposed each other except positions of the 4'-oxygen and 4'-sulfur. Because the sulfur atom has a longer van der Waals radius than the oxygen atom, the 4'-sulfur was positioned slightly outside of the 4'-oxygen when two cytidine analogs were superimposed. However, the distance between the heterocyclic base and 5'-hydroxy group, which has been considered as the key factor to bind to nucleoside kinases, is similar in the two classes as shown in FIG. 19-a (Wang, P.; Hong, J. H.; Cooperwood, J. S.; Chu, C. K. Recent advances in L-nucleosides: chemistry and biology. *Antiviral Res.* 1998, 40, 19–44; Herdewijn, P. Structural requirements for activiral activity in nucleosides. *Drug Discov. Today*, 1997, 2, 235–242). Both β-L-2'F4'S-d4C L-17 and β-L-2'F-d4C may be potentially the substrates of nucleoside kinases, such as deoxycytidine kinase. After the initial phosphorylation of the synthesized nucleosides, their triphosphates could be readily synthesized by nucleotide kinases as the first phosphorylation step is considered as the rate-limiting step (Gaubert, G.; Gosselin, G.; Boudou, V.; Imbach, J. -L.; Eriksson, S.; Maury, G. Low enatioselectivities of human deoxycytidine kinase and human deoxyguanosine kinase with respect to 2'-deoxyadenosine, 2'-deoxyguanosine and their anlolgs. *Biochimie*, 1999, 81; 1041–1047). The triphosphates of geometry-optimized β-L-2'F-4'S-d4C L-17 and β-L-2'F-d4C, β-L-2'F-4'S-d4CTP and β-L-2'F-d4CTP were manually docked into the truncated catalytic site of HIV-1 RT (Lys1~Pro243 in p66 subunit), and the complexes were energy-minimized using Kollman-All-Atom force field (Weiner, S. J.; Kollman, P. A.; Nguyen, D. T.; Case, D. A. An all atom force field for simulations for proteins and nucleic acids. *J. Comput. Chem.* 1986, 7, 230–252). Both minimized structures showed that the triph osphates of β-L-2'F4'S-d4C L-17 and β-L-2'F-d4C bound tightly to the active site of HIV-1 RT (FIGS. 19-c and 19-d). In addition to the structural similarity, which was shown in FIG. 19-a, their binding modes to the HIV-1 RT were also similar in several aspects. Arg72 at the active site of HIV-1 RT plays a key role in binding the triphosphates of β-L-2'F-4'S-d4C L-17 and β-L-2'F-d4C: The guanidinium moiety of Arg72 approaches the active site in order to establish multiple hydrogen bonds with the triphosphates of β-L-2'F-4'S-d4CTP and β-L-2'F-d4CTP, resulting in stabilization of the nucleoside triphosphates. The backbone amides, which are part of 3'-OH pocket residues (Asp113 and Ala114), also stabilize the triphosphates through the hydrogen bonding interaction. Even though the 4'-sulfur atom in β-L-2'F-4'S-d4C L-17 is closer to Arg72 compared to the 4'-oxygen in β-L-2'F-d4C, there was no destabilizing steric hindrance between the 4'-sulfur atom and the guanidinium moiety of Arg72, which allowed stable orientation of β-L-2'F4'S-d4C L-17 at the active site (FIG. 19-b). The conformational analysis and binding affinity from the modeling studies indicate that β-L-2'F-4'S-d4C L-17 and β-L-2'F-d4C have similar structures, and the substitution of a sulfur atom is well tolerated at the polymerase level, which could explain their similar antiviral potency in the wild-type viral RT. However, the M184V mutation in HIV-1 RT causes a serious problem in positioning the L-configured nucleoside triphosphates at the active site, because the branched methyl groups of Val184 tend to occupy the space where the sugar moiety of L-2'F-2',3'-unsaturated nucleosides projected. The resulting steric hindrance destabilized the L-2'F-2',3'-unsaturated nucleoside triphosphate/RT complex (FIG. 19-e), which can be confirmed by the highly decreased relative binding energies for L-nucleosides (Table 9). On the other hand, the structure of β-D-2'F-d4CTP/RT complex does not show any significant steric crash between Val184 and the sugar moiety of nucleoside triphosphate because the natural D-configured sugar moiety was located at the opposite side (FIG. 19-f). Therefore,the antiviral data of β-D-2'F-d4C against the 3TC-resistant mutant is predicted to maintain the antiviral activity against the 3TC-resistant strain. The potent anti-HIV-$1_{M184V}$ activity of its 5-fluoro analogue, β-D-2'F-d4FC, supports this idea. In this context, it is interesting that M184V RT is cross-resistant to the natural D-configured β-D-2'F-4'S-d4C.[24] The molecular modeling study showed that the longer van der Waals radius of 4'-sulfur and the longer C—S bond length place the 4'-sulfur atom close enough to Val184, which resulted in steric hindrance, and thereby reduced relative binding affinity and antiviral potency.

The pyrimidine analogs, β-L-2'F-4'S-d4C L-17 and β-L-2'F4'S-d4–5FC L-18 showed potent antiviral activity against HIV-1. The cytidine analogue, β-L-2'F4'S-d4C L-17, however, did not show any significant antiviral activity against the 3TC-resistant mutant RT. Based on the molecular modeling studies, the similar pattern of anti-HIV-1 activity of β-L-2'F-4'S-d4N and β-L-2'F-d4N can be explained by their conformational and structural similarities. The unnatural L-configuration of sugar moiety was found to provide steric hindrance with the side chain of Val184 in 3TC-resistant RT, which destabilized the RT-nucleoside analog complex.

TABLE 9

Correlation of relative binding energy difference ($\Delta E_{rel}$) with fold increase (FI)

| Compound | WT (xxBRU) Activity (EC$_{90}$, μM) | WT (xxBRU) E$_{rel}$[a] (kcal/mol) | M184V Activity (EC$_{90}$, μM) | M184V E$_{rel}$[a] (kcal/mol) | F1[b] | $\Delta E_{rel}$[c] (kcal/mol) |
|---|---|---|---|---|---|---|
| β-L-2'F-4'S-d4C (L-17) | 1.4 | 86.0 | >100 | −21.5 | >100 | 107.5 |
| β-L-2'F-d4C | 2.1 | 36.8 | >100 | −70.0 | >100 | 106.8 |
| β-D-2'F-4'S-d4C[d] | 5.0 | 82.6 | 125 | −14.8 | 25 | 97.4 |
| (D-17) β-D-2'F-d4C | —[e] | 44.3 | —[e] | −6.5 | —[e] | 50.8 |
| β-D-2'F-d4FC[f] | 3.1[g] | —[h] | 9.6[g] | — | 3[g] | —[h] |

[a]relative binding energy (E$_{rel}$) = binding energy of nucleoside triphosphate - binding energy of dCTP, [b]EC$_{90}$ HIV-1$_{M184V}$/EC$_{90}$ HIV-1$_{xxBRU}$, [c]relative binding energy difference ($\Delta E_{rel}$) = E$_{rel}$(WT) − E$_{rel}$(M184V), [d]Ref. 24, [e]not available, [f]Ref. 23, [g]anti-HIV activity or fold increase in EC$_{50}$ (μM), [h]not determined This invention has been described with reference to its preferred embodiments. Variations and modifications of the invention, will be obvious to those skilled in the art from the foregoing detailed description of the invention. It is intended that all of these variations and modifications be included within the scope of this invention.

We claim:

1. A method for the treatment of an HIV infection in a host, comprising administering an effective treatment amount of a β-D or β-L-3'-halonucleoside of the formula (II):

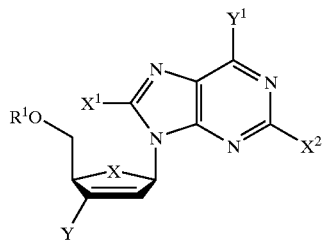

(II)

or its pharmaceutically acceptable salt, optionally in combination with a pharmaceutically acceptable carrier, wherein X is S;

Y is fluoro, chloro, bromo or iodo;

$R^1$ is hydrogen, straight chained, branched or cyclic alkyl, CO-alkyl, CO-aryl, CO-alkoxyalkyl, CO-aryloxyalkyl, CO-substituted aryl, aryl, alkylsufonyl, arylsulfonyl, aralkylsulfonyl, amino acid residue, mono, di or triphosphate or a phosphate derivative;

$Y^1$ is OH, $OR^2$, $NH_2$, $NHR^2$, $NR^2R^3$, SH, $SR^2$ or halogen;

$X^1$ and $X^2$ are independently selected from the group consisting of H, straight chained, branched or cyclic alkyl, CO-alkyl, CO-aryl, CO-alkoxyalkyl, halogen, OH, $OR^4$, $NH_2$, $NHR^2$, $NR^4R^5$, SH or $SR^4$; and $R^2$, $R^3$, $R^4$ and $R^5$ are independently H, straight chained, branched or cyclic alkyl, dialkylaminoalkylene, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate.

2. A method for the treatment of an HIV infection in a host, comprising administering an effective treatment amount of a β-D or β-L-3'-halonucleoside of the formula (II):

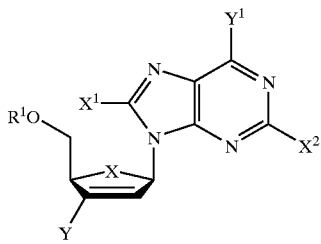

(II)

or its pharmaceutically acceptable salt, in combination or alternation with one or more other effective anti-HIV agent, optionally in combination with a pharmaceutically acceptable carrier, wherein X is S;

Y is fluoro, chloro, bromo or iodo;

$R^1$ is hydrogen, straight chained, branched or cyclic alkyl, CO-alkyl, CO-aryl, CO-alkoxyalkyl, CO-aryloxyalkyl, CO-substituted aryl, aryl, alkylsufonyl, arylsulfonyl, aralkylsulfonyl, amino acid residue, mono, di or triphosphate or a phosphate derivative;

$Y^1$ is OH, $OR^2$, $NH_2$, $NHR^2$, $NR^2R^3$, SH, $SR^2$ or halogen;

$X^1$ and $X^2$ are independently selected from the group consisting of H, straight chained, branched or cyclic alkyl, CO-alkyl, CO-aryl, CO-alkoxyalkyl, halogen, OH, $OR^4$, $NH_2$, $NHR^2$, $NR^4R^5$, SH or $SR^4$; and $R^2$, $R^3$, $R^4$ and $R^5$ are independently H, straight chained, branched or cyclic alkyl, dialkylaminoalkylene, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate.

3. A method for the treatment of an HIV infection in a host, comprising administering an effective treatment amount of a β-D or β-L-3'-halonucleoside of the formula (II):

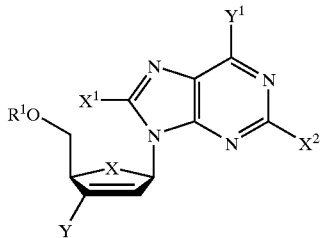

(II)

or its pharmaceutically acceptable salt, optionally in combination with a pharmaceutically acceptable carrier, wherein X is O or S;

Y is fluoro, chloro, bromo or iodo;

$R^1$ is hydrogen, straight chained, branched or cyclic alkyl, CO-alkyl, CO-aryl, CO-alkoxyalkyl, CO aryloxyalkyl, CO-substituted aryl, aryl, alkylsufonyl, arylsulfonyl, aralkylsulfonyl, amino acid residue, mono, di or triphosphate or a phosphate derivative;

$Y^1$ is OH, $OR^2$, SH, $SR^2$ or halogen;

$X^1$ and $X^2$ are independently selected from the group consisting of H, straight chained, branched or cyclic alkyl, CO-alkyl, CO-aryl, CO-alkoxyalkyl, halogen, OH, $OR^4$, $NH_2$, $NHR^2$, $NR^4R^5$, SH or $SR^4$; and $R^2$, $R^3$, $R^4$ and $R^5$ are independently H, straight chained, branched or cyclic alkyl, dialkylaminoalkylene, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate.

4. The method of claim 3 wherein X is O.
5. The method of claim 3 wherein X is S.
6. The method of claim 3 wherein Y is F.
7. A method for the treatment of an HIV infection in a host, comprising administering an effective treatment amount of a β-D or β-L-3'-halonucleoside of the formula (II):

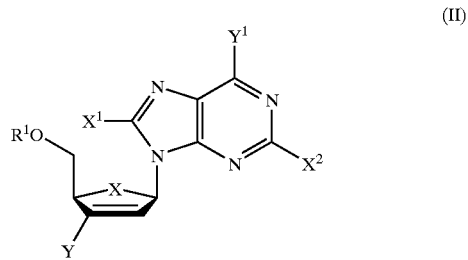

(II)

or its pharmaceutically acceptable salt, in combination or alternation with one or more other effective anti-HIV agent, optionally in combination with a pharmaceutically acceptable carrier, wherein X is O or S;

Y is fluoro, chloro, bromo or iodo;

$R^1$ is hydrogen, straight chained, branched or cyclic alkyl, CO-alkyl, CO-aryl, CO-alkoxyalkyl, CO aryloxyalkyl, CO-substituted aryl, aryl, alkylsufonyl, arylsulfonyl, aralkylsulfonyl, amino acid residue, mono, di or triphosphate or a phosphate derivative;

$Y^1$ is OH, $OR^2$, SH, $SR^2$ or halogen;

$X^1$ and $X^2$ are independently selected from the group consisting of H, straight chained, branched or cyclic alkyl, CO-alkyl, CO-aryl, CO-alkoxyalkyl, halogen OH, $OR^4$, $NH_2$, $NHR^2$, $NR^4R^5$, SH or $SR^4$; and $R^2$, $R^3$, $R^4$ and $R^5$ are independently H, straight chained, branched or cyclic alkyl dialkylaminoalkylene, dimethylaminomethylene, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate.

8. The method of claim 7, wherein X is O.
9. The method of claim 7, wherein X is S.
10. The method of claim 7, wherein Y is F.
11. The method of any one of claims 3, 4–6, 7 or 8–10, wherein the host is a human.
12. A method for the treatment of an HBV infection in a host, comprising administering an effective treatment amount of a β-D or β-L-3'-halonucleoside of the formula (II):

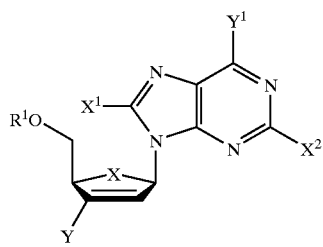

(II)

or its pharmaceutically acceptable salt, optionally in combination with a pharmaceutically acceptable carrier, wherein X is O, S, SO$_2$;

Y is fluoro, chloro, bromo or iodo;

R$^1$ is hydrogen, straight chained, branched or cyclic alkyl, CO-alkyl, CO-aryl, CO-alkoxyalkyl, CO aryloxyalkyl, CO-substituted aryl, aryl, alkylsufonyl, arylsulfonyl, aralkylsulfonyl, amino acid residue, mono, di or triphosphate or a phosphate derivative;

Y$^1$ is OH, OR$^2$, NH$_2$, NHR$^2$, NR$^2$R$^3$, SH, SR$^2$ or halogen;

X$^1$ and X$^2$ are independently selected from the group consisting of H, straight chained, branched or cyclic alkyl, CO-alkyl, CO-aryl, CO-alkoxyalkyl, halogen, OH, OR$^4$, NH$_2$, NHR$^2$, NR$^4$R$^5$, SH or SR$^4$; and R$^2$, R$^3$, R$^4$ and R$^5$ are independently H, straight chained, branched or cyclic alkyl, dialkylaminoalkylene, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate.

13. A method for the treatment of an HBV infection in a host, comprising administering an effective treatment amount of a β-D or β-L-3'-halonucleoside of the formula (II):

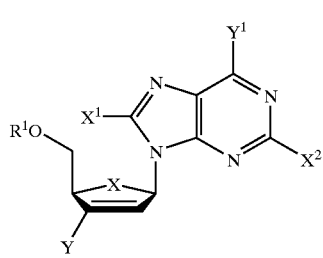

(II)

or its pharmaceutically acceptable salt, in combination or alternation with one or more other effective anti-HBV agents optionally in combination with a pharmaceutically acceptable carrier, wherein X is O, S, SO$_2$ or CH$_2$;

Y is fluoro, chloro, bromo or iodo;

R$^1$ is hydrogen, straight chained, branched or cyclic alkyl, CO-alkyl, CO-aryl, CO-alkoxyalkyl, CO aryloxyalkyl, CO-substituted aryl, aryl, alkylsufonyl, arylsulfonyl, aralkylsulfonyl, amino acid residue, mono, di or triphosphate or a phosphate derivative Y$^1$ is OH, OR$^2$, NH$_2$, NHR$^2$, NR$^2$R$^3$, SH, SR$^2$ or halogen;

X$^1$ and X$^2$ are independently selected from the group consisting of H, straight chained, branched or cyclic alkyl, CO-alkyl, CO-aryl, CO-alkoxyalkyl, halogen, OH, OR$^4$, NH$_2$, NHR$^2$, NR$^4$R$^5$, SH or SR$^4$; and R$^2$, R$^3$, R$^4$ and R$^5$ are independently H, straight chained, branched or cyclic alkyl, dialkylaminoalkylene, dimethylaminomethylene, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate.

14. The method of claim 12 or 13, wherein the host is a human.

15. The method of claim 12 or 13, wherein Y is F.

16. The method of any of claims 3, 7, 1 or 2 wherein R$^1$ is hydrogen.

17. The method of any of claims 3, 7, 1 or 2 wherein Y$^1$ is OH.

18. The method of any of claims 1 or 2 wherein Y$^1$ is NH$_2$.

19. The method of any of claims 1 or 2 wherein Y$^1$ is NHR$^2$.

20. The method of any of claims 3, 7, 1 or 2 wherein Y$^1$ is Cl.

21. The method of any of claims 3, 7, 1 or 2 wherein X$^1$ and X$^2$ are independently H.

22. The method of any of claims 3, 7, 1 or 2 wherein X$^1$ and X$^2$ are independently OH.

23. The method of any of claims 3, 7, 1 or 2 wherein X$^1$ and X$^2$ are independently NH$_2$.

24. The method of any of claims 3, 7, 1 or 2 wherein R$^2$, R$^3$, R$^4$ and R$^5$ are independently H.

25. The method of any of claims 3, 7, 1 or 2 wherein R$^2$, R$^3$, R$^4$ and R$^5$ are independently alkyl.

26. The method of any of claims 3, 7, 1 or 2 wherein R$^2$, R$^3$, R$^4$ and R$^5$ are independently amino acid residue.

27. The method of any of claims 3, 7, 1 or 2 wherein R$^2$, R$^3$, R$^4$ and R$^5$ are independently mono-phosphate.

28. The method of any of claims 3, 7, 1 or 2 wherein R$^2$, R$^3$, R$^4$ and R$^5$ are independently di-phosphate.

29. The method of any of claims 3, 7, 1 or 2 wherein R$^2$, R$^3$, R$^4$ and R$^5$ are independently tri-phosphate.

30. The method of claim 13, wherein the other effective anti-HBV agent is selected from the group consisting of (−)-enantiomer of 2-hydroxymethyl-5-(cytosin-1-yl)-1,3-oxathiolane (3TC), cis-2-hydroxymethyl-5-(5-fluorocytosin-1-yl)-1,3-oxathiolane (FTC), L-FMAU, interferon, β-D-dioxolanyl-guanine (DXG), β-D-dioxolanyl-2,6-diaminopurine (DAPD), and β-D-dioxolanyl-6-chloropurine (ACP), famciclovir, penciclovir, BMS-200475, bis porn PMEA; lobucavir, ganciclovir, and ribavarin.

31. The method of claim 7 or 2, wherein the other effective anti-HIV agent is selected from the group consisting of a protease inhibitor, cis-2-hydroxymethyl-5-(5-fluorocytosin-1-yl)-1,3-oxathiolane (FTC), the (−)-enantiomer of 2-hydroxymethyl-5-(cytosin-1-yl)-1,3-oxathiolane (3TC), carbovir, acyclovir, foscarnet, interferon, AZT, DDI, DDC, D4T, CS-87 (3'-azido-2',3'-dideoxy-uridine), and β-D-dioxolane nucleosides, and MKC-442 (6-benzyl-1-(ethoxymethyl)-5-isopropyl uracil.

32. The method of one of claims 1or 2 wherein Y is F.

33. The method of one of claims 1 or 2 wherein X$^1$ and X$^2$ are each H and Y$^1$ is NH$_2$.

34. The method of one of claims 3, 7, 1 or 2 wherein R$^1$ is CO-alkyl.

35. The method of one of claims 3, 7, 1 or 2 wherein wherein X$^2$ is NH$_2$.

36. The method of one of claims 3, 7, 1 or 2 wherein X$^2$ is F.

37. The method of claim 3, wherein the 3'-halonucleoside is a β-D nucleoside.

38. The method of claim 7 wherein the 3'-halonucleoside is a β-D nucleoside.

39. The method of claim 1 wherein the 3'-halonucleoside is a β-D nucleoside.

40. The method of claim 2 wherein the 3'-halonucleoside is a β-D nucleoside.

41. The method of claim 3, wherein the 3'-halonucleoside is a β-L nucleoside.

42. The method of claim 7 wherein the 3'-halonucleoside is a β-L nucleoside.

43. The method of claim 1 wherein the 3'-halonucleoside is a β-L nucleoside.

44. The method of claim 2 wherein the 3'-halonucleoside is a β-L nucleoside.

* * * * *

SEQUENCE LISTING

<160> NUMBER OF SEQ ID NOS: 12

<210> SEQ ID NO 1
<211> LENGTH: 33
<212> TYPE: DNA
<213> ORGANISM: Artificial
<220> FEATURE:
<223> OTHER INFORMATION: quenched fluorescent probe
<220> FEATURE:
<221> NAME/KEY: misc_feature
<222> LOCATION: (1)..(1)
<223> OTHER INFORMATION: n=FAM modified thymine
<220> FEATURE:
<221> NAME/KEY: misc_feature
<222> LOCATION: (33)..(33)
<223> OTHER INFORMATION: n=TAMRA modified thymine

<400> SEQUENCE: 1
nttctggcag cactataggc tgtactgtcc atn                          33

<210> SEQ ID NO 2
<211> LENGTH: 23
<212> TYPE: DNA
<213> ORGANISM: Artificial
<220> FEATURE:
<223> OTHER INFORMATION: sense primer

<400> SEQUENCE: 2
tgggttatga actccatcct gat                                     23

<210> SEQ ID NO 3
<211> LENGTH: 22
<212> TYPE: DNA
<213> ORGANISM: Artificial
<220> FEATURE:
<223> OTHER INFORMATION: antisense primer

<400> SEQUENCE: 3
tgtcattgac agtccagcgt ct                                      22

```
<210> SEQ ID NO 4
<211> LENGTH: 29
<212> TYPE: DNA
<213> ORGANISM: Artificial
<220> FEATURE:
<223> OTHER INFORMATION: probe
<220> FEATURE:
<221> NAME/KEY: misc_feature
<222> LOCATION: (1)..(1)
<223> OTHER INFORMATION: n=6FAM
<220> FEATURE:
<221> NAME/KEY: misc_feature
<222> LOCATION: (29)..(29)
<223> OTHER INFORMATION: n=TAMRA

<400> SEQUENCE: 4
naaatcctcc taacaagcgg gttccaggn                                29

<210> SEQ ID NO 5
<211> LENGTH: 23
<212> TYPE: DNA
<213> ORGANISM: Artificial
<220> FEATURE:
<223> OTHER INFORMATION: sense primer

<400> SEQUENCE: 5
agccttcagt ttcttgctga tgt                                      23

<210> SEQ ID NO 6
<211> LENGTH: 20
<212> TYPE: DNA
<213> ORGANISM: Artificial
<220> FEATURE:
<223> OTHER INFORMATION: antisense primer

<400> SEQUENCE: 6
tgttgcgaaa ggaccaacag                                          20

<210> SEQ ID NO 7
<211> LENGTH: 17
<212> TYPE: DNA
<213> ORGANISM: Artificial
<220> FEATURE:
<223> OTHER INFORMATION: sense primer

<400> SEQUENCE: 7
tgcccgccat catccta                                             17

<210> SEQ ID NO 8
<211> LENGTH: 23
<212> TYPE: DNA
<213> ORGANISM: Artificial
<220> FEATURE:
<223> OTHER INFORMATION: probe
<220> FEATURE:
<221> NAME/KEY: misc_feature
<222> LOCATION: (1)..(1)
<223> OTHER INFORMATION: n=TET
<220> FEATURE:
<221> NAME/KEY: misc_feature
<222> LOCATION: (23)..(23)
<223> OTHER INFORMATION: n=TAMRA

<400> SEQUENCE: 8
ntcctcatcg ccctcccatc ccn                                      23

<210> SEQ ID NO 9
<211> LENGTH: 23
<212> TYPE: DNA
```

```
-continued

<213> ORGANISM: Artificial
<220> FEATURE:
<223> OTHER INFORMATION: antisense probe

<400> SEQUENCE: 9
cgtctgttat gtaaaggatg cgt                                              23

<210> SEQ ID NO 10
<211> LENGTH: 17
<212> TYPE: DNA
<213> ORGANISM: Artificial
<220> FEATURE:
<223> OTHER INFORMATION: sense primer

<400> SEQUENCE: 10
gcgcggctac agcttca                                                     17

<210> SEQ ID NO 11
<211> LENGTH: 20
<212> TYPE: DNA
<213> ORGANISM: Artificial
<220> FEATURE:
<223> OTHER INFORMATION: probe
<220> FEATURE:
<221> NAME/KEY: misc_feature
<222> LOCATION: (1)..(1)
<223> OTHER INFORMATION: n=6FAM
<220> FEATURE:
<221> NAME/KEY: misc_feature
<222> LOCATION: (20)..(20)
<223> OTHER INFORMATION: n=6TAMRA

<400> SEQUENCE: 11
ncaccacggc cgagcgggan                                                  20

<210> SEQ ID NO 12
<211> LENGTH: 22
<212> TYPE: DNA
<213> ORGANISM: Artificial
<220> FEATURE:
<223> OTHER INFORMATION: antisense probe

<400> SEQUENCE: 12
tctccttaat gtcacgcacg at                                               22
```